US009464330B2

(12) United States Patent
Allen et al.

(10) Patent No.: US 9,464,330 B2
(45) Date of Patent: Oct. 11, 2016

(54) GENETIC LOCI ASSOCIATED WITH SOYBEAN CYST NEMATODE RESISTANCE AND METHODS OF USE

(71) Applicant: Pioneer Hi-Bred International, Inc., Johnston, IA (US)

(72) Inventors: Jonathan B. Allen, Polk City, IA (US); Bryce Daines, Johnston, IA (US); David Hyten, Jr., Johnston, IA (US); Donald Kyle, Princeton, IL (US); Clinton W. Mapel, Edwardsville, IL (US); Joshua M. Shendelman, Ankeny, IA (US); Jeffrey A. Thompson, Edwardsville, IA (US); John B. Woodward, Ankeny, IA (US); Yanwen Xiong, Johnston, IA (US); Meizhu Yang, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 591 days.

(21) Appl. No.: 13/786,948

(22) Filed: Mar. 6, 2013

(65) Prior Publication Data
US 2014/0182009 A1    Jun. 26, 2014

Related U.S. Application Data

(60) Provisional application No. 61/745,002, filed on Dec. 21, 2012.

(51) Int. Cl.
*C12Q 1/68* (2006.01)
*A01H 1/04* (2006.01)

(52) U.S. Cl.
CPC ............... *C12Q 1/6895* (2013.01); *A01H 1/04* (2013.01); *C12Q 2600/156* (2013.01)

(58) Field of Classification Search
CPC .................................................. C12Q 1/6895
See application file for complete search history.

(56) References Cited

U.S. PATENT DOCUMENTS

| | | | |
|---|---|---|---|
| 5,491,081 | A | 2/1996 | Webb |
| 6,096,944 | A | 8/2000 | Vierling et al. |
| 6,162,967 | A | 12/2000 | Webb |
| 6,300,541 | B1 | 10/2001 | Lightfoot et al. |
| 6,538,175 | B1 | 3/2003 | Webb |
| 7,154,021 | B2 | 12/2006 | Hauge et al. |
| 7,485,770 | B2 | 2/2009 | Hauge et al. |
| 7,872,171 | B2 | 1/2011 | Webb |
| 2002/0144310 | A1 | 10/2002 | Lightfoot et al. |
| 2004/0031072 | A1 | 2/2004 | La Rosa et al. |
| 2007/0083945 | A1 | 4/2007 | Byrum et al. |
| 2009/0100537 | A1* | 4/2009 | Concibido ............... A01H 1/04 800/265 |
| 2011/0083234 | A1* | 4/2011 | Nguyen ................... A01H 1/00 800/301 |

FOREIGN PATENT DOCUMENTS

| | | |
|---|---|---|
| WO | WO 99/31964 A1 | 7/1999 |
| WO | WO 2005/075685 A1 | 8/2005 |
| WO | WO 2014/100346 | 6/2014 |

OTHER PUBLICATIONS

Thomas, 1985, J. Opt. Soc. Am. 2: 1457-1467.*
Yue et al., 2000, Euphytica 116: 181-186.*
Batley and Edwards, 2007, In; Association Mapping in Plants, pp. 95-102.*
Suzuki et al., GenBank accession No. AB506488, Jun. 6, 2009.*
Hyten et al., 2010, Crop Science 50: 960-968.*
Ferdous et al., 2006, Breeding Science 56: 155-163.*
International Search Report and Written Opinion mailed on May 9, 2014 for PCT/US2013/076414 filed Dec. 19, 2013 and published as WO 2014/100346 on Jun. 26, 2014 (Applicants—Pioneer Hi-Bred International, Inc. // Inventors—Allen et al.) (7 pages).
U.S. Appl. No. 12/961,684, filed Apr. 7, 2011, David M. Webb.
U.S. Appl. No. 13/544,470, filed Nov. 1, 2012, David M. Webb.
U.S. Appl. No. 13/779,957, filed Feb. 28, 2013, Daines et al.
U.S. Appl. No. 13/780,390, filed Feb. 28, 2013, Shendelman et al.
U.S. Appl. No. 13/781,963, filed Mar. 1, 2013, Shendelman et al.
Anand, S.C., "Identification of Additional Soybean Germplasm with Resistant to Race 3 of the Soybean Cyst Nematode," *Plant. Disease*, 1984, vol. 68(7), pp. 593-595.
Anand, S.C., "Sources of resistance to the soybean cyst nematode," In Lamberti F., Taylor CE (eds) Cyst nematodes. NATO advanced study institute series. Plenum Press, New York, pp. 269-276.
Anand, S.C., "Genetic Diversity for Resistance to *Heterodera glycines* Race 5 in Soybean," *J. Nematol*, 1994, vol. 26(1), pp. 76-79.
Anand, S.C., et al., "Genetic Analyses of Soybean Genotypes Resistant to Soybean Cyst Nematode Race 5," *Crop. Sci.*, 1989, vol. 29, pp. 1181-1184.
Anand, S.C, et al., "Variation in Parasitic Potential of *Heterodera glycines* Populations," *Crop. Sci.*, 1994, vol. 34, pp. 1452-1454.
Arondel, V., et al., "Map-Based Cloning of a Gene Controlling Omega-3 Fatty Acid Desaturation in *Arabidopsis,*" *Science*, 1992, vol. 258, pp. 1353-1355.
Baltazar, B.M., et al., "Identification of restriction fragment length polymorphisms (RFLPs) to map soybean cyst nematode resistance genes in soybean," *Soybean Genet. Newsletter*, 1992, vol. 19, pp. 120-122.

(Continued)

*Primary Examiner* — David T Fox
*Assistant Examiner* — Bratislav Stankovic

(57) ABSTRACT

Various methods and compositions are provided for identifying and/or selecting soybean plants or soybean germplasm with improved resistance to soybean cyst nematode. In certain embodiments, the method comprises detecting at least one marker locus that is associated with resistance to soybean cyst nematode. In other embodiments, the method further comprises detecting at least one marker profile or haplotype associated with resistance to soybean cyst nematode. In further embodiments, the method comprises crossing a selected soybean plant with a second soybean plant. Further provided are markers, primers, probes and kits useful for identifying and/or selecting soybean plants or soybean germplasm with improved resistance to soybean cyst nematode.

16 Claims, 25 Drawing Sheets

(56) References Cited

OTHER PUBLICATIONS

Bent, A., et al., "SCN Resistance Determinants at the Rhg1 Locus," *Molecular & Cellular Biology of the Soybean Conference*, Aug. 12-15, 2012, Abstract.
Box, G.E.P., and Draper, N.R., "Adequacy of Estimation and the Use of Transformation," *Response Surfaces, Mixtures, and Ridge Analyses*, 2007, pp. 271-302, John Wiley & Sons, Inc.
Caldwell, B.E., et al., "Inheritance of Resistance of Soybeans to the Cyst Nematode, *Heterodera glycines*," *Agronomy Journal*, 1960, vol. 52, pp. 635-636.
Concibido, V.C., et al., "A Decade of QTL Mapping for Cyst Nematode Resistance in Soybean," Crop Science, 2004, vol. 44, pp. 1121-1131.
Cook, D.E., et al., "Copy Number Variation of Multiple Genes at Rhg1 Mediates Nematode Resistance in Soybean," Science, Nov. 30, 2012; 1206-9, 338(6111); doi: 10.1126/science.1228746. Epub Oct. 11, 2012.
Gibson, S., et al., "Isolating plant genes," *Trends Biotech*, 1993, vol. 11(7), pp. 306-313.
Golden, A.M., et al., "Terminology and Identity of Infraspecific Forms of the Soybean Cyst Nematode (*Heterodera glycines*)," *Plant Disease Reporter*, 1970, vol. 54(7), pp. 544-546.
Hartwig, E.E., et al., "Breeding Productive Soybeans with Resistance to the Soybean Cyst Nematode," In: Shibles R. (ed) Proceedings World Soy Res Conf. III, Westview Press, Boulder, Colo., pp. 394-399.
Keim, P., et al., "RFLP Analysis of Soybean Breeding Populations: I. Genetic Structure Differences due to Inbreeding Methods," *Crop Science*, 1994, vol. 34, pp. 55-61.
Keim, P., et al., "A rapid protocol for isolating soybean DNA," *Soybean Genet. Newsletter*, 1988, vol. 15, pp. 150-152.
Keim, P., et al., "Construction of a random recombinant DNA library that is primarily single copy sequences," *Soybean Genet. Newsletter*, 1988, vol. 15, pp. 147-148.
Keim, P., et al., "Restriction fragment length polymorphism diversity in soybean," *Theor. Appl. Genet.*, 1989, vol. 77, pp. 786-792.
Kim, M., et al., "Fine Mapping of the SCN Resistance Locus *rhg1-b* from PI 88788," *The Plant Genome*, 2010, vol. 3(2), pp. 81-89.
Knapp, S.J., et al., "Mapping quantitative trait loci using nonsimultaneous and simultaneous estimators and hypothesis tests," *Plant Genomes: Methods for Genetic and Physical Mapping*, 1992, pp. 209-237, Kluwer Academic Publishers, The Netherlands.
Lande, R., et al., "Efficiency of Marker Assisted Selection in the Improvement of Quantitative Traits," *Genetics*, 1990, vol. 124, pp. 743-756.
Lander, E.S., et al., "Strategies for studying heterogeneous genetic traits in humans by using a linkage map of restriction fragment length polymorphisms," *Proc. Natl. Acad. Sci. USA*, 1986, vol. 83, pp. 7353-7357.
Lander, E.S., et al., "Mapping Mendelian Factors Underlying Quantitative Traits Using RFLP Linkage Maps," *Genetics*, 1989, vol. 121, pp. 185-199.
Landry, B.S., and Hubert, N., "A genetic map for *Brassica napus* based on restriction fragment length polymorphisms detected with expressed DNA sequences," *Genome*, 1991, vol. 34 pp. 543-552.
Lee, T.G., et al., "Copy Number Polymorphism in the SCN Resistance Lodus rhg1-b From PI 88788," *Molecular & Cellular Biology of the Soybean Conference*, Aug. 12-15, 2012, Abstract.
Lewers, K., et al., "A physical map of a gene-dense region in soybean linkage group A2 near the black seed coat and $Rhg_4$ loci," *Theor. Appl. Genet.*, 2002, vol. 104, pp. 254-260.
Lincoln, S.E., et al., "MAPMAKER/EXP," Whitehead Institute of Biomedical Research, Cambridge, Mass., (1993).
Lincoln, S.E., et al., "MAPMAKER/QTL," Whitehead Institute of Biomedical Research, Cambridge, Mass., (1990).
Liu, S., et al., "A soybean cyst nematode resistance gene points to a new mechanism of plant resistance to pathogens," *Nature*, 2012, vol. 492, pp. 256-263.

Mansur, L.M., et al., "Generation Mean Analysis of Resistance to Race 3 of Soybean Cyst Nematode," *Crop Sci.*, 1993, vol. 33, pp. 1249-1253.
Marek, L.F., "Construction and Size Characterization of a Bacterial Artificial Chromosome (BAC) Library from Soybean," *Soybean Genet. Newsletter*, 1996, vol. 23, pp. 126-129.
Martin, G.B., et al., "Map-Based Cloning of a Protein Kinase Gene Conferring Disease Resistance in Tomato," *Science*, 1993, vol. 262, pp. 1432-1436.
McCann, J., et al., "Selection and Reproduction of Soybean Cyst Nematodes on Resistant Soybeans," *Crop Science*, 1982, vol. 22, pp. 78-80.
Mulrooney, R.P., "Soybean Disease Loss Estimate for Southern United States in 1987," *Plant Dis.*, 1988, vol. 72, p. 915.
Murray, M., and Thompson, W.F., "Rapid isolation of high molecular weight plant DNA," *Nucleic Acids Research*, 1980, vol. 8(19), pp. 4321-4325.
Myers, G.O., and Anand, S.C., "Inheritance of resistance and genetic relationships among soybean plant introductions to races of soybean cyst nematode," *Euphytica*, 1991, vol. 55, pp. 197-201.
Nelson, R.L., et al., "Evaluation of the USDA Soybean Germplasm Collection: Maturity Groups 000 to IV (PI 427.136 to PI 445.845)," *USDA-ARS Technical Bulletin*, 1988, No. 1726.
Niblack, T.L., et al., "Soybean Yield Losses Due to *Heterodera glycines* in Iowa," *Plant Dis.*, 1992, vol. 76(9), pp. 943-948.
Parrish, J.E., and Nelson, D.L., "Methods for Finding Genes a Major Rate-Limiting Step in Positional Cloning," *GATA*, 1993, vol. 10(2), pp. 29-41.
Rao-Arelli, A.P., and Anand, S.C., "Genetic Relationships Among Soybean Plant Introductions for Resistance to Race 3 of Soybean Cyst Nematode," *Crop Sci.*, 1988, vol. 28, pp. 650-652.
Rao-Arelli, A.P., et al., "Additional dominant gene in PI 88.788 conferring resistance to soybean cyst nematode race 3," *Soybean Genet. Newsletter*, 1991, vol. 18, pp. 221-224.
Rao-Arelli, A.P., et al., "Soybean Resistance to Soybean Cyst Nematode Race 3 is Conditioned by an Additional Dominant Gene," *Crop Science*, 1992, vol. 32, pp. 862-864.
Rao-Arelli, A.P., and Clark, K.M., "Inheritance of Soybean Cyst Nematode Resistance Genes in Soybean Germplasm," *Agronomy Abstraces*, ASA, Madison, Wis., p. 100, Abstract.
Rao-Arelli, A.P., et al., "A Rapid Method for Inoculating Soybean Seedlings with *Heterodera glycines*," *Plant Disease*, 1991, vol. 75, pp. 594-595.
Rao-Arelli, A.P., et al., "Genetic Diversity Among Isolates of *Heterodera glycines* and Sources of Resistance in Soybeans," *Plant Disease*, 1992, vol. 76(9), pp. 894-896.
Riggs, R.D., and Schmitt, D.P., "Complete Characterization of the Race Scheme for *Heterodera glycines*," *Journal of Nematologists*, 1988, vol. 20(3), pp. 392-395.
Rommens, J.M., et al., "Identification of the Cystic Fibrosis Gene: Chromosome Walking and Jumping," *Science*, 1989, vol. 245, pp. 1059-1065.
Shoemaker, R.C., and Specht, J.E., "Integration of the Soybean Molecular and Classical Genetic Linkage Groups," *Crop Sci.*, 1995, vol. 35, pp. 436-446.
Tachibana, H., et al., "Registration of 'BSR101' Soybean," *Crop Science*, 1987, vol. 27, pp. 612, Abstract.
Triantaphyllou, A., "Genetic Structure of Races of *Heterodera glycines* and Inheritance of Ability to Reproduce on Resistant Soybeans," *Journal of Nematology*, 1975, vol. 7(4), pp. 356-364.
Webb, D.M., et al., "Genetic mapping of soybean cyst nematode race-3 resistance loci in the soybean PI 437.654," *Theor. Appl. Genet.*, 1995, vol. 91, pp. 574-581.
Weisemann, J.M., et al., "Molecular markers located proximal to the soybean cyst nematode resistance gene, *Rhg4*," *Theor. Appl. Genet.*, 1992, vol. 85, pp. 136-138.
Weiss, M.G., "Genetic Linkage in Soybeans: Linkage Group VII," *Crop Science*, 1970, vol. 10, pp. 627-629.
Wicking, C., et al., "From linked marker to gene," *Trends Genet.*, 1991, vol. 7(9), pp. 288-289.
Winstead, N.N., et al., "Soybean Cyst Nematode in North Carolina," *Plant Dis. Rep.*, 1955, vol. 39(1), pp. 9-11.

(56) References Cited

OTHER PUBLICATIONS

Young, L.D., "Reproduction of Differentially Selected Soybean Cyst Nematode Populations on Soybeans," *Crop Science*, 1982, vol. 22, pp. 385-388.

Young, L.D., "Changes in the Reproduction of Heterodera glycines on Different Lines of Glycine max," *Journal of Nematology*, 1984, vol. 16(3), pp. 304-309.

Zhang, H-B., et al, "Map-based cloning in crop plants: tomato as a model system II. Isolation and characterization of a set of overlapping yeast artificial chromosomes encompassing the jointless locus," *Mol. Gen. Genet.*, 1994, vol. 244, pp. 613-621.

Zhu, et al., "Characterization and application of soybean YACs to molecular cytogenetics," *Mol. Gen. Genet.*, 1996, vol. 252, pp. 483-488.

* cited by examiner

Figure 1A

| Locus Name | LG | Physical | Estimated Public Consensus4.0 Positions | Approximate Centromere |
|---|---|---|---|---|
| BARCSOYSSR_04_0025 | C1_(4) | 433,582 | 0.00 | |
| Sct_186 | C1_(4) | 433,582 | 0.00 | |
| BARCSOYSSR_04_0026 | C1_(4) | 447,227 | 2.11 | |
| Satt690 | C1_(4) | 447,227 | 2.11 | |
| BARCSOYSSR_04_0035 | C1_(4) | 525,154 | 2.97 | |
| SOYGPATR | C1_(4) | 525,154 | 2.97 | |
| BARC-030305-06851 | C1_(4) | 963,864 | 5.03 | |
| BARC-044617-08741 | C1_(4) | 982,287 | 5.58 | |
| BARC-018919-03036 | C1_(4) | 1,089,217 | 6.17 | |
| BARC-031853-07222 | C1_(4) | 1,163,728 | 6.77 | |
| BARC-057913-15004 | C1_(4) | 1,250,289 | 10.04 | |
| BARC-014277-01301 | C1_(4) | 1,431,400 | 10.61 | |
| BARC-016959-02166 | C1_(4) | 1,710,562 | 11.51 | |
| BARC-030765-06943 | C1_(4) | 1,891,388 | 11.97 | |
| BARC-054289-12451 | C1_(4) | 2,069,710 | 12.19 | |
| BARC-029425-06191 | C1_(4) | 2,207,639 | 12.33 | |
| BARCSOYSSR_04_0125 | C1_(4) | 2,402,268 | 13.37 | |
| Satt194 | C1_(4) | 2,402,268 | 13.37 | |
| BARC-039239-07481 | C1_(4) | 2,507,250 | 14.03 | |
| BARC-016519-02081 | C1_(4) | 2,843,396 | 15.58 | |
| BARC-015981-02030 | C1_(4) | 3,205,314 | 16.51 | |
| BARC-022353-04316 | C1_(4) | 3,348,266 | 16.72 | |
| BARC-031733-07217 | C1_(4) | 4,054,929 | 19.50 | |
| BARC-044709-08764 | C1_(4) | 4,120,312 | 20.56 | |
| BARCSOYSSR_04_0228 | C1_(4) | 4,172,835 | 20.97 | |
| Sat_337 | C1_(4) | 4,172,835 | 20.97 | |
| BARC-020447-04622 | C1_(4) | 5,392,117 | 27.44 | |
| BARC-014361-01331 | C1_(4) | 5,468,471 | 27.65 | |
| BARC-022437-04324 | C1_(4) | 5,468,475 | 27.71 | |
| BARC-044691-08761 | C1_(4) | 6,322,293 | 32.27 | |
| BARC-044521-08714 | C1_(4) | 6,378,204 | 33.11 | |
| BARC-040777-07848 | C1_(4) | 6,428,283 | 34.00 | |
| BARC-025825-05102 | C1_(4) | 6,684,059 | 36.48 | |
| BARCSOYSSR_04_0416 | C1_(4) | 7,819,458 | 40.86 | |
| Satt578 | C1_(4) | 7,819,458 | 40.86 | |
| BARC-041405-07979 | C1_(4) | 7,882,994 | 41.75 | |
| BARC-038309-10010 | C1_(4) | 8,030,160 | 42.42 | |

Figure 1B

| | | | | | |
|---|---|---|---|---|---|
| BARCSOYSSR_04_0430 | C1_(4) | | 8,093,779 | 43.17 | |
| Satt607 | C1_(4) | | 8,093,779 | 43.17 | |
| BARC-062641-17963 | C1_(4) | | 8,154,438 | 44.48 | |
| BARC-017023-02178 | C1_(4) | | 8,224,268 | 45.67 | |
| BARC-029943-06758 | C1_(4) | | 8,465,328 | 45.96 | |
| BARCSOYSSR_04_0460 | C1_(4) | | 8,830,940 | 46.01 | |
| Satt646 | C1_(4) | | 8,830,940 | 46.01 | |
| BARC-015923-02016 | C1_(4) | | 8,915,160 | 46.45 | |
| BARC-046068-10219 | C1_(4) | | 9,120,496 | 47.07 | |
| BARC-064923-19002 | C1_(4) | | 9,168,034 | 47.07 | |
| BARC-063455-18377 | C1_(4) | | 9,170,865 | 47.07 | |
| BARC-053223-11766 | C1_(4) | | 9,236,857 | 48.48 | |
| BARC-053219-11764 | C1_(4) | | 9,300,071 | 48.87 | |
| BARC-058645-15349 | C1_(4) | | 9,789,291 | 50.76 | |
| BARCSOYSSR_04_0579 | C1_(4) | | 12,529,635 | 50.97 | x |
| Sat_404 | C1_(4) | | 12,529,635 | 50.97 | x |
| BARC-055359-13232 | C1_(4) | | 14,079,084 | 51.08 | x |
| BARC-007901-00205 | C1_(4) | | 14,985,510 | 51.13 | x |
| BARC-060187-16464 | C1_(4) | | 16,789,799 | 51.74 | x |
| BARC-020889-03981 | C1_(4) | | 18,904,768 | 51.75 | x |
| BARC-057291-14674 | C1_(4) | | 19,337,323 | 52.35 | x |
| BARC-063099-18239 | C1_(4) | | 26,870,515 | 52.49 | x |
| BARCSOYSSR_04_0881 | C1_(4) | | 33,321,553 | 52.71 | x |
| Satt399 | C1_(4) | | 33,321,553 | 52.71 | x |
| BARC-063667-18427 | C1_(4) | | 34,928,793 | 52.72 | x |
| BARC-058775-15427 | C1_(4) | | 35,970,986 | 52.72 | x |
| BARC-060917-16967 | C1_(4) | | 36,250,476 | 52.72 | x |
| BARC-061273-17145 | C1_(4) | | 36,403,199 | 52.72 | x |
| BARCSOYSSR_04_0953 | C1_(4) | | 37,475,216 | 53.17 | x |
| Sat_416 | C1_(4) | | 37,475,216 | 53.17 | x |
| BARC-063499-18381 | C1_(4) | | 38,018,967 | 53.30 | x |
| BARC-059291-15718 | C1_(4) | | 38,496,133 | 53.84 | x |
| BARC-059947-16237 | C1_(4) | | 38,929,141 | 53.84 | x |
| BARC-061329-17168 | C1_(4) | | 40,179,629 | 54.89 | |
| BARC-061983-17604 | C1_(4) | | 40,650,236 | 55.78 | |
| BARCSOYSSR_04_1062 | C1_(4) | | 40,871,939 | 56.46 | |
| Satt476 | C1_(4) | | 40,871,939 | 56.46 | |
| BARCSOYSSR_04_1072 | C1_(4) | | 41,223,589 | 58.35 | |
| Sat_042 | C1_(4) | | 41,223,589 | 58.35 | |
| BARC-020509-04645 | C1_(4) | | 41,667,200 | 59.31 | |
| BARC-038989-07419 | C1_(4) | | 41,667,225 | 59.34 | |

Figure 1C

| | | | | |
|---|---|---|---|---|
| BARC-056153-14127 | C1_(4) | 41,872,671 | 60.01 | |
| BARCSOYSSR_04_1140 | C1_(4) | 42,571,776 | 63.13 | |
| Satt670 | C1_(4) | 42,571,776 | 63.13 | |
| S07162-1 | C1_(4) | 42,916,770 | 65.27 | |
| BARCSOYSSR_04_1172 | C1_(4) | 43,039,754 | 66.04 | |
| Sat_311 | C1_(4) | 43,039,754 | 66.04 | |
| BARC-030647-06914 | C1_(4) | 43,097,230 | 66.35 | |
| BARC-042189-08197 | C1_(4) | 43,684,210 | 68.85 | |
| BARC-040387-07722 | C1_(4) | 44,012,162 | 75.21 | |
| BARC-044373-08692 | C1_(4) | 44,746,648 | 80.76 | |
| BARC-052267-11398 | C1_(4) | 45,015,005 | 82.17 | |
| BARC-022447-04328 | C1_(4) | 46,306,130 | 96.50 | |
| BARC-019093-03301 | C1_(4) | 46,484,136 | 96.83 | |
| BARC-013699-01240 | C1_(4) | 46,578,102 | 97.43 | |
| BARC-024187-04790 | C1_(4) | 46,813,397 | 100.53 | |
| BARC-015121-02570 | C1_(4) | 46,896,236 | 100.57 | |
| BARCSOYSSR_04_1362 | C1_(4) | 46,964,916 | 101.22 | |
| Satt338 | C1_(4) | 46,964,916 | 101.22 | |
| BARC-044427-08705 | C1_(4) | 47,116,996 | 102.47 | |
| BARCSOYSSR_04_1382 | C1_(4) | 47,335,984 | 104.01 | |
| Satt682 | C1_(4) | 47,335,984 | 104.01 | |
| BARC-061009-17004 | C1_(4) | 47,396,872 | 104.61 | |
| BARC-018629-03208 | C1_(4) | 47,621,366 | 105.84 | |
| BARC-028671-05985 | C1_(4) | 48,121,255 | 108.24 | |
| BARC-062835-18113 | C1_(4) | 48,196,149 | 108.93 | |
| BARC-032045-07244 | C1_(4) | 48,918,109 | 110.22 | |
| BARC-041047-07901 | C1_(4) | 48,959,049 | 110.26 | |
| BARC-029125-06087 | C1_(4) | 49,173,958 | 112.20 | |

Figure 2A

| Locus Name | LG | Physical | Estimated Public Consensus4.0 Positions | Approximate Centromere |
|---|---|---|---|---|
| BARC-061409-17191 | B1_(11) | 15,208,402 | 68.33 | |
| BARC-053713-11954 | B1_(11) | 15,545,136 | 69.17 | |
| BARC-040309-07711 | B1_(11) | 15,576,761 | 69.17 | |
| BARCSOYSSR_11_0828 | B1_(11) | 16,893,706 | 72.09 | |
| Sat_348 | B1_(11) | 16,893,706 | 72.09 | |
| BARCSOYSSR_11_0839 | B1_(11) | 17,065,539 | 74.21 | |
| Satt597 | B1_(11) | 17,065,539 | 74.21 | |
| BARC-059803-16097 | B1_(11) | 17,822,677 | 76.86 | |
| BARC-050205-09457 | B1_(11) | 17,822,703 | 76.86 | |
| BARC-012485-00902 | B1_(11) | 26,826,723 | 83.37 | x |
| BARCSOYSSR_11_1022 | B1_(11) | 27,078,672 | 81.43 | x |
| Satt430 | B1_(11) | 27,078,672 | 81.43 | x |
| BARCSOYSSR_11_1065 | B1_(11) | 29,344,254 | 80.54 | x |
| Sat_095 | B1_(11) | 29,344,254 | 80.54 | x |
| BARC-040407-07733 | B1_(11) | 30,159,992 | 77.34 | x |
| BARC-040075-07652 | B1_(11) | 30,160,057 | 77.16 | x |
| BARCSOYSSR_11_1138 | B1_(11) | 31,594,042 | 83.86 | x |
| Sat_364 | B1_(11) | 31,594,042 | 83.86 | x |
| BARCSOYSSR_11_1225 | B1_(11) | 34,635,285 | 84.70 | |
| Satt444 | B1_(11) | 34,635,285 | 84.70 | |
| BARCSOYSSR_11_1324 | B1_(11) | 36,229,282 | 91.55 | |
| Satt665 | B1_(11) | 36,229,282 | 91.55 | |
| BARC-027874-06697 | B1_(11) | 36,435,055 | 94.75 | |
| BARCSOYSSR_11_1355 | B1_(11) | 36,660,512 | 96.15 | |
| Sat_123 | B1_(11) | 36,660,512 | 96.15 | |
| BARC-013547-01157 | B1_(11) | 36,767,922 | 96.89 | |
| S04937-1 | B1_(11) | 36,954,799 | 97.95 | |
| S04938-1 | B1_(11) | 36,954,994 | 97.95 | |
| S06786-1 | B1_(11) | 37,311,443 | 99.97 | |
| S06787-1 | B1_(11) | 37,333,894 | 100.09 | |
| S06803-1 | B1_(11) | 37,334,507 | 100.10 | |
| BARC-054049-12291 | B1_(11) | 37,627,423 | 101.75 | |
| BARCSOYSSR_11_1443 | B1_(11) | 37,892,771 | 109.34 | |
| AQ851479 | B1_(11) | 37,892,771 | 109.34 | |
| BARC-061787-17389 | B1_(11) | 37,893,613 | 109.38 | |
| BARC-062275-17736 | B1_(11) | 38,020,213 | 109.91 | |
| BARC-044669-08757 | B1_(11) | 38,119,874 | 110.17 | |
| BARC-054037-12260 | B1_(11) | 38,223,594 | 110.29 | |

Figure 2B

| | | | | |
|---|---|---|---|---|
| BARCSOYSSR_11_1469 | B1_(11) | 38,377,047 | 110.73 | |
| Sat_331 | B1_(11) | 38,377,047 | 110.73 | |
| BARC-007704-00081 | B1_(11) | 38,424,149 | 111.04 | |
| BARC-010169-00539 | B1_(11) | 38,424,182 | 111.29 | |
| BARC-048441-10595 | B1_(11) | 38,424,387 | 111.29 | |
| BARC-032029-07241 | B1_(11) | 38,597,714 | 112.69 | |
| BARC-904050-01007 | B1_(11) | 38,635,673 | 112.74 | |
| BARC-900554-00951 | B1_(11) | 38,736,229 | 113.54 | |
| BARC-900336-00920 | B1_(11) | 38,769,105 | 113.62 | |
| BARC-021459-04106 | B1_(11) | 38,902,697 | 114.92 | |
| BARC-055333-13216 | B1_(11) | 38,937,276 | 115.55 | |
| BARC-018869-03031 | B1_(11) | 38,951,794 | 115.97 | |

Figure 3A

| Locus Name | LG | Physical | Estimated Public Consensus4.0 Positions | Approximate Centromere |
|---|---|---|---|---|
| BARC-014389-01344 | D2_(17) | 691,002 | 4.04 | |
| BARC-020357-04569 | D2_(17) | 789,741 | 5.07 | |
| BARC-014483-01560 | D2_(17) | 967,506 | 5.57 | |
| BARCSOYSSR_17_0071 | D2_(17) | 1,174,808 | 6.56 | |
| Sat_296 | D2_(17) | 1,174,808 | 6.56 | |
| BARC-031827-07220 | D2_(17) | 1,786,102 | 8.16 | |
| BARC-016645-02157 | D2_(17) | 2,031,988 | 9.70 | |
| BARC-030219-06835 | D2_(17) | 2,102,971 | 10.29 | |
| BARC-050393-09582 | D2_(17) | 2,437,228 | 11.44 | |
| BARC-024287-04825 | D2_(17) | 2,804,349 | 13.20 | |
| BARCSOYSSR_17_0152 | D2_(17) | 2,841,432 | 13.32 | |
| Sct_192 | D2_(17) | 2,841,432 | 13.32 | |
| BARC-046618-12673 | D2_(17) | 2,855,550 | 13.82 | |
| BARC-057345-14694 | D2_(17) | 2,892,902 | 13.83 | |
| BARC-015033-01953 | D2_(17) | 3,248,163 | 14.62 | |
| BARC-048819-10727 | D2_(17) | 3,537,279 | 16.65 | |
| BARC-025461-06505 | D2_(17) | 3,586,138 | 17.01 | |
| BARCSOYSSR_17_0219 | D2_(17) | 4,131,242 | 18.57 | |
| Satt328 | D2_(17) | 4,131,242 | 18.57 | |
| BARC-029195-06120 | D2_(17) | 4,275,310 | 18.96 | |
| BARC-018645-03217 | D2_(17) | 4,367,926 | 19.42 | |
| BARC-044189-08643 | D2_(17) | 4,398,714 | 19.73 | |
| BARC-044417-08703 | D2_(17) | 4,640,324 | 20.36 | |
| BARC-043087-08524 | D2_(17) | 4,899,001 | 21.03 | |
| BARC-056107-14093 | D2_(17) | 5,029,797 | 21.27 | |
| BARC-030909-06973 | D2_(17) | 5,183,578 | 22.44 | |
| BARC-055705-13616 | D2_(17) | 5,353,996 | 22.64 | |
| BARC-028485-05923 | D2_(17) | 5,940,941 | 23.50 | |
| BARCSOYSSR_17_0337 | D2_(17) | 6,053,081 | 24.40 | |
| Satt458 | D2_(17) | 6,053,081 | 24.40 | |
| BARCSOYSSR_17_0343 | D2_(17) | 6,156,551 | 25.48 | |
| Satt135 | D2_(17) | 6,156,551 | 25.48 | |
| BARCSOYSSR_17_0384 | D2_(17) | 6,740,508 | 28.39 | |
| Satt014 | D2_(17) | 6,740,508 | 28.39 | |
| BARC-021191-03999 | D2_(17) | 7,387,314 | 33.62 | |
| BARC-022037-04267 | D2_(17) | 7,417,105 | 33.63 | |
| BARCSOYSSR_17_0444 | D2_(17) | 7,811,400 | 36.12 | |
| Satt372 | D2_(17) | 7,811,400 | 36.12 | |

Figure 3B

| | | | | |
|---|---|---|---|---|
| BARC-062339-1754 | D2_(17) | 7,862,447 | 36.48 | |
| BARC-018859-03262 | D2_(17) | 7,992,564 | 37.30 | |
| BARC-056481-14397 | D2_(17) | 8,231,251 | 38.00 | |
| BARC-042751-08400 | D2_(17) | 8,314,319 | 38.21 | |
| BARC-049645-09086 | D2_(17) | 8,354,406 | 38.47 | |
| BARC-052295-11407 | D2_(17) | 8,360,848 | 38.55 | |
| BARC-064695-18779 | D2_(17) | 8,477,659 | 39.03 | |
| BARC-062955-18179 | D2_(17) | 8,585,149 | 39.48 | |
| BARC-020373-04573 | D2_(17) | 8,698,627 | 40.64 | |
| BARC-048381-10555 | D2_(17) | 8,840,733 | 41.55 | |
| BARC-048379-10554 | D2_(17) | 8,840,734 | 41.68 | |
| BARC-012687-00367 | D2_(17) | 8,987,706 | 42.45 | |
| BARCSOYSSR_17_0510 | D2_(17) | 9,088,821 | 42.69 | |
| Satt002 | D2_(17) | 9,088,821 | 42.69 | |
| BARC-024449-04894 | D2_(17) | 9,260,050 | 44.74 | |
| BARCSOYSSR_17_0554 | D2_(17) | 9,863,263 | 46.77 | |
| Satt154 | D2_(17) | 9,863,263 | 46.77 | |
| BARCSOYSSR_17_0561 | D2_(17) | 9,949,913 | 47.18 | |
| Satt582 | D2_(17) | 9,949,913 | 47.18 | |
| BARC-031145-07005 | D2_(17) | 10,534,591 | 50.41 | |
| BARC-025885-05138 | D2_(17) | 11,157,614 | 55.59 | |
| BARC-025885-05137 | D2_(17) | 11,157,614 | 55.78 | |
| BARC-017191-02247 | D2_(17) | 11,260,712 | 57.18 | |
| BARC-063551-18386 | D2_(17) | 11,372,457 | 57.33 | |
| BARCSOYSSR_17_0669 | D2_(17) | 11,724,512 | 58.74 | |
| Satt397 | D2_(17) | 11,724,512 | 58.74 | |
| BARC-013637-01186 | D2_(17) | 11,915,457 | 59.92 | |
| BARC-013969-01290 | D2_(17) | 12,666,290 | 62.79 | |
| BARCSOYSSR_17_0731 | D2_(17) | 12,771,421 | 62.88 | |
| Sat_292 | D2_(17) | 12,771,421 | 62.88 | |
| BARCSOYSSR_17_0754 | D2_(17) | 13,150,232 | 63.94 | |
| Sat_222 | D2_(17) | 13,150,232 | 63.94 | |
| BARC-047685-10379 | D2_(17) | 13,354,764 | 64.72 | |
| BARCSOYSSR_17_0807 | D2_(17) | 14,024,929 | 68.20 | |
| Satt389 | D2_(17) | 14,024,929 | 68.20 | |
| BARC-051665-11191 | D2_(17) | 14,849,946 | 72.14 | |
| BARC-047829-10399 | D2_(17) | 14,938,405 | 72.23 | |
| BARC-048389-10562 | D2_(17) | 15,128,584 | 72.65 | |
| BARC-059581-15926 | D2_(17) | 16,113,309 | 73.34 | x |
| BARC-060511-16708 | D2_(17) | 17,995,210 | 73.34 | x |
| BARC-062079-17648 | D2_(17) | 18,355,304 | 73.34 | x |

Figure 3C

| | | | | |
|---|---|---|---|---|
| BARC-062127-17661 | D2_(17) | 18,480,666 | 73.34 | x |
| BARCSOYSSR_17_0930 | D2_(17) | 18,770,886 | 73.91 | x |
| Satt514 | D2_(17) | 18,770,886 | 73.91 | x |
| BARCSOYSSR_17_0973 | D2_(17) | 19,746,681 | 74.20 | x |
| Satt082 | D2_(17) | 19,746,681 | 74.20 | x |
| BARCSOYSSR_17_0988 | D2_(17) | 20,710,130 | 74.25 | x |
| Sat_300 | D2_(17) | 20,710,130 | 74.25 | x |
| BARC-010289-00577 | D2_(17) | 24,102,133 | 75.05 | x |
| BARC-028773-06009 | D2_(17) | 24,177,949 | 75.06 | x |
| BARC-065605-19580 | D2_(17) | 25,895,720 | 75.44 | x |
| BARC-060353-16626 | D2_(17) | 27,486,421 | 75.44 | x |
| BARC-065169-19205 | D2_(17) | 28,115,010 | 75.44 | x |
| BARC-065239-19278 | D2_(17) | 31,882,561 | 75.85 | x |
| BARC-057449-14753 | D2_(17) | 34,117,998 | 76.12 | x |
| S07161-1 | D2_(17) | 34,888,681 | 76.54 | x |
| BARC-050501-09705 | D2_(17) | 36,462,106 | 77.39 | x |
| BARC-040583-07786 | D2_(17) | 37,275,595 | 78.31 | |
| BARC-019787-04375 | D2_(17) | 37,418,900 | 78.52 | |
| BARC-064095-18554 | D2_(17) | 37,769,021 | 79.94 | |
| BARC-037179-06731 | D2_(17) | 38,089,554 | 82.62 | |
| BARCSOYSSR_17_1425 | D2_(17) | 38,091,254 | 84.17 | |
| GMHSP179 | D2_(17) | 38,091,254 | 84.17 | |
| BARC-013653-01222 | D2_(17) | 38,730,417 | 86.45 | |
| BARC-025927-05161 | D2_(17) | 38,916,720 | 87.84 | |
| BARCSOYSSR_17_1477 | D2_(17) | 39,057,375 | 90.28 | |
| Satt310 | D2_(17) | 39,057,375 | 90.28 | |
| BARC-049255-10878 | D2_(17) | 39,399,533 | 95.97 | |
| BARCSOYSSR_17_1511 | D2_(17) | 39,561,506 | 98.51 | |
| Sat_326 | D2_(17) | 39,561,506 | 98.51 | |
| BARCSOYSSR_17_1540 | D2_(17) | 40,043,057 | 100.96 | |
| Satt413 | D2_(17) | 40,043,057 | 100.96 | |
| BARC-010861-00784 | D2_(17) | 40,052,990 | 101.43 | |
| BARC-055793-13720 | D2_(17) | 40,053,275 | 101.43 | |
| BARC-029859-06448 | D2_(17) | 40,146,564 | 104.31 | |
| BARC-029279-06138 | D2_(17) | 41,007,685 | 109.10 | |
| BARC-014747-01639 | D2_(17) | 41,146,946 | 110.80 | |
| BARC-019021-03292 | D2_(17) | 41,237,076 | 111.26 | |
| BARCSOYSSR_17_1639 | D2_(17) | 41,333,788 | 114.29 | |
| Sat_220 | D2_(17) | 41,333,788 | 114.29 | |
| BARC-039151-07458 | D2_(17) | 41,489,936 | 116.10 | |
| BARC-051411-11102 | D2_(17) | 41,520,637 | 117.24 | |

Figure 3D

| BARC-030531-06894 | D2_(17) | 41,806,677 | 117.79 | |
| BARC-001489-00142 | D2_(17) | 41,821,321 | 118.12 | |

Figure 4A

| Locus Name | LG | Physical | Estimated Public Consensus4.0 Positions | Approximate Centromere |
|---|---|---|---|---|
| BARC-017811-02392 | B1_(11) | 29,924 | 5.55 | |
| BARC-058339-15238 | B1_(11) | 559,320 | 4.58 | |
| BARC-062833-18109 | B1_(11) | 560,024 | 4.58 | |
| BARC-017915-02450 | B1_(11) | 1,481,336 | 2.82 | |
| BARC-018583-02981 | B1_(11) | 1,656,830 | 2.54 | |
| BARCSOYSSR_11_0142 | B1_(11) | 2,710,565 | 18.03 | |
| Sat_272 | B1_(11) | 2,710,565 | 18.03 | |
| BARC-041095-07905 | B1_(11) | 3,684,393 | 23.86 | |
| BARCSOYSSR_11_0227 | B1_(11) | 4,224,531 | 25.64 | |
| Sat_270 | B1_(11) | 4,224,531 | 25.64 | |
| BARC-014611-01591 | B1_(11) | 4,250,965 | 26.17 | |
| BARC-018713-03241 | B1_(11) | 5,089,529 | 31.61 | |
| BARC-042439-08267 | B1_(11) | 5,123,196 | 31.81 | |
| BARC-018099-02516 | B1_(11) | 5,270,796 | 32.12 | |
| BARC-032437-08975 | B1_(11) | 5,287,056 | 32.13 | |
| BARC-032333-08951 | B1_(11) | 5,287,077 | 32.13 | |
| S04348-1 | B1_(11) | 5,916,329 | 37.62 | |
| BARC-042989-08491 | B1_(11) | 5,938,208 | 37.81 | |
| BARC-017097-02199 | B1_(11) | 6,020,848 | 37.95 | |
| BARC-900941-00964 | B1_(11) | 6,166,382 | 38.32 | |
| BARC-016137-02291 | B1_(11) | 6,174,078 | 38.37 | |
| BARCSOYSSR_11_0380 | B1_(11) | 6,961,225 | 40.95 | |
| Satt638 | B1_(11) | 6,961,225 | 40.95 | |
| BARC-040851-07854 | B1_(11) | 7,619,584 | 44.65 | |
| BARC-044037-08588 | B1_(11) | 7,688,341 | 45.33 | |
| BARC-025873-05130 | B1_(11) | 7,847,370 | 45.37 | |
| BARC-061085-17035 | B1_(11) | 7,952,601 | 45.43 | |
| BARC-038623-10188 | B1_(11) | 7,996,138 | 45.45 | |
| BARC-031547-07108 | B1_(11) | 8,492,168 | 46.25 | |
| BARC-050091-09377 | B1_(11) | 8,582,563 | 46.56 | |
| BARCSOYSSR_11_0482 | B1_(11) | 8,879,510 | 49.07 | |

Figure 4B

| | | | | |
|---|---|---|---|---|
| Satt197 | B1_(11) | 8,879,510 | 49.07 | |
| BARCSOYSSR_11_0496 | B1_(11) | 9,078,586 | 52.06 | |
| Sat_247 | B1_(11) | 9,078,586 | 52.06 | |
| S01209-1 | B1_(11) | 9,963,410 | 54.57 | |
| BARC-032817-09052 | B1_(11) | 10,319,338 | 55.57 | |
| BARC-016279-02316 | B1_(11) | 10,804,852 | 61.61 | |
| S01999-1 | B1_(11) | 11,202,391 | 63.22 | |
| BARC-022123-04287 | B1_(11) | 11,269,342 | 63.49 | |
| BARC-050929-13806 | B1_(11) | 11,532,769 | 65.62 | |
| BARC-054421-12081 | B1_(11) | 12,295,534 | 66.70 | |
| BARC-061409-17191 | B1_(11) | 15,208,402 | 68.33 | |
| BARC-053713-11954 | B1_(11) | 15,545,136 | 69.17 | |
| BARC-040309-07711 | B1_(11) | 15,576,761 | 69.17 | |
| BARCSOYSSR_11_0828 | B1_(11) | 16,893,706 | 72.09 | |
| Sat_348 | B1_(11) | 16,893,706 | 72.09 | |
| BARCSOYSSR_11_0839 | B1_(11) | 17,065,539 | 74.21 | |
| Satt597 | B1_(11) | 17,065,539 | 74.21 | |
| BARC-059803-16097 | B1_(11) | 17,822,677 | 76.86 | |
| BARC-050205-09457 | B1_(11) | 17,822,703 | 76.86 | |
| BARC-012485-00902 | B1_(11) | 26,826,723 | 83.37 | x |
| BARCSOYSSR_11_1022 | B1_(11) | 27,078,672 | 81.43 | x |
| Satt430 | B1_(11) | 27,078,672 | 81.43 | x |
| BARCSOYSSR_11_1065 | B1_(11) | 29,344,254 | 80.54 | x |
| Sat_095 | B1_(11) | 29,344,254 | 80.54 | x |
| BARC-040407-07733 | B1_(11) | 30,159,992 | 77.34 | x |
| BARC-040075-07652 | B1_(11) | 30,160,057 | 77.16 | x |
| BARCSOYSSR_11_1138 | B1_(11) | 31,594,042 | 83.86 | x |
| Sat_364 | B1_(11) | 31,594,042 | 83.86 | x |
| BARCSOYSSR_11_1225 | B1_(11) | 34,635,285 | 84.70 | |
| Satt444 | B1_(11) | 34,635,285 | 84.70 | |
| BARCSOYSSR_11_1324 | B1_(11) | 36,229,282 | 91.55 | |
| Satt665 | B1_(11) | 36,229,282 | 91.55 | |
| BARC-027874-06697 | B1_(11) | 36,435,055 | 94.75 | |
| BARCSOYSSR_11_1355 | B1_(11) | 36,660,512 | 96.15 | |

Figure 4C

| | | | | |
|---|---|---|---|---|
| Sat_123 | B1 (11) | 36,660,512 | 96.15 | |
| BARC-013547-01157 | B1_(11) | 36,767,922 | 96.89 | |
| Satt359 | B1_(11) | 36,868,291 | ~97 | |
| S04937-2 | B1_(11) | 36,954,416 | 97.94 | |
| S04937-1 | B1_(11) | 36,954,799 | 97.95 | |
| S04938-1 | B1_(11) | 36,954,994 | 97.95 | |
| S04938-2 | B1_(11) | 36,955,430 | 97.95 | |
| S06786-2 | B1_(11) | 37,311,026 | 99.96 | |
| S06786-3 | B1_(11) | 37,311,370 | 99.97 | |
| S06786-1 | B1_(11) | 37,311,443 | 99.97 | |
| S06787-2 | B1_(11) | 37,333,749 | 100.09 | |
| S06787-1 | B1_(11) | 37,333,894 | 100.09 | |
| S06803-1 | B1_(11) | 37,334,507 | 100.10 | |
| S06804-1 | B1_(11) | 37,335,483 | 100.10 | |
| S06788-1 | B1_(11) | 37,405,385 | 100.50 | |
| S06805-1 | B1_(11) | 37,492,596 | 100.99 | |
| BARC-054049-12291 | B1_(11) | 37,627,423 | 101.75 | |
| BARCSOYSSR_11_1443 | B1_(11) | 37,892,771 | 109.34 | |
| AQ851479 | B1_(11) | 37,892,771 | 109.34 | |
| BARC-061787-17389 | B1_(11) | 37,893,613 | 109.38 | |
| S06789-1 | B1_(11) | 37,923,651 | 109.51 | |
| BARC-062275-17736 | B1_(11) | 38,020,213 | 109.91 | |
| S06790-1 | B1_(11) | 38,041,618 | 109.97 | |
| BARC-044669-08757 | B1_(11) | 38,119,874 | 110.17 | |
| S06791-2 | B1_(11) | 38,197,612 | 110.26 | |
| S06791-1 | B1_(11) | 38,197,663 | 110.26 | |
| BARC-054037-12260 | B1_(11) | 38,223,594 | 110.29 | |
| S06792-1 | B1_(11) | 38,279,360 | 110.45 | |
| Satt453 | B1_(11) | 38,360,633 | ~110.5 | |
| BARCSOYSSR_11_1469 | B1_(11) | 38,377,047 | 110.73 | |
| Sat_331 | B1_(11) | 38,377,047 | 110.73 | |
| BARC-007704-00081 | B1_(11) | 38,424,149 | 111.04 | |
| BARC-010169-00539 | B1_(11) | 38,424,182 | 111.29 | |
| BARC-048441-10595 | B1_(11) | 38,424,387 | 111.29 | |

Figure 4D

| BARC-032029-07241 | B1_(11) | 38,597,714 | 112.69 | |
|---|---|---|---|---|
| BARC-904050-01007 | B1_(11) | 38,635,673 | 112.74 | |
| BARC-900554-00951 | B1_(11) | 38,736,229 | 113.54 | |
| BARC-900336-00920 | B1_(11) | 38,769,105 | 113.62 | |
| BARC-021459-04106 | B1_(11) | 38,902,697 | 114.92 | |
| BARC-055333-13216 | B1_(11) | 38,937,276 | 115.55 | |
| BARC-018869-03031 | B1_(11) | 38,951,794 | 115.97 | |

Figure 5 A

| Locus Name | LG | Physical Position | Genetic position (cM) | Approximate Centromere |
|---|---|---|---|---|
| BARCSOYSSR_02_0676 | D1b_(2) | 12,956,582 | 61.84 | |
| Satt542 | D1b_(2) | 12,956,582 | 61.84 | |
| BARC-031301-07041 | D1b_(2) | 14,031,310 | 65.18 | |
| BARC-048815-10726 | D1b_(2) | 14,106,291 | 66.18 | |
| BARC-013487-00500 | D1b_(2) | 14,418,339 | 68.12 | |
| BARC-047945-10443 | D1b_(2) | 14,851,469 | 71.70 | |
| BARC-043983-08572 | D1b_(2) | 15,490,882 | 76.90 | |
| BARC-018819-03259 | D1b_(2) | 15,718,441 | 79.16 | |
| BARC-018781-03247 | D1b_(2) | 15,718,559 | 79.16 | |
| BARC-027390-06561 | D1b_(2) | 16,502,802 | 79.17 | |
| BARCSOYSSR_02_0846 | D1b_(2) | 17,474,784 | 81.46 | |
| Satt428 | D1b_(2) | 17,474,784 | 81.46 | |
| BARCSOYSSR_02_0855 | D1b_(2) | 19,409,056 | 82.59 | x |
| Satt579 | D1b_(2) | 19,409,056 | 82.59 | x |
| BARC-061653-17307 | D1b_(2) | 30,848,974 | 83.01 | x |
| BARCSOYSSR_02_1048 | D1b_(2) | 32,526,214 | 83.26 | x |
| Satt600 | D1b_(2) | 32,526,214 | 83.26 | x |
| BARC-057711-14907 | D1b_(2) | 36,102,833 | 83.35 | x |
| BARC-052515-11484 | D1b_(2) | 38,644,397 | 83.36 | x |
| BARC-060135-16407 | D1b_(2) | 39,922,914 | 83.38 | x |
| BARC-018381-03605 | D1b_(2) | 40,362,445 | 83.93 | |
| BARC-049713-09132 | D1b_(2) | 40,552,642 | 84.11 | |
| BARC-053163-11724 | D1b_(2) | 40,596,174 | 84.31 | |
| BARC-063685-18434 | D1b_(2) | 40,623,295 | 84.31 | |
| BARC-053161-11723 | D1b_(2) | 40,704,043 | 84.69 | |
| BARCSOYSSR_02_1257 | D1b_(2) | 40,884,780 | 85.66 | |
| Sat_169 | D1b_(2) | 40,884,780 | 85.66 | |
| BARCSOYSSR_02_1268 | D1b_(2) | 41,290,043 | 87.01 | |
| Satt644 | D1b_(2) | 41,290,043 | 87.01 | |
| BARC-032679-09011 | D1b_(2) | 41,923,345 | 88.86 | |
| BARC-055839-13759 | D1b_(2) | 42,622,375 | 90.55 | |
| S00479-1 | D1b_(2) | 42,982,998 | 91.61 | |
| BARCSOYSSR_02_1386 | D1b_(2) | 43,775,594 | 93.94 | |
| Satt546 | D1b_(2) | 43,775,594 | 93.94 | |
| BARC-018115-02528 | D1b_(2) | 44,075,539 | 94.55 | |
| S02136-1 | D1b_(2) | 44,096,100 | 94.75 | |
| BARC-032025-07239 | D1b_(2) | 44,109,165 | 94.88 | |
| BARC-024409-04868 | D1b_(2) | 44,522,551 | 95.29 | |

Figure 5B

| | | | | |
|---|---|---|---|---|
| BARC-021561-04146 | D1b_(2) | 44,574,118 | 95.45 | |
| BARCSOYSSR 02 1436 | D1b_(2) | 44,879,014 | 98.37 | |
| Sat_139 | D1b_(2) | 44,879,014 | 98.37 | |
| BARCSOYSSR_02_1500 | D1b_(2) | 45,655,561 | 103.25 | |
| Satt703 | D1b_(2) | 45,655,561 | 103.25 | |
| BARC-030479-06875 | D1b_(2) | 45,682,686 | 103.61 | |
| BARC-040187-07679 | D1b_(2) | 45,948,050 | 103.90 | |
| BARC-021647-04164 | D1b_(2) | 46,042,031 | 103.90 | |
| BARCSOYSSR 02 1540 | D1b_(2) | 46,353,760 | 105.87 | |
| Sat_069 | D1b_(2) | 46,353,760 | 105.87 | |
| BARCSOYSSR 02 1602 | D1b_(2) | 47,404,748 | 113.32 | |
| Sat_183 | D1b_(2) | 47,404,748 | 113.32 | |
| S00875-1 | D1b_(2) | 47,471,551 | 113.96 | |
| S12875-1 | D1b_(2) | 47,529,446 | 114.51 | |
| BARC-017895-02427 | D1b_(2) | 47,548,016 | 114.69 | |
| S12950-1 | D1b_(2) | 47,556,177 | 114.71 | |
| S12947-1 | D1b_(2) | 47,576,630 | 114.78 | |
| S12933-1 | D1b_(2) | 47,765,197 | 115.35 | |
| BARC-045013-08865 | D1b_(2) | 48,138,016 | 116.48 | |
| BARC-028373-05856 | D1b_(2) | 48,185,260 | 116.49 | |
| S12853-1 | D1b_(2) | 48,204,176 | 116.68 | |
| S03246-1 | D1b_(2) | 48,336,665 | 117.97 | |
| BARC-054149-12354 | D1b_(2) | 48,374,309 | 118.34 | |
| BARCSOYSSR_02_1682 | D1b_(2) | 48,621,937 | 119.18 | |
| Sat_198 | D1b_(2) | 48,621,937 | 119.18 | |
| S01519-1 | D1b_(2) | 48,686,902 | 120.16 | |
| BARC-057665-14892 | D1b_(2) | 48,703,378 | 120.41 | |
| S12962-1 | D1b_(2) | 49,371,792 | 125.66 | |
| BARC-040169-07675 | D1b_(2) | 49,388,450 | 125.79 | |
| S00144-1 | D1b_(2) | 49,461,261 | 126.03 | |
| S08166-1 | D1b_(2) | 49,505,295 | 126.17 | |
| BARC-044747-08795 | D1b_(2) | 49,530,080 | 126.26 | |
| BARC-054217-12380 | D1b_(2) | 49,541,234 | 126.26 | |
| BARCSOYSSR_02_1759 | D1b_(2) | 50,122,136 | 129.78 | |
| Sat_289 | D1b_(2) | 50,122,136 | 129.78 | |
| BARC-059321-15931 | D1b_(2) | 50,231,557 | 130.71 | |
| BARC-051677-11199 | D1b_(2) | 50,270,411 | 130.81 | |
| S08177-1 | D1b_(2) | 50,529,112 | 131.45 | |
| BARC-039799-07588 | D1b_(2) | 50,691,457 | 131.85 | |
| S01081-1 | D1b_(2) | 50,775,206 | 132.07 | |
| BARC-019805-04379 | D1b_(2) | 51,243,272 | 133.30 | |

Figure 5C

| | | | | |
|---|---|---|---|---|
| BARC-041469-08004 | D1b_(2) | 51,407,018 | 133.85 | |
| S02621-1 | D1b_(2) | 51,490,811 | 133.95 | |
| BARC-020293-04543 | D1b_(2) | 51,541,368 | 134.02 | |
| BARC-906743-01012 | D1b_(2) | 51,549,897 | 134.02 | |

Figure 6A

| Locus Name | LG | Physical Position | Genetic position (cM) | Approximate Centromere |
|---|---|---|---|---|
| BARC-018663-03235 | C2_(6) | 11,898,756 | 71.60 | |
| BARC-039613-07521 | C2_(6) | 11,938,892 | 71.86 | |
| BARC-031571-07112 | C2_(6) | 12,129,054 | 72.39 | |
| BARC-022299-04310 | C2_(6) | 12,273,626 | 72.39 | |
| BARCSOYSSR_06_0667 | C2_(6) | 12,310,043 | 73.19 | |
| Satt322 | C2_(6) | 12,310,043 | 73.19 | |
| BARC-028177-05786 | C2_(6) | 13,551,011 | 80.28 | |
| BARC-017285-02260 | C2_(6) | 13,674,273 | 81.14 | |
| BARC-013837-01254 | C2_(6) | 14,247,199 | 86.27 | |
| BARC-052917-11675 | C2_(6) | 14,272,287 | 86.96 | |
| BARC-016423-02585 | C2_(6) | 14,285,575 | 86.96 | |
| BARC-014305-01308 | C2_(6) | 14,424,366 | 87.41 | |
| BARC-015081-02562 | C2_(6) | 14,424,385 | 87.41 | |
| BARC-047715-10388 | C2_(6) | 14,849,172 | 88.14 | |
| BARCSOYSSR_06_0840 | C2_(6) | 15,756,463 | 89.71 | |
| Satt363 | C2_(6) | 15,756,463 | 89.71 | |
| BARCSOYSSR_06_0850 | C2_(6) | 15,958,859 | 90.53 | |
| Sat_076 | C2_(6) | 15,958,859 | 90.53 | |
| BARC-021735-04194 | C2_(6) | 15,980,393 | 90.88 | |
| BARC-020031-04407 | C2_(6) | 16,050,227 | 91.43 | |
| BARC-054075-12325 | C2_(6) | 16,050,267 | 92.10 | |
| BARCSOYSSR_06_0858 | C2_(6) | 16,057,524 | 92.67 | |
| Satt643 | C2_(6) | 16,057,524 | 92.67 | |
| BARC-041165-07922 | C2_(6) | 16,155,041 | 93.21 | |
| BARCSOYSSR_06_0876 | C2_(6) | 16,367,712 | 94.58 | |
| Sat_402 | C2_(6) | 16,367,712 | 94.58 | |
| BARC-025707-05008 | C2_(6) | 16,659,438 | 97.81 | |
| BARC-056573-14503 | C2_(6) | 16,914,099 | 98.55 | |
| BARC-063591-18406 | C2_(6) | 16,927,469 | 98.55 | |
| BARC-013687-01230 | C2_(6) | 16,941,331 | 98.55 | |
| BARC-014491-01561 | C2_(6) | 17,424,176 | 100.17 | |
| BARC-064115-18558 | C2_(6) | 17,899,364 | 100.94 | |
| BARC-020405-04602 | C2_(6) | 18,123,648 | 101.71 | |
| BARC-065853-19796 | C2_(6) | 18,860,236 | 101.76 | x |
| BARC-040213-07685 | C2_(6) | 18,953,546 | 101.85 | x |
| BARCSOYSSR_06_1041 | C2_(6) | 20,018,876 | 102.23 | x |
| Satt557 | C2_(6) | 20,018,876 | 102.23 | x |
| BARC-029239-06133 | C2_(6) | 21,487,556 | 102.83 | x |
| BARC-054471-12090 | C2_(6) | 21,745,662 | 102.83 | x |

Figure 6B

| | | | | |
|---|---|---|---|---|
| S03252-1 | C2_(6) | 21,822,996 | 102.83 | x |
| BARC-050867-09934 | C2_(6) | 22,004,492 | 102.83 | x |
| BARCSOYSSR_06_1129 | C2_(6) | 23,874,403 | 103.22 | x |
| Satt489 | C2_(6) | 23,874,403 | 103.22 | x |
| BARC-060711-16810 | C2_(6) | 25,068,452 | 103.28 | x |
| BARC-057907-14996 | C2_(6) | 27,768,566 | 103.30 | x |
| BARCSOYSSR_06_1255 | C2_(6) | 35,215,338 | 103.32 | x |
| Sat_312 | C2_(6) | 35,215,338 | 103.32 | x |
| BARC-024923-10366 | C2_(6) | 36,069,731 | 103.45 | x |
| BARC-015077-02559 | C2_(6) | 38,136,028 | 103.88 | x |
| BARC-061147-17083 | C2_(6) | 39,878,533 | 104.50 | x |
| BARC-056379-14289 | C2_(6) | 41,204,571 | 105.16 | x |
| BARC-029025-06051 | C2_(6) | 41,308,555 | 105.73 | x |
| BARC-058239-15169 | C2_(6) | 42,603,052 | 106.26 | x |
| BARC-011045-00827 | C2_(6) | 42,963,664 | 106.36 | x |
| BARC-059303-15722 | C2_(6) | 42,991,306 | 106.36 | x |
| BARC-023203-03824 | C2_(6) | 43,185,037 | 106.47 | x |
| BARC-023277-05311 | C2_(6) | 43,397,269 | 106.59 | x |
| BARCSOYSSR_06_1476 | C2_(6) | 43,950,998 | 106.85 | x |
| Satt079 | C2_(6) | 43,950,998 | 106.85 | x |
| BARC-051929-11299 | C2_(6) | 45,363,053 | 107.60 | x |
| S02112-1 | C2_(6) | 45,770,644 | 108.15 | x |
| BARC-062515-17881 | C2_(6) | 46,063,176 | 108.55 | x |
| BARCSOYSSR_06_1579 | C2_(6) | 46,273,201 | 109.58 | |
| Sct_028 | C2_(6) | 46,273,201 | 109.58 | |
| BARCSOYSSR_06_1581 | C2_(6) | 46,286,900 | 109.96 | |
| Satt307 | C2_(6) | 46,286,900 | 109.96 | |
| BARC-010777-00746 | C2_(6) | 47,413,265 | 113.05 | |
| BARC-021425-04104 | C2_(6) | 47,782,099 | 113.24 | |
| BARCSOYSSR_06_1680 | C2_(6) | 47,820,539 | 114.18 | |
| Satt202 | C2_(6) | 47,820,539 | 114.18 | |
| BARCSOYSSR_06_1726 | C2_(6) | 48,582,450 | 116.34 | |
| Sat_252 | C2_(6) | 48,582,450 | 116.34 | |
| BARC-038923-07396 | C2_(6) | 48,635,024 | 126.95 | |
| BARC-047703-10385 | C2_(6) | 48,635,266 | 126.95 | |
| BARC-042663-08339 | C2_(6) | 48,658,985 | 126.95 | |
| BARC-016969-02170 | C2_(6) | 48,677,811 | 126.95 | |
| BARCSOYSSR_06_1762 | C2_(6) | 49,159,652 | 127.93 | |
| Satt371 | C2_(6) | 49,159,652 | 127.93 | |
| BARC-064859-18826 | C2_(6) | 49,329,186 | 128.37 | |
| BARC-064297-18613 | C2_(6) | 49,411,956 | 129.53 | |

Figure 6C

| BARC-038861-07350 | C2_(6) | 49,975,437 | 132.41 | |
|---|---|---|---|---|
| BARC-025179-06455 | C2_(6) | 50,324,535 | 135.04 | |
| BARC-030551-06898 | C2_(6) | 50,372,013 | 135.04 | |
| BARC-030551-06899 | C2_(6) | 50,372,013 | 136.12 | |
| BARC-018915-03279 | C2_(6) | 50,602,830 | 136.51 | |

Figure 7A

| Locus Name | LG | Physical Position | Genetic position (cM) | Approximate Centromere |
|---|---|---|---|---|
| BARC-013365-00489 | B2_(14) | 96,681 | 3.28 | |
| BARC-030905-06965 | B2_(14) | 432,316 | 4.27 | |
| BARC-014285-01304 | B2_(14) | 594,759 | 4.94 | |
| BARCSOYSSR_14_0036 | B2_(14) | 668,820 | 5.47 | |
| Satt577 | B2_(14) | 668,820 | 5.47 | |
| BARC-014457-01378 | B2_(14) | 807,094 | 6.37 | |
| BARC-058633-15342 | B2_(14) | 849,008 | 7.88 | |
| BARC-061447-18864 | B2_(14) | 884,932 | 9.97 | |
| BARC-028553-05949 | B2_(14) | 1,359,496 | 10.43 | |
| BARCSOYSSR_14_0096 | B2_(14) | 1,843,817 | 10.95 | |
| Sat_264 | B2_(14) | 1,843,817 | 10.95 | |
| BARC-028723-05998 | B2_(14) | 2,186,526 | 11.89 | |
| BARC-040733-07831 | B2_(14) | 2,204,606 | 12.47 | |
| BARC-065411-19443 | B2_(14) | 2,250,759 | 13.10 | |
| BARC-051559-11161 | B2_(14) | 2,597,962 | 14.48 | |
| BARC-020561-04671 | B2_(14) | 2,684,286 | 14.85 | |
| BARCSOYSSR_14_0147 | B2_(14) | 2,954,859 | 15.50 | |
| Sat_342 | B2_(14) | 2,954,859 | 15.50 | |
| S02874-1 | B2_(14) | 3,945,680 | 20.07 | |
| BARC-021353-04044 | B2_(14) | 4,305,870 | 21.73 | |
| BARC-031661-06454 | B2_(14) | 4,534,340 | 22.28 | |
| BARC-031365-07064 | B2_(14) | 4,822,808 | 23.73 | |
| BARC-039595-07510 | B2_(14) | 5,028,861 | 25.62 | |
| S04785-1 | B2_(14) | 5,096,522 | 26.08 | |
| BARCSOYSSR_14_0281 | B2_(14) | 5,177,348 | 26.64 | |
| Sat_287 | B2_(14) | 5,177,348 | 26.64 | |
| BARC-015539-02002 | B2_(14) | 5,429,630 | 27.38 | |
| BARC-055975-13947 | B2_(14) | 6,740,624 | 35.52 | |
| BARC-020449-04623 | B2_(14) | 6,968,818 | 35.76 | |
| BARC-050249-09527 | B2_(14) | 7,132,727 | 38.37 | |
| BARC-065455-19481 | B2_(14) | 7,264,008 | 39.39 | |
| BARC-016505-02073 | B2_(14) | 7,318,792 | 39.86 | |
| BARC-044549-08718 | B2_(14) | 7,379,590 | 40.03 | |
| BARCSOYSSR_14_0440 | B2_(14) | 7,818,064 | 43.15 | |
| Sct_034 | B2_(14) | 7,818,064 | 43.15 | |
| BARC-064873-18956 | B2_(14) | 8,340,001 | 45.46 | |
| BARCSOYSSR_14_0485 | B2_(14) | 8,642,764 | 45.66 | |
| Satt416 | B2_(14) | 8,642,764 | 45.66 | |
| BARC-030967-06981 | B2_(14) | 8,902,647 | 50.05 | |

Figure 7B

| | | | | |
|---|---|---|---|---|
| BARC-055677-13598 | B2_(14) | 9,318,033 | 53.92 | |
| BARC-014309-01312 | B2_(14) | 9,642,001 | 54.51 | |
| BARC-052759-11611 | B2_(14) | 10,018,294 | 55.50 | |
| BARC-052757-11610 | B2_(14) | 10,149,510 | 55.50 | |
| BARC-057817-14938 | B2_(14) | 10,667,555 | 55.79 | |
| BARC-054615-12115 | B2_(14) | 10,699,554 | 56.10 | |
| BARC-059553-15907 | B2_(14) | 10,708,292 | 56.10 | |
| BARC-051601-11175 | B2_(14) | 11,283,799 | 56.33 | x |
| BARC-051599-11174 | B2_(14) | 11,320,165 | 56.36 | x |
| BARC-065009-19043 | B2_(14) | 12,765,699 | 56.60 | x |
| BARCSOYSSR_14_0663 | B2_(14) | 13,784,029 | 56.81 | x |
| Sat_355 | B2_(14) | 13,784,029 | 56.81 | x |

Figure 8A

| Locus Name | LG | Physical Position | Genetic position (cM) | ~Centromere |
|---|---|---|---|---|
| BARC-044707-08763 | E_(15) | 11,564,044 | 56.54 | |
| BARC-028607-05972 | E_(15) | 11,630,781 | 57.24 | |
| BARC-017755-03124 | E_(15) | 11,798,929 | 59.38 | |
| BARC-018461-02916 | E_(15) | 12,256,121 | 61.36 | |
| BARC-062799-18070 | E_(15) | 13,676,958 | 66.03 | |
| BARC-066103-17539 | E_(15) | 13,735,240 | 66.03 | |
| BARC-057283-14667 | E_(15) | 13,762,803 | 68.06 | |
| BARC-030079-06803 | E_(15) | 14,032,584 | 68.46 | |
| BARC-038377-10061 | E_(15) | 14,329,242 | 69.39 | |
| BARC-054023-12243 | E_(15) | 14,753,749 | 69.79 | |
| BARCSOYSSR_15_0692 | E_(15) | 14,918,775 | 70.47 | |
| Satt606 | E_(15) | 14,918,775 | 70.47 | |
| BARC-054095-12332 | E_(15) | 15,100,427 | 70.60 | |
| BARC-016029-02040 | E_(15) | 15,100,540 | 70.60 | |
| BARC-023525-05447 | E_(15) | 15,443,300 | 71.20 | |
| BARC-060905-16966 | E_(15) | 15,743,043 | 71.42 | |
| BARCSOYSSR_15_0753 | E_(15) | 16,668,418 | 72.02 | |
| Sat_136 | E_(15) | 16,668,418 | 72.02 | |
| BARCSOYSSR_15_0765 | E_(15) | 17,025,474 | 74.32 | |
| Sat_380 | E_(15) | 17,025,474 | 74.32 | |
| BARCSOYSSR_15_0766 | E_(15) | 17,054,779 | 74.37 | |
| Satt706 | E_(15) | 17,054,779 | 74.37 | |
| BARC-029637-06273 | E_(15) | 17,582,453 | 74.81 | |
| BARCSOYSSR_15_0800 | E_(15) | 17,692,405 | 75.28 | |
| Sat_107 | E_(15) | 17,692,405 | 75.28 | |
| BARC-052575-11504 | E_(15) | 18,539,487 | 75.81 | x |
| BARC-054787-12166 | E_(15) | 19,024,123 | 75.94 | x |
| BARC-059455-15814 | E_(15) | 20,019,884 | 76.10 | x |
| BARC-030059-06795 | E_(15) | 20,686,689 | 76.37 | x |
| BARC-059689-16003 | E_(15) | 21,179,215 | 76.60 | x |
| BARC-061007-17001 | E_(15) | 22,274,650 | 76.87 | x |
| BARC-059873-16177 | E_(15) | 23,625,526 | 77.04 | x |
| BARC-062747-18029 | E_(15) | 30,330,055 | 77.04 | x |
| BARC-059537-15899 | E_(15) | 32,251,236 | 77.04 | x |
| BARCSOYSSR_15_1125 | E_(15) | 34,902,080 | 77.04 | x |
| Satt483 | E_(15) | 34,902,080 | 77.04 | x |
| BARC-039931-07614 | E_(15) | 36,577,083 | 77.27 | x |
| BARC-063963-18516 | E_(15) | 37,088,862 | 77.41 | x |
| BARC-051429-11107 | E_(15) | 37,297,779 | 77.49 | x |

Figure 8B

| | | | | |
|---|---|---|---|---|
| BARC-058493-15308 | E_(15) | 39,652,366 | 78.62 | x |
| BARC-007650-00171 | E_(15) | 41,305,413 | 78.64 | x |
| BARC-001485-00045 | E_(15) | 41,305,449 | 78.64 | x |
| BARC-014501-01563 | E_(15) | 41,841,189 | 78.66 | x |
| BARC-044083-08609 | E_(15) | 43,374,464 | 79.23 | x |
| BARC-028805-06018 | E_(15) | 43,849,421 | 79.25 | x |
| BARC-028221-05799 | E_(15) | 43,851,079 | 79.27 | x |
| BARC-050947-10881 | E_(15) | 45,424,612 | 80.37 | |
| BARC-055571-13451 | E_(15) | 47,021,065 | 81.62 | |
| BARC-055527-13350 | E_(15) | 47,080,727 | 82.28 | |
| BARC-051565-11166 | E_(15) | 47,427,853 | 82.70 | |
| BARC-040965-07871 | E_(15) | 48,222,867 | 84.93 | |
| S00350-1 | E_(15) | 48,657,373 | 85.49 | |
| BARC-016083-02061 | E_(15) | 48,657,557 | 85.49 | |
| BARC-043041-08509 | E_(15) | 48,694,488 | 85.88 | |
| BARC-052379-11435 | E_(15) | 48,781,847 | 86.52 | |
| BARC-020425-04614 | E_(15) | 48,863,918 | 86.64 | |
| BARC-016131-02290 | E_(15) | 49,621,518 | 88.47 | |
| BARC-013073-00440 | E_(15) | 49,883,172 | 90.16 | |
| S02183-1 | E_(15) | 49,934,844 | 90.49 | |
| BARC-022009-04249 | E_(15) | 50,061,005 | 91.30 | |
| BARC-042937-08466 | E_(15) | 50,114,250 | 92.37 | |
| BARCSOYSSR_15_1568 | E_(15) | 50,282,274 | 92.75 | |
| Sat_381 | E_(15) | 50,282,274 | 92.75 | |
| BARC-013235-00458 | E_(15) | 50,334,269 | 93.35 | |
| BARC-025839-05112 | E_(15) | 50,395,865 | 93.42 | |
| BARC-017767-03127 | E_(15) | 50,396,230 | 93.53 | |
| BARCSOYSSR_15_1582 | E_(15) | 50,497,750 | 96.42 | |
| Satt231 | E_(15) | 50,497,750 | 96.42 | |

Figure 9A

| Locus Name | LG | Physical Position | Genetic position (cM) | ~Centromere |
|---|---|---|---|---|
| BARCSOYSSR_19_0017 | L_(19) | 206,205 | 0.14 | |
| Sat_408 | L_(19) | 206,205 | 0.14 | |
| BARC-060295-16596 | L_(19) | 215,739 | 0.00 | |
| BARC-043223-08561 | L_(19) | 581,962 | 0.00 | |
| BARCSOYSSR_19_0046 | L_(19) | 650,680 | 2.74 | |
| Satt495 | L_(19) | 650,680 | 2.74 | |
| BARC-039375-07304 | L_(19) | 805,921 | 3.36 | |
| BARC-039375-07306 | L_(19) | 805,921 | 3.74 | |
| BARCSOYSSR_19_0110 | L_(19) | 1,634,229 | 10.42 | |
| Satt446 | L_(19) | 1,634,229 | 10.42 | |
| BARCSOYSSR_19_0132 | L_(19) | 2,014,582 | 13.07 | |
| Satt182 | L_(19) | 2,014,582 | 13.07 | |
| S02074-1 | L_(19) | 2,901,398 | 17.63 | |
| BARC-065445-19463 | L_(19) | 2,977,006 | 18.02 | |
| BARC-050993-10894 | L_(19) | 2,997,175 | 18.16 | |
| BARCSOYSSR_19_0212 | L_(19) | 3,303,354 | 18.83 | |
| Sat_071 | L_(19) | 3,303,354 | 18.83 | |
| BARCSOYSSR_19_0257 | L_(19) | 4,212,666 | 21.14 | |
| Satt388 | L_(19) | 4,212,666 | 21.14 | |
| BARCSOYSSR_19_0360 | L_(19) | 7,155,405 | 25.57 | |
| Satt523 | L_(19) | 7,155,405 | 25.57 | |
| BARC-057829-14944 | L_(19) | 8,345,791 | 27.38 | |
| BARC-058553-15312 | L_(19) | 9,409,584 | 28.68 | |
| BARC-013093-01432 | L_(19) | 11,340,071 | 29.32 | x |
| BARC-055799-13726 | L_(19) | 15,925,255 | 29.32 | x |
| BARCSOYSSR_19_0507 | L_(19) | 15,995,252 | 29.32 | x |
| Sat_134 | L_(19) | 15,995,252 | 29.32 | x |
| BARC-055237-13132 | L_(19) | 16,513,696 | 29.32 | x |
| BARC-047428-12928 | L_(19) | 16,641,861 | 29.32 | x |
| S03991-1 | L_(19) | 18,029,354 | 29.32 | x |
| BARC-058347-15244 | L_(19) | 19,376,541 | 29.32 | x |
| BARC-054881-12190 | L_(19) | 20,699,444 | 29.32 | x |
| BARC-052985-11687 | L_(19) | 20,928,966 | 29.32 | x |
| BARC-049759-09138 | L_(19) | 20,937,783 | 29.32 | x |
| BARC-065719-19673 | L_(19) | 21,108,088 | 29.32 | x |
| BARC-061139-17079 | L_(19) | 24,755,826 | 29.32 | x |
| BARC-058601-15327 | L_(19) | 24,937,205 | 29.32 | x |
| BARC-061553-17266 | L_(19) | 25,005,200 | 29.32 | x |
| BARC-061163-17087 | L_(19) | 27,061,961 | 29.32 | x |

Figure 9B

| | | | | |
|---|---|---|---|---|
| BARC-047250-12895 | L_(19) | 27,283,751 | 29.32 | x |
| BARC-047144-12870 | L_(19) | 27,295,235 | 29.32 | x |
| BARC-047086-12837 | L_(19) | 27,297,715 | 29.32 | x |
| BARC-047244-12890 | L_(19) | 27,298,477 | 29.32 | x |
| BARCSOYSSR_19_0758 | L_(19) | 33,692,499 | 29.40 | |
| Sat_397 | L_(19) | 33,692,499 | 29.40 | |
| BARCSOYSSR_19_0775 | L_(19) | 34,184,335 | 30.19 | |
| Sat_320 | L_(19) | 34,184,335 | 30.19 | |
| BARCSOYSSR_19_0788 | L_(19) | 34,589,380 | 32.30 | |
| Satt313 | L_(19) | 34,589,380 | 32.30 | |
| BARC-050839-09924 | L_(19) | 34,696,220 | 32.61 | |
| BARC-040695-07821 | L_(19) | 34,926,706 | 33.22 | |
| BARCSOYSSR_19_0813 | L_(19) | 35,095,401 | 33.40 | |
| Satt613 | L_(19) | 35,095,401 | 33.40 | |
| BARC-055761-13695 | L_(19) | 35,305,449 | 33.80 | |
| BARCSOYSSR_19_0832 | L_(19) | 35,484,455 | 33.94 | |
| Satt284 | L_(19) | 35,484,455 | 33.94 | |
| BARC-064129-18562 | L_(19) | 35,769,071 | 34.40 | |
| BARC-018885-03269 | L_(19) | 36,397,670 | 35.12 | |
| BARC-059725-16059 | L_(19) | 36,693,633 | 36.36 | |
| BARC-022029-04261 | L_(19) | 37,003,494 | 37.66 | |
| BARC-013203-00448 | L_(19) | 37,244,259 | 39.34 | |
| BARCSOYSSR_19_0921 | L_(19) | 37,501,595 | 41.40 | |
| AW508247 | L_(19) | 37,501,595 | 41.40 | |
| BARC-025567-06523 | L_(19) | 39,766,002 | 49.52 | |
| BARCSOYSSR_19_1041 | L_(19) | 40,072,246 | 50.22 | |
| Sat_150 | L_(19) | 40,072,246 | 50.22 | |
| BARCSOYSSR_19_1045 | L_(19) | 40,127,099 | 51.38 | |
| Satt481 | L_(19) | 40,127,099 | 51.38 | |
| BARCSOYSSR_19_1073 | L_(19) | 40,445,843 | 52.55 | |
| Sat_340 | L_(19) | 40,445,843 | 52.55 | |
| BARCSOYSSR_19_1112 | L_(19) | 41,187,677 | 54.14 | |
| Sct_010 | L_(19) | 41,187,677 | 54.14 | |
| BARCSOYSSR_19_1128 | L_(19) | 41,423,108 | 55.66 | |
| Satt076 | L_(19) | 41,423,108 | 55.66 | |
| BARC-055739-13676 | L_(19) | 42,048,498 | 59.18 | |
| BARCSOYSSR_19_1176 | L_(19) | 42,110,356 | 59.44 | |
| Sat_113 | L_(19) | 42,110,356 | 59.44 | |

SEQUENCE LISTING

<160> NUMBER OF SEQ ID NOS: 377

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gccatcctag ctagccctgt                                              20

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
ttgacctgtt gattatttcg taatg                                        25

```
<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
gccatcctag ctagccctgt atat                                              24

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gtgttaggtg tcatcgaggc at                                                22

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
tcctagctag ccctgtatat tttga                                             25

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
taggtgtcat cgaggcatcg                                                   20

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
aattatcttg acctgttgat tatttcg                                           27

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ccacaaccta ttgttgaagc ac                                                22

<210> SEQ ID NO 9
<211> LENGTH: 20
<212> TYPE: DNA
<213> ORGANISM: Artificial Sequence
<220> FEATURE:
<223> OTHER INFORMATION: Primer
```

<400> SEQUENCE: 9
tgtgcactcc tgactgcttt    20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tcaaccgtgg aaagtaacca    20

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
gttcttgaaa gttggagact raatg    25

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tccttggaag gttcggtaga    20

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
tcaatttagt tcttgaaagt tggagac    27

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
aaccgtggaa agtaaccaaa aa    22

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
acctcaaccg tggaaagtaa cc    22

<210> SEQ ID NO 16
<211> LENGTH: 25

```
<212> TYPE: DNA
<213> ORGANISM: Artificial Sequence
<220> FEATURE:
<223> OTHER INFORMATION: Primer

<400> SEQUENCE: 16
ggaatgacat taacttggtt tttga                                           25

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
tgacattaac ttggtttttg atcct                                           25

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
cgacaccaat ttctccatcc                                                 20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
atgtcggaac ttggcatctt                                                 20

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
cacgacacca atttctccat cctctca                                         27

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21
caacattccc agtcgacacg tcttct                                          26

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
```
aaggcatgtc ggaacttggc atct                                              24

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
tgatttccaa tgtaaatcaa ccatt                                             25

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
aatacccttc cacgacacca                                                   20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cggaacttgg catctttgat                                                   20

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
tcaaacttga caaagccaca a                                                 21

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
tgcaaagagg gtaaggactt g                                                 21

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28 ccattttttgg agaatctcgt gtccgtag                                         28

<210> SEQ ID NO 29
<211> LENGTH: 32
<212> TYPE: DNA
<213> ORGANISM: Artificial Sequence
<220> FEATURE:
<223> OTHER INFORMATION: Primer

<400> SEQUENCE: 29
gacttaccaa atgagtttga ccaggttttta cc                                32

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
gatgatycca aatctgcttc a                                             21

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ttgttctccc gyttacacca                                               20

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
tgatacaacg ycccattctt c                                             21

<210> SEQ ID NO 33
<211> LENGTH: 31
<212> TYPE: DNA
<213> ORGANISM: Artificial Sequence
<220> FEATURE:
<223> OTHER INFORMATION: Primer

<400> SEQUENCE: 33
ggtcaaactc atttggtaag tctragtttg c                                  31

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
cccattcttc atgtactcat acaccaagag                                    30

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ttctcccgyt tacaccacaa                                               20

```
<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
caacgyccca ttcttcatgt                                               20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ggttgcaatc aagagggta                                                20

<210> SEQ ID NO 38
<211> LENGTH: 21
<212> TYPE: DNA
<213> ORGANISM: Artificial Sequence
<220> FEATURE:
<223> OTHER INFORMATION: Primer

<400> SEQUENCE: 38
tgatgataca acgycccatt c                                             21

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
gctttagacg tgtcctcctc a                                             21

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
ccacttggaa agagtgggtt a                                             21

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
agacgtgtcc tcctcaacca                                               20

<210> SEQ ID NO 42
<211> LENGTH: 20
<212> TYPE: DNA
<213> ORGANISM: Artificial Sequence
<220> FEATURE:
<223> OTHER INFORMATION: Primer
```

```
<400> SEQUENCE: 42
aggagaaccc ttcacactcg                                                  20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
cacactcgcg agcatagaac                                                  20

<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44
ttcaatttgt tgaagccttt tca                                              23

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
gaggagaacc cttcacactc g                                                21

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
tagacgtgtc ctcctcaacc at                                               22

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
aaccacttgg aaagagtggg tta                                              23

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
tcaatttgtt gaagccttttt ca                                              22

<210> SEQ ID NO 49
```

```
<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
tgaggctttt gaggagaacc                                               20

<210> SEQ ID NO 50
<211> LENGTH: 25
<212> TYPE: DNA
<213> ORGANISM: Artificial Sequence
<220> FEATURE:
<223> OTHER INFORMATION: Primer

<400> SEQUENCE: 50
tgctgttcca taattagaat tggag                                         25

<210> SEQ ID NO 51
<211> LENGTH: 22
<212> TYPE: DNA
<213> ORGANISM: Artificial Sequence
<220> FEATURE:
<223> OTHER INFORMATION: Primer

<400> SEQUENCE: 51
cctgcatcaa gatgaacaag aa                                            22

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
gccaatggtc catcaaaatg                                               20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
aacatcgaag gctgagaacg                                               20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
gtgttgtgtg tgctgttcca                                               20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
```

```
gttggccaat caatgaaggt                                            20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
ggtttcagtt ccaccacctg                                            20

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
agtgttgtgt gtgctgttcc a                                          21

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
agttccacca cctgcatcaa                                            20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
gcttcaacat caccagcaga                                            20

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
gaaggctgag aacggacaag                                            20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
catcaccagc agaaactgga                                            20

<210> SEQ ID NO 62
<211> LENGTH: 20
<212> TYPE: DNA
```

```
<213> ORGANISM: Artificial Sequence
<220> FEATURE:
<223> OTHER INFORMATION: Primer

<400> SEQUENCE: 62
ctgcttcaac atcaccagca                                              20

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
tgcatcctgc ttttctgctt                                              20

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
tgcctaatgg gagagatgaa g                                            21

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
cgcaggttct gttactcgaa g                                            21

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
aatgcctaat gggagagatg aa                                           22

<210> SEQ ID NO 67
<211> LENGTH: 27
<212> TYPE: DNA
<213> ORGANISM: Artificial Sequence
<220> FEATURE:
<223> OTHER INFORMATION: Primer

<400> SEQUENCE: 67
tttatattgt agtgtaggtg ccttgtc                                      27

<210> SEQ ID NO 68
<211> LENGTH: 28
<212> TYPE: DNA
<213> ORGANISM: Artificial Sequence
<220> FEATURE:
<223> OTHER INFORMATION: Primer

<400> SEQUENCE: 68
tgaatatata aatgcctaat gggagaga                                     28
```

```
<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
ttgggttgaa gccttttatg g                                          21

<210> SEQ ID NO 70
<211> LENGTH: 28
<212> TYPE: DNA
<213> ORGANISM: Artificial Sequence
<220> FEATURE:
<223> OTHER INFORMATION: Primer

<400> SEQUENCE: 70
acaagtaaag tatggataag atgtgcaa                                   28

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
tcgcaggttc tgttactcga a                                          21

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
aatgcagggc cagttacaat                                            20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
aattgccccc atctttctc                                             20

<210> SEQ ID NO 74
<211> LENGTH: 40
<212> TYPE: DNA
<213> ORGANISM: Artificial Sequence
<220> FEATURE:
<223> OTHER INFORMATION: Primer

<400> SEQUENCE: 74
cagttacaat acatacatac gcataaccaa aacagtaaca                      40

<210> SEQ ID NO 75
<211> LENGTH: 40
<212> TYPE: DNA
<213> ORGANISM: Artificial Sequence
<220> FEATURE:
```

<223> OTHER INFORMATION: Primer

<400> SEQUENCE: 75
actactggat tttaatgtag gtttcttcca tgtagctatg                    40

<210> SEQ ID NO 76
<211> LENGTH: 26
<212> TYPE: DNA
<213> ORGANISM: Artificial Sequence
<220> FEATURE:
<223> OTHER INFORMATION: Primer

<400> SEQUENCE: 76
aaccaaaaca gtaacatcaa tggaac                                  26

<210> SEQ ID NO 77
<211> LENGTH: 29
<212> TYPE: DNA
<213> ORGANISM: Artificial Sequence
<220> FEATURE:
<223> OTHER INFORMATION: Primer

<400> SEQUENCE: 77
caaatggttg tgttttctt agaaatttc                                29

<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78
accaaaacag taacatcaat ggaa                                    24

<210> SEQ ID NO 79
<211> LENGTH: 26
<212> TYPE: DNA
<213> ORGANISM: Artificial Sequence
<220> FEATURE:
<223> OTHER INFORMATION: Primer

<400> SEQUENCE: 79
tttaatgtag gtttcttcca tgtagc                                  26

<210> SEQ ID NO 80
<211> LENGTH: 24
<212> TYPE: DNA
<213> ORGANISM: Artificial Sequence
<220> FEATURE:
<223> OTHER INFORMATION: Primer

<400> SEQUENCE: 80
acgcataacc aaaacagtaa catc                                    24

<210> SEQ ID NO 81
<211> LENGTH: 26
<212> TYPE: DNA
<213> ORGANISM: Artificial Sequence
<220> FEATURE:
<223> OTHER INFORMATION: Primer

<400> SEQUENCE: 81
atgtaggttt cttccatgta gctatg                                  26

```
<210> SEQ ID NO 82
<211> LENGTH: 24
<212> TYPE: DNA
<213> ORGANISM: Artificial Sequence
<220> FEATURE:
<223> OTHER INFORMATION: Primer

<400> SEQUENCE: 82
tgcttatctt gtctgaaaac cact                                          24

<210> SEQ ID NO 83
<211> LENGTH: 26
<212> TYPE: DNA
<213> ORGANISM: Artificial Sequence
<220> FEATURE:
<223> OTHER INFORMATION: Primer

<400> SEQUENCE: 83
tgactttaag gcaattcaac tgtatc                                        26

<210> SEQ ID NO 84
<211> LENGTH: 25
<212> TYPE: DNA
<213> ORGANISM: Artificial Sequence
<220> FEATURE:
<223> OTHER INFORMATION: Primer

<400> SEQUENCE: 84
acctaatgtg atgagcatcc ttaat                                         25

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
cttgtctgaa aaccactaat gctc                                          24

<210> SEQ ID NO 86
<211> LENGTH: 25
<212> TYPE: DNA
<213> ORGANISM: Artificial Sequence
<220> FEATURE:
<223> OTHER INFORMATION: Primer

<400> SEQUENCE: 86
ctaatgtgat gagcatcctt aattg                                         25

<210> SEQ ID NO 87
<211> LENGTH: 20
<212> TYPE: DNA
<213> ORGANISM: Artificial Sequence
<220> FEATURE:
<223> OTHER INFORMATION: Probe

<400> SEQUENCE: 87
attcctaaag atagtccaat                                               20

<210> SEQ ID NO 88
<211> LENGTH: 19
<212> TYPE: DNA
<213> ORGANISM: Artificial Sequence
<220> FEATURE:
<223> OTHER INFORMATION: Probe
```

```
<400> SEQUENCE: 88
ctaaagatac atgcaagtc                                                19

<210> SEQ ID NO 89
<211> LENGTH: 17
<212> TYPE: DNA
<213> ORGANISM: Artificial Sequence
<220> FEATURE:
<223> OTHER INFORMATION: Probe

<400> SEQUENCE: 89
ttctgataga cgaaacc                                                  17

<210> SEQ ID NO 90
<211> LENGTH: 17
<212> TYPE: DNA
<213> ORGANISM: Artificial Sequence
<220> FEATURE:
<223> OTHER INFORMATION: Probe

<400> SEQUENCE: 90
ctgatagatg aaaccca                                                  17

<210> SEQ ID NO 91
<211> LENGTH: 14
<212> TYPE: DNA
<213> ORGANISM: Artificial Sequence
<220> FEATURE:
<223> OTHER INFORMATION: Probe

<400> SEQUENCE: 91
caaactgcaa gatt                                                     14

<210> SEQ ID NO 92
<211> LENGTH: 15
<212> TYPE: DNA
<213> ORGANISM: Artificial Sequence
<220> FEATURE:
<223> OTHER INFORMATION: Probe

<400> SEQUENCE: 92
cacaaaccgc aagat                                                    15

<210> SEQ ID NO 93
<211> LENGTH: 19
<212> TYPE: DNA
<213> ORGANISM: Artificial Sequence
<220> FEATURE:
<223> OTHER INFORMATION: Probe

<400> SEQUENCE: 93
cggagaataa ataaataag                                                19

<210> SEQ ID NO 94
<211> LENGTH: 19
<212> TYPE: DNA
<213> ORGANISM: Artificial Sequence
<220> FEATURE:
<223> OTHER INFORMATION: Probe

<400> SEQUENCE: 94
cggagaataa ataagtaag                                                19

<210> SEQ ID NO 95
<211> LENGTH: 16
```

```
<212> TYPE: DNA
<213> ORGANISM: Artificial Sequence
<220> FEATURE:
<223> OTHER INFORMATION: Probe

<400> SEQUENCE: 95
ttagtggaca gtgcca                                                        16

<210> SEQ ID NO 96
<211> LENGTH: 18
<212> TYPE: DNA
<213> ORGANISM: Artificial Sequence
<220> FEATURE:
<223> OTHER INFORMATION: Probe

<400> SEQUENCE: 96
ttagttgaca gtgccata                                                      18

<210> SEQ ID NO 97
<211> LENGTH: 21
<212> TYPE: DNA
<213> ORGANISM: Artificial Sequence
<220> FEATURE:
<223> OTHER INFORMATION: Probe

<400> SEQUENCE: 97
tttgtgaaga aaaatatgaa a                                                  21

<210> SEQ ID NO 98
<211> LENGTH: 19
<212> TYPE: DNA
<213> ORGANISM: Artificial Sequence
<220> FEATURE:
<223> OTHER INFORMATION: Probe

<400> SEQUENCE: 98
ttgtgaacaa aaagatgaa                                                     19

<210> SEQ ID NO 99
<211> LENGTH: 17
<212> TYPE: DNA
<213> ORGANISM: Artificial Sequence
<220> FEATURE:
<223> OTHER INFORMATION: Probe

<400> SEQUENCE: 99
ctcagtatat catcttc                                                       17

<210> SEQ ID NO 100
<211> LENGTH: 15
<212> TYPE: DNA
<213> ORGANISM: Artificial Sequence
<220> FEATURE:
<223> OTHER INFORMATION: Probe

<400> SEQUENCE: 100
ccctcagtag atcat                                                         15

<210> SEQ ID NO 101
<211> LENGTH: 15
<212> TYPE: DNA
<213> ORGANISM: Artificial Sequence
<220> FEATURE:
<223> OTHER INFORMATION: Probe

<400> SEQUENCE: 101
```
cacctaagga acaat                                                    15

<210> SEQ ID NO 102
<211> LENGTH: 16
<212> TYPE: DNA
<213> ORGANISM: Artificial Sequence
<220> FEATURE:
<223> OTHER INFORMATION: Probe

<400> SEQUENCE: 102
cctaatgaac aatacc                                                   16

<210> SEQ ID NO 103
<211> LENGTH: 15
<212> TYPE: DNA
<213> ORGANISM: Artificial Sequence
<220> FEATURE:
<223> OTHER INFORMATION: Probe

<400> SEQUENCE: 103
cttccagtgg ctgct                                                    15

<210> SEQ ID NO 104
<211> LENGTH: 13
<212> TYPE: DNA
<213> ORGANISM: Artificial Sequence
<220> FEATURE:
<223> OTHER INFORMATION: Probe

<400> SEQUENCE: 104
ccttccagcg gct                                                      13

<210> SEQ ID NO 105
<211> LENGTH: 18
<212> TYPE: DNA
<213> ORGANISM: Artificial Sequence
<220> FEATURE:
<223> OTHER INFORMATION: Probe

<400> SEQUENCE: 105
ctactaccat acctaaac                                                 18

<210> SEQ ID NO 106
<211> LENGTH: 17
<212> TYPE: DNA
<213> ORGANISM: Artificial Sequence
<220> FEATURE:
<223> OTHER INFORMATION: Probe

<400> SEQUENCE: 106
tactaccatc cctaaac                                                  17

<210> SEQ ID NO 107
<211> LENGTH: 18
<212> TYPE: DNA
<213> ORGANISM: Artificial Sequence
<220> FEATURE:
<223> OTHER INFORMATION: Probe

<400> SEQUENCE: 107
aataggacac aattatta                                                 18

<210> SEQ ID NO 108
<211> LENGTH: 17
<212> TYPE: DNA
<213> ORGANISM: Artificial Sequence

```
<220> FEATURE:
<223> OTHER INFORMATION: Probe

<400> SEQUENCE: 108
ataggacaca atcatta                                                  17

<210> SEQ ID NO 109
<211> LENGTH: 15
<212> TYPE: DNA
<213> ORGANISM: Artificial Sequence
<220> FEATURE:
<223> OTHER INFORMATION: Probe

<400> SEQUENCE: 109
tcagtgagaa taaaa                                                    15

<210> SEQ ID NO 110
<211> LENGTH: 15
<212> TYPE: DNA
<213> ORGANISM: Artificial Sequence
<220> FEATURE:
<223> OTHER INFORMATION: Probe

<400> SEQUENCE: 110
tcagtgtgaa taaaa                                                    15

<210> SEQ ID NO 111
<211> LENGTH: 236
<212> TYPE: DNA
<213> ORGANISM: Artificial Sequence
<220> FEATURE:
<223> OTHER INFORMATION: Amplicon
<220> FEATURE:
<221> NAME/KEY: misc_feature
<222> LOCATION: 33, 34, 37
<223> OTHER INFORMATION: n = A,T,C or G

<400> SEQUENCE: 111
gccatcctag ctagccctgt atattttgat tannttnatg ggaagaaaaa attaaatatt    60
tttatttaat tgaagagtaa gttaatttta tgaaaacaaa aatttaacat tttcttactt   120
atcttttaat tcaaatttta tttttatttc tcttattcca acaataattc ctaaagatag   180
tccaatatgt ttaactcatc acatttaatt tcattacgaa ataatcaaca ggtcaa       236

<210> SEQ ID NO 112
<211> LENGTH: 243
<212> TYPE: DNA
<213> ORGANISM: Artificial Sequence
<220> FEATURE:
<223> OTHER INFORMATION: Amplicon
<220> FEATURE:
<221> NAME/KEY: misc_feature
<222> LOCATION: 33, 34, 37
<223> OTHER INFORMATION: n = A,T,C or G

<400> SEQUENCE: 112
gccatcctag ctagccctgt atattttgat tannttnatg ggaagaaaaa attaaatatt    60
tttatttaat tgaagagtaa gttaatttta tgaaaacaaa aatttaacat tttcttactt   120
atcttttaat tcaaatttta tttttatttc tcttattcca acaataattc ctaaagatac   180
atgcaagtcc aatatgttta actcatcaca tttaatttca ttacgaaata atcaacaggt   240
caa                                                                243

<210> SEQ ID NO 113
```

```
<211> LENGTH: 101
<212> TYPE: DNA
<213> ORGANISM: Artificial Sequence
<220> FEATURE:
<223> OTHER INFORMATION: Amplicon

<400> SEQUENCE: 113
tgtgcactcc tgactgcttt tacatttagt gtcttcattt cattgggttt cctctatcag      60
aattcagtga taagaaacag tgcttcaaca ataggttgtg g                         101

<210> SEQ ID NO 114
<211> LENGTH: 101
<212> TYPE: DNA
<213> ORGANISM: Artificial Sequence
<220> FEATURE:
<223> OTHER INFORMATION: Amplicon

<400> SEQUENCE: 114
tgtgcactcc tgactgcttt tacatttagt gtcttcattt cattgggttt cttctatcag      60
aattcagtga taagaaacag tgcttcaaca ataggttgtg g                         101

<210> SEQ ID NO 115
<211> LENGTH: 224
<212> TYPE: DNA
<213> ORGANISM: Artificial Sequence
<220> FEATURE:
<223> OTHER INFORMATION: Amplicon

<400> SEQUENCE: 115
tcaatttagt tcttgaaagt tggagactra atgtcctcta aataaattga catcaatgta      60
gatcctcaat aatagaaaga tgacatcaat ttastcccta aatcttgctg tttgtgcata    120
gaaggatggt tttttggtta ctttccacgg ttgaggtact aaattgatgc aatatctctt    180
agggagttag aggacaaagt gatgtctacc gaaccttcca agga                     224

<210> SEQ ID NO 116
<211> LENGTH: 224
<212> TYPE: DNA
<213> ORGANISM: Artificial Sequence
<220> FEATURE:
<223> OTHER INFORMATION: Amplicon

<400> SEQUENCE: 116
tcaatttagt tcttgaaagt tggagactra atgtcctcta aataaattga catcaatgta      60
gatcctcaat aatagaaaga tgacatcaat ttastcccta aatcttgccg tttgtgcata    120
gaaggatggt tttttggtta ctttccacgg ttgaggtact aaattgatgc aatatctctt    180
agggagttag aggacaaagt gatgtctacc gaaccttcca agga                     224

<210> SEQ ID NO 117
<211> LENGTH: 112
<212> TYPE: DNA
<213> ORGANISM: Artificial Sequence
<220> FEATURE:
<223> OTHER INFORMATION: Amplicon

<400> SEQUENCE: 117
cgacaccaat ttctccatcc tctcattgaa aaacaaaatt aatcatctta cttatttatt      60
ctccgaaaat ggttgattta cattggaaat caaagatgcc aagttccgac at            112

<210> SEQ ID NO 118
<211> LENGTH: 112
```

```
<212> TYPE: DNA
<213> ORGANISM: Artificial Sequence
<220> FEATURE:
<223> OTHER INFORMATION: Amplicon

<400> SEQUENCE: 118
cgacaccaat ttctccatcc tctcattgaa aaacaaaatt aatcatctta tttatttatt    60
ctccgaaaat ggttgattta cattggaaat caaagatgcc aagttccgac at           112

<210> SEQ ID NO 119
<211> LENGTH: 286
<212> TYPE: DNA
<213> ORGANISM: Artificial Sequence
<220> FEATURE:
<223> OTHER INFORMATION: Amplicon

<400> SEQUENCE: 119
gacttaccaa atgagtttga ccaggtttta cccctcttga ttgcaacctc acgaccatca    60
acgagtttgc ctctgtactc aacaacaaag cctccggtac caatcttgtt gtcaaatgag   120
aaattattgg tggctgcttt aagttcagcg agggtgaata atggtgcagc aaaagcatgc   180
actggggaag gggatgatyc caaatctgct tcactggcac tactactcct tatggcactg   240
tccactaatg aagcaaaact acggacacga gattctccaa aaatgg                  286

<210> SEQ ID NO 120
<211> LENGTH: 286
<212> TYPE: DNA
<213> ORGANISM: Artificial Sequence
<220> FEATURE:
<223> OTHER INFORMATION: Amplicon

<400> SEQUENCE: 120
gacttaccaa atgagtttga ccaggtttta cccctcttga ttgcaacctc acgaccatca    60
acgagtttgc ctctgtactc aacaacaaag cctccggtac caatcttgtt gtcaaatgag   120
aaattattgg tggctgcttt aagttcagcg agggtgaata atggtgcagc aaaagcatgc   180
actggggaag gggatgatyc caaatctgct tcactggcac tactactcct tatggcactg   240
tcaactaatg aagcaaaact acggacacga gattctccaa aaatgg                  286

<210> SEQ ID NO 121
<211> LENGTH: 110
<212> TYPE: DNA
<213> ORGANISM: Artificial Sequence
<220> FEATURE:
<223> OTHER INFORMATION: Amplicon

<400> SEQUENCE: 121
ttgttctccc gyttacacca caagaatttg gttgggctgg ttggattttg tgaacaaaaa    60
gatgaaaggc tcttggtgta tgagtacatg aagaatgggr cgttgtatca              110

<210> SEQ ID NO 122
<211> LENGTH: 110
<212> TYPE: DNA
<213> ORGANISM: Artificial Sequence
<220> FEATURE:
<223> OTHER INFORMATION: Amplicon

<400> SEQUENCE: 122
ttgttctccc gyttacacca caagaatttg gttgggctgg ttggattttg tgaagaaaaa    60
tatgaaaggc tcttggtgta tgagtacatg aagaatgggr cgttgtatca              110
```

<210> SEQ ID NO 123
<211> LENGTH: 130
<212> TYPE: DNA
<213> ORGANISM: Artificial Sequence
<220> FEATURE:
<223> OTHER INFORMATION: Amplicon

<400> SEQUENCE: 123
ccacttggaa agagtgggtt actagcatga tttttagtga ggcttttgag gagaaccctt    60
cacactcgcg agcatagaac attgaagatg atatactgag ggaaatggtt gaggaggaca   120
cgtctaaagc                                                          130

<210> SEQ ID NO 124
<211> LENGTH: 130
<212> TYPE: DNA
<213> ORGANISM: Artificial Sequence
<220> FEATURE:
<223> OTHER INFORMATION: Amplicon

<400> SEQUENCE: 124
ccacttggaa agagtgggtt actagcatga tttttagtga ggcttttgag gagaaccctt    60
cacactcgcg agcatagaac attgaagatg atctactgag ggaaatggtt gaggaggaca   120
cgtctaaagc                                                          130

<210> SEQ ID NO 125
<211> LENGTH: 175
<212> TYPE: DNA
<213> ORGANISM: Artificial Sequence
<220> FEATURE:
<223> OTHER INFORMATION: Amplicon

<400> SEQUENCE: 125
tgctgttcca taattagaat tggagtttta cttaccttag taatatgtat aattctaatt    60
ggagaacagt acaaacaaaa acacctaagg aacaatacct tagttttaat catatttgtt   120
ttgttcatat agcttatcaa taagtgaagt attttcttgt tcatcttgat gcagg        175

<210> SEQ ID NO 126
<211> LENGTH: 175
<212> TYPE: DNA
<213> ORGANISM: Artificial Sequence
<220> FEATURE:
<223> OTHER INFORMATION: Amplicon

<400> SEQUENCE: 126
tgctgttcca taattagaat tggagtttta cttaccttag taatatgtat aattctaatt    60
ggagaacagt acaaacaaaa acacctaatg aacaatacct tagttttaat catatttgtt   120
ttgttcatat agcttatcaa taagtgaagt attttcttgt tcatcttgat gcagg        175

<210> SEQ ID NO 127
<211> LENGTH: 144
<212> TYPE: DNA
<213> ORGANISM: Artificial Sequence
<220> FEATURE:
<223> OTHER INFORMATION: Amplicon

<400> SEQUENCE: 127
aacatcgaag gctgagaacg gacaagccac ggggagagca gccactggaa ggacagaaaa    60
aggagtccct ccagtttctg ctggtgatgt tgaagcaggt ggggaggctg gagggaaact   120
agtccatttt gatggaccat tggc                                          144

<210> SEQ ID NO 128
<211> LENGTH: 144
<212> TYPE: DNA
<213> ORGANISM: Artificial Sequence
<220> FEATURE:
<223> OTHER INFORMATION: Amplicon

<400> SEQUENCE: 128

```
aacatcgaag gctgagaacg gacaagccac ggggagagca gccgctggaa ggacagaaaa      60
aggagtccct ccagtttctg ctggtgatgt tgaagcaggt ggggaggctg gagggaaact     120
agtccatttt gatggaccat tggc                                            144
```

<210> SEQ ID NO 129
<211> LENGTH: 200
<212> TYPE: DNA
<213> ORGANISM: Artificial Sequence
<220> FEATURE:
<223> OTHER INFORMATION: Amplicon

<400> SEQUENCE: 129

```
tgcctaatgg gagagatgaa gattaaagtt attattatat acataaatat aaaattggaa      60
atgaatattt gttttaaatg gagtatgaag atcatacact atccagtatc tactaccrgt     120
atctactacc atccctaaac tcgacaaggc acctacacta caatataaat atagtaaggc     180
ttcgagtaac agaacctgcg                                                 200
```

<210> SEQ ID NO 130
<211> LENGTH: 200
<212> TYPE: DNA
<213> ORGANISM: Artificial Sequence
<220> FEATURE:
<223> OTHER INFORMATION: Amplicon

<400> SEQUENCE: 130

```
tgcctaatgg gagagatgaa gattaaagtt attattatat acataaatat aaaattggaa      60
atgaatattt gttttaaatg gagtatgaag atcatacact atccagtatc tactaccrgt     120
atctactacc atacctaaac tcgacaaggc acctacacta caatataaat atagtaaggc     180
ttcgagtaac agaacctgcg                                                 200
```

<210> SEQ ID NO 131
<211> LENGTH: 205
<212> TYPE: DNA
<213> ORGANISM: Artificial Sequence
<220> FEATURE:
<223> OTHER INFORMATION: Amplicon

<400> SEQUENCE: 131

```
aatgcagggc cagttacaat acatacatac gcataaccaa aacagtaaca tcaatggaac      60
agtaatagga cacaatcatt attatttttt tgttaaggaa atttctaaga aaacacaac     120 catttgtaca aaaaaggtat taatacatag ctacatggaa gaaacctaca ttaaaatcca    180
gtagtgagaa aagatggggg caatt                                           205
```

<210> SEQ ID NO 132
<211> LENGTH: 205
<212> TYPE: DNA
<213> ORGANISM: Artificial Sequence
<220> FEATURE:
<223> OTHER INFORMATION: Amplicon

<400> SEQUENCE: 132

```
aatgcagggc cagttacaat acatacatac gcataaccaa acagtaaca tcaatggaac    60
agtaatagga cacaattatt attattttt tgttaaggaa atttctaaga aaacacaac    120
catttgtaca aaaaggtat taatacatag ctacatggaa gaaacctaca ttaaaatcca   180
gtagtgagaa aagatgggggg caatt                                       205
```

<210> SEQ ID NO 133
<211> LENGTH: 156
<212> TYPE: DNA
<213> ORGANISM: Artificial Sequence
<220> FEATURE:
<223> OTHER INFORMATION: Amplicon

<400> SEQUENCE: 133

```
tgcttatctt gtctgaaaac cactaatgct ctcttcagtg agaataaaag ggctacaaga    60
tatcatacat atgctttaat attatatcac taaatacaat taaggatgct catcacatta   120
ggttaggtta gatacagttg aattgcctta aagtca                            156
```

<210> SEQ ID NO 134
<211> LENGTH: 156
<212> TYPE: DNA
<213> ORGANISM: Artificial Sequence
<220> FEATURE:
<223> OTHER INFORMATION: Amplicon

<400> SEQUENCE: 134

```
tgcttatctt gtctgaaaac cactaatgct ctcttcagtg tgaataaaag ggctacaaga    60
tatcatacat atgctttaat attatatcac taaatacaat taaggatgct catcacatta   120
ggttaggtta gatacagttg aattgcctta aagtca                            156
```

<210> SEQ ID NO 135
<211> LENGTH: 405
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 34, 35, 38
<223> OTHER INFORMATION: n = A,T,C or G

<400> SEQUENCE: 135

```
tgccatccta gctagccctg tatattttga ttannttnat gggaagaaaa aattaaatat    60
ttttatttaa ttgaagagta agttaatttt atgaaaacaa aaatttaaca ttttcttact   120
tatcttttaa ttcaaatttt atttttatttt ctcttattcc aacaataatt cctaaagata   180
gtccaatatg tttaactcat cacatttaat ttcattacga ataatcaac aggtcaagat    240
aattttaaga caaattagat tataaggatt gttattttct tttaaaatat attattacac   300
aactttttgtc atatatatta tgcgcccgat gcctcgatga cacctaacac atatataaaa   360
cctttttttat aattaagaat taaaaaagag agagagaggg aagat                 405
```

<210> SEQ ID NO 136
<211> LENGTH: 412
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 34, 35, 38
<223> OTHER INFORMATION: n = A,T,C or G

<400> SEQUENCE: 136

```
tgccatccta gctagccctg tatattttga ttannttnat gggaagaaaa aattaaatat    60
ttttatttaa ttgaagagta agttaattt atgaaaacaa aaatttaaca ttttcttact    120
tatcttttaa ttcaaatttt attttatttt ctcttattcc aacaataatt cctaaagata   180
catgcaagtc caatatgttt aactcatcac atttaatttc attacgaaat aatcaacagg   240
tcaagataat tttaagacaa attagattat aaggattgtt attttctttt aaaatatatt   300
attacacaac ttttgtcata tatattatgc gcccgatgcc tcgatgacac ctaacacata   360
tataaaacct tttttataat taagaattaa aaaagagaga gagagggaag at           412
```

<210> SEQ ID NO 137
<211> LENGTH: 649
<212> TYPE: DNA
<213> ORGANISM: Artificial Sequence
<220> FEATURE:
<223> OTHER INFORMATION: Consensus reference sequence

<400> SEQUENCE: 137

```
aacagctatg accatgcgaa ccttccaagg accaaaatga attttcactc taaaatttat    60
gtgcactcct gactgctttt acatttagtg tcttcatttc attgggtttc ctctatcaga   120
attcagtgat aagaaacagt gcttcaacaa taggttgtgg aacatgtttt tctgagaggt   180
aaggtagtca caatgaaaaa aaggacaaaa cttagatcca aagctatgtt gcattgatta   240
acaaagtaat cacataattt tggtgtcatt ttctaataag aattggagtt tcatcttgaa   300
agtttatgtt gacctgtaat gcaaacctgt attgcataga ttagtgaagt aaaactttgt   360
tttttattag agaataacat caaaagcatt tatggatctg catgagtttt tcctaaaaag   420
gtgtgaaata gggggaaaaa agccacactg gatgtcaaaa ccattgttca tctggtatat   480
attttcatct ccwtatgata rttttttttt cttttctgat ttcttgtgaa atatattaat   540
taactkcctt cttttacatg taaatgagaa tgttgttaat taatatgtta acctaaacga   600
tatctttaat gygttgtcat cttctattcg ttttgcagtg atggtatcc              649
```

<210> SEQ ID NO 138
<211> LENGTH: 649
<212> TYPE: DNA
<213> ORGANISM: Artificial Sequence
<220> FEATURE:
<223> OTHER INFORMATION: Consensus reference sequence

<400> SEQUENCE: 138

```
aacagctatg accatgcgaa ccttccaagg accaaaatga attttcactc taaaatttat    60
gtgcactcct gactgctttt acatttagtg tcttcatttc attgggtttc ttctatcaga   120
attcagtgat aagaaacagt gcttcaacaa taggttgtgg aacatgtttt tctgagaggt   180
aaggtagtca caatgaaaaa aaggacaaaa cttagatcca aagctatgtt gcattgatta   240
acaaagtaat cacataattt tggtgtcatt ttctaataag aattggagtt tcatcttgaa   300
agtttatgtt gacctgtaat gcaaacctgt attgcataga ttagtgaagt aaaactttgt   360
tttttattag agaataacat caaaagcatt tatggatctg catgagtttt tcctaaaaag   420
gtgtgaaata gggggaaaaa agccacactg gatgtcaaaa ccattgttca tctggtatat   480
attttcatct ccwtatgata rttttttttt cttttctgat ttcttgtgaa atatattaat   540
```

```
taactkcctt cttttacatg taaatgagaa tgttgttaat taatatgtta acctaaacga    600
tatctttaat gygttgtcat cttctattcg ttttgcagtg atggtatcc                649
```

<210> SEQ ID NO 139
<211> LENGTH: 590
<212> TYPE: DNA
<213> ORGANISM: Artificial Sequence
<220> FEATURE:
<223> OTHER INFORMATION: Consensus reference sequence

<400> SEQUENCE: 139

```
gaatgcttgt ttcacgtaag cttcttgact ttatcrttct ctcccccgcc ccccaaatac     60
cacaaaaatt ccgaacgctg tcatattgca atctaattgt ttaatacccca aatccttccc   120 tagctctttt ccagtatctt gagcttgtaa tcttccatct taaaagcata ctgactgatg   180
caatcttctg attaatttag acctgcatca gttacttgct tgcaagttgt agaatctctt   240 attttyctttt tcacttcact ggtttgcatg tccatacaat tcgaactatt ttttatctttt   300 caaagattgg aatgacatta acttggtttt tgatcctaat agataagtca tatcaattta    360
gttcttgaaa gttggagact raatgtcctc taaataaatt gacatcaatg tagatcctca   420
ataatagaaa gatgacatca atttastccc taaatcttgc tgtttgtgca tagaaggatg    480
gttttttggt tactttccac ggttgaggta ctaaattgat gcaatatctc ttagggagtt   540
agaggacaaa gtgatgtcta ccgaaccttc caaggaactg gccgtcgttt                590
```

<210> SEQ ID NO 140
<211> LENGTH: 590
<212> TYPE: DNA
<213> ORGANISM: Artificial Sequence
<220> FEATURE:
<223> OTHER INFORMATION: Consensus reference sequence

<400> SEQUENCE: 140

```
gaatgcttgt ttcacgtaag cttcttgact ttatcrttct ctcccccgcc ccccaaatac     60
cacaaaaatt ccgaacgctg tcatattgca atctaattgt ttaatacccca aatccttccc   120 tagctctttt ccagtatctt gagcttgtaa tcttccatct taaaagcata ctgactgatg   180
caatcttctg attaatttag acctgcatca gttacttgct tgcaagttgt agaatctctt   240 attttyctttt tcacttcact ggtttgcatg tccatacaat tcgaactatt ttttatctttt   300 caaagattgg aatgacatta acttggtttt tgatcctaat agataagtca tatcaattta    360
gttcttgaaa gttggagact raatgtcctc taaataaatt gacatcaatg tagatcctca   420
ataatagaaa gatgacatca atttastccc taaatcttgc cgtttgtgca tagaaggatg    480
gttttttggt tactttccac ggttgaggta ctaaattgat gcaatatctc ttagggagtt   540
agaggacaaa gtgatgtcta ccgaaccttc caaggaactg gccgtcgttt                590
```

<210> SEQ ID NO 141
<211> LENGTH: 300
<212> TYPE: DNA
<213> ORGANISM: Artificial Sequence
<220> FEATURE:
<223> OTHER INFORMATION: Consensus reference sequence

<400> SEQUENCE: 141

```
aatccctcgt tcttcatgcc ccccaaccca acattcccag tcgacacgtc ttctactcct     60
taatttcctc cttctttcaa acttgacaaa gccacaactc ttctctcatc tcatataaat   120
acccttccac gacaccaatt tctccatcct ctcattgaaa aacaaaatta atcatcttac   180
```
ttatttattc tccgaaaatg gttgatttac attggaaatc aaagatgcca agttccgaca  240
tgccttccaa aactctaaaa ctctctctct ccgacaacaa gtccttaccc tctttgcaac  300

<210> SEQ ID NO 142
<211> LENGTH: 300
<212> TYPE: DNA
<213> ORGANISM: Artificial Sequence
<220> FEATURE:
<223> OTHER INFORMATION: Consensus reference sequence

<400> SEQUENCE: 142
aatccctcgt tcttcatgcc ccccaaccca acattcccag tcgacacgtc ttctactcct   60
taatttcctc cttctttcaa acttgacaaa gccacaactc ttctctcatc tcatataaat  120
acccttccac gacaccaatt tctccatcct ctcattgaaa aacaaaatta atcatcttat  180
ttatttattc tccgaaaatg gttgatttac attggaaatc aaagatgcca agttccgaca  240
tgccttccaa aactctaaaa ctctctctct ccgacaacaa gtccttaccc tctttgcaac  300

<210> SEQ ID NO 143
<211> LENGTH: 515
<212> TYPE: DNA
<213> ORGANISM: Artificial Sequence
<220> FEATURE:
<223> OTHER INFORMATION: Consensus reference sequence

<400> SEQUENCE: 143
caagcaaact tagacttacc aaatgagttt gaccaggttt taccccctctt gattgcaacc   60
tcacgaccat caacgagttt gcctctgtac tcaacaacaa agcctccggt accaatcttg  120
ttgtcaaatg agaaattatt ggtggctgct ttaagttcag cgagggtgaa taatggtgca  180
gcaaaagcat gcactgggga aggggatgat yccaaatctg cttcactggc actactactc  240
cttatggcac tgtccactaa tgaagcaaaa ctacggacac gagattctcc aaaaatggac  300
ccagtatcac tccttatgtc gctgtcgact gccatgctaa aactccttgc atcatctgtg  360
ttatccctca catcaattct ctcaacggtt tcagtatcca tttttatttga tttggtaagt  420
gaaagtatgt actaagtgct ttggcagagg cactgagcac atatrtcata tacagagacc  480
aaagcacata catatatata tatatattaa ttgag                              515

<210> SEQ ID NO 144
<211> LENGTH: 515
<212> TYPE: DNA
<213> ORGANISM: Artificial Sequence
<220> FEATURE:
<223> OTHER INFORMATION: Consensus reference sequence

<400> SEQUENCE: 144
caagcaaact tagacttacc aaatgagttt gaccaggttt taccccctctt gattgcaacc   60
tcacgaccat caacgagttt gcctctgtac tcaacaacaa agcctccggt accaatcttg  120
ttgtcaaatg agaaattatt ggtggctgct ttaagttcag cgagggtgaa taatggtgca  180
gcaaaagcat gcactgggga aggggatgat yccaaatctg cttcactggc actactactc  240
cttatggcac tgtcaactaa tgaagcaaaa ctacggacac gagattctcc aaaaatggac  300
ccagtatcac tccttatgtc gctgtcgact gccatgctaa aactccttgc atcatctgtg  360
ttatccctca catcaattct ctcaacggtt tcagtatcca tttttatttga tttggtaagt  420
gaaagtatgt actaagtgct ttggcagagg cactgagcac atatrtcata tacagagacc  480

```
aaagcacata catatatata tatatattaa ttgag                                   515

<210> SEQ ID NO 145
<211> LENGTH: 799
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 5, 7, 779
<223> OTHER INFORMATION: n = A,T,C or G

<400> SEQUENCE: 145
cttcncngca ccttctcaat taatatatat atgtatgtgg tttggtgtct gtatatgaca        60
tatgtgctca gtgcctccgc caaagcaaat aaaatggata ctgaaatggt tgagagcatt       120
gatgtcacag atgatgcaag gagttttagc tgggcagtgg acagcgccat aaggagtgat       180
actgggtcca tttttggaga atctcgtgtc cgtagctttg cttcgttagt ggacagtgcc       240
ataaggagta gtagtgctac tgaagcagat ttggaatcat cccttgtcca ggcagaagac       300
agggcgatga ggactgttgc agcacgatta acaaaagccg tgtcaaatgc aaaaagacat       360
tttgctaaag gattatttac ccgggctgag cttataccag tcacccaggc tgagcttgaa       420
ccagccacca acaatttccm rssayyawta wttwcycwkk atsaccwyar mkccagccac       480
caataatttc tcatttgaca acaagattgg tactggaggc tttggtgttg ttgagtacag       540
aggcaaactc attgatggtc gtgaggttgc aatcaagagg ggtaaaacct ggtcaaactc       600
atttggtaag tctragtttg ccttgttctc ccgyttacac cacaagaatt tggttgggct       660
ggttggattt tgtgaacaaa agatgaaag gctcttggtg tatgagtaca tgaagaatgg       720
grcgttgtat catcatttgc atrrcaagaa gggtarcagt gtgttgaatt ggtaaawanr       780
ygrasrwrgs watswgtgk                                                   799

<210> SEQ ID NO 146
<211> LENGTH: 799
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 5, 7, 779
<223> OTHER INFORMATION: n = A,T,C or G

<400> SEQUENCE: 146
cttcncngca ccttctcaat taatatatat atgtatgtgg tttggtgtct gtatatgaca        60
tatgtgctca gtgcctccgc caaagcaaat aaaatggata ctgaaatggt tgagagcatt       120
gatgtcacag atgatgcaag gagttttagc tgggcagtgg acagcgccat aaggagtgat       180
actgggtcca tttttggaga atctcgtgtc cgtagctttg cttcgttagt ggacagtgcc       240
ataaggagta gtagtgctac tgaagcagat ttggaatcat cccttgtcca ggcagaagac       300
agggcgatga ggactgttgc agcacgatta acaaaagccg tgtcaaatgc aaaaagacat       360
tttgctaaag gattatttac ccgggctgag cttataccag tcacccaggc tgagcttgaa       420
ccagccacca acaatttccm rssayyawta wttwcycwkk atsaccwyar mkccagccac       480
caataatttc tcatttgaca acaagattgg tactggaggc tttggtgttg ttgagtacag       540
aggcaaactc attgatggtc gtgaggttgc aatcaagagg ggtaaaacct ggtcaaactc       600
atttggtaag tctragtttg ccttgttctc ccgyttacac cacaagaatt tggttgggct       660
```

```
ggttggattt tgtgaagaaa aatatgaaag gctcttggtg tatgagtaca tgaagaatgg    720
grcgttgtat catcatttgc atrrcaagaa gggtarcagt gtgttgaatt ggtaaawanr    780
ygrasrwrgs watswgtgk                                                 799
```

<210> SEQ ID NO 147
<211> LENGTH: 765
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 757
<223> OTHER INFORMATION: n = A,T,C or G

<400> SEQUENCE: 147

```
stattgcacs cgcttttcgt cccggtcaag aaaagatggt ttatgtgtat cagctcttgg     60
caacaggcac attggaggaa gataagtaca taagaaccac ttggaaagag tgggttacta   120
gcatgatttt tagtgaggct tttgaggaga acccttcaca ctcgcgagca tagaacattg   180
aagatgatat actgagggaa atggttgagg aggacacgtc taaagcaatt catatgattc   240
taaagaatga aaaggcttca ayaaattgaa gagaggtaat tacgcttttt tcatatgaaa   300
acatgtgctt aatttatgtt tatatatctt aatcctacat tctccctatt agtgttattt   360
acagtgtttg cactagatca ctagaatgct tgttggcatt caccttcagt gttggagaca   420
gatttgacac ttgtcgtctc gaatgccagg gcaagttcga gtttagtaga aacttatcat   480
ccaaaattaa aattgaaagc actaatacaa aatgcacaat ttgaagccat tcatgtcctc   540
tcttggtctg agtcttgtca ttttgtggat tgaattcatg gtttctctta tccggtgaca   600
ttgttrmcaa gtaatactac tataaattca gatttggata tcagataacc atggtcatta   660
atagtaatac taacatacta tacatataat accttacagg accttgtccg aaacttgaaa   720
caggatcagg gacagcgaaa aacaaacatg gtcawancyk kttyy                   765
```

<210> SEQ ID NO 148
<211> LENGTH: 765
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 757
<223> OTHER INFORMATION: n = A,T,C or G

<400> SEQUENCE: 148

```
stattgcacs cgcttttcgt cccggtcaag aaaagatggt ttatgtgtat cagctcttgg     60
caacaggcac attggaggaa gataagtaca taagaaccac ttggaaagag tgggttacta   120
gcatgatttt tagtgaggct tttgaggaga acccttcaca ctcgcgagca tagaacattg   180
aagatgatct actgagggaa atggttgagg aggacacgtc taaagcaatt catatgattc   240
taaagaatga aaaggcttca ayaaattgaa gagaggtaat tacgcttttt tcatatgaaa   300
acatgtgctt aatttatgtt tatatatctt aatcctacat tctccctatt agtgttattt   360
acagtgtttg cactagatca ctagaatgct tgttggcatt caccttcagt gttggagaca   420
gatttgacac ttgtcgtctc gaatgccagg gcaagttcga gtttagtaga aacttatcat   480
ccaaaattaa aattgaaagc actaatacaa aatgcacaat ttgaagccat tcatgtcctc   540
```

```
tcttggtctg agtcttgtca ttttgtggat tgaattcatg gtttctctta tccggtgaca    600
ttgttrmcaa gtaatactac tataaattca gatttggata tcagataacc atggtcatta    660
atagtaatac taacatacta tacatataat accttacagg accttgtccg aaacttgaaa    720
caggatcagg gacagcgaaa aacaaacatg gtcawancyk kttyy                    765

<210> SEQ ID NO 149
<211> LENGTH: 637
<212> TYPE: DNA
<213> ORGANISM: Artificial Sequence
<220> FEATURE:
<223> OTHER INFORMATION: Consensus reference sequence

<400> SEQUENCE: 149
ttacaaatag gagaaaactt agatatacat agttctttaa gtttgattac attacaaata     60
ggagaaaact taaacataca tagttcttta agtgttgtgt gtgctgttcc ataattagaa    120
ttggagtttt acttaccttta gtaatatgta taattctaat tggagaacag tacaaacaaa    180
aacacctaag gaacaatacc ttagttttaa tcatatttgt tttgttcata tagcttatca    240
ataagtgaag tattttcttg ttcatcttga tgcaggtggt ggaactgaaa ccttcattga    300
ttggccaaca aggatgaaaa tagcacagga catgactcgt ggcttgtttt gtcttcattc    360
cctggagaac attatacatg ggaacctcac atccagcaat gtgttgcttg atgagaacac    420
aaatgctaaa attgcagatt ttggtctttc tcggttgatg tcaactgctg ctaactccaa    480
cgtgatagct actgctggag cattgggata ccgggcacca gagctctcaa agctcaagaa    540
agcaaacact aaaactgata tatacagtct tggtgttatc ttgttagaac tcctaactag    600
gaagtcacct ggggtgtcta tcatggtcat agctgtt                             637

<210> SEQ ID NO 150
<211> LENGTH: 637
<212> TYPE: DNA
<213> ORGANISM: Artificial Sequence
<220> FEATURE:
<223> OTHER INFORMATION: Consensus reference sequence

<400> SEQUENCE: 150
ttacaaatag gagaaaactt agatatacat agttctttaa gtttgattac attacaaata     60
ggagaaaact taaacataca tagttcttta agtgttgtgt gtgctgttcc ataattagaa    120
ttggagtttt acttaccttta gtaatatgta taattctaat tggagaacag tacaaacaaa    180
aacacctaat gaacaatacc ttagttttaa tcatatttgt tttgttcata tagcttatca    240
ataagtgaag tattttcttg ttcatcttga tgcaggtggt ggaactgaaa ccttcattga    300
ttggccaaca aggatgaaaa tagcacagga catgactcgt ggcttgtttt gtcttcattc    360
cctggagaac attatacatg ggaacctcac atccagcaat gtgttgcttg atgagaacac    420
aaatgctaaa attgcagatt ttggtctttc tcggttgatg tcaactgctg ctaactccaa    480
cgtgatagct actgctggag cattgggata ccgggcacca gagctctcaa agctcaagaa    540
agcaaacact aaaactgata tatacagtct tggtgttatc ttgttagaac tcctaactag    600
gaagtcacct ggggtgtcta tcatggtcat agctgtt                             637

<210> SEQ ID NO 151
<211> LENGTH: 670
<212> TYPE: DNA
<213> ORGANISM: Artificial Sequence
<220> FEATURE:
<223> OTHER INFORMATION: Consensus reference sequence
```

<400> SEQUENCE: 151

```
ttgcgtaatc tttctgttct gattttgagt aggaaccaat ttagtggaca tattccttca    60
agcattgcaa acatttccat gcttaggcag cttgatttgt cactgaataa tctcagtgga   120
gaaattccag tctcctttga aagtcaacgt agtcttgatt tcttcaatgt ttcttacaat   180
agcctttcag gttctgttcc acctctactt gccaagaaat ttaactcaag ctcatttgtg   240
ggaaatattc aactatgtgg gtatagccct tcaaccccat gtctttcaca agctccatca   300
caaggagtca ttgccccaac tccagaagta ctgtcagaac agcaccatcg taggaacctc   360
agtaccaaag acataattct catagtagca ggagttctcc tagtagtcct gattatactt   420
tgttgcatcc tgcttttctg cttgatcaga aagagatcaa catcgaaggc tgagaacgga   480
caagccacgg ggagagcagc cactggaagg acagaaaaag gagtccctcc agtttctgct   540
ggtgatgttg aagcaggtgg ggaggctgga gggaaactag tccattttga tggaccattg   600
gcttttacag ccgatgatct cttgtgtgca actgctgaga tcatgggaaa gagccatggt   660
catagcctgt                                                           670
```

<210> SEQ ID NO 152
<211> LENGTH: 670
<212> TYPE: DNA
<213> ORGANISM: Artificial Sequence
<220> FEATURE:
<223> OTHER INFORMATION: Consensus reference sequence

<400> SEQUENCE: 152

```
ttgcgtaatc tttctgttct gattttgagt aggaaccaat ttagtggaca tattccttca    60
agcattgcaa acatttccat gcttaggcag cttgatttgt cactgaataa tctcagtgga   120
gaaattccag tctcctttga aagtcaacgt agtcttgatt tcttcaatgt ttcttacaat   180
agcctttcag gttctgttcc acctctactt gccaagaaat ttaactcaag ctcatttgtg   240
ggaaatattc aactatgtgg gtatagccct tcaaccccat gtctttcaca agctccatca   300
caaggagtca ttgccccaac tccagaagta ctgtcagaac agcaccatcg taggaacctc   360
agtaccaaag acataattct catagtagca ggagttctcc tagtagtcct gattatactt   420
tgttgcatcc tgcttttctg cttgatcaga aagagatcaa catcgaaggc tgagaacgga   480
caagccacgg ggagagcagc cgctggaagg acagaaaaag gagtccctcc agtttctgct   540
ggtgatgttg aagcaggtgg ggaggctgga gggaaactag tccattttga tggaccattg   600
gcttttacag ccgatgatct cttgtgtgca actgctgaga tcatgggaaa gagccatggt   660
catagcctgt                                                           670
```

<210> SEQ ID NO 153
<211> LENGTH: 647
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 42, 43, 46, 82, 83, 87
<223> OTHER INFORMATION: n = A,T,C or G

<400> SEQUENCE: 153

```
tttcttaagt tatatgttat ttcatttaag tcctaactgt cnnttnactc ctcttcttgc    60
tattgtcatt agtattcact tnnttnaat aactgtggaa gcaaaatgat cgttgtgtaa   120
```

```
tttttttattg tatattagat tattaggttt ataatgttgt tttgttatgt tatatatttg    180
aatgactcga gtttatgttt ttattttttaa tgctacgttt ggatgattta agagtaaaat    240
attaatttat ttatagtaaa ttttttaatt aatatttgt attcattggt tgaatttata     300
acaagtaaag tatggataag atgtgcaata atgaatatat aaatgcctaa tgggagagat    360
gaagattaaa gttattatta tatacataaa tataaaattg gaaatgaata tttgttttaa    420
atggagtatg aagatcatac cctatccagt atctactacc rgtatctact accatcccta    480
aactcgacaa ggcacctaca ctacaatata aatatagtaa ggcttcgagt aacagaacct    540
gcgacatata ataagccata aaaggcttca acccaaagac cctacgttac gagaaaagaa    600
gaaaacattt gttgaagtga accacaacaa cgcaatggca tggtcat                 647
```

<210> SEQ ID NO 154
<211> LENGTH: 647
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 42, 43, 46, 82, 83, 87
<223> OTHER INFORMATION: n = A,T,C or G

<400> SEQUENCE: 154

```
tttcttaagt tatatgttat ttcatttaag tcctaactgt cnnttnactc ctcttcttgc     60
tattgtcatt agtattcact tnnttttnaat aactgtggaa gcaaaatgat cgttgtgtaa   120 tttttttattg tatattagat tattaggttt ataatgttgt tttgttatgt tatatatttg   180
aatgactcga gtttatgttt ttattttttaa tgctacgttt ggatgattta agagtaaaat   240
attaatttat ttatagtaaa ttttttaatt aatatttgt attcattggt tgaatttata    300
acaagtaaag tatggataag atgtgcaata atgaatatat aaatgcctaa tgggagagat   360
gaagattaaa gttattatta tatacataaa tataaaattg gaaatgaata tttgttttaa   420
atggagtatg aagatcatac cctatccagt atctactacc rgtatctact accataccta   480
aactcgacaa ggcacctaca ctacaatata aatatagtaa ggcttcgagt aacagaacct   540
gcgacatata ataagccata aaaggcttca acccaaagac cctacgttac gagaaaagaa   600
gaaaacattt gttgaagtga accacaacaa cgcaatggca tggtcat                647
```

<210> SEQ ID NO 155
<211> LENGTH: 737
<212> TYPE: DNA
<213> ORGANISM: Artificial Sequence
<220> FEATURE:
<223> OTHER INFORMATION: Consensus reference sequence

<400> SEQUENCE: 155

```
cgcaattaac cctcactaaa gggaacaaaa gcttgcatgc ctgcagcaat ataaccagga     60
ttcagaatta atctagttag tatatcatac aatgcagggc cagttacaat acatacatac   120
gcataaccaa aacagtaaca tcaatggaac agtaatagga cacaatcatt attattttt   180 tgttaaggaa atttctaaga aaaacacaac catttgtaca aaaaaggtat taatacatag   240
ctacatggaa gaaacctaca ttaaaatcca gtagtgagaa aagatggggg caattatgat   300
aatctcggaa agcctctgcc aagggtcagc attcaaaatt gagttcctta gcctgctgtc   360
tgcatatgct tatccacaag gaatattgtc tccgtgagga ttaaccaaaa gcatacctca   420
atgggtccag atatcctgaa gatagcgccc aatttgctga gcaccaaaat atagggcatc   480
```

```
ggcaacgaga aagactccaa tctacgccac aaatgtcaaa cttgtgaatg tcaaggttaa      540
gaaataagat ttacaattga aggtctacag cagatagatt accaggcgtg cagaaaacac      600
taatctatat ccccaacctt ccttggctgc aggtcgactc tagaggatcc ccgggtaccg      660
agctcgaatt cgccctatag tgagtcgtat tacaccctat agtgagtcgt attacgccct      720
atagtgagtc gtattac                                                    737

<210> SEQ ID NO 156
<211> LENGTH: 737
<212> TYPE: DNA
<213> ORGANISM: Artificial Sequence
<220> FEATURE:
<223> OTHER INFORMATION: Consensus reference sequence

<400> SEQUENCE: 156
cgcaattaac cctcactaaa gggaacaaaa gcttgcatgc ctgcagcaat ataaccagga      60
ttcagaatta atctagttag tatatcatac aatgcagggc cagttacaat acatacatac      120
gcataaccaa aacagtaaca tcaatggaac agtaatagga cacaattatt attatttttt      180
tgttaaggaa atttctaaga aaacacaac catttgtaca aaaaggtat taatacatag        240 ctacatggaa gaaacctaca ttaaaatcca gtagtgagaa aagatggggg caattatgat      300
aatctcggaa agcctctgcc aagggtcagc attcaaaatt gagttcctta gcctgctgtc      360
tgcatatgct tatccacaag gaatattgtc tccgtgagga ttaaccaaaa gcatacctca      420
atgggtccag atatcctgaa gatagcgccc aatttgctga gcaccaaaat atagggcatc      480
ggcaacgaga aagactccaa tctacgccac aaatgtcaaa cttgtgaatg tcaaggttaa      540
gaaataagat ttacaattga aggtctacag cagatagatt accaggcgtg cagaaaacac      600
taatctatat ccccaacctt ccttggctgc aggtcgactc tagaggatcc ccgggtaccg      660
agctcgaatt cgccctatag tgagtcgtat tacaccctat agtgagtcgt attacgccct      720
atagtgagtc gtattac                                                    737

<210> SEQ ID NO 157
<211> LENGTH: 985
<212> TYPE: DNA
<213> ORGANISM: Artificial Sequence
<220> FEATURE:
<223> OTHER INFORMATION: Consensus reference sequence

<400> SEQUENCE: 157
cttgaagtta taagttttga gagagatttt atgcttatct tgtctgaaaa ccactaatgc      60
tctcttcagt gagaataaaa gggctacaag atatcataca tatgctttaa tattatatca      120
ctaaatacaa ttaaggatgc tcatcacatt aggttaggtt agatacagtt gaattgcctt      180
aaagtcaaaa tttccacaag acaacagtaa cagttaccaa aaaccatgcc cacaacaagc      240
aatattggct gcgtgactta aaaactgttt aaacatctca actgatgtct tacaaggaaa      300
ggtaacctaa tgaaaagaca tcaatctaga aatcaaggca cttcagtgag aagacaaatg      360
aagtccaact gattgcattt tgtcttgtca tattaggact taacattaga agcaagttgc      420
atatagaaca aatctgaagg atcatttat atatatttaa caactactgg ttgaccaccc       480
aatacgataa acaggaacaa ccacacaaaa gctcttgatc aacataaaga aaacaaaatt      540
aaacacaaaa aactgctaca gaattttaaaa aacactttag cagacgtaac agaagtacag     600
aacaaattct gtcagcaatt aagctaacta gataccaaac aggatacttc cattgtagta      660
```

```
gaaaaggtga aacactatag aaaaattcaa cagtctaggt gattaaatct agactcaaat    720
ctctcaatgt ataaatggtc ctcttaaaaa ccaaccctgc caatggtagc aaatcccctg    780
gacataatga agcacacgaa ccaacaaaga atccaataga ataaaaccaa aaaccaaaaa    840
acttaaagtc caaacaacaa atacacaggc aatcaaatca accaaacaaa atgatgtaca    900
cacatacaca aaatgatgta cacatacata taattaggct taaatatgtt tttgattcct    960
taaatttgga gtttgaacaa ttttg                                          985
```

<210> SEQ ID NO 158
<211> LENGTH: 985
<212> TYPE: DNA
<213> ORGANISM: Artificial Sequence
<220> FEATURE:
<223> OTHER INFORMATION: Consensus reference sequence

<400> SEQUENCE: 158

```
cttgaagtta taagttttga gagagatttt atgcttatct tgtctgaaaa ccactaatgc     60
tctcttcagt gtgaataaaa gggctacaag atatcataca tatgctttaa tattatatca    120
ctaaatacaa ttaaggatgc tcatcacatt aggttaggtt agatacagtt gaattgcctt    180
aaagtcaaaa tttccacaag acaacagtaa cagttaccaa aaaccatgcc cacaacaagc    240
aatattggct gcgtgactta aaaactgttt aaacatctca actgatgtct tacaaggaaa    300
ggtaacctaa tgaaaagaca tcaatctaga atcaaggca cttcagtgag aagacaaatg    360
aagtccaact gattgcattt tgtcttgtca tattaggact taacattaga agcaagttgc    420
atatagaaca aatctgaagg atcattttat atatatttaa caactactgg ttgaccaccc    480
aatacgataa acaggaacaa ccacacaaaa gctcttgatc aacataaaga aaacaaaatt    540
aaacacaaaa aactgctaca gaatttaaaa aacactttag cagacgtaac agaagtacag    600
aacaaattct gtcagcaatt aagctaacta gataccaaac aggatacttc cattgtagta    660
gaaaaggtga aacactatag aaaaattcaa cagtctaggt gattaaatct agactcaaat    720
ctctcaatgt ataaatggtc ctcttaaaaa ccaaccctgc caatggtagc aaatcccctg    780
gacataatga agcacacgaa ccaacaaaga atccaataga ataaaaccaa aaaccaaaaa    840
acttaaagtc caaacaacaa atacacaggc aatcaaatca accaaacaaa atgatgtaca    900
cacatacaca aaatgatgta cacatacata taattaggct taaatatgtt tttgattcct    960
taaatttgga gtttgaacaa ttttg                                          985
```

<210> SEQ ID NO 159
<211> LENGTH: 20
<212> TYPE: DNA
<213> ORGANISM: Artificial Sequence
<220> FEATURE:
<223> OTHER INFORMATION: Primer

<400> SEQUENCE: 159

```
gcaattcgtc cttccaaatg                                                 20
```

<210> SEQ ID NO 160
<211> LENGTH: 20
<212> TYPE: DNA
<213> ORGANISM: Artificial Sequence
<220> FEATURE:
<223> OTHER INFORMATION: Primer

<400> SEQUENCE: 160

```
gagtgtgctt ttgctcgttg                                                 20
```

<210> SEQ ID NO 161
<211> LENGTH: 20
<212> TYPE: DNA
<213> ORGANISM: Artificial Sequence
<220> FEATURE:
<223> OTHER INFORMATION: Primer

<400> SEQUENCE: 161
cttgtagcgc agctccagat                                               20

<210> SEQ ID NO 162
<211> LENGTH: 21
<212> TYPE: DNA
<213> ORGANISM: Artificial Sequence
<220> FEATURE:
<223> OTHER INFORMATION: Primer

<400> SEQUENCE: 162
accatgaagt ccttgaagca g                                             21

<210> SEQ ID NO 163
<211> LENGTH: 20
<212> TYPE: DNA
<213> ORGANISM: Artificial Sequence
<220> FEATURE:
<223> OTHER INFORMATION: Primer

<400> SEQUENCE: 163
tttgggaatg gagacagagg                                               20

<210> SEQ ID NO 164
<211> LENGTH: 20
<212> TYPE: DNA
<213> ORGANISM: Artificial Sequence
<220> FEATURE:
<223> OTHER INFORMATION: Primer

<400> SEQUENCE: 164
gccctattgg cattcttgat                                               20

<210> SEQ ID NO 165
<211> LENGTH: 24
<212> TYPE: DNA
<213> ORGANISM: Artificial Sequence
<220> FEATURE:
<223> OTHER INFORMATION: Primer

<400> SEQUENCE: 165
tcatgcactg cccataccta aagg                                          24

<210> SEQ ID NO 166
<211> LENGTH: 29
<212> TYPE: DNA
<213> ORGANISM: Artificial Sequence
<220> FEATURE:
<223> OTHER INFORMATION: Primer

<400> SEQUENCE: 166
aaacggatgt ggatggttaa gaattagac                                     29

<210> SEQ ID NO 167
<211> LENGTH: 24
<212> TYPE: DNA
<213> ORGANISM: Artificial Sequence
<220> FEATURE:

-continued

<223> OTHER INFORMATION: Primer

<400> SEQUENCE: 167
ggctgccgtt tatgttgtta gcat                                          24

<210> SEQ ID NO 168
<211> LENGTH: 35
<212> TYPE: DNA
<213> ORGANISM: Artificial Sequence
<220> FEATURE:
<223> OTHER INFORMATION: Primer

<400> SEQUENCE: 168
aggtatttag aatcagtcca agaagtgaat taact                              35

<210> SEQ ID NO 169
<211> LENGTH: 22
<212> TYPE: DNA
<213> ORGANISM: Artificial Sequence
<220> FEATURE:
<223> OTHER INFORMATION: Primer

<400> SEQUENCE: 169
acgcctcatt atccgtgacc ct                                            22

<210> SEQ ID NO 170
<211> LENGTH: 22
<212> TYPE: DNA
<213> ORGANISM: Artificial Sequence
<220> FEATURE:
<223> OTHER INFORMATION: Primer

<400> SEQUENCE: 170
ttcacaattc tgtgcagccg ac                                            22

<210> SEQ ID NO 171
<211> LENGTH: 20
<212> TYPE: DNA
<213> ORGANISM: Artificial Sequence
<220> FEATURE:
<223> OTHER INFORMATION: Primer

<400> SEQUENCE: 171
ggacgtggct caagagagtt                                               20

<210> SEQ ID NO 172
<211> LENGTH: 21
<212> TYPE: DNA
<213> ORGANISM: Artificial Sequence
<220> FEATURE:
<223> OTHER INFORMATION: Primer

<400> SEQUENCE: 172
tgaatgtgat caaaagcgag a                                             21

<210> SEQ ID NO 173
<211> LENGTH: 22
<212> TYPE: DNA
<213> ORGANISM: Artificial Sequence
<220> FEATURE:
<223> OTHER INFORMATION: Primer

<400> SEQUENCE: 173
ggtatgtgca cagatcctat gg                                            22

<210> SEQ ID NO 174
<211> LENGTH: 20
<212> TYPE: DNA
<213> ORGANISM: Artificial Sequence
<220> FEATURE:
<223> OTHER INFORMATION: Primer

<400> SEQUENCE: 174
ggcatcatgc aaaacaaaaa                                          20

<210> SEQ ID NO 175
<211> LENGTH: 23
<212> TYPE: DNA
<213> ORGANISM: Artificial Sequence
<220> FEATURE:
<223> OTHER INFORMATION: Primer

<400> SEQUENCE: 175
ttggtgactg atcacaagat acg                                      23

<210> SEQ ID NO 176
<211> LENGTH: 21
<212> TYPE: DNA
<213> ORGANISM: Artificial Sequence
<220> FEATURE:
<223> OTHER INFORMATION: Primer

<400> SEQUENCE: 176
tggacaaaaa gaagccaaag g                                        21

<210> SEQ ID NO 177
<211> LENGTH: 20
<212> TYPE: DNA
<213> ORGANISM: Artificial Sequence
<220> FEATURE:
<223> OTHER INFORMATION: Primer

<400> SEQUENCE: 177
tcttaggtcg caaatcacga                                          20

<210> SEQ ID NO 178
<211> LENGTH: 23
<212> TYPE: DNA
<213> ORGANISM: Artificial Sequence
<220> FEATURE:
<223> OTHER INFORMATION: Primer

<400> SEQUENCE: 178
tgcaatcata taaggtttcg ttg                                      23

<210> SEQ ID NO 179
<211> LENGTH: 22
<212> TYPE: DNA
<213> ORGANISM: Artificial Sequence
<220> FEATURE:
<223> OTHER INFORMATION: Primer

<400> SEQUENCE: 179
tttttccgcg atcaactatt tt                                       22

<210> SEQ ID NO 180
<211> LENGTH: 20
<212> TYPE: DNA
<213> ORGANISM: Artificial Sequence
<220> FEATURE:
<223> OTHER INFORMATION: Primer

<400> SEQUENCE: 180
acgatcccta attgctttgc                                                20

<210> SEQ ID NO 181
<211> LENGTH: 21
<212> TYPE: DNA
<213> ORGANISM: Artificial Sequence
<220> FEATURE:
<223> OTHER INFORMATION: Primer

<400> SEQUENCE: 181
tccgacggta ttgagttaag g                                              21

<210> SEQ ID NO 182
<211> LENGTH: 22
<212> TYPE: DNA
<213> ORGANISM: Artificial Sequence
<220> FEATURE:
<223> OTHER INFORMATION: Primer

<400> SEQUENCE: 182
gcaacgtatt tatgcaactc ca                                             22

<210> SEQ ID NO 183
<211> LENGTH: 20
<212> TYPE: DNA
<213> ORGANISM: Artificial Sequence
<220> FEATURE:
<223> OTHER INFORMATION: Primer

<400> SEQUENCE: 183
ttgccatgga agggtaaagt                                                20

<210> SEQ ID NO 184
<211> LENGTH: 21
<212> TYPE: DNA
<213> ORGANISM: Artificial Sequence
<220> FEATURE:
<223> OTHER INFORMATION: Primer

<400> SEQUENCE: 184
tgcaccactg caattagttt g                                              21

<210> SEQ ID NO 185
<211> LENGTH: 23
<212> TYPE: DNA
<213> ORGANISM: Artificial Sequence
<220> FEATURE:
<223> OTHER INFORMATION: Primer

<400> SEQUENCE: 185
agcttcagag gcacgactac cag                                            23

<210> SEQ ID NO 186
<211> LENGTH: 22
<212> TYPE: DNA
<213> ORGANISM: Artificial Sequence
<220> FEATURE:
<223> OTHER INFORMATION: Primer

<400> SEQUENCE: 186
ggcaccatca tctccaccaa tc                                             22

<210> SEQ ID NO 187
<211> LENGTH: 21

<212> TYPE: DNA
<213> ORGANISM: Artificial Sequence
<220> FEATURE:
<223> OTHER INFORMATION: Primer

<400> SEQUENCE: 187
ttgaattcca cacgacattt g                                              21

<210> SEQ ID NO 188
<211> LENGTH: 20
<212> TYPE: DNA
<213> ORGANISM: Artificial Sequence
<220> FEATURE:
<223> OTHER INFORMATION: Primer

<400> SEQUENCE: 188
gagcgttatg gggagctaga                                                20

<210> SEQ ID NO 189
<211> LENGTH: 21
<212> TYPE: DNA
<213> ORGANISM: Artificial Sequence
<220> FEATURE:
<223> OTHER INFORMATION: Primer

<400> SEQUENCE: 189
aacagcttta gccttcaacc a                                              21

<210> SEQ ID NO 190
<211> LENGTH: 20
<212> TYPE: DNA
<213> ORGANISM: Artificial Sequence
<220> FEATURE:
<223> OTHER INFORMATION: Primer

<400> SEQUENCE: 190
gttgtgtcca agaagcagca                                                20

<210> SEQ ID NO 191
<211> LENGTH: 21
<212> TYPE: DNA
<213> ORGANISM: Artificial Sequence
<220> FEATURE:
<223> OTHER INFORMATION: Primer

<400> SEQUENCE: 191
caggctcgya gtagttttgg a                                              21

<210> SEQ ID NO 192
<211> LENGTH: 16
<212> TYPE: DNA
<213> ORGANISM: Artificial Sequence
<220> FEATURE:
<223> OTHER INFORMATION: Primer

<400> SEQUENCE: 192
ccaacctctg tagcaa                                                    16

<210> SEQ ID NO 193
<211> LENGTH: 26
<212> TYPE: DNA
<213> ORGANISM: Artificial Sequence
<220> FEATURE:
<223> OTHER INFORMATION: Primer

<400> SEQUENCE: 193
ttccttttaa tttgcccaat gtgaga                                              26

<210> SEQ ID NO 194
<211> LENGTH: 28
<212> TYPE: DNA
<213> ORGANISM: Artificial Sequence
<220> FEATURE:
<223> OTHER INFORMATION: Primer

<400> SEQUENCE: 194
tcctatgtta gtcccagcat gaaacttc                                            28

<210> SEQ ID NO 195
<211> LENGTH: 23
<212> TYPE: DNA
<213> ORGANISM: Artificial Sequence
<220> FEATURE:
<223> OTHER INFORMATION: Primer

<400> SEQUENCE: 195
ccttccttga tatcttgagg ttg                                                 23

<210> SEQ ID NO 196
<211> LENGTH: 21
<212> TYPE: DNA
<213> ORGANISM: Artificial Sequence
<220> FEATURE:
<223> OTHER INFORMATION: Primer

<400> SEQUENCE: 196
cattacaatg tgtgccctgt g                                                   21

<210> SEQ ID NO 197
<211> LENGTH: 20
<212> TYPE: DNA
<213> ORGANISM: Artificial Sequence
<220> FEATURE:
<223> OTHER INFORMATION: Primer

<400> SEQUENCE: 197
ctgtcagcca tgtcgatttc                                                     20

<210> SEQ ID NO 198
<211> LENGTH: 20
<212> TYPE: DNA
<213> ORGANISM: Artificial Sequence
<220> FEATURE:
<223> OTHER INFORMATION: Primer

<400> SEQUENCE: 198
ctgccagcaa aaacagctaa                                                     20

<210> SEQ ID NO 199
<211> LENGTH: 20
<212> TYPE: DNA
<213> ORGANISM: Artificial Sequence
<220> FEATURE:
<223> OTHER INFORMATION: Primer

<400> SEQUENCE: 199
tccgaaataa ggcacctgtt                                                     20

<210> SEQ ID NO 200
<211> LENGTH: 20
<212> TYPE: DNA
<213> ORGANISM: Artificial Sequence

```
<220> FEATURE:
<223> OTHER INFORMATION: Primer

<400> SEQUENCE: 200
ttgcgtgagt ttgggtatga                                               20

<210> SEQ ID NO 201
<211> LENGTH: 20
<212> TYPE: DNA
<213> ORGANISM: Artificial Sequence
<220> FEATURE:
<223> OTHER INFORMATION: Primer

<400> SEQUENCE: 201
gcatggtctt gcaccttttt                                               20

<210> SEQ ID NO 202
<211> LENGTH: 20
<212> TYPE: DNA
<213> ORGANISM: Artificial Sequence
<220> FEATURE:
<223> OTHER INFORMATION: Primer

<400> SEQUENCE: 202
catggctcat ttcccttgtt                                               20

<210> SEQ ID NO 203
<211> LENGTH: 20
<212> TYPE: DNA
<213> ORGANISM: Artificial Sequence
<220> FEATURE:
<223> OTHER INFORMATION: Primer

<400> SEQUENCE: 203
caatcacacc accaccaaga                                               20

<210> SEQ ID NO 204
<211> LENGTH: 20
<212> TYPE: DNA
<213> ORGANISM: Artificial Sequence
<220> FEATURE:
<223> OTHER INFORMATION: Primer

<400> SEQUENCE: 204
ctttgacaag gccatcgagt                                               20

<210> SEQ ID NO 205
<211> LENGTH: 20
<212> TYPE: DNA
<213> ORGANISM: Artificial Sequence
<220> FEATURE:
<223> OTHER INFORMATION: Primer

<400> SEQUENCE: 205
ttcctgaaga gcggagacag                                               20

<210> SEQ ID NO 206
<211> LENGTH: 20
<212> TYPE: DNA
<213> ORGANISM: Artificial Sequence
<220> FEATURE:
<223> OTHER INFORMATION: Primer

<400> SEQUENCE: 206
gcacggagct tctcataagg                                               20
```

<210> SEQ ID NO 207
<211> LENGTH: 20
<212> TYPE: DNA
<213> ORGANISM: Artificial Sequence
<220> FEATURE:
<223> OTHER INFORMATION: Primer

<400> SEQUENCE: 207
ccccaaagtc ggagaagaat                                               20

<210> SEQ ID NO 208
<211> LENGTH: 20
<212> TYPE: DNA
<213> ORGANISM: Artificial Sequence
<220> FEATURE:
<223> OTHER INFORMATION: Primer

<400> SEQUENCE: 208
tgttatatgg gaggggtga                                                20

<210> SEQ ID NO 209
<211> LENGTH: 25
<212> TYPE: DNA
<213> ORGANISM: Artificial Sequence
<220> FEATURE:
<223> OTHER INFORMATION: Primer

<400> SEQUENCE: 209
gcttcttgac tttatcrttc tctcc                                         25

<210> SEQ ID NO 210
<211> LENGTH: 21
<212> TYPE: DNA
<213> ORGANISM: Artificial Sequence
<220> FEATURE:
<223> OTHER INFORMATION: Primer

<400> SEQUENCE: 210
agctagggaa ggatttgggt a                                             21

<210> SEQ ID NO 211
<211> LENGTH: 20
<212> TYPE: DNA
<213> ORGANISM: Artificial Sequence
<220> FEATURE:
<223> OTHER INFORMATION: Primer

<400> SEQUENCE: 211
tcaaccgtgg aaagtaacca                                               20

<210> SEQ ID NO 212
<211> LENGTH: 27
<212> TYPE: DNA
<213> ORGANISM: Artificial Sequence
<220> FEATURE:
<223> OTHER INFORMATION: Primer

<400> SEQUENCE: 212
tcaatttagt tcttgaaagt tggagac                                       27

<210> SEQ ID NO 213
<211> LENGTH: 22
<212> TYPE: DNA
<213> ORGANISM: Artificial Sequence
<220> FEATURE:
<223> OTHER INFORMATION: Primer

```
<400> SEQUENCE: 213
ccacaaccta ttgttgaagc ac                                          22

<210> SEQ ID NO 214
<211> LENGTH: 20
<212> TYPE: DNA
<213> ORGANISM: Artificial Sequence
<220> FEATURE:
<223> OTHER INFORMATION: Primer

<400> SEQUENCE: 214
tgtgcactcc tgactgcttt                                             20

<210> SEQ ID NO 215
<211> LENGTH: 21
<212> TYPE: DNA
<213> ORGANISM: Artificial Sequence
<220> FEATURE:
<223> OTHER INFORMATION: Primer

<400> SEQUENCE: 215
tcaaaaccat tgttcatctg g                                           21

<210> SEQ ID NO 216
<211> LENGTH: 28
<212> TYPE: DNA
<213> ORGANISM: Artificial Sequence
<220> FEATURE:
<223> OTHER INFORMATION: Primer

<400> SEQUENCE: 216
gaatagaaga tgacaacrca ttaaagat                                    28

<210> SEQ ID NO 217
<211> LENGTH: 20
<212> TYPE: DNA
<213> ORGANISM: Artificial Sequence
<220> FEATURE:
<223> OTHER INFORMATION: Primer

<400> SEQUENCE: 217
cggacaaggt cctgtaaggt                                             20

<210> SEQ ID NO 218
<211> LENGTH: 22
<212> TYPE: DNA
<213> ORGANISM: Artificial Sequence
<220> FEATURE:
<223> OTHER INFORMATION: Primer

<400> SEQUENCE: 218
ttttgtggat tgaattcatg gt                                          22

<210> SEQ ID NO 219
<211> LENGTH: 28
<212> TYPE: DNA
<213> ORGANISM: Artificial Sequence
<220> FEATURE:
<223> OTHER INFORMATION: Primer

<400> SEQUENCE: 219
tgcaaacact gtaaataaca ctaatagg                                    28

<210> SEQ ID NO 220
```

```
<211> LENGTH: 20
<212> TYPE: DNA
<213> ORGANISM: Artificial Sequence
<220> FEATURE:
<223> OTHER INFORMATION: Primer

<400> SEQUENCE: 220
aaatggttga ggaggacacg                                          20

<210> SEQ ID NO 221
<211> LENGTH: 20
<212> TYPE: DNA
<213> ORGANISM: Artificial Sequence
<220> FEATURE:
<223> OTHER INFORMATION: Primer

<400> SEQUENCE: 221
agacgtgtcc tcctcaacca                                          20

<210> SEQ ID NO 222
<211> LENGTH: 20
<212> TYPE: DNA
<213> ORGANISM: Artificial Sequence
<220> FEATURE:
<223> OTHER INFORMATION: Primer

<400> SEQUENCE: 222
aggagaaccc ttcacactcg                                          20

<210> SEQ ID NO 223
<211> LENGTH: 20
<212> TYPE: DNA
<213> ORGANISM: Artificial Sequence
<220> FEATURE:
<223> OTHER INFORMATION: Primer

<400> SEQUENCE: 223
attgctggat gtgaggttcc                                          20

<210> SEQ ID NO 224
<211> LENGTH: 20
<212> TYPE: DNA
<213> ORGANISM: Artificial Sequence
<220> FEATURE:
<223> OTHER INFORMATION: Primer

<400> SEQUENCE: 224
tggccaacaa ggatgaaaat                                          20

<210> SEQ ID NO 225
<211> LENGTH: 25
<212> TYPE: DNA
<213> ORGANISM: Artificial Sequence
<220> FEATURE:
<223> OTHER INFORMATION: Primer

<400> SEQUENCE: 225
tgctgttcca taattagaat tggag                                    25

<210> SEQ ID NO 226
<211> LENGTH: 22
<212> TYPE: DNA
<213> ORGANISM: Artificial Sequence
<220> FEATURE:
<223> OTHER INFORMATION: Primer

<400> SEQUENCE: 226
```

-continued

```
cctgcatcaa gatgaacaag aa                                            22

<210> SEQ ID NO 227
<211> LENGTH: 20
<212> TYPE: DNA
<213> ORGANISM: Artificial Sequence
<220> FEATURE:
<223> OTHER INFORMATION: Primer

<400> SEQUENCE: 227
gcttcaacat caccagcaga                                               20

<210> SEQ ID NO 228
<211> LENGTH: 20
<212> TYPE: DNA
<213> ORGANISM: Artificial Sequence
<220> FEATURE:
<223> OTHER INFORMATION: Primer

<400> SEQUENCE: 228
gaaggctgag aacggacaag                                               20

<210> SEQ ID NO 229
<211> LENGTH: 22
<212> TYPE: DNA
<213> ORGANISM: Artificial Sequence
<220> FEATURE:
<223> OTHER INFORMATION: Primer

<400> SEQUENCE: 229
aggtttctgt cctttgcttc ag                                            22

<210> SEQ ID NO 230
<211> LENGTH: 20
<212> TYPE: DNA
<213> ORGANISM: Artificial Sequence
<220> FEATURE:
<223> OTHER INFORMATION: Primer

<400> SEQUENCE: 230
gccaataaag cttggtggaa                                               20

<210> SEQ ID NO 231
<211> LENGTH: 20
<212> TYPE: DNA
<213> ORGANISM: Artificial Sequence
<220> FEATURE:
<223> OTHER INFORMATION: Primer

<400> SEQUENCE: 231
aagaaacccc accaataggg                                               20

<210> SEQ ID NO 232
<211> LENGTH: 20
<212> TYPE: DNA
<213> ORGANISM: Artificial Sequence
<220> FEATURE:
<223> OTHER INFORMATION: Primer

<400> SEQUENCE: 232
aacggtttca gggaacattg                                               20

<210> SEQ ID NO 233
<211> LENGTH: 26
<212> TYPE: DNA
```

```
<213> ORGANISM: Artificial Sequence
<220> FEATURE:
<223> OTHER INFORMATION: Primer

<400> SEQUENCE: 233
gatgaaatgt tctggcttg aaatta                                           26

<210> SEQ ID NO 234
<211> LENGTH: 20
<212> TYPE: DNA
<213> ORGANISM: Artificial Sequence
<220> FEATURE:
<223> OTHER INFORMATION: Primer

<400> SEQUENCE: 234
cctggaaact tgcatgagtg                                                 20

<210> SEQ ID NO 235
<211> LENGTH: 20
<212> TYPE: DNA
<213> ORGANISM: Artificial Sequence
<220> FEATURE:
<223> OTHER INFORMATION: Primer

<400> SEQUENCE: 235
cgtcagctat tccacccttc                                                 20

<210> SEQ ID NO 236
<211> LENGTH: 20
<212> TYPE: DNA
<213> ORGANISM: Artificial Sequence
<220> FEATURE:
<223> OTHER INFORMATION: Primer

<400> SEQUENCE: 236
ggtgagatca agagggcatt                                                 20

<210> SEQ ID NO 237
<211> LENGTH: 20
<212> TYPE: DNA
<213> ORGANISM: Artificial Sequence
<220> FEATURE:
<223> OTHER INFORMATION: Primer

<400> SEQUENCE: 237
tcctgaaatc ccaagcaatc                                                 20

<210> SEQ ID NO 238
<211> LENGTH: 20
<212> TYPE: DNA
<213> ORGANISM: Artificial Sequence
<220> FEATURE:
<223> OTHER INFORMATION: Primer

<400> SEQUENCE: 238
cttcaatggg tcgcaaaaag                                                 20

<210> SEQ ID NO 239
<211> LENGTH: 20
<212> TYPE: DNA
<213> ORGANISM: Artificial Sequence
<220> FEATURE:
<223> OTHER INFORMATION: Primer

<400> SEQUENCE: 239
atgcggaaga tcaayagcag                                                 20
```

<210> SEQ ID NO 240
<211> LENGTH: 20
<212> TYPE: DNA
<213> ORGANISM: Artificial Sequence
<220> FEATURE:
<223> OTHER INFORMATION: Primer

<400> SEQUENCE: 240
atgcagaccc aattcatgct                                           20

<210> SEQ ID NO 241
<211> LENGTH: 22
<212> TYPE: DNA
<213> ORGANISM: Artificial Sequence
<220> FEATURE:
<223> OTHER INFORMATION: Primer

<400> SEQUENCE: 241
acaacgwaag gtatgaggtc aa                                        22

<210> SEQ ID NO 242
<211> LENGTH: 19
<212> TYPE: DNA
<213> ORGANISM: Artificial Sequence
<220> FEATURE:
<223> OTHER INFORMATION: Primer

<400> SEQUENCE: 242
atcggtgagc aagggaaac                                            19

<210> SEQ ID NO 243
<211> LENGTH: 21
<212> TYPE: DNA
<213> ORGANISM: Artificial Sequence
<220> FEATURE:
<223> OTHER INFORMATION: Primer

<400> SEQUENCE: 243
tcaaccaaaa gtttcccttc c                                         21

<210> SEQ ID NO 244
<211> LENGTH: 21
<212> TYPE: DNA
<213> ORGANISM: Artificial Sequence
<220> FEATURE:
<223> OTHER INFORMATION: Primer

<400> SEQUENCE: 244
gcagccacct aacagaacaa a                                         21

<210> SEQ ID NO 245
<211> LENGTH: 21
<212> TYPE: DNA
<213> ORGANISM: Artificial Sequence
<220> FEATURE:
<223> OTHER INFORMATION: Primer

<400> SEQUENCE: 245
catgttgctc gcgaccttga c                                         21

<210> SEQ ID NO 246
<211> LENGTH: 24
<212> TYPE: DNA
<213> ORGANISM: Artificial Sequence
<220> FEATURE:

<223> OTHER INFORMATION: Primer

<400> SEQUENCE: 246
gaaggtgatt gaggtggtga agga                                          24

<210> SEQ ID NO 247
<211> LENGTH: 25
<212> TYPE: DNA
<213> ORGANISM: Artificial Sequence
<220> FEATURE:
<223> OTHER INFORMATION: Primer

<400> SEQUENCE: 247
gcttggaata ttaatctatg gctgt                                         25

<210> SEQ ID NO 248
<211> LENGTH: 22
<212> TYPE: DNA
<213> ORGANISM: Artificial Sequence
<220> FEATURE:
<223> OTHER INFORMATION: Primer

<400> SEQUENCE: 248
cgcgttacaa attaaagcat gt                                            22

<210> SEQ ID NO 249
<211> LENGTH: 20
<212> TYPE: DNA
<213> ORGANISM: Artificial Sequence
<220> FEATURE:
<223> OTHER INFORMATION: Probe

<400> SEQUENCE: 249
ctctattact atctgtcttt                                               20

<210> SEQ ID NO 250
<211> LENGTH: 14
<212> TYPE: DNA
<213> ORGANISM: Artificial Sequence
<220> FEATURE:
<223> OTHER INFORMATION: Probe

<400> SEQUENCE: 250
acaggacgat actc                                                     14

<210> SEQ ID NO 251
<211> LENGTH: 18
<212> TYPE: DNA
<213> ORGANISM: Artificial Sequence
<220> FEATURE:
<223> OTHER INFORMATION: Probe

<400> SEQUENCE: 251
ctttgcattt tagatcat                                                 18

<210> SEQ ID NO 252
<211> LENGTH: 17
<212> TYPE: DNA
<213> ORGANISM: Artificial Sequence
<220> FEATURE:
<223> OTHER INFORMATION: Probe

<400> SEQUENCE: 252
caagtgatgt ttatttt                                                  17

```
<210> SEQ ID NO 253
<211> LENGTH: 16
<212> TYPE: DNA
<213> ORGANISM: Artificial Sequence
<220> FEATURE:
<223> OTHER INFORMATION: Probe

<400> SEQUENCE: 253
actcgaatgt actctc                                                     16

<210> SEQ ID NO 254
<211> LENGTH: 18
<212> TYPE: DNA
<213> ORGANISM: Artificial Sequence
<220> FEATURE:
<223> OTHER INFORMATION: Probe

<400> SEQUENCE: 254
tcaagatcat tcactatt                                                   18

<210> SEQ ID NO 255
<211> LENGTH: 15
<212> TYPE: DNA
<213> ORGANISM: Artificial Sequence
<220> FEATURE:
<223> OTHER INFORMATION: Probe

<400> SEQUENCE: 255
ccacgtattg ttctt                                                      15

<210> SEQ ID NO 256
<211> LENGTH: 15
<212> TYPE: DNA
<213> ORGANISM: Artificial Sequence
<220> FEATURE:
<223> OTHER INFORMATION: Probe

<400> SEQUENCE: 256
ccagccttcg tagca                                                      15

<210> SEQ ID NO 257
<211> LENGTH: 18
<212> TYPE: DNA
<213> ORGANISM: Artificial Sequence
<220> FEATURE:
<223> OTHER INFORMATION: Probe

<400> SEQUENCE: 257
aaattttgtg ctatccac                                                   18

<210> SEQ ID NO 258
<211> LENGTH: 16
<212> TYPE: DNA
<213> ORGANISM: Artificial Sequence
<220> FEATURE:
<223> OTHER INFORMATION: Probe

<400> SEQUENCE: 258
tcaaacactg attctc                                                     16

<210> SEQ ID NO 259
<211> LENGTH: 17
<212> TYPE: DNA
<213> ORGANISM: Artificial Sequence
<220> FEATURE:
<223> OTHER INFORMATION: Probe
```

```
<400> SEQUENCE: 259
atgctacccg tgtatat                                                  17

<210> SEQ ID NO 260
<211> LENGTH: 17
<212> TYPE: DNA
<213> ORGANISM: Artificial Sequence
<220> FEATURE:
<223> OTHER INFORMATION: Probe

<400> SEQUENCE: 260
cctatgctat cagtttt                                                  17

<210> SEQ ID NO 261
<211> LENGTH: 18
<212> TYPE: DNA
<213> ORGANISM: Artificial Sequence
<220> FEATURE:
<223> OTHER INFORMATION: Probe

<400> SEQUENCE: 261
ttgaatggtc tccacatg                                                 18

<210> SEQ ID NO 262
<211> LENGTH: 17
<212> TYPE: DNA
<213> ORGANISM: Artificial Sequence
<220> FEATURE:
<223> OTHER INFORMATION: Probe

<400> SEQUENCE: 262
ttcacaagtg tataacc                                                  17

<210> SEQ ID NO 263
<211> LENGTH: 15
<212> TYPE: DNA
<213> ORGANISM: Artificial Sequence
<220> FEATURE:
<223> OTHER INFORMATION: Probe

<400> SEQUENCE: 263
acatctccca ctggc                                                    15

<210> SEQ ID NO 264
<211> LENGTH: 14
<212> TYPE: DNA
<213> ORGANISM: Artificial Sequence
<220> FEATURE:
<223> OTHER INFORMATION: Probe

<400> SEQUENCE: 264
caaccatgac tttc                                                     14

<210> SEQ ID NO 265
<211> LENGTH: 16
<212> TYPE: DNA
<213> ORGANISM: Artificial Sequence
<220> FEATURE:
<223> OTHER INFORMATION: Probe

<400> SEQUENCE: 265
ccaacctcta tagcaa                                                   16

<210> SEQ ID NO 266
<211> LENGTH: 15
```

<212> TYPE: DNA
<213> ORGANISM: Artificial Sequence
<220> FEATURE:
<223> OTHER INFORMATION: Probe

<400> SEQUENCE: 266
tctttcacaa tctac                                                    15

<210> SEQ ID NO 267
<211> LENGTH: 16
<212> TYPE: DNA
<213> ORGANISM: Artificial Sequence
<220> FEATURE:
<223> OTHER INFORMATION: Probe

<400> SEQUENCE: 267
ctactcttgc gttgtt                                                   16

<210> SEQ ID NO 268
<211> LENGTH: 16
<212> TYPE: DNA
<213> ORGANISM: Artificial Sequence
<220> FEATURE:
<223> OTHER INFORMATION: Probe

<400> SEQUENCE: 268
tcaaacaagg atctcc                                                   16

<210> SEQ ID NO 269
<211> LENGTH: 18
<212> TYPE: DNA
<213> ORGANISM: Artificial Sequence
<220> FEATURE:
<223> OTHER INFORMATION: Probe

<400> SEQUENCE: 269
attctggttc ttcacttg                                                 18

<210> SEQ ID NO 270
<211> LENGTH: 15
<212> TYPE: DNA
<213> ORGANISM: Artificial Sequence
<220> FEATURE:
<223> OTHER INFORMATION: Probe

<400> SEQUENCE: 270
cctcacaaat tacca                                                    15

<210> SEQ ID NO 271
<211> LENGTH: 16
<212> TYPE: DNA
<213> ORGANISM: Artificial Sequence
<220> FEATURE:
<223> OTHER INFORMATION: Probe

<400> SEQUENCE: 271
acaaatgtac accgcc                                                   16

<210> SEQ ID NO 272
<211> LENGTH: 15
<212> TYPE: DNA
<213> ORGANISM: Artificial Sequence
<220> FEATURE:
<223> OTHER INFORMATION: Probe

<400> SEQUENCE: 272
cttccagagc agtgc                                        15

<210> SEQ ID NO 273
<211> LENGTH: 16
<212> TYPE: DNA
<213> ORGANISM: Artificial Sequence
<220> FEATURE:
<223> OTHER INFORMATION: Probe

<400> SEQUENCE: 273 cataccccttt acaagc                                      16

<210> SEQ ID NO 274
<211> LENGTH: 18
<212> TYPE: DNA
<213> ORGANISM: Artificial Sequence
<220> FEATURE:
<223> OTHER INFORMATION: Probe

<400> SEQUENCE: 274
tcctatgttg gtctggtc                                     18

<210> SEQ ID NO 275
<211> LENGTH: 15
<212> TYPE: DNA
<213> ORGANISM: Artificial Sequence
<220> FEATURE:
<223> OTHER INFORMATION: Probe

<400> SEQUENCE: 275
ttggctttga atcac                                        15

<210> SEQ ID NO 276
<211> LENGTH: 15
<212> TYPE: DNA
<213> ORGANISM: Artificial Sequence
<220> FEATURE:
<223> OTHER INFORMATION: Probe

<400> SEQUENCE: 276
ccgaacgtgt catat                                        15

<210> SEQ ID NO 277
<211> LENGTH: 14
<212> TYPE: DNA
<213> ORGANISM: Artificial Sequence
<220> FEATURE:
<223> OTHER INFORMATION: Probe

<400> SEQUENCE: 277
caaactgcaa gatt                                         14

<210> SEQ ID NO 278
<211> LENGTH: 17
<212> TYPE: DNA
<213> ORGANISM: Artificial Sequence
<220> FEATURE:
<223> OTHER INFORMATION: Probe

<400> SEQUENCE: 278
ttctgataga cgaaacc                                      17

<210> SEQ ID NO 279
<211> LENGTH: 19
<212> TYPE: DNA
<213> ORGANISM: Artificial Sequence
<220> FEATURE:
<223> OTHER INFORMATION: Probe

<400> SEQUENCE: 279
attaacttcc ttcttttac                                                    19

<210> SEQ ID NO 280
<211> LENGTH: 15
<212> TYPE: DNA
<213> ORGANISM: Artificial Sequence
<220> FEATURE:
<223> OTHER INFORMATION: Probe

<400> SEQUENCE: 280
ttacttggca acaat                                                        15

<210> SEQ ID NO 281
<211> LENGTH: 16
<212> TYPE: DNA
<213> ORGANISM: Artificial Sequence
<220> FEATURE:
<223> OTHER INFORMATION: Probe

<400> SEQUENCE: 281
caatttgttg aagcct                                                       16

<210> SEQ ID NO 282
<211> LENGTH: 17
<212> TYPE: DNA
<213> ORGANISM: Artificial Sequence
<220> FEATURE:
<223> OTHER INFORMATION: Probe

<400> SEQUENCE: 282
ctcagtatat catcttc                                                      17

<210> SEQ ID NO 283
<211> LENGTH: 14
<212> TYPE: DNA
<213> ORGANISM: Artificial Sequence
<220> FEATURE:
<223> OTHER INFORMATION: Probe

<400> SEQUENCE: 283
aagccacgag tcat                                                         14

<210> SEQ ID NO 284
<211> LENGTH: 15
<212> TYPE: DNA
<213> ORGANISM: Artificial Sequence
<220> FEATURE:
<223> OTHER INFORMATION: Probe

<400> SEQUENCE: 284
cacctaagga acaat                                                        15

<210> SEQ ID NO 285
<211> LENGTH: 15
<212> TYPE: DNA
<213> ORGANISM: Artificial Sequence
<220> FEATURE:
<223> OTHER INFORMATION: Probe

<400> SEQUENCE: 285
cttccagtgg ctgct                                                        15

<210> SEQ ID NO 286
<211> LENGTH: 14
<212> TYPE: DNA
<213> ORGANISM: Artificial Sequence
<220> FEATURE:
<223> OTHER INFORMATION: Probe

<400> SEQUENCE: 286
ctcaccggag caat                                                        14

<210> SEQ ID NO 287
<211> LENGTH: 16
<212> TYPE: DNA
<213> ORGANISM: Artificial Sequence
<220> FEATURE:
<223> OTHER INFORMATION: Probe

<400> SEQUENCE: 287
ctaacctcca gaacac                                                      16

<210> SEQ ID NO 288
<211> LENGTH: 18
<212> TYPE: DNA
<213> ORGANISM: Artificial Sequence
<220> FEATURE:
<223> OTHER INFORMATION: Probe

<400> SEQUENCE: 288
cacttgtctt tacaacat                                                    18

<210> SEQ ID NO 289
<211> LENGTH: 18
<212> TYPE: DNA
<213> ORGANISM: Artificial Sequence
<220> FEATURE:
<223> OTHER INFORMATION: Probe

<400> SEQUENCE: 289
tctctatttt ccgaaatg                                                    18

<210> SEQ ID NO 290
<211> LENGTH: 14
<212> TYPE: DNA
<213> ORGANISM: Artificial Sequence
<220> FEATURE:
<223> OTHER INFORMATION: Probe

<400> SEQUENCE: 290
ccacattttc ttcc                                                        14

<210> SEQ ID NO 291
<211> LENGTH: 17
<212> TYPE: DNA
<213> ORGANISM: Artificial Sequence
<220> FEATURE:
<223> OTHER INFORMATION: Probe

<400> SEQUENCE: 291
accttacgtt gtagatc                                                     17

<210> SEQ ID NO 292
<211> LENGTH: 14
<212> TYPE: DNA
<213> ORGANISM: Artificial Sequence
<220> FEATURE:
<223> OTHER INFORMATION: Probe

```
<400> SEQUENCE: 292
ctgctgttga tctt                                                        14

<210> SEQ ID NO 293
<211> LENGTH: 15
<212> TYPE: DNA
<213> ORGANISM: Artificial Sequence
<220> FEATURE:
<223> OTHER INFORMATION: Probe

<400> SEQUENCE: 293
acgaacacgt cctga                                                       15

<210> SEQ ID NO 294
<211> LENGTH: 19
<212> TYPE: DNA
<213> ORGANISM: Artificial Sequence
<220> FEATURE:
<223> OTHER INFORMATION: Probe

<400> SEQUENCE: 294
tctattactg tctgtcttt                                                   19

<210> SEQ ID NO 295
<211> LENGTH: 16
<212> TYPE: DNA
<213> ORGANISM: Artificial Sequence
<220> FEATURE:
<223> OTHER INFORMATION: Probe

<400> SEQUENCE: 295
acaggatgat actcac                                                      16

<210> SEQ ID NO 296
<211> LENGTH: 17
<212> TYPE: DNA
<213> ORGANISM: Artificial Sequence
<220> FEATURE:
<223> OTHER INFORMATION: Probe

<400> SEQUENCE: 296
ctttgcattt gagatca                                                     17

<210> SEQ ID NO 297
<211> LENGTH: 17
<212> TYPE: DNA
<213> ORGANISM: Artificial Sequence
<220> FEATURE:
<223> OTHER INFORMATION: Probe

<400> SEQUENCE: 297
caagtgatgt tcatttt                                                     17

<210> SEQ ID NO 298
<211> LENGTH: 15
<212> TYPE: DNA
<213> ORGANISM: Artificial Sequence
<220> FEATURE:
<223> OTHER INFORMATION: Probe

<400> SEQUENCE: 298
ctcgaacgta ctctc                                                       15

<210> SEQ ID NO 299
```

```
<211> LENGTH: 18
<212> TYPE: DNA
<213> ORGANISM: Artificial Sequence
<220> FEATURE:
<223> OTHER INFORMATION: Probe

<400> SEQUENCE: 299
tcaagatcat ccactatt                                                   18

<210> SEQ ID NO 300
<211> LENGTH: 14
<212> TYPE: DNA
<213> ORGANISM: Artificial Sequence
<220> FEATURE:
<223> OTHER INFORMATION: Probe

<400> SEQUENCE: 300
ccacgtgttg ttct                                                       14

<210> SEQ ID NO 301
<211> LENGTH: 16
<212> TYPE: DNA
<213> ORGANISM: Artificial Sequence
<220> FEATURE:
<223> OTHER INFORMATION: Probe

<400> SEQUENCE: 301
ccagccttag tagcag                                                     16

<210> SEQ ID NO 302
<211> LENGTH: 18
<212> TYPE: DNA
<213> ORGANISM: Artificial Sequence
<220> FEATURE:
<223> OTHER INFORMATION: Probe

<400> SEQUENCE: 302
aaaatttgtg ctatccac                                                   18

<210> SEQ ID NO 303
<211> LENGTH: 16
<212> TYPE: DNA
<213> ORGANISM: Artificial Sequence
<220> FEATURE:
<223> OTHER INFORMATION: Probe

<400> SEQUENCE: 303
tcaaacagtg attctc                                                     16

<210> SEQ ID NO 304
<211> LENGTH: 16
<212> TYPE: DNA
<213> ORGANISM: Artificial Sequence
<220> FEATURE:
<223> OTHER INFORMATION: Probe

<400> SEQUENCE: 304
ctacccgtgt gtatac                                                     16

<210> SEQ ID NO 305
<211> LENGTH: 17
<212> TYPE: DNA
<213> ORGANISM: Artificial Sequence
<220> FEATURE:
<223> OTHER INFORMATION: Probe

<400> SEQUENCE: 305
```

```
cctatgctat cggtttt                                                    17

<210> SEQ ID NO 306
<211> LENGTH: 16
<212> TYPE: DNA
<213> ORGANISM: Artificial Sequence
<220> FEATURE:
<223> OTHER INFORMATION: Probe

<400> SEQUENCE: 306
tttgaacggt ctccac                                                     16

<210> SEQ ID NO 307
<211> LENGTH: 18
<212> TYPE: DNA
<213> ORGANISM: Artificial Sequence
<220> FEATURE:
<223> OTHER INFORMATION: Probe

<400> SEQUENCE: 307
ttcacaagtc tataacct                                                   18

<210> SEQ ID NO 308
<211> LENGTH: 14
<212> TYPE: DNA
<213> ORGANISM: Artificial Sequence
<220> FEATURE:
<223> OTHER INFORMATION: Probe

<400> SEQUENCE: 308
catctcccac cggc                                                       14

<210> SEQ ID NO 309
<211> LENGTH: 14
<212> TYPE: DNA
<213> ORGANISM: Artificial Sequence
<220> FEATURE:
<223> OTHER INFORMATION: Probe

<400> SEQUENCE: 309
caaccatgcc tttc                                                       14

<210> SEQ ID NO 310
<211> LENGTH: 16
<212> TYPE: DNA
<213> ORGANISM: Artificial Sequence
<220> FEATURE:
<223> OTHER INFORMATION: Probe

<400> SEQUENCE: 310
ccaacctctg tagcaa                                                     16

<210> SEQ ID NO 311
<211> LENGTH: 15
<212> TYPE: DNA
<213> ORGANISM: Artificial Sequence
<220> FEATURE:
<223> OTHER INFORMATION: Probe

<400> SEQUENCE: 311
tctttgacaa tctac                                                      15

<210> SEQ ID NO 312
<211> LENGTH: 15
<212> TYPE: DNA
```

```
<213> ORGANISM: Artificial Sequence
<220> FEATURE:
<223> OTHER INFORMATION: Probe

<400> SEQUENCE: 312
ctcttgcgct gttaa                                                    15

<210> SEQ ID NO 313
<211> LENGTH: 16
<212> TYPE: DNA
<213> ORGANISM: Artificial Sequence
<220> FEATURE:
<223> OTHER INFORMATION: Probe

<400> SEQUENCE: 313
tcaaactagg atctcc                                                   16

<210> SEQ ID NO 314
<211> LENGTH: 17
<212> TYPE: DNA
<213> ORGANISM: Artificial Sequence
<220> FEATURE:
<223> OTHER INFORMATION: Probe

<400> SEQUENCE: 314
attctggtcc ttcactt                                                  17

<210> SEQ ID NO 315
<211> LENGTH: 13
<212> TYPE: DNA
<213> ORGANISM: Artificial Sequence
<220> FEATURE:
<223> OTHER INFORMATION: Probe

<400> SEQUENCE: 315
cctcaccaat tac                                                      13

<210> SEQ ID NO 316
<211> LENGTH: 16
<212> TYPE: DNA
<213> ORGANISM: Artificial Sequence
<220> FEATURE:
<223> OTHER INFORMATION: Probe

<400> SEQUENCE: 316
acaaacgtac accgcc                                                   16

<210> SEQ ID NO 317
<211> LENGTH: 14
<212> TYPE: DNA
<213> ORGANISM: Artificial Sequence
<220> FEATURE:
<223> OTHER INFORMATION: Probe

<400> SEQUENCE: 317
ttccagagca gcgc                                                     14

<210> SEQ ID NO 318
<211> LENGTH: 15
<212> TYPE: DNA
<213> ORGANISM: Artificial Sequence
<220> FEATURE:
<223> OTHER INFORMATION: Probe

<400> SEQUENCE: 318
ccataccccg tacaa                                                    15
```

```
<210> SEQ ID NO 319
<211> LENGTH: 17
<212> TYPE: DNA
<213> ORGANISM: Artificial Sequence
<220> FEATURE:
<223> OTHER INFORMATION: Probe

<400> SEQUENCE: 319
tcctatgctg gtctggt                                                     17

<210> SEQ ID NO 320
<211> LENGTH: 15
<212> TYPE: DNA
<213> ORGANISM: Artificial Sequence
<220> FEATURE:
<223> OTHER INFORMATION: Probe

<400> SEQUENCE: 320
ttggctttga attac                                                       15

<210> SEQ ID NO 321
<211> LENGTH: 14
<212> TYPE: DNA
<213> ORGANISM: Artificial Sequence
<220> FEATURE:
<223> OTHER INFORMATION: Probe

<400> SEQUENCE: 321
ccgaacgctg tcat                                                        14

<210> SEQ ID NO 322
<211> LENGTH: 15
<212> TYPE: DNA
<213> ORGANISM: Artificial Sequence
<220> FEATURE:
<223> OTHER INFORMATION: Probe

<400> SEQUENCE: 322
cacaaaccgc aagat                                                       15

<210> SEQ ID NO 323
<211> LENGTH: 17
<212> TYPE: DNA
<213> ORGANISM: Artificial Sequence
<220> FEATURE:
<223> OTHER INFORMATION: Probe

<400> SEQUENCE: 323
ctgatagatg aaaccca                                                     17

<210> SEQ ID NO 324
<211> LENGTH: 16
<212> TYPE: DNA
<213> ORGANISM: Artificial Sequence
<220> FEATURE:
<223> OTHER INFORMATION: Probe

<400> SEQUENCE: 324
attaactgcc ttcttt                                                      16

<210> SEQ ID NO 325
<211> LENGTH: 18
<212> TYPE: DNA
<213> ORGANISM: Artificial Sequence
<220> FEATURE:
```

```
<223> OTHER INFORMATION: Probe

<400> SEQUENCE: 325
acttgttaac aatgtcac                                              18

<210> SEQ ID NO 326
<211> LENGTH: 18
<212> TYPE: DNA
<213> ORGANISM: Artificial Sequence
<220> FEATURE:
<223> OTHER INFORMATION: Probe

<400> SEQUENCE: 326
caatttattg aagccttt                                              18

<210> SEQ ID NO 327
<211> LENGTH: 15
<212> TYPE: DNA
<213> ORGANISM: Artificial Sequence
<220> FEATURE:
<223> OTHER INFORMATION: Probe

<400> SEQUENCE: 327
ccctcagtag atcat                                                 15

<210> SEQ ID NO 328
<211> LENGTH: 14
<212> TYPE: DNA
<213> ORGANISM: Artificial Sequence
<220> FEATURE:
<223> OTHER INFORMATION: Probe

<400> SEQUENCE: 328
aagccacgag ccat                                                  14

<210> SEQ ID NO 329
<211> LENGTH: 16
<212> TYPE: DNA
<213> ORGANISM: Artificial Sequence
<220> FEATURE:
<223> OTHER INFORMATION: Probe

<400> SEQUENCE: 329
cctaatgaac aatacc                                                16

<210> SEQ ID NO 330
<211> LENGTH: 13
<212> TYPE: DNA
<213> ORGANISM: Artificial Sequence
<220> FEATURE:
<223> OTHER INFORMATION: Probe

<400> SEQUENCE: 330
ccttccagcg gct                                                   13

<210> SEQ ID NO 331
<211> LENGTH: 16
<212> TYPE: DNA
<213> ORGANISM: Artificial Sequence
<220> FEATURE:
<223> OTHER INFORMATION: Probe

<400> SEQUENCE: 331
caacttgctc acagga                                                16
```

```
<210> SEQ ID NO 332
<211> LENGTH: 18
<212> TYPE: DNA
<213> ORGANISM: Artificial Sequence
<220> FEATURE:
<223> OTHER INFORMATION: Probe

<400> SEQUENCE: 332
ctctctaacc tctagaac                                                   18

<210> SEQ ID NO 333
<211> LENGTH: 17
<212> TYPE: DNA
<213> ORGANISM: Artificial Sequence
<220> FEATURE:
<223> OTHER INFORMATION: Probe

<400> SEQUENCE: 333
acacttgcct ttacaac                                                    17

<210> SEQ ID NO 334
<211> LENGTH: 18
<212> TYPE: DNA
<213> ORGANISM: Artificial Sequence
<220> FEATURE:
<223> OTHER INFORMATION: Probe

<400> SEQUENCE: 334
tctctattct ccgaaatg                                                   18

<210> SEQ ID NO 335
<211> LENGTH: 14
<212> TYPE: DNA
<213> ORGANISM: Artificial Sequence
<220> FEATURE:
<223> OTHER INFORMATION: Probe

<400> SEQUENCE: 335
ccacatttgc ttcc                                                       14

<210> SEQ ID NO 336
<211> LENGTH: 17
<212> TYPE: DNA
<213> ORGANISM: Artificial Sequence
<220> FEATURE:
<223> OTHER INFORMATION: Probe

<400> SEQUENCE: 336
acctttcgtt gtagatc                                                    17

<210> SEQ ID NO 337
<211> LENGTH: 15
<212> TYPE: DNA
<213> ORGANISM: Artificial Sequence
<220> FEATURE:
<223> OTHER INFORMATION: Probe

<400> SEQUENCE: 337
ctgctattga tcttc                                                      15

<210> SEQ ID NO 338
<211> LENGTH: 15
<212> TYPE: DNA
<213> ORGANISM: Artificial Sequence
<220> FEATURE:
<223> OTHER INFORMATION: Probe
```

```
<400> SEQUENCE: 338
caacgaacag gtcct                                                   15

<210> SEQ ID NO 339
<211> LENGTH: 531
<212> TYPE: DNA
<213> ORGANISM: Artificial Sequence
<220> FEATURE:
<223> OTHER INFORMATION: Consensus reference sequence

<400> SEQUENCE: 339
mmrgctatga ccatggggaa gtgcatgagt gcttttcag atacctactt ataagtaggt    60
ttgaattaaa ttgattatat tgtcctagta gaagtggcta tataatattt tttgagtgag  120
tgtgcttttg ctcgttgcat gatatagcag atatgctatc tgaatgctaa aggtactcta  180
ttactrtctg tcttttcttc tcattcctta tccatacata ttttgaacca attttacatt  240
tggaaggacg aattgctgcc aatggtgcaa tctagcaatc ttaccttgtc attttcaact  300
gaaagttcaa ttgaggaaga actaaagaga gaaagcactg cagatgtcat aacaatactc  360
gtaagaaatt tctgtttctt tcaactaaat gtgaaaacat gatttgtgtt gtgtgtaagc  420
taatgaactg attagtttgg ttgtggcttc ataaagatgt gctttattgg aatatacaat  480
aaatgtcttc tccaacatat tattaggtga gctatattgt aatgttgctt a           531

<210> SEQ ID NO 340
<211> LENGTH: 372
<212> TYPE: DNA
<213> ORGANISM: Artificial Sequence
<220> FEATURE:
<223> OTHER INFORMATION: Consensus reference sequence

<400> SEQUENCE: 340
gatgggtaga ccaatacaca agtttgcaag cattgtagga tatagagagg gtaagatgta   60 tacaactta ccaccataag aagagaggct gcttctgaga ctagaaaatt tgaccaccag   120
gtcacaagct tacaacctta taactgcacg aaggtttact ttctaatatg aagaaatacc  180
accttttgtc atgtaaatat ttaagtttac taaattgaaa tgttgataac aatgcaaaga  240
aaagagtagt cagtgactca attcaaaagt tgatgatacc aaacaaacct gaagcttgta  300
gcgcagctcc agatttcatg attggctccc caacaggayg atactcacag cctgcttcaa  360
ggacttcatg gt                                                     372

<210> SEQ ID NO 341
<211> LENGTH: 801
<212> TYPE: DNA
<213> ORGANISM: Artificial Sequence
<220> FEATURE:
<223> OTHER INFORMATION: Consensus reference sequence

<400> SEQUENCE: 341
agtaccaagg gaggacatgc attgtgttgc acagtttttt tccaggacat gggaactgca   60
agtgctggtt gctgcttgtt tagcccttcc atgataaaag aaaatgcccc aaaagtgaga  120
cagctctgca gaagagcttg tggtgcacct gtaaaaccct agaatataag tcctaataac  180
aaaacaagta cacagaatga aatttacatg tgtatttagc tgaacaatga attgttgaat  240
tttaacaata gcaatgattg gaagccattc tgagtcagca aaatttcccc cctcctccat  300
ttaaggtgat ggtttgggaa tggagacaga ggattccaga gtaatacatc tcaagaaaca  360
aattaccaca ctgattatgg acaaaattat ctttgcattt kagatcatat gactatgctt  420
```

```
ttaaagagag atcaagaatg ccaatagggc ctattcagaa tagtcagatt ggcaagtcct    480
ttatcctaat tctttcttat agatttcaaa aagagggcaa acccatcaat ttgaataaat    540
aaataagaga tacctggaaa acttagagca agaccagtgc aacatccagc aacacccgca    600
ttaatgactg caaatgcaaa agaattcaca ttaccgagg aagatcactt aaaagcaaaa     660
gtgacaaatt ttacaactaa atattcatac catcatcttt tcctctaagc cttttcaaga    720
tgcaaacaac caaactatga actccagaca aaactgcaaa tgtctaatga cataaagaac    780
aacacaatta cttacaatct a                                              801
```

<210> SEQ ID NO 342
<211> LENGTH: 526
<212> TYPE: DNA
<213> ORGANISM: Artificial Sequence
<220> FEATURE:
<223> OTHER INFORMATION: Consensus reference sequence

<400> SEQUENCE: 342

```
mtgcatgcat ggattttaag caaataaatt aatgtgaagt atttcaatgt atgcccgtgc     60
myhkahcaca tctcatgcac tgcccatacc taaaggataa aatatcaagt gatgttyatt    120
ttttaatctc cccttcaaaa tgaccaatta atgtagagaa ccttctaagt tctatagatt    180
ttaacacttg tctaattctt aaccatccac atccgtttct catgtacctt tatagtttca    240
attatttcaa caataacgcc aacactgtaa agttttgcc gttaccagtt ccaaattcta     300
ccttttttct tttctgtaac agctggattc actgtactaa aatccaaaaa gtgtctgaaa    360
ccggagtttg tctatttgcc atggtcaarb bbddtyycyv vbddbbrbrd vbbvdbdbvb    420
bhdvmvbbbr vhddvvddrd rbbrvvddbb bwbvhbwbbd hhhwbybmbh dhbbbmbbhr    480
bhbwbbbbbv bbbbdrbbdr bbkrbbdvbb dwdwkkwdws amarkd                   526
```

<210> SEQ ID NO 343
<211> LENGTH: 510
<212> TYPE: DNA
<213> ORGANISM: Artificial Sequence
<220> FEATURE:
<223> OTHER INFORMATION: Consensus reference sequence

<400> SEQUENCE: 343

```
attttatttt attttttctg agataaacaa tgagccaata gtttaaaatg gctgccgttt     60
atgttgttag catataaaga ttctcaataa tattcaatta ctcgaaygta ctctctaaaa    120
taaacaagtt aattcacttc ttggactgat tctaaatacc tgttaactgc agcatataac    180
ctgtactaac ttcccaattt aagagtaatc taacaaacaa tattaagaat tttataatgc    240
aaatagacag aaagaatctt actcccacat ggttaactat tttagcctag gtggtgcatt    300
gtaatttgct attatacagt aattttgtaa ttacartaca tagaaaaagg tcaagagtaa    360
gtgaattaga ttttagaatt aataggtgct gacactatag atccacacct atgaaggtct    420
ccaggttgtc ctgatgaggt cctaaactta cccatatgcc atgcatgtct gacagaatga    480
cacttcacca ccacatggtc atagcykkkt                                     510
```

<210> SEQ ID NO 344
<211> LENGTH: 509
<212> TYPE: DNA
<213> ORGANISM: Artificial Sequence
<220> FEATURE:
<223> OTHER INFORMATION: Consensus reference sequence

<400> SEQUENCE: 344

```
tcgcgaccat ccaagagttt gcctttataa acaacaccat agcttccagc accaatctyt    60
caatcaaggg cgaaattatt ggtggcagca acaagctcag ccaaagtgaa ctcctcagcc   120
ctctcaggat gctttgtgga tgatgttcca ctcctttgac gcctcattat ccgtgaccct   180
tgacgcctaa tagtgratga tcttgaagga ggactaatgc tattattaga accacccaca   240
ccatttacac tgccacctct agtgattgtc ggctgcacag aattgtgaac tttcttcttc   300
ccaaaacaaa ccccagtcca caaacaataa atcgcagtgc atatcccagc aacacctccc   360
acgcatccaa caatggcaaa tgccaacaac cccttagtca aggccttcga ccgagaagct   420
gcaggccccg gtggtgatgc tggcaccacc gcaggtggag ccggcaccag catttcaggc   480
caacaagcat ggtcatagaa tgtttccaa                                     509
```

<210> SEQ ID NO 345
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 345

```
taaacagttt tctaactagt gaaatttcat ttcggtatca ttggaaacgg agaattccaa    60
tatagcagaa aacatgaaca gaacgcgttg ttccaaagca aagccaataa taactcacag   120
tgttcccact gctaatagac gttgaatgtg atcaaaagcg agaatagacg cattagatgg   180
aacgccatag tgaagaacaa yacgtggatc aaaattcccc gacggaaaac tctcttgagc   240
cacgtcctgt tgctgaacgg cgcgaaaaat gttcagaaac aacgtcagct tcaggatttg   300
cgttcatata taaataaact tctacgaatg cactattatt atcattaaaa aaaaacaaaa   360
aacaaaaggc tccctagcat tattcgtaac cgcaagaaaa a                       401
```

<210> SEQ ID NO 346
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 346

```
tcggcgccca atttcaccct gaaaaaaata catatagatg taggggaaga cctaaaagaa    60
gaaattaaat caaacagaaa cataggagac aaacaattta gtaaattgag aaacatagga   120
gacataggta ttattattta gaatgaaacg gcatcatgca aaacaaaaaa gaatcatgaa   180
agaaatttat gcactgctac kaaggctggt ttgttcaaaa tacagaccat aggatctgtg   240
cacataccag acagataata tcatgcaagc aaacaacttt gataaaccaa ttcctaaaca   300
cacaagtgca caaatgataa tagattataa atatatcaaa acttcaagct aattgcatat   360
aatggaagtg gaaagaggaa acaataatgt aaaacatagt a                       401
```

<210> SEQ ID NO 347
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 347

```
aactgcaaaa cataatggac caagacatta agccattttt aaaatagtcc aagttctgga    60
```

```
caaaaagaag ccaagggtt aatttaaaaa aaaaaaaaaa aattgtaatc ttttttccta      120
gatccttttt tataaatgtt acacaacata aaaggtatag tagtaaattt tgcagtgtat      180
caattggtgg atagcacaaa wttttttcg tatcttgtga tcagtcacca aacagctcct      240
atacaaataa tatcctgtga ctcaacgagt tgaaatgtgc tgttttgttt gtttgtctct      300
ccatacacat caaatacaaa aaattataca attttacata agtggagggc agggagcaca      360
accctcactc tatgagctgg ctattggagt tgagttaggc t                         401

<210> SEQ ID NO 348
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 348
aagacctaaa aaattataat ttttttttt ataaatttta gtcaattata aaaatgatac       60
tcaaaagaat gtgttaaaaa gtatgttatc aacatttttt taatattata tacatatttc     120
taacacaaat gattgatgca atcatataag gtttcgttgt gtttatataa gtgaaaacga     180
tctagttaat atgagaatca stgtttgatt cccactattg caaaatttta tcaaacaaac     240
aaaattaggg aacactcgtg atttgcgacc taagacaaaa gagacatcaa agttcaaaaa     300
acactactta catatcaagt taagttatgg attacaagat cttcgtatttt acaatgaaaa     360 ttcatattgc atatgaaaag tagattatgc atttcagtta t                         401

<210> SEQ ID NO 349
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 349
atgacatatc tcttttttgtt ttttcaaatg ttaaattaat attgaggtgc ttatatttgg     60
caattttgaa ttaagtctga atattttaaa aatttgtgat tgagacaatg ttataatatt    120
tttaacgtgc tctaactatt aattttcctt ttttttttccg cgatcaacta ttttaatttc    180
caatagtatg ctacccgtgt rtatacacag gttatctaag aattgagatc tgctagaaat    240
gcaaagcaat tagggatcgt gtacaagata tattaaacat tttaccaact aaccatagaa    300
tctttttcat caacacgact agatattttt aaaagaaatc aacacaagta tttaagcaag    360
ttttgatttg aaaattctgc ataatccccc aaaaggaaaa g                         401

<210> SEQ ID NO 350
<211> LENGTH: 418
<212> TYPE: DNA
<213> ORGANISM: Artificial Sequence
<220> FEATURE:
<223> OTHER INFORMATION: Consensus reference sequence

<400> SEQUENCE: 350 aacttttat gattgacttg gttctcaaat tccgacggta ttgagttaag gaattttaat      60
ggtgcctatg ctatcrgttt tggaataacg attatgaggt ttggatgaat atttggagtt    120
gcataaatac gttgctacaa aggtttattt ttctcttctg gtagtaatat ggaataacag    180
gttacaacct attgatttaa tattaatata ataggggagg agtgtatttt ttgaaacaga    240
```

```
atattttgg aaatcgggca ctgcctccta gacgttaaga ctgaaatcta cagttttggg      300
cttatattgg gtttgctttt attactattg ggctgcatac atacaatata gttatttaa     360 ttaattttct ttatgctcta acactttggt tggcagggta caatttgcag ctcatggt      418
```

<210> SEQ ID NO 351
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 351

```
tgcaatggtc agactactca acacaactct tgttgactta ttgttctta aatttctaat      60 ttctttcttc caaaaatgat tttgagagga tgaatagaat aaaattctta gaagcttcct    120
tcctgcaagc tgaggaagat tacttactag gagtgataac ttggtgcacc actgcaatta    180
gtttgatcca tgtggagacc rttcaaaaaa atttacattg atttctctag atgcatcatg    240
gatcgcaatt caaaactaaa ctttacccctt ccatggcaat gacttcccta ccttattgag    300
gaactccact ttttttatta cagaagaagt ggctcaagga attttttgtgt aacttacaaa    360 ataagtaagt gctaaagaac caaagactct tggcagctta a                         401
```

<210> SEQ ID NO 352
<211> LENGTH: 695
<212> TYPE: DNA
<213> ORGANISM: Artificial Sequence
<220> FEATURE:
<223> OTHER INFORMATION: Consensus reference sequence

<400> SEQUENCE: 352

```
tttttttttt tttttttttt tttttttttt ttttttagaaa atatccactc attattattt      60
ccaacatgaa acgcttgttc cacatattca acaaaccatt ttattttctt ttttcaagaa    120
gaaagaaact tccaaacatg catcaatttt attgtactaa tctctccctt gccttgagct    180
tacaggaaca ttgttacaat tggtgttctg cttgctcatg ataaaaccca aatcaacacc    240
acataattta ggaagtgaat tggccttgtt ttcgagcaag gaaggaaggc gagttgctac    300
gtcgaaaaag cacttacatg cagccattcg ttgaatttgt gttggtgctg atgctttcac    360
tgcattaaca ctttggcaac aaacacctga aggggcacca tcatctccac caatcatgta    420
atctacgcac gaaactaaca ggttatasac ttgtgaacaa ttgtagtcat ttgatgctga    480
atttgtttta actggtagtc gtgcctctga agctttcgct gtaagaacaa atacaactag    540
cacagctaaa aatgtgacaa acactttctt cattttgtga aattgaagct agtttctata    600
tatctcaatc aacttttttag gatttgcttg tgttttgccg cgtgggtcga ccagggtatt    660
ccggaccggt acctgcaggc gtaccagctt tccct                                 695
```

<210> SEQ ID NO 353
<211> LENGTH: 801
<212> TYPE: DNA
<213> ORGANISM: Artificial Sequence
<220> FEATURE:
<223> OTHER INFORMATION: Consensus reference sequence

<400> SEQUENCE: 353

```
atgagttccg tatgaaaaat atactgttct ggatgaattg tggcacgaac catacatcca      60
tgtatatata tcctaatact gtcctaccgt ccacttacaa tgattgtgca aagttcttca    120
atgagaaaat aagtcctaaa aacggtagag cttaatgaca acaaagaaaa taaccaatgc    180
```

```
gttaccatat tggcaactat aactaaatgt gagtgcatgt cattccaaat tacgcatttc    240
tgcgttattc acgagattat tcatactctg ggagtcacag cacctcccat tgaattccac    300
acgacatttg acaatggatg ccacccggaa gagggctgca taaagtctcc tgagattaca    360
aacgagagat ctggaggggt atcactgaaa catctcccac yggcgggaac aaatctagct    420
ccccataacg ctccaggaca cgcatcctgc agtcctcagc agccatcatt ccagtagagt    480
atgcaccatg cacagacccc gtatacaaca tacttgttgc ttcccctgca agaataaat    540 tgtctacagg aacccgtagc ttctcataca gatcatgtgg tttcccaact gcatcatagc    600
tataggaacc tagtgtatta atatctgtac cccatcgaga cacaagatac tgaatctgca    660
tgattgaaac aaattgcatc ttcaaaacac caacaacata ctagtcactg aaaaacaact    720
tattaaattc aatcatatag cgattgaact aaaatgaata aaacttagga ctttaggagt    780
ctgccactta taaaaatatg g                                              801

<210> SEQ ID NO 354
<211> LENGTH: 496
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 11
<223> OTHER INFORMATION: n = A,T,C or G

<400> SEQUENCE: 354
acgtactttc nttttctttt tattattaat tctaacagct ttagccttca accatttttt    60
atggtttgtt caaccatgmc tttccgttcc ttgagactgg tttaaacttg tggtcaaaag    120 cctttttgc tgctgctgct tcttggacac aacatgggtg tgatacaaaa tgatattagg    180
cttcatatcg aagtacctta taaaatgatc tgctgttgca tcttgtacct gttgatcttg    240
aakaagatct ttaattgctt caggcatrgg ttsgtcattc atcattttct tccaataatc    300
ccccaggtct tttcttgcat ggcttaagtt gatgttggca acctatttat tagtagagat    360
aacatagaaa astcataaac cataattagc acaaactcaa tggttcaaat tttaaaacaa    420
atragttrct actgaaaagc ttaccaggag aagmgamaag actamgaasa aggcaaagrt    480
cakggtcata gcykkt                                                    496

<210> SEQ ID NO 355
<211> LENGTH: 566
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 5, 6, 34, 35, 45, 48, 57, 62, 63, 64, 65, 69, 73, 79,
      80, 82, 83, 85, 86, 87, 89, 90, 91, 93, 94, 95, 96, 97, 98,
      99, 100, 101, 102, 103, 524
<223> OTHER INFORMATION: n = A,T,C or G

<400> SEQUENCE: 355
gaccnntgct tacatccagt ccccamrwmm csynntyrgg agwtncantw kskrkcnaat    60
cnnnnacanw ttntgaaann cnntnnntnn ntnnnnnnnn nnnaccatgg gaggaccttg    120
atgatgtcgg atcaccatac ccccactttg cttttcaaac raagtattat gaggaacatc    180
tttctcayct aaaaacataa ttctatgttc aaaaacaaat atacaaggca taaaagtacr    240
```

```
tgtatccaaa aktagcatga ataaaaactc gataccttgg ggttgattag aaggaatcaa      300
agtagtcgac ttctccacgt gcttgtcatt aacatcaaca ttagtgatcg acttctcatc      360
gttatktggt tggatcacat caacattcct acccttagta gcaggctcgy agtagttttg      420
gactrrgctt gttyagtttt gtcactttgt tggccaacct ctrtagcaac tcttttcctt      480
ttctttggct tcactaggtc ggcaaagtgt tggtggtatg ctangattat gagatttcga      540
catggaagcc caaaccttcc tgaaat                                           566

<210> SEQ ID NO 356
<211> LENGTH: 977
<212> TYPE: DNA
<213> ORGANISM: Artificial Sequence
<220> FEATURE:
<223> OTHER INFORMATION: Consensus reference sequence

<400> SEQUENCE: 356
tgggttgttt ggtgagaacg ataagtttgc cacaggaaca gaggtaagaa taataaaata       60
ataaatcatc cattgctttt gaaagatttt gcaagactgt ctcactgtaa agtacttcca      120
gtccaaatat tggattcttc tttataagcc tggttacatc acttgtactc aagtcttcag      180
atttgggcca ttattcatgg atcaaactgt gaaaaaaag ttaaacaaaa tttatttaca       240
attgaaaatc agttatcttc cttttaattt gcccaatgtg agagaaatgc attagagtct      300
ttsacaatct acaatgggaa gtttcatgct gggactaaca taggacgaca attttatct       360 attttctttt acttatttca tgcttctgtt gtaggttaga aaaygatact gccatagtgg      420
tattagtata atataatata ctacatctgy tttagaaaaa gatatgcatt tatctgaaac      480
tatatcatgc atatgttaaa ctctgagaag ctctttgata gatgtgcaac tgtaaaactt      540
cagagcatta catgcactaa tgaaaagctc tttgatgctt taaatctga acttgaaac       600 ttctataaaa tttgatgtac ttgatcacta gtaactgaag actctaccct ttttgtgcac      660
aggctatagc caagaaactg gcagagctga gtgggaaggg agtgacaacc atcattggag      720
gaggtgactc cgttgccgct gtggagaagg ttggacttgc agacaagatg agccacatct      780
ccactggtgg tggtgccagc ttagagcttc ttgagggaaa gcaactccct ggtgtccttg      840
ctcttgatga tgcttgagca aaaatcattc gttcctttga agtttgtgct ttatattatt      900 attatgggttg ggtttcagcc aacagtggat taaggtacaa tgagagctgc gaagttcttg      960
ctccctgaaa ggcttaa                                                     977

<210> SEQ ID NO 357
<211> LENGTH: 570
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 6
<223> OTHER INFORMATION: n = A,T,C or G

<400> SEQUENCE: 357 atggantct aaaagaatgc cttgtatgtg acgcgtacca ttctaatcct aactatattt        60
ctttatattc cttatttcac aaaaagacac attacaatgt gtgccctgtg agggaaatat      120
tgtaaatgtt aacarcgcaa gagtagttta cacaacctca agatatcaag gaaggtatta      180
gtgtgtaatt ttgctcattt ttttaagaga caacaaaatt ttattctcat atacttatca      240
aagccacaag atgtgaccta aatatataag ccaaacatta cagaaattat ttttgccat      300
```

```
atggttgcag caccaaatta acatcatccc taaacacaag aaaatttgaa cactaaatcc    360
atctagaaag ccttcktaaa catagttttt ctaggcttag aaaccacaat cctagaatca    420
aataaacata aagactccaa ccatagtgta attttgctca ttttattttt gatacaaagt    480
gctaggacat taaaacatat tctttctcta atgaaacctc ctctaaaaaa ctagycggag    540
aatcccacca acagaaccat gtgtcatggt                                    570
```

<210> SEQ ID NO 358
<211> LENGTH: 430
<212> TYPE: DNA
<213> ORGANISM: Artificial Sequence
<220> FEATURE:
<223> OTHER INFORMATION: Consensus reference sequence

<400> SEQUENCE: 358

```
agcttatycc ccaagacgct gtcagccatg tcgatttcat tgtcaaacwa ggatctcctc     60
cctatgaagt tccactccca acctacatct gtgtgactcc ctatgtgctg aattagctgt    120
ttttgctggc aggaaatgtg atatagctta ggatattttg ttattagtgg agcatcatta    180
gcaattccat tttgaaagac attgcccgtg tgcgattggt ggaacaccgc ctttaggtcc    240
tgccaccata aagattcatt gttgcctctt gttacgtcat ccatgcacct ccagccacca    300
tattttgaat ccaatattct ggcccatagt tcccctkggt gctgaaatar awccsatctc    360
catcttccaa gcagtgctag aktgraggtg ttgatgtcct tcatgctcta acacatacct    420
gtttccatcc                                                          430
```

<210> SEQ ID NO 359
<211> LENGTH: 240
<212> TYPE: DNA
<213> ORGANISM: Artificial Sequence
<220> FEATURE:
<223> OTHER INFORMATION: Consensus reference sequence

<400> SEQUENCE: 359

```
attcagtgat tttacctgtt tgcttgcgag attcaggagg aggggcccca tattgacgag     60
gcaagaaaac cccygttcca gcgcaacccc ttttagtaac accggatcca ccttgcaacc    120
cgggtcgcga cccggatccg aaataaggca cctgttgggt attctggtyc ttcacttgaa    180
gagggtgcca tgcaragtga ggcaaaacgt gcgtgcawtt cacagcttca tagtcatacc    240
```

<210> SEQ ID NO 360
<211> LENGTH: 495
<212> TYPE: DNA
<213> ORGANISM: Artificial Sequence
<220> FEATURE:
<223> OTHER INFORMATION: Consensus reference sequence

<400> SEQUENCE: 360

```
gtattatgca gctatggtca agacatactc atactagcaa acagcatta atttgatgat      60 ttgactcatg gctcatttcc cttgtttaaa tatagccatg tggaagttca ctttgttatg    120
gattccaytt tcctattcat gtgagggatt tggtaattkg tgaggcacga ccaaggagaa    180
gggaaaataa aaaaggtgca agaccatgct aaaaaggcta aagaaacta taaatcctga    240 tattgttgtt gagaaagaag tggtttgatt tgtgataaat aaatgataat atctcacaca    300
accggccwgc ttcatcttac ccacacagtt atttcataaa ctttagaaga waacgtaaac    360
ttatagtagt tgattagaaa attaacagtt gaaattgtga ttaaatacat tcacatatgt    420
```
tcgaaaatat agaattgtta tccactaacg tgtatcaagc tcttttttgcg ggatcttgca    480 tggtcatagc ykktt    495

<210> SEQ ID NO 361
<211> LENGTH: 754
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 49, 50, 51, 52, 53
<223> OTHER INFORMATION: n = A,T,C or G

<400> SEQUENCE: 361
khvkwywhaa yywratgarm agkgmatrkg rtaacwkrsm kwscagagnn nnngagacta    60
gaaccattaa cattagccag agccacaaaa ggtctaataa aaacatatca tgaaaataat    120
tttctaaaaa gagcagcaaa agacctgtgc catcacagtt gtaggaatct gaataaaatt    180
aacaccacgt aggaaggcag aggcagcaaa gccacacatg tcgccaatca caccaccacc    240
aagagcaaca aaygtacacc gccggtcgag ccgcgactcg atggccttgt caaagacttt    300
cataagagta tcctatcagt tgaacacaca aagactttct tatgcaattc tcaagagtgc    360
caacaaacac cacagccaat tcaaaacaca tgagacctac catgtccttg tactgctcac    420
catcaggtaa aattacactc tccacagaaa cattcgggtt tccccttgtc aaagcatcaa    480
caaccttgtc tagataaagt ggcgcaacgg tttcgttagt tacaactagg actctctttc    540
catgcacatg cctattccaa tagtgagaac agagcacttc agaataaata ttaaacaaga    600
aataaaatcc atgccttgtt agaaacttta attgaattga acttctccca catacyatta    660
aattttatag aagctctttc atttaaagtc tccaaaagtt gaggcacata tgttgatttt    720
agcttagagg agacttcaat tcattctatc ttct    754

<210> SEQ ID NO 362
<211> LENGTH: 464
<212> TYPE: DNA
<213> ORGANISM: Artificial Sequence
<220> FEATURE:
<223> OTHER INFORMATION: Consensus reference sequence

<400> SEQUENCE: 362
aatactaagc tgaaggaatc gattgcaaaa taataaccct tagaaaacac tacggctttg    60
taaatcataa accctaagct ctctcgcccc taatcctacg agctagctga atgtccttgg    120
gcataatggt aaccctctta gcatgaatag cgcagaggtt ggtatcctca aagagcccaa    180
cgaggtaggc ctcagcggct tcctgaagag cggagacagc rctgtctctgg aagcgtagat    240 cggtcttgaa gtcytgagcg atttccctta cgagcctctg gaaggaagc ttccttatga    300 gaagctccgt gctcttctgg tacttccgaa tctccctcag agccactgtc cccggcctga    360
aacggtgggg cttcttcacg ccgcccgtcg ccggagcgga cttrcstgct gccttggtgg    420
cgagctgctt ccttggagct tttcctccat ggtcatagct gttt    464

<210> SEQ ID NO 363
<211> LENGTH: 533
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 26, 43
<223> OTHER INFORMATION: n = A,T,C or G

<400> SEQUENCE: 363

| | | | | | |
|---|---|---|---|---|---|
| camcggcgat | taagcagcca | tatttnctgg | tcaacaccaa | gmnwgtctta | agttcccttc | 60 |
| agctactctt | tggtctaatt | ttgataggaa | cctgtctcag | accaagccta | aggtttaatt | 120 |
| ccataggccc | aaaagggcaa | atgcgtccta | ggtgaaaaga | agttagttag | agatgagaca | 180 |
| gtgtgagtga | ggggtctgtt | atatgggagg | gggtgaggct | tgtamggggt | atggatgaat | 240 |
| ttggaatgtg | aattggagtc | tagagattct | tctccgactt | tggggagcac | ttgctctcac | 300 |
| ttctttctgt | gtgttttctg | ttttcagctt | gttttctaa | ttctgcagct | tccctctgat | 360 |
| acaatatgta | tcattggtgc | tttcattgag | agatttgttc | caatcascat | atgcaaacga | 420 |
| ggatgacgtc | ctgcctygat | gctgttgaat | aaaaaawmtc | taccatcgac | ttcmtccttm | 480 |
| aawcwcatcw | ycaaymamtt | makywacatt | ccdyycmcat | ggtcawagsh | dkt | 533 |

<210> SEQ ID NO 364
<211> LENGTH: 518
<212> TYPE: DNA
<213> ORGANISM: Artificial Sequence
<220> FEATURE:
<223> OTHER INFORMATION: Consensus reference sequence

<400> SEQUENCE: 364

| | | | | | |
|---|---|---|---|---|---|
| ccatagatct | gaaacagaga | tcacaaggtt | aacgctttta | ttctccattg | gatgttaccc | 60 |
| caaacacccc | gyacctataa | tctagcacca | atccaacccg | ttttcactcg | gatctaggac | 120 |
| ctcaggtaat | cccccatgaa | ttttcaatta | ttatcaatgc | ttttttcaact | ttagtttatt | 180 |
| aattcagcya | gggtttagtg | tctaagtgaa | taaggttggg | atttgygatg | gctccgacra | 240 |
| tgrtccggaa | ggtgattgag | gtggtgaagg | accagaccar | cataggaata | gtcaaggtcg | 300 |
| cgagcaacat | ggcgtcggag | atggaggtca | cgattgtgaa | ggcgatgagc | cacgaagatg | 360 |
| accctgycag | tgacaagtac | ataagaraga | tcttgaacct | catgtctcac | tcryrcgrct | 420 |
| acatccacac | atgtgtcacc | gccatgtcca | agcgattggg | taagatgcrc | gaatggattg | 480 |
| tgtcgctcaa | ggcrctgatg | ctcgtgaaca | ggctcatg | | | 518 |

<210> SEQ ID NO 365
<211> LENGTH: 532
<212> TYPE: DNA
<213> ORGANISM: Artificial Sequence
<220> FEATURE:
<223> OTHER INFORMATION: Consensus reference sequence

<400> SEQUENCE: 365

| | | | | | |
|---|---|---|---|---|---|
| gtagcataac | tgaaaatata | aattcccaat | gctcctattc | ttcaagaagc | aattcaaact | 60 |
| ataagacaag | ttatatgacc | ttcaaaagtg | tgcccataga | aagtgtgttt | ttaaggtttt | 120 |
| tcgttgtcct | ggtaataatt | taactaacta | gatggcttgt | agtactgtca | gaacatgttc | 180 |
| tcacttgtta | aatttctatt | ttgtggtacg | gtcccagctc | aaagatgttt | gctttataca | 240 |
| aattacgcgt | tacaaattaa | agcatgttaa | acaaggttta | tgagagagga | agttttgacg | 300 |
| trattcaaag | ccaaaccaat | aagtggttag | acatgtattt | ataatagaac | atagatttac | 360 |
| cataacagcc | atagattaat | attccaagct | aattaagtgg | ttgacaaccc | cgacaatacc | 420 |
| aatatatact | gaaattcctg | attacacgcc | ctctctccaa | cgtgttgctg | aattktcaag | 480 |
| aggctttcct | atgtggctgg | atatattgca | tcacacaaca | tctgggcacc | at | 532 |

<210> SEQ ID NO 366
<211> LENGTH: 590
<212> TYPE: DNA
<213> ORGANISM: Artificial Sequence
<220> FEATURE:
<223> OTHER INFORMATION: Consensus reference sequence

<400> SEQUENCE: 366

```
gaatgcttgt tcacgtaag cttcttgact ttatcrttct ctcccccgcc ccccaaatac      60
cacwaaaatt ccgaacgctg tcatattgca atctaattgt ttaatacccca aatccttccc    120 tagctctttt ccagtatctt gagcttgtaa tcttccatct taaaagcata ctgactgatg    180
caatcttctg attaatttag acctgcatca gttacttgct tgcaagttgt agaatctctt    240
attttycttt tcacttcact ggtttgcatg tccatacaat tcgaactatt ttttatcttt    300
caaagattgg aatgacatta acttggtttt tgatcctaat agataagtca tatcaattta    360
gttcttgaaa gttggagact raatgtcctc taaataaatt gacatcaatg tagatcctca    420
ataatagaaa gatgacatca atttastccc taaatcttgc rgtttgtgca tagaaggatg    480
gttttttggt tactttccac ggttgaggtw ctaaaytgat gcaatatctc ttakggagtt    540
arrrvmmaaa gtgatgtcta ccgaaccttc caaggaactg gccgwmgttt                590
```

<210> SEQ ID NO 367
<211> LENGTH: 650
<212> TYPE: DNA
<213> ORGANISM: Artificial Sequence
<220> FEATURE:
<223> OTHER INFORMATION: Consensus reference sequence

<400> SEQUENCE: 367

```
ammakytatg accatkcgaa ccttccaass mccaaaakgr awtttcactc ywaaatwtat      60
gtscactcct gactgctttt acatttagtg tyttcatttc attgggtttc rtctatcaga    120
attcagtgat aagaaacagt gcttcaacaa taggttgtgg aacatgtttt tytgagaggt    180
aaggtagtca caatgaaaaa aaggacaaaa cttagatcca aagctatgtt gcattgatta    240
acaaagtaat cacataattt tggtgtcatt ttctaataag aattggagtt tcatcttgaa    300
agtttatgtt gacctgtaat gcaaacctgt attgcataga ttagtgaagt aaaactttgt    360
tttttattag agaataacat caaaagcatt tatggatctg catgagtttt ktcctaaaaa    420
ggtgtgaaat agggggaaaa aagccacact ggatgtcaaa accattgttc atctggtata    480
tattttcatc tccwtatgat arttttttt tcttttctga tttcttgtga aatatattaa      540
ttaactkcct tcttttacak gtaaatgaga atgttgttaa ttaatatgtt aacctaaacs    600
atatctttaa tgygttkyca tyttctwttc gttttgcagt gatggtatcc                650
```

<210> SEQ ID NO 368
<211> LENGTH: 765
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 757
<223> OTHER INFORMATION: n = A,T,C or G

<400> SEQUENCE: 368

```
stattgcacs cgcttttcgt cccggtcaag aaaagatggt ttatgtgtat cagctcttgg      60
caacaggcac attggaggaa gataagtaca taagaaccac ttggaaagag tgggttacta    120
```

```
gcatgatttt tagtgaggct tttgaggaga acccttcaca ctcgcgagca tagaacattg    180
aagatgatmt actgagggaa atggttgagg aggacacgtc taaagcaatt catatgattc    240
taaagaatga aaaggcttca ayaaattgaa gagaggtaat tacgcttttt tcatatgaaa    300
acatgtgctt aatttatgtt tatatatctt aatcctacat tctccctatt agtgttattt    360
acagtgtttg cactagatca ctagaatgct tgttggcatt caccttcagt gttggagaca    420
gatttgacac ttgtcgtctc gaatgccagg gcaagttcga gtttagtaga aacttatcat    480
ccaaaattaa aattgaaagc actaatacaa aatgcacaat ttgaagccat tcatgtcctc    540
tcttggtctg agtcttgtca ttttgtggat tgaattcatg gtttctctta tccggtgaca    600
ttgttrmcaa gtaatactac tataaattca gatttggata tcagataacc atggtcatta    660 atagtaaatac taacatacta tacatataat accttacagg accttgtccg aaacttgaaa    720
caggatcagg gacagcgaaa aacaaacatg gtcawancyk kttyy                    765
```

`<210>` SEQ ID NO 369
`<211>` LENGTH: 637
`<212>` TYPE: DNA
`<213>` ORGANISM: Artificial Sequence
`<220>` FEATURE:
`<223>` OTHER INFORMATION: Consensus reference sequence

`<400>` SEQUENCE: 369

```
ttacaaatag grraaaactt agatatacat agttctttaa gtttgattac attacaaata    60
ggagaaaact taaayatrca tagttcttta agtgttgtgt gtgctgttcc ataattagaa    120
ttggagtttt acttaccttta gtaatatgta taattctaat tggagaacag tacaaacaaa    180
aacacctaak gaacaatacc ttagttttaa tcatatttgt tttgttcata tagcttatca    240
ataagtgaag tattttcttg ttcatcttga tgcaggtggt ggaactgaaa ccttcattga    300
ttggccaaca aggatgaaaa tagcacagga catgrctcgt ggcttgtttt gtcttcattc    360
cctggagaac attatacatg ggaacctcac atccagcaat gtgttgcttg atgagaacac    420
aaatgctaaa attgcagatt ttggtctttc tcggttgatg tcaactgctg ctaactccaa    480
cgtgatagct actgctggag cattgggata ccgggcacca gagctctcaa agctcaagaa    540
agcaaacact aaaactgata tatacagtct tggtgttatc ttgttagaac tcctaactag    600
gaagtcacct ggggtgtcta tcatggycaw agctkkt                             637
```

`<210>` SEQ ID NO 370
`<211>` LENGTH: 670
`<212>` TYPE: DNA
`<213>` ORGANISM: Artificial Sequence
`<220>` FEATURE:
`<223>` OTHER INFORMATION: Consensus reference sequence

`<400>` SEQUENCE: 370

```
ttgcgtaatc tttctgttct gattttgagt aggaaccaat ttagtggaca tattccttca    60
agcattgcaa acatttccat gcttaggcag cttgatttgt cactgaataa tctcagtgga    120
gaaattccag tctccttttga aagtcaacgt agtcttgatt tcttcaatgt ttcttacaat    180
agcctttcag gttctgttcc acctctactt gccaagaaat ttaactcaag ctcatttgtg    240
ggaaatattc aactatgtgg gtatagccct tcaaccccat gtctttcaca agctccatca    300
caaggagtca ttgccccaac tccagaagta ctgtcagaac agcaccatcg taggaacctc    360
agtaccaaag acataattct catagtagca ggagttctcc tagtagtcct gattatactt    420
```

```
tgttgcatcc tgcttttctg cttgatcaga aagagatcaa catcgaaggc tgagaacgga      480
caagccacgg ggagagcagc crctggaagg acagaaaaag gagtccctcc agtttctgct      540
ggtgatgttg aagcaggtgg ggaggctgga gggaaactag tccattttga tggaccattg      600
gcttttacag ccgatgatct cttgtgtgca actgctgaga tcatgggaaa gagccatggt      660
catagcctgt                                                              670
```

<210> SEQ ID NO 371
<211> LENGTH: 695
<212> TYPE: DNA
<213> ORGANISM: Artificial Sequence
<220> FEATURE:
<223> OTHER INFORMATION: Consensus reference sequence

<400> SEQUENCE: 371

```
tttgtttctc ttatgtatgt ggagtcttgt tgtgctccct tcatgcgtga gaccagcttt       60
gtgtgaagat gaaagttggg acggagtggt tgtgacagca tcaaacctct tagcacttca      120
agctttcaag caagagttgg tggacccaga agggttcttg cggagctgga acgacagtgg      180
ctatggtgct tgttcaggag gttgggttgg aatcaagtgt gctcagggac aggttatcgt      240
gatccagctt ccttggaagg gtttgaaggg tcgaatcact gacaaaattg gccaacttca      300
aggccttagg aagcttagtc ttcatgataa ccaaattggt ggttcaatcc cttcaacttt      360
gggacttctt cccaacctta gaggggttca gttattcaac aataggttaa ctggttccat      420
cccttcttct ttaggtttct gtcctttgct tcagtctctt gacctcagca acaacttgct      480
cacmggagca atcccttata gccttgccaa ttccaccaag ctttattggc ttaacttgag      540
tttcaactcc ttctctggta ctttaccaac tagcctaact cactcatttt ctctcacttt      600
cctttctctt caaataata atctttctgg caaccttcct aactcttggg gtgggagtcc      660
caagagtggc ttctttaggc atggtcatag ctgtt                                  695
```

<210> SEQ ID NO 372
<211> LENGTH: 788
<212> TYPE: DNA
<213> ORGANISM: Artificial Sequence
<220> FEATURE:
<223> OTHER INFORMATION: Consensus reference sequence

<400> SEQUENCE: 372

```
gtatttgatt agttaaaccg caacgcggaa tctcttttct cgaactggct aactctcagg       60
caagtggttc ggacgctgat tccagcaaca agcggctggt gctcgcactg tatgacgccc      120
taaactccgg cgactccgac gccgtcgtca agatcgtcgc cgccgacctc gagtggtggt      180
tccatggtcc gccctcacac cagttttttga tgcgcatgct caccggcgac tccgctgccg      240
acaactcctt ccgcttcctt ccgcagtcca tgccgccctt cggctccacc gtcatcgtcg      300
agggctgcga caccgcccgc aacattgcct gggtccacgc ctgcaccgtc acggatggga      360
taattactca gatcagagag tacttcaaca ccgccctcac cgtcacccgc atccacgatt      420
ccggcgagat tgttccggct agctccggcg ccggccgttt gccccctgtgt ctgggaaagc      480 agcgtctccg gtcgggtcgg gaaatcccgta cccggtttgg ttcttgcaat ataaaataat      540
tattaacaag taattaggga agaacgcggt cacgtgtgaa taataattaa ataaggaggt      600
tgtgcacgtg gcggtgactg ggtcgaacgg tttcagggaa cattgatata ttttcgtagt      660
attggtgtgt tctrgaggtt agagagatgt gagaccctat tggtgggggtt tcttatttct      720 ttaatttct caggtttggt ttgttttttgt tttgtttgct tgtgtgtttt gggcatggtc      780
```

```
atagcckk                                                              788

<210> SEQ ID NO 373
<211> LENGTH: 679
<212> TYPE: DNA
<213> ORGANISM: Artificial Sequence
<220> FEATURE:
<223> OTHER INFORMATION: Consensus reference sequence

<400> SEQUENCE: 373
tattttaatt aagaaaataa aggagtttgt ttatgctgca atttatgatc tagatccaat     60
atagggaaga tgaatgctag taaggcacta tttattgggt aaaatccatg tgggtcccaa    120
tccatattta ctagttctca ctccgtactt agtgtaactt acatgtgtca tccgattatg    180
gagtgttgtg ctagcatttc tcttatatag ggaattaggg atacaaaatg gctttcccta    240
cttttcgtgg gcaaccccaa tttgataact tggccacttt atggctagac ttcagcctaa    300
tttatgtact agatatagta tatgaattta tacataactt cacatgccct gaaattttcc    360
acttgatttg caggcaattg tgacagaaga ggatggaatg gagtcaatag ctcatagatt    420
tctttctgct gctgtcaagg tagagttcca tccacctgat tctattttg atgaaatgtt     480
tctggcttga aattattact atatttatta ttgtatttta acacttgyct ttacaacatg    540
tagtataata ctataattac actcatgcaa gtttccaggt ccatctttac aaaattgtaa    600
atactaacac tgcagraatt tggaaagtta tagtagtagt cgtctaccat ctacggccaa    660
amcmwkgkym wwrsybkkt                                                  679

<210> SEQ ID NO 374
<211> LENGTH: 765
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 742
<223> OTHER INFORMATION: n = A,T,C or G

<400> SEQUENCE: 374
ggsttyccca aataggtcag cctctccata aaccctcaag agcgtattat agctaatgac     60
gttgggttga atccccattt tcctcatgct ccagaagagg cggtcggctt ccttgggcat    120
gtgaagctgg ccataaacat caatcatgat gttacaagtg gtgagatcaa gagggcattt    180
agcttcattc atttcggara atagagaaag tgcttcaaca aacttttggt tgtcaacgta    240
gatggcaaga agggtggaat agctgacggt gtcgggttga acggcattgt ctctcatctc    300
ttgaagaaga aggcgagcct cacggaagag cttggctttt ccaaagacat tgatcatgga    360
gttataagca ataaggtcgg gggtaatagt ggaggctttc aatctggaga agatagaaat    420
ggccttggaa taatcggaca acttgcgggc aaggtcaatc aagttactgt agagaacgag    480
gtcgccggag acgttgtctt gctccatctg ctggagccaa agagggaag aatcaaacaa     540
gccgtgtttg ccgaaacaag taattagggt ggagtaagtg tacctatcgg gggagaggcc    600
cttttggcgc atttcatcga acaggccgtg tgcgaggtgc cactgcttgg cccgaaggac    660
gttgcggaga aggacgtggt gggcgamgwk gsrgrramrr wmgwkgbmck yswmswkkrw    720
ssvwbgdymk agsbbbttby mnwtgatccm tggtcatagc ykktt                    765

<210> SEQ ID NO 375
```

<211> LENGTH: 735
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 708
<223> OTHER INFORMATION: n = A,T,C or G

<400> SEQUENCE: 375

```
gwcwmkwwtt kgcamasrmk cvargctcga cmctgktcta taatcttacc cctgatagaa      60
ccttcaagtt caggccttgg agctccggtg aaagtgaaca agtatggccg cttttgatgt     120
ctgattttc tctgccaccg gtaaacatga gtgtcctctg atgggtggaa agaagttggg     180
tacggaattg cgtagtcatt attccacgaa cttgcttcaa ctgctaacat ggacatgttc     240
atggattcgg gtataaacct gaacttacta ccccaatagg acgcatcatc atattgtctc     300
ctgaaatccc aagcaatcct cccagaaaca aggaaatgat ctctgcccca catttkcttc     360
cactcgggtc tttttgcgac ccattgaaga agatcacgac cagaggaatc tctctctgtg     420
agattagaga gccaaaggaa acggctaaca tcaagaccag catagaatgg gacgaaaatt     480
gcagaggcga gggaggaatc gttggtcaag cagccatatt tggtcatcct gttgtgaaaa     540
ataacttcca acaagaactg gttggtggca tagcaagtgt tgttggagaa aagcccttgg     600
gagtaggtaa tgtgaggacc taaaccattg ttttgcatgt atggacacat gttgggtttg     660
tcagtgcctc tagtgaggga ctggcaattc tgaagcaagt aatcgttnaa gcgggagcat     720
ggtcatagcb kkttt                                                      735
```

<210> SEQ ID NO 376
<211> LENGTH: 663
<212> TYPE: DNA
<213> ORGANISM: Artificial Sequence
<220> FEATURE:
<223> OTHER INFORMATION: Consensus reference sequence

<400> SEQUENCE: 376

```
tacbtaattt taagtaggtt gaaatgtytc ttacccttg tatgagatct ctgtttgatt      60
caccctagaaa gtgttccttc acaagtgaca tatataattg aatcggtgag caagggaaac     120
atgcggaaga tcaayagcag ttaaacattg aymaaagaaa gaaagsataa ttgacctcat     180
accttwcgtt gtagatcaga aagctgatcc agcatgaatt gggtctgcat atatagaatg     240
ctatgagaaa agttgatata gaccattgac cattggagatt atatgaagg ttatgagaaa     300
gatcaactaa tttcttctat tctttattgc acagctaaaa aaaaaatgat tatatatgtc     360
aaaatggaaa ttggcaacgt tggaaacttt agtaccctta ttgatctgat ttgtttcaaa     420
gacgaatcta gctgcctttc aagtgactca agctctttgc tgcttagagg accaagatct     480
tctcccataa ggttcctaat gagtatcgac cagtcaaata tatattaata actcatcagt     540
tcgtattatg tagctagcat atacttctag acatagtcga gtctagctct ttacctttga     600
gaacgctgaa gagcttcata acgcgcttc agcctcaagt attcttcatg gtcatagcyk     660
ktt                                                                   663
```

<210> SEQ ID NO 377
<211> LENGTH: 712
<212> TYPE: DNA
<213> ORGANISM: Artificial Sequence
<220> FEATURE:
<223> OTHER INFORMATION: Consensus reference sequence

```
-continued

<220> FEATURE:
<221> NAME/KEY: misc_feature
<222> LOCATION: 12
<223> OTHER INFORMATION: n = A,T,C or G

<400> SEQUENCE: 377
kwrtwaactt cnattccwta tcrtctctat gatcaryats rgcataagtt tcagaagaag        60
taattggaga gttgtcttca accaaaagtt tcccttcctt agctgcaacg aacasgtcct       120
gaataggacc atacaaggca ttgtgatttg ttctgttagg tggctgcgga aaatcagtca       180
aactctccct tatcaaacta cattgtttct ctatgcttaa tgccccagga ataaaataaa       240
agcctgcaaa ttaagtatca ccaagtgtgc ttgagttcat tagttacaaa tgcacttatg       300
attagtttct aatcactaat taattatccc agtcaagtac aattcaagcc atttgtttca       360
agttactaag ataaacggca aataaaagaa aaagaaaat acctgggcga ttttgtaaag        420
caaaaaccgg agaggtgaac ttgtcgtgaa gaacgataac acccgaagga agcacagcgt       480
tttggtgata gcattctaga atagatctaa agtcaaggac ctccgctaag tccacgggtt       540
taggttgttt tttcctgtta agaaagggaa tttcaattas aatttgcaga gattacaact       600
gaaacaatct acgttcaaag gaaatgaaat agtaaaatac tttttgttct tggaagaagc       660
attgtagtcs tagtagagct tgtacttctt ctctgcatgg tcawagcskk tt              712
```

GENETIC LOCI ASSOCIATED WITH SOYBEAN CYST NEMATODE RESISTANCE AND METHODS OF USE

CROSS-REFERENCE TO RELATED APPLICATIONS

This application claims the benefit of U.S. Provisional Application No. 61/745,002, filed Dec. 21, 2012, which is hereby incorporated herein in its entirety by reference.

FIELD OF THE INVENTION

This invention relates to methods of identifying and/or selecting soybean plants or germplasm that display improved resistance to Soybean Cyst Nematode.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 430287seqlist.txt, a creation date of Feb. 26, 2013 and a size of 111 KB. The sequence listing filed via EFS-Web is part of the specification and is hereby incorporated in its entirety by reference herein.

BACKGROUND

Soybeans (*Glycine max* L. Merr.) are a major cash crop and investment commodity in North America and elsewhere. Soybean oil is one of the most widely used edible oils, and soybeans are used worldwide both in animal feed and in human food production. Additionally, soybean utilization is expanding to industrial, manufacturing, and pharmaceutical applications.

Soybean Cyst Nematode (SCN) is a parasitic pest which has threatened soybean production in the U.S. for more than fifty years. Soybean cyst nematode resistance is an economically important trait as infection can substantially reduce yields. Molecular characterization of soybean cyst nematode resistance would have important implications for soybean cultivar improvement.

There remains a need for soybean plants with improved resistance to soybean cyst nematode and methods for identifying and selecting such plants.

SUMMARY

Various methods and compositions are provided for identifying and/or selecting soybean plants or soybean germplasm with improved resistance to soybean cyst nematode. In certain embodiments, the method comprises detecting at least one marker locus that is associated with resistance to soybean cyst nematode. In other embodiments, the method further comprises detecting at least one marker profile or haplotype associated with resistance to soybean cyst nematode. In further embodiments, the method comprises crossing a selected soybean plant with a second soybean plant. Further provided are markers, primers, probes and kits useful for identifying and/or selecting soybean plants or soybean germplasm with improved resistance to soybean cyst nematode, as well as soybean plants and seeds comprising one or more soybean cyst nematode loci.

BRIEF DESCRIPTION OF THE FIGURES

FIG. 1 A-C provides a genetic map for loci on linkage group C1.

FIG. 2 A-B provides a genetic map for loci on linkage group B1.

FIG. 3 A-D provides a genetic map for loci on linkage group D2.

FIG. 4 A-D provide a genetic map for loci on LG B1. Genetic map positions are based on the public integrated map (Hyten et al. (2010) Crop Sci 50:960-968). Physical map positions are based on the public physical map Glyma1 Williams82 soybean reference assembly (Schmutz et al. (2010) Nature 463:178-183; and phytozome.net/soybean).

FIG. 5 A-C provides a genetic map for loci on linkage group D1b.

FIG. 6 A-C provides a genetic map for loci on linkage group C2.

FIG. 7 A-B provides a genetic map for loci on linkage group B2.

FIG. 8 A-B provides a genetic map for loci on linkage group E.

FIG. 9 A-B provides a genetic map for loci on linkage group L.

DETAILED DESCRIPTION

Before describing the present invention in detail, it is to be understood that this invention is not limited to particular embodiments, which can, of course, vary. It is also to be understood that the terminology used herein is for the purpose of describing particular embodiments only, and is not intended to be limiting.

Certain definitions used in the specification and claims are provided below. In order to provide a clear and consistent understanding of the specification and claims, including the scope to be given such terms, the following definitions are provided:

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include examples encompassed by the terms "consisting essentially of" and "consisting of." Similarly, the term "consisting essentially of" is intended to include examples encompassed by the term "consisting of."

"Agronomics," "agronomic traits," and "agronomic performance" refer to the traits (and underlying genetic elements) of a given plant variety that contribute to yield over the course of a growing season. Individual agronomic traits include emergence vigor, vegetative vigor, stress resistance, disease resistance or resistance, insect resistance or resistance, herbicide resistance, branching, flowering, seed set, seed size, seed density, standability, threshability, and the like.

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term "amplifying" in the context of nucleic acid amplification is any process whereby additional copies of a selected nucleic acid (or a transcribed form thereof) are produced. An "amplicon" is an amplified nucleic acid, e.g., a nucleic acid that is produced by amplifying a template nucleic acid by any available amplification method An "ancestral line" is a parent line used as a source of genes, e.g., for the development of elite lines.

An "ancestral population" is a group of ancestors that have contributed the bulk of the genetic variation that was used to develop elite lines.

"Backcrossing" is a process in which a breeder crosses a progeny variety back to one of the parental genotypes one or more times.

The term "chromosome segment" designates a contiguous linear span of genomic DNA that resides in planta on a single chromosome. "Chromosome interval" refers to a chromosome segment defined by specific flanking marker loci.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic linkage relationships among loci on one or more chromosomes (or linkage groups) within a given species, generally depicted in a diagrammatic or tabular form.

"Genotype" is a description of the allelic state at one or more loci.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Introgression" means the entry or introduction of a gene, QTL, haplotype, marker profile, trait, or trait locus from the genome of one plant into the genome of another plant.

The terms "label" or "detectable label" refer to a molecule capable of detection. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state non-radiatively transfers to the quencher where it either dissipates non-radiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, resistance, etc.).

"Linkage" refers to the tendency for alleles to segregate together more often than expected by chance if their transmission was independent. Typically, linkage refers to alleles on the same chromosome. Genetic recombination occurs with an assumed random frequency over the entire genome. Genetic maps are constructed by measuring the frequency of recombination between pairs of traits or markers, the lower the frequency of recombination, and the greater the degree of linkage.

"Linkage disequilibrium" or "LD" is a non-random association of alleles at two or more loci and can occur between unlinked markers. It is based on allele frequencies within a population and is influenced by but not dependent on linkage.

"Linkage group" (LG) refers to traits or markers that generally co-segregate. A linkage group generally corresponds to a chromosomal region containing genetic material that encodes the traits or markers.

"Locus" is a defined segment of DNA.

A "map location" or "map position" is an assigned location on a genetic map relative to linked genetic markers where a specified marker can be found within a given species. Map positions are generally provided in centimorgans (cM), unless otherwise indicated, genetic positions provided are based on the *Glycine max* consensus map v 4.0 as provided by Hyten et al. (2010) Crop Sci 50:960-968. A "physical position" or "physical location" or "physical map location" is the position, typically in nucleotides bases, of a particular nucleotide, such as a SNP nucleotide, on a chromosome. Unless otherwise indicated, the physical position within the soybean genome provided is based on the Glyma 1.0 genome sequence described in Schmutz et al. (2010) Nature 463:178-183, available from the Phytozome website (phytozome-dot-net/soybean).

"Mapping" is the process of defining the linkage relationships of loci through the use of genetic markers, populations segregating for the markers, and standard genetic principles of recombination frequency.

"Marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest.

"Marker assisted selection" refers to the process of selecting a desired trait or traits in a plant or plants by detecting one or more nucleic acids from the plant, where the nucleic acid is linked to the desired trait, and then selecting the plant or germplasm possessing those one or more nucleic acids.

"Haplotype" refers to a combination of particular alleles present within a particular plant's genome at two or more linked marker loci, for instance at two or more loci on a particular linkage group. For instance, in one example, two specific marker loci on LG-O are used to define a haplotype for a particular plant. In still further examples, 3, 4, 5, 6, 7, 8, 9, 10, 11, 12, 13, 14, 15, 16, 17, 18, 19, 20, or more linked marker loci are used to define a haplotype for a particular plant.

As used herein, a "marker profile" means a combination of particular alleles present within a particular plant's genome at two or more marker loci which are not linked, for instance two or more loci on two or more different linkage groups or two or more chromosomes. For instance, in one example, a particular combination of marker loci or a particular combination of haplotypes define the marker profile of a particular plant.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells and the like.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid," "nucleic acid molecule," "nucleic acid sequence," "nucleic acid fragment," and "oligonucleotide" are used interchangeably herein to indicate a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Resistance and "improved resistance" are used interchangeably herein and refer to any type of increase in resistance or resistance to, or any type of decrease in susceptibility. A "resistant plant" or "resistant plant variety" need not possess absolute or complete resistance. Instead, a "resistant plant," "resistant plant variety," or a plant or plant variety with "improved resistance" will have a level of resistance or resistance which is higher than that of a comparable susceptible plant or variety.

"Self-crossing" or "self-pollination" or "selfing" is a process through which a breeder crosses a plant with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome.

The term "yield" refers to the productivity per unit area of a particular plant product of commercial value. For example, yield of soybean is commonly measured in bushels of seed per acre or metric tons of seed per hectare per season. Yield is affected by both genetic and environmental factors.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Typically, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein, culture media or other chemical components.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Methods are provided for identifying and/or selecting a soybean plant or soybean germplasm that displays improved resistance to soybean cyst nematode. The method comprises detecting in the soybean plant or germplasm, or a part thereof, at least one marker locus associated with resistance to soybean cyst nematode. Also provided are isolated polynucleotides and kits for use in identifying and/or detecting a soybean plant or soybean germplasm that displays improved resistance to soybean cyst nematode, and soybean plants, cells, and/or seeds comprising at least one marker locus conferring improved resistance to soybean cyst nematode, and soybean plants, cells, and/or seeds comprising at least one marker locus conferring improved resistance to soybean cyst nematode.

Provided herein are marker loci associated with soybean cyst nematode resistance that have been identified and mapped to genomic loci on linkage groups D b, B2, B1, C2, E, C1, D2, and L. These genomic regions represent both major and minor QTLs associated with soybean cyst nematode resistance.

These findings have important implications for soybean production, as identifying markers that can be used for selection of soybean cyst nematode resistance will greatly expedite the development of soybean cyst nematode resistance into elite cultivars.

Marker loci, haplotypes and marker profiles associated with resistance to soybean cyst nematode, are provided. Further provided are genomic loci that are associated with soybean resistance to soybean cyst nematode.

In certain embodiments, soybean plants or germplasm are identified that have at least one favorable allele, marker locus, haplotype or marker profile that positively correlates with resistance or improved resistance to soybean cyst nematode. However, in other embodiments, it is useful for exclusionary purposes during breeding to identify alleles, marker loci, haplotypes, or marker profiles that negatively correlate with resistance, for example, to eliminate such plants or germplasm from subsequent rounds of breeding.

In one embodiment, marker loci useful for identifying a first soybean plant or first soybean germplasm that displays improved resistance to soybean cyst nematode are between about marker Sat_123 and about marker Satt453 on linkage group B1. In a specific embodiment, the marker locus comprises one or more of S04196-1-B, S04938-1-A, S04937-1-Q1, S08344-1-Q1, S08343-1-Q1, S08346-1-Q1, S06786-1, S06787-1, S06803-1, S04197-1 or a closely linked marker.

In another embodiment, marker loci useful for identifying a first soybean plant or first soybean germplasm that displays improved resistance to soybean cyst nematode are between about marker Sat_207 and about marker Satt713 on linkage group C1. In a specific embodiment, the marker locus comprises S07162-1-Q1, or a closely linked marker.

In yet another embodiment, marker loci useful for identifying a first soybean plant or first soybean germplasm that displays improved resistance to soybean cyst nematode are between about marker Satt574 and about marker Satt615 on linkage group D2. In a specific embodiment, the marker locus comprises S07161-1-Q1, or a closely linked marker.

Non-limiting examples of marker loci located within, linked to, or closely linked to these genomic loci are provided in Table 1 and Table 9 and FIGS. 1, 2, 3, 4, 5, 6, 7, 8 and 9.

TABLE 1

Marker Positions For Marker Loci Associated With Resistance to Soybean Cyst Nematode.

| Marker Name | Linkage Group | Flanking Public Markers* | Public Map Position Region (CM)* | Public Physical Map Position Region* | Marker Physical Map Position** | Allele (R/S) | Source |
|---|---|---|---|---|---|---|---|
| S04196-1-B | B1 | Sat_123-Satt453 | 100.87-123.95 | 37220324-37220725 | 37220579 | *******/CATGCAA | Peking |
| S04938-1-A | B1 | Sat_123-Satt453 | 100.87-123.95 | 36954900-36955533 | 36954994 | C/T | Peking |
| S04937-1-Q1 | B1 | Sat_123-Satt453 | 100.87-123.95 | 36954339-36954916 | 36954799 | T/C | Peking |
| S08344-1-Q1 | B1 | Sat_123-Satt453 | 100.87-123.95 | 36781634-36781933 | 36781754 | C/T | Peking |
| S08343-1-Q1 | B1 | Sat_123-Satt453 | 100.87-123.95 | 37020146-37020659 | 37020399 | C/A | PI437654 |
| S08346- | B1 | Sat_123-Satt453 | 100.87-123.95 | 37020037- | 37020092 | CA . . . G/ | PI437654 |

TABLE 1-continued

Marker Positions For Marker Loci Associated With Resistance to Soybean Cyst Nematode.

| Marker Name | Linkage Group | Flanking Public Markers* | Public Map Position Region (CM)* | Public Physical Map Position Region* | Marker Physical Map Position** | Allele (R/S) | Source |
|---|---|---|---|---|---|---|---|
| 1-Q1 | | Satt453 | 123.95 | 37020146 | | GA . . . T | |
| S06786-1 | B1 | Sat_123-Satt453 | 100.87-123.95 | 37310886-37311630 | 37311443 | A/C | |
| S06787-1 | B1 | Sat_123-Satt453 | 100.87-123.95 | 37333461-37334083 | 37333894 | G/T | |
| S06803-1 | B1 | Sat_123-Satt453 | 100.87-123.95 | 37334355-37335008 | 37334507 | A/G | |
| S04197-1 | B1 | Sat_123-Satt453 | 100.87-123.95 | 37117156-37117406 | 37117244 | C/A | Peking |
| S07162-1-Q1 | C1 | sat_207-satt713 | 87.3-88.94 | 42916694-42916901 | 42916770 | C/T | PI437654 |
| S07161-1-Q1 | D2 | satt574-satt615 | 87.66-91.2 | 34888639-34888798 | 34888681 | A/T | PI437654 |

*Gm composite v4.0 Genetic Map
**JGI Glyma1 assembly

In certain embodiments, multiple marker loci that collectively make up the soybean cyst nematode resistance haplotype of interest are investigated. For example, 2, 3, 4, 5, 6, 7, 8, 9, 10, or more of the various marker loci provided herein can comprise a soybean cyst nematode resistance haplotype. In some embodiments, the haplotype comprises: (a) two or more marker loci found between about marker Sat_123 and about marker Satt453 on linkage group B1; (b) two or more marker loci comprising S04196-1-B, S04938-1-A, S04937-1-Q1, S08344-1-Q1, S08343-1-Q1, S08346-1-Q1, S06786-1, S06787-1, S06803-1, S04197-1 on linkage group B1, or a closely linked marker; (c) two or more marker loci between about marker Sat_207 and about marker Satt713 on linkage group C1; and/or (d) two or more marker loci between about marker Satt574 and about marker Satt615 on linkage group D2.

In one embodiment, marker loci useful for identifying a first soybean plant or first soybean germplasm that displays improved resistance to soybean cyst nematode are in an interval flanked by and including marker locus S00875 and about marker S02621 on linkage group D1b. In some examples, the marker locus is in an interval flanked by and including S00479 and S02136. In some examples, the marker is within 30 cM of one or more of S00479, S02136, S00875, S12875, S12950, S12947, S12933, S12853, S03246, S01519, S12962, S00144, S08166, S08177, S01081, and S02621. In some examples, the marker is within 10 cM of one or more of S00479, S02136, S00875, S12875, S12950, S12947, S12933, S12853, S03246, S01519, S12962, S00144, S08166, S08177, S01081, and S02621. In a specific embodiment, the marker locus comprises one or more of S01519-1-A; S08177-1-Q1; S00479-1-A; S02136-1-A; S00875-1-A; S12875-1-Q1; S12950-1-Q1; S12947-1-Q1; S12933-1-Q1; S12853-1-Q1; S03246-1-A or S12962-1-Q1 S00144-1-A, S08166-1-Q1, S01081, and S02621-1-A, or a marker closely linked thereto.

In another embodiment, marker loci useful for identifying a first soybean plant or first soybean germplasm that displays improved resistance to soybean cyst nematode are in an interval flanked by and including Sat_264 and about BARC-020449-04623 on linkage group B2. In some examples one or more loci are in an interval flanked by and including S02874 and S04785—on linkage group B2. In some examples, the marker is within 30 cM of one or more of S02864 and S04785. In some examples, the marker is within 10 cM of one or more of S02864 and S04785. In a specific embodiment, the marker locus comprises S02874-1-A, S04785-1-A, or a marker closely linked thereto.

In yet another embodiment, marker loci useful for identifying a first soybean plant or first soybean germplasm that displays improved resistance to soybean cyst nematode in an interval flanked by and including S04348 and S01999 on linkage group B1. In some examples, the marker is within 30 cM of one or more of S04348, S01209, or S01999. In some examples, the marker is within 10 cM of one or more of S04348, S01209, or S01999. In a specific embodiment, the marker locus comprises S04348-1-A, S01209-1-A, S01999-1-A, or a marker closely linked thereto.

In another embodiment, marker loci useful for identifying a first soybean plant or first soybean germplasm that displays improved resistance to soybean cyst nematode in an interval flanked by and including S01209 and S01999 on linkage group B1.

In another embodiment, marker loci useful for identifying a first soybean plant or first soybean germplasm that displays improved resistance to soybean cyst nematode associated with one or more marker locus selected from the group consisting of S04937-2-A, S04937-1-Q1, S04938-1-A, S04938-2-A, S06786-2-Q1, S06786-3-Q1, S06786-1-Q1, S06787-2-Q1, S06787-1-Q1, S06803-1-Q1, S06804-1-Q1, S06788-1-Q1, S06805-1-Q1, S06789-1-Q1, S06790-1-Q1, S06791-2-Q1, S06791-1-Q1, S06792-1-Q1.

In another embodiment, marker loci useful for identifying a first soybean plant or first soybean germplasm that displays improved resistance to soybean cyst in an interval flanked by and including Satt557 and Satt307 on linkage group C2. In some examples the interval is flanked by and includes S03252 and S02112 on linkage group C2. In some examples, the marker is within 30 cM of one or more of S03252 or S02112. In some examples, the marker is within 10 cM of one or more of S03252 or S02112. In a specific embodiment, the marker locus comprises S03252-1-A, S02112-1-A, or a marker closely linked thereto.

In another embodiment, marker loci useful for identifying a first soybean plant or first soybean germplasm that displays improved resistance to soybean cyst nematode in an interval comprising the bottom 30 cM of linkage group E, for example from about 66 cM to the end. In some example the interval is flanked by and includes BARC-062799-18070 to the end of linkage group E. In some examples the interval is flanked by and includes Sat_107 to the end of linkage group E. In some examples the interval is flanked by and includes S00350 to S02183 on linkage group E. In some examples, the marker is within 30 cM of one or more of S00350 or S02183. In some examples, the marker is within 10 cM of one or more of S00350 or S02183. In a specific embodiment, the marker locus comprises S00350-1-A, S02183-1-A, or a marker closely linked thereto.

In another embodiment, marker loci useful for identifying a first soybean plant or first soybean germplasm that displays improved resistance to soybean cyst nematode in an interval comprising the top 30 cM of linkage group L, for example from about 0-30 cM. In some examples the interval is flanked by and comprises S02074 and S03991 on linkage group L. In some examples, the marker is within 30 cM of one or more of S02074 or S03991. In some examples, the marker is within 10 cM of one or more of S02074 or S03991. In a specific embodiment, the marker locus comprises S02074-1-A, S03991-1-A, or a marker closely linked thereto.

Non-limiting examples of marker loci located within, linked to, or closely linked to these genomic loci are provided in Table 1 and 9 and FIGS. 1, 2, 3, 4, 5, 6, 7, 8 and 9.

In certain embodiments, multiple marker loci that collectively make up the soybean cyst nematode resistance haplotype of interest are investigated. For example, 2, 3, 4, 5, 6, 7, 8, 9, 10, or more of the various marker loci provided herein can comprise a soybean cyst nematode resistance haplotype. In some embodiments, the haplotype comprises: (a) two or more marker locus flanked by and including S04348 and S01999 on linkage group B1; (b) two or more marker locus within 30 cM of one or more of S04348, S01209, or S01999 on linkage group B1; (c) two or more marker locus within 10 cM of one or more of S04348, S01209, or S01999 on linkage group B1; (d) two or more marker locus comprising S04348-1-A, S01209-1-A, S01999-1-A, or a marker closely linked thereto on linkage group B1; (e) two or more marker locus flanked by and including S01209 and S01999 on linkage group B1; (f) two or more marker locus selected from the group consisting of S04937-2-A, S04937-1-Q1, S04938-1-A, S04938-2-A, S06786-2-Q1, S06786-3-Q1, S06786-1-Q1, S06787-2-Q1, S06787-1-Q1, S06803-1-Q1, S06804-1-Q1, S06788-1-Q1, S06805-1-Q1, S06789-1-Q1, S06790-1-Q1, S06791-2-Q1, S06791-1-Q1, or S06792-1-Q1 on linkage group B1; (g) two or more marker locus flanked by Satt557 and Satt307 on linkage group C2; (h) two or more marker locus flanked by S03252 and S02112 on linkage group C2; (i) two or more marker locus within 30 cM of one or more of S03252 or S02112 on linkage group C2; (j) two or more marker locus within 10 cM of one or more of S03252 or S02112 on linkage group C2; (k) two or more marker locus comprising S03252-1-A, S02112-1-A, or a marker closely linked thereto on linkage group C2; (l) two or more marker locus an interval comprising the bottom 30 cM of linkage group E, for example from about 66 cM to the end; (m) two or more marker locus flanked by BARC-062799-18070 to the end of linkage group E; (n) two or more marker locus flanked by Sat_107 to the end of linkage group E; (o) two or more marker locus flanked by S00350 to S02183 on linkage group E; (p) two or more marker locus within 30 cM of one or more of S00350 or S02183 on linkage group E; (q) two or more marker locus within 10 cM of one or more of S00350 or S02183 on linkage group E; (r) two or more marker locus comprising S00350-1-A, S02183-1-A, or a marker closely linked thereto on linkage group E; (s) two or more marker locus in an interval comprising the top 30 cM of linkage group L, for example from about 0-30 cM; (t) two or more marker locus in an interval is flanked by S02074 and S03991 on linkage group L; (u) two or more marker locus within 30 cM of one or more of S02074 or S03991 on linkage group L; (v) two or more marker locus within 10 cM of one or more of S02074 or S03991 on linkage group L; (w) two or more marker locus comprising S02074-1-A, S03991-1-A, or a marker closely linked thereto on linkage group L; (x) two or more marker locus flanked by marker locus S00875 and about marker S02621 on linkage group D1b; (y) two or more marker locus flanked by S00479 and S02136 on linkage group D1b; (z) two or more maker locus within 30 cM of one or more of S00479, S02136, S00875, S12875, S12950, S12947, S12933, S12853, S03246, S01519, S12962, S00144, S08166, S08177, S01081, and S02621 on linkage group D1b; (aa) two or more marker locus within 10 cM of one or more of S00479, S02136, S00875, S12875, S12950, S12947, S12933, S12853, S03246, S01519, S12962, S00144, S08166, S08177, S01081, and S02621 on linkage group D1b; (ab) two or more marker locus comprising one or more of S01519-1-A; S08177-1-Q1; S00479-1-A; S02136-1-A; S00875-1-A; S12875-1-Q1; S12950-1-Q1; S12947-1-Q1; S12933-1-Q1; S12853-1-Q1; S03246-1-A or S12962-1-Q1 S00144-1-A, S08166-1-Q1, S01081, and S02621-1-A, or a marker closely linked thereto on linkage group D1b; (ac) two or more marker locus flanked by Sat_264 and about BARC-020449-04623 on linkage group B2; (ad) two or more marker locus flanked by S02874 and S04785 on linkage group B2; (ae) two or more marker locus within 30 cM of one or more of S02864 and S04785 on linkage group B2; (af) two or more marker locus within 10 cM of one or more of S02864 and S04785 on linkage group B2; and/or (ag) two or more marker locus comprises S02874-1-A, S04785-1-A, or a marker closely linked thereto on linkage group B2.

In one embodiment, the method of identifying a first soybean plant or a first soybean germplasm that displays improved resistance to soybean cyst nematode comprises detecting in the genome of the first soybean plant or in the genome of the first soybean germplasm at least one haplotype that is associated with the resistance, wherein the at least one haplotype comprises at least two of the various marker loci provided herein.

In certain embodiments, two or more marker loci or haplotypes can collectively make up a marker profile. The marker profile can comprise any two or more marker loci comprising: (a) any marker loci between about marker Sat_123 and about marker Satt453 on linkage group B1; (b) marker loci comprising S04196-1-B, S04938-1-A, S04937-1-Q1, S08344-1-Q1, S08343-1-Q1, S08346-1-Q1, S06786-1, S06787-1, S06803-1, S04197-1 on linkage group B1, or a closely linked marker; (c) any marker loci between about marker Sat_207 and about marker Satt713 on linkage group C1; (d) marker loci comprising S07162-1-Q1 on linkage group C1, or a closely linked marker; (e) any marker loci between about marker Satt574 and about marker Satt615 on linkage group D2; and/or (f) marker loci comprising S07161-1-Q1 on linkage group D2, or a closely linked marker; (g) marker loci comprising S07160-1 on linkage group A2, or a closely linked marker; (h) any marker loci associated with the rhg4 locus on linkage group A2; (i) any marker loci associated with the rhg1 locus on linkage group G, or a closely linked marker; (j) any marker loci associated with the rhg2 locus on linkage group M; and/or (k) any marker loci associated with resistance to soybean cyst nematode.

In certain embodiments, two or more marker loci or haplotypes can collectively make up a marker profile. The marker profile can comprise any two or more marker loci comprising: (a) two or more marker locus flanked by and including S04348 and S01999 on linkage group B1; (b) two or more marker locus within 30 cM of one or more of S04348, S01209, or S01999 on linkage group B1; (c) two or more marker locus within 10 cM of one or more of S04348, S01209, or S01999 on linkage group B1; (d) two or more marker locus comprising S04348-1-A, S01209-1-A, S01999-1-A, or a marker closely linked thereto on linkage group B1; (e) two or more marker locus flanked by and including S01209 and S01999 on linkage group B1; (f) two or more marker locus selected from the group consisting of S04937-2-A, S04937-1-Q1, S04938-1-A, S04938-2-A, S06786-2-Q1, S06786-3-Q1, S06786-1-Q1, S06787-2-Q1, S06787-1-Q1, S06803-1-Q1, S06804-1-Q1, S06788-1-Q1, S06805-1-Q1, S06789-1-Q1, S06790-1-Q1, S06791-2-Q1, S06791-1-Q1, or S06792-1-Q1 on linkage group B1; (g) two or more marker locus flanked by Satt557 and Satt307 on linkage group C2; (h) two or more marker locus flanked by S03252 and S02112 on linkage group C2; (i) two or more marker locus within 30 cM of one or more of S03252 or S02112 on linkage group C2; (j) two or more marker locus within 10 cM of one or more of S03252 or S02112 on linkage group C2; (k) two or more marker locus comprising S03252-1-A, S02112-1-A, or a marker closely linked thereto on linkage group C2; (l) two or more marker locus an interval comprising the bottom 30 cM of linkage group E, for example from about 66 cM to the end; (m) two or more marker locus flanked by BARC-062799-18070 to the end of linkage group E; (n) two or more marker locus flanked by Sat_107 to the end of linkage group E; (o) two or more marker locus flanked by S00350 to S02183 on linkage group E; (p) two or more marker locus within 30 cM of one or more of S00350 or S02183 on linkage group E; (q) two or more marker locus within 10 cM of one or more of S00350 or S02183 on linkage group E; (r) two or more marker locus comprising S00350-1-A, S02183-1-A, or a marker closely linked thereto on linkage group E; (s) two or more marker locus in an interval comprising the top 30 cM of linkage group L, for example from about 0-30 cM; (t) two or more marker locus in an interval is flanked by S02074 and S03991 on linkage group L; (u) two or more marker locus within 30 cM of one or more of S02074 or S03991 on linkage group L; (v) two or more marker locus within 10 cM of one or more of S02074 or S03991 on linkage group L; (w) two or more marker locus comprising S02074-1-A, S03991-1-A, or a marker closely linked thereto on linkage group L; (x) two or more marker locus flanked by marker locus S00875 and about marker S02621 on linkage group D1b; (y) two or more marker locus flanked by S00479 and S02136 on linkage group D1b; (z) two or more maker locus within 30 cM of one or more of S00479, S02136, S00875, S12875, S12950, S12947, S12933, S12853, S03246, S01519, S12962, S00144, S08166, S08177, S01081, and S02621 on linkage group D1b; (aa) two or more marker locus within 10 cM of one or more of S00479, S02136, S00875, S12875, S12950, S12947, S12933, S12853, S03246, S01519, S12962, S00144, S08166, S08177, S01081, and S02621 on linkage group D1b; (ab) two or more marker locus comprising one or more of S01519-1-A; S08177-1-Q1; S00479-1-A; S02136-1-A; S00875-1-A; S12875-1-Q1; S12950-1-Q1; S12947-1-Q1; S12933-1-Q1; S12853-1-Q1; S03246-1-A or S12962-1-Q1 S00144-1-A, S08166-1-Q1, S01081, and S02621-1-A, or a marker closely linked thereto on linkage group D1b; (ac) two or more marker locus flanked by Sat_264 and about BARC-020449-04623 on linkage group B2; (ad) two or more marker locus flanked by S02874 and S04785 on linkage group B2; (ae) two or more marker locus within 30 cM of one or more of S02864 and S04785 on linkage group B2; (af) two or more marker locus within 10 cM of one or more of S02864 and S04785 on linkage group B2; and/or (ag) two or more marker locus comprises S02874-1-A, S04785-1-A, or a marker closely linked thereto on linkage group B2; (ah) marker loci comprising S07160-1 on linkage group A2, or a closely linked marker; (ai) any marker loci associated with the rhg4 locus on linkage group A2; (aj) any marker loci associated with the rhg1 locus on linkage group G, or a closely linked marker; (ak) any marker loci associated with the rhg2 locus on linkage group M; and/or (al) any marker loci associated with resistance to soybean cyst nematode.

Any of the marker loci in any of the genomic loci disclosed herein can be combined in the marker profile. For example, the marker profile can comprise 2, 3, 4, 5, 6, 7, 8, 9, 10, 11, 12, 13, 14, 15, 16, 17, 18, 19, 20, or more marker loci or haplotypes associated with resistance to soybean cyst nematode provided herein.

In one embodiment, a method of identifying a first soybean plant or a first soybean germplasm that displays improved resistance to soybean cyst nematode comprises detecting in the genome of the first soybean plant or in the genome of the first soybean germplasm at least one marker profile that is associated with the resistance, wherein the at least one marker profile comprises at least two of the various marker loci provided herein.

Not only can one detect the various markers provided herein, it is recognized that one could detect any markers that are closely linked to the various markers discussed herein.

In addition to the markers discussed herein, information regarding useful soybean markers can be found, for example, on the USDA's Soybase website, available at soybase.org. One of skill in the art will recognize that the identification of favorable marker alleles may be germplasm-specific. The determination of which marker alleles correlate with resistance (or susceptibility) is determined for the particular germplasm under study. One of skill will also recognize that methods for identifying the favorable alleles are routine and well known in the art, and furthermore, that the identification and use of such favorable alleles is well within the scope of the invention.

Various methods are provided to identify soybean plants and/or germplasm with improved resistance to soybean cyst nematode. In one embodiment, the method of identifying comprises detecting at least one marker locus associated with resistance to soybean cyst nematode. The term "associated with" in connection with a relationship between a marker locus and a phenotype refers to a statistically significant dependence of marker frequency with respect to a quantitative scale or qualitative gradation of the phenotype. Thus, an allele of a marker is associated with a trait of interest when the allele of the marker locus and the trait phenotypes are found together in the progeny of an organism more often than if the marker genotypes and trait phenotypes segregated separately.

Any combination of the marker loci provided herein can be used in the methods to identify a soybean plant or soybean germplasm that displays improved resistance to soybean cyst nematode. Any one marker locus or any combination of the markers set forth in Table 1 and 9 or FIG. 1, 2, 3, 4, 5, 6, 7, 8 or 9, or any closely linked marker can be used to aid in identifying and selecting soybean plants or soybean germplasm with improved resistance to soybean cyst nematode.

In one embodiment, a method of identifying a first soybean plant or a first soybean germplasm that displays improved resistance to soybean cyst nematode is provided. The method comprises detecting in the genome of the first soybean plant or first soybean germplasm an allele of at least one marker locus that is associated with resistance. In such a method, the at least one marker locus: (A) can be between about marker Sat_123 and about marker Satt453 on linkage group B1; (B) can comprise one or more of the marker loci S04196-1-B, S04938-1-A, S04937-1-Q1, S08344-1-Q1, S08343-1-Q1, S08346-1-Q1, S06786-1, S06787-1, S06803-1, S04197-1 on linkage group B1, or a closely linked marker; (C) can be between about marker Sat_207 and about marker Satt713 on linkage group C1; (D) can comprise the marker locus S07162-1-Q1, or a closely linked marker; (E) can be between about marker Satt574 and about marker Satt615 on linkage group D2; and/or (F) can comprise the marker locus S07161-1-Q1, or a closely linked marker.

In one embodiment, a method of identifying a first soybean plant or a first soybean germplasm that displays improved resistance to soybean cyst nematode is provided. The method comprises detecting in the genome of the first soybean plant or first soybean germplasm at least one marker locus that is associated with resistance. In such a method, the at least one marker locus (a) is flanked by S04348 and S01999 on linkage group B1; (b) two or more marker locus within 30 cM of one or more of S04348, S01209, or S01999 on linkage group B1; (c) is within 10 cM of one or more of S04348, S01209, or S01999 on linkage group B1; (d) comprises S04348-1-A, S01209-1-A, S01999-1-A, or a marker closely linked thereto on linkage group B1; (e) is flanked by S01209 and S01999 on linkage group B1; (f) is selected from the group consisting of S04937-2-A, S04937-1-Q1, S04938-1-A, S04938-2-A, S06786-2-Q1, S06786-3-Q1, S06786-1-Q1, S06787-2-Q1, S06787-1-Q1, S06803-1-Q1, S06804-1-Q1, S06788-1-Q1, S06805-1-Q1, S06789-1-Q1, S06790-1-Q1, S06791-2-Q1, S06791-1-Q1, or S06792-1-Q1 or a marker closely linked thereto on linkage group B1; (g) is flanked by Satt557 and Satt307 on linkage group C2; (h) is flanked by S03252 and S02112 on linkage group C2; (i) is within 30 cM of one or more of S03252 or S02112 on linkage group C2; (j) is within 10 cM of one or more of S03252 or S02112 on linkage group C2; (k) comprises S03252-1-A, S02112-1-A, or a marker closely linked thereto on linkage group C2; (l) is in an interval comprising the bottom 30 cM of linkage group E, for example from about 66 cM to the end; (m) is flanked by BARC-062799-18070 to the end of linkage group E; (n) is flanked by Sat_107 to the end of linkage group E; (o) is flanked by S00350 to S02183 on linkage group E; (p) is within 30 cM of one or more of S00350 or S02183 on linkage group E; (q) is within 10 cM of one or more of S00350 or S02183 on linkage group E; (r) comprises S00350-1-A, S02183-1-A, or a marker closely linked thereto on linkage group E; (s) is in an interval comprising the top 30 cM of linkage group L, for example from about 0-30 cM; (t) is in an interval is flanked by S02074 and S03991 on linkage group L; (u) is within 30 cM of one or more of S02074 or S03991 on linkage group L; (v) is within 10 cM of one or more of S02074 or S03991 on linkage group L; (w) comprises S02074-1-A, S03991-1-A, or a marker closely linked thereto on linkage group L; (x) is flanked by marker locus S00875 and about marker S02621 on linkage group D1b; (y) is flanked by S00479 and S02136 on linkage group D1b; (z) is within 30 cM of one or more of S00479, S02136, S00875, S12875, S12950, S12947, S12933, S12853, S03246, S01519, S12962, S00144, S08166, S08177, S01081, and S02621 on linkage group D1b; (aa) is within 10 cM of one or more of S00479, S02136, S00875, S12875, S12950, S12947, S12933, S12853, S03246, S01519, S12962, S00144, S08166, S08177, S01081, and S02621 on linkage group D1b; (ab) comprises one or more of S01519-1-A; S08177-1-Q1; S00479-1-A; S02136-1-A; S00875-1-A; S12875-1-Q1; S12950-1-Q1; S12947-1-Q1; S12933-1-Q1; S12853-1-Q1; S03246-1-A or S12962-1-Q1 S00144-1-A, S08166-1-Q1, S01081, and S02621-1-A, or a marker closely linked thereto on linkage group D1b; (ac) is flanked by Sat_264 and about BARC-020449-04623 on linkage group B2; (ad) is flanked by S02874 and S04785 on linkage group B2; (ae) is within 30 cM of one or more of S02864 and S04785 on linkage group B2; (af) is within 10 cM of one or more of S02864 and S04785 on linkage group B2; and/or (ag) comprises S02874-1-A, S04785-1-A, or a marker closely linked thereto on linkage group B2.

In other embodiments, two or more marker loci are detected in the method. In a specific embodiment, the germplasm is a soybean variety.

In other embodiments, the method further comprises crossing the selected first soybean plant or first soybean germplasm with a second soybean plant or second soybean germplasm. In a further embodiment of the method, the second soybean plant or second soybean germplasm comprises an exotic soybean strain or an elite soybean strain.

In specific embodiments, the first soybean plant or first soybean germplasm comprises a soybean variety. Any soybean line known to the art or disclosed herein may be used. Non-limiting examples of soybean varieties and their associated soybean cyst nematode resistance alleles encompassed by the methods provided herein include, for example, those listed in Table 1 and 9 and FIGS. 1, 2, 3, 4, 5, 6, 7, 8 and 9.

In another embodiment, the detection method comprises amplifying at least one marker locus and detecting the resulting amplified marker amplicon. In such a method, amplifying comprises (a) admixing an amplification primer or amplification primer pair for each marker locus being amplified with a nucleic acid isolated from the first soybean plant or the first soybean germplasm such that the primer or primer pair is complementary or partially complementary to a variant or fragment of the genomic locus comprising the marker locus and is capable of initiating DNA polymerization by a DNA polymerase using the soybean nucleic acid as a template; and (b) extending the primer or primer pair in a DNA polymerization reaction comprising a DNA polymerase and a template nucleic acid to generate at least one amplicon. In such a method, the primer or primer pair can comprise a variant or fragment of one or more of the genomic loci provided herein.

In one embodiment, the method involves amplifying a variant or fragment of one or more polynucleotides comprising SEQ ID NOS: 135, 136, 137, 138, 139, 140, 141, 142, 143, 144, 145, 146, 147, 148, 149, 150, 151, 152, 153, 154, 155, 156, 157, 158, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, and/or 377 or variants or fragments thereof. In one embodiment, the primer or primer pair can comprise a variant or fragment of one or more polynucleotides comprising SEQ ID NOS: 135, 136, 137, 138, 139, 140, 141, 142, 143, 144, 145, 146, 147, 148, 149, 150, 151, 152, 153, 154, 155, 156, 157, 158, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, and/or 377 or complements thereof. In specific embodiments, the primer or primer pair comprises a nucleic acid sequence comprising SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, and/or 248 or variants or fragments thereof.

In a specific embodiment, the primer pair comprises SEQ ID NO: 1 and SEQ ID NO:2, SEQ ID NO: 8 and SEQ ID NO:9, SEQ ID NO: 10 and SEQ ID NO: 13, SEQ ID NO: 18 and SEQ ID NO:19, SEQ ID NO: 31 and SEQ ID NO:32, SEQ ID NO: 39 and SEQ ID NO:40, SEQ ID NO: 50 and SEQ ID NO:51, SEQ ID NO: 64 and SEQ ID NO:65, SEQ ID NO: 66 and SEQ ID NO:67, SEQ ID NO: 72 and SEQ ID NO:73, or SEQ ID NO: 82 and SEQ ID NO:83 or the primer pairs set forth in Table 3.

In another embodiment, the method further comprises providing one or more labeled nucleic acid probes suitable for detection of each marker locus being amplified. In such a method, the labeled nucleic acid probe can comprise a sequence comprising a variant or fragment of one or more of the genomic loci provided herein. In one embodiment, the labeled nucleic acid probe can comprise a sequence comprising a variant or fragment of one or more polynucleotides comprising SEQ ID NOS: 135, 136, 137, 138, 139, 140, 141, 142, 143, 144, 145, 146, 147, 148, 149, 150, 151, 152, 153, 154, 155, 156, 157, 158, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, and/or 377 or complements thereof. In specific embodiments, the labeled nucleic acid probe comprises a nucleic acid sequence comprising SEQ ID NOS: 87, 88, 89, 90, 91, 92, 93, 94, 95, 96, 97, 98, 99, 100, 101, 102, 103, 104, 105, 106, 107, 108, 109, 110, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, and/or 338 or variants or fragments thereof.

Non-limiting examples of primers, probes, genomic loci and amplicons that can be used in the methods and compositions provided herein are summarized in Tables 2, 3, 4, 5, 6, 7, and 8.

TABLE 2

Non-Limiting Examples of Primer Sequences.

| Marker position | Linkage Group (ch) | Locus | Primer Name | SEQ ID NO | Primer Sequence | Allele (Res/Sus) |
|---|---|---|---|---|---|---|
| 37220579 | B1 (Gm11) | S04196-1 | 141527 | 1 | GCCATCCTAGCTAGCCCTGT | *******/CATGCAA |
| 37220579 | B1 (Gm11) | S04196-1 | 141528 | 2 | TTGACCTGTTGATTATTTCGTAATG | *******/CATGCAA |
| 37220579 | B1 (Gm11) | S04196-1 | S4196-F2 | 3 | GCCATCCTAGCTAGCCCTGTATAT | *******/CATGCAA |
| 37220579 | B1 (Gm11) | S04196-1 | S4196-R2 | 4 | GTGTTAGGTGTCATCGAGGCAT | *******/CATGCAA |
| 37220579 | B1 (Gm11) | S04196-1 | S4196-F3 | 5 | TCCTAGCTAGCCCTGTATATTTTGA | CATGCAA |
| 37220579 | B1 (Gm11) | S04196-1 | S4196-R3 | 6 | TAGGTGTCATCGAGGCATCG | *******/CATGCAA |
| 37220579 | B1 (Gm11) | 504196-1 | S4196-R4 | 7 | AATTATCTTGACCTGTTGATTATTTCG | *******/CATGCAA |
| 36954994 | B1 (Gm11) | S04938-1 | S04938-F1 | 8 | CCACAACCTATTGTTGAAGCAC | C/T |
| 36954994 | B1 (Gm11) | S04938-1 | S04938-R1 | 9 | TGTGCACTCCTGACTGCTTT | C/T |

TABLE 2-continued

Non-Limiting Examples of Primer Sequences.

| Marker position | Linkage Group (ch) | Locus | Primer Name | SEQ ID NO | Primer Sequence | Allele (Res/Sus) |
|---|---|---|---|---|---|---|
| 36954799 | B1 (Gm11) | S04937-1 | 141535, S04937-F1 | 10 | TCAACCGTGGAAAGTAACCA | T/C |
| 36954799 | B1 (Gm11) | S04937-1 | 141536 | 11 | GTTCTTGAAAGTTGGAGACTRAATG | T/C |
| 36954799 | B1 (Gm11) | S04937-1 | 148638, | 12 | TCCTTGGAAGGTTCGGTAGA | T/C |
| 36954799 | B1 (Gm11) | S04937-1 | 148639, S04937-1 R3 | 13 | TCAATTTAGTTCTTGAAAGTTGGAGAC | T/C |
| 36954799 | B1 (Gm11) | S04937-1 | S04937-F3 | 14 | AACCGTGGAAAGTAACCAAAAA | T/C |
| 36954799 | B1 (Gm11) | S04937-1 | S04937-F4 | 15 | ACCTCAACCGTGGAAAGTAACC | T/C |
| 36954799 | B1 (Gm11) | S04937-1 | S04937-R4 | 16 | GGAATGACATTAACTTGGTTTTTGA | T/C |
| 36954799 | B1 (Gm11) | S04937-1 | S04937-R5 | 17 | TGACATTAACTTGGTTTTTGATCCT | T/C |
| 36781754 | B1 (Gm11) | S08344-1 | 136830 | 18 | CGACACCAATTFCTCCATCC | C/T |
| 36781754 | B1 (Gm11) | S08344-1 | 136831 | 19 | ATGTCGGAACTTGGCATCTT | C/T |
| 36781754 | B1 (Gm11) | S08344-1 | P12198A1-F(128-)76806 | 20 | CACGACACCAATTTCTCCATCCTCTCA | C/T |
| 36781754 | B1 (Gm11) | S08344-1 | 86074: P12198A-1T66A218F | 21 | CAACATTCCCAGTCGACACGTCTTCT | C/T |
| 36781754 | B1 (Gm11) | S08344-1 | 86075: P12198A-1T66A218R | 22 | AAGGCATGTCGGAACTTGGCATCT | C/T |
| 36781754 | B1 (Gm11) | S08344-1 | 92472-p12198A1_R | 23 | TGATTTCCAATGTAAATCAACCATT | C/T |
| 36781754 | B1 (Gm11) | S08344-1 | 136828 | 24 | AATACCCTTCCACGACACCA | C/T |
| 36781754 | B1 (Gm11) | S08344-1 | 136829 | 25 | CGGAACTTGGCATCTTTGAT | C/T |
| 36781754 | B1 (Gm11) | S08344-1 | 136832 | 25 | TCAAACTTGACAAAGCCACAA | C/T |
| 36781754 | B1 (Gm11) | S08344-1 | 136833 | 27 | TGCAAAGAGGGTAAGGACTTG | C/T |
| 37020399 | B1 (Gm11) | S08343-1 | 19661 | 28 | CCATTTTTGGAGAATCTCGTGTCCGTAG | C/A |
| 37020399 | B1 (Gm11) | S08343-1 | 19389 | 29 | GACTTACCAAATGAGTTTGACCAGGTTTTACC | C/A |
| 37020399 | B1 (Gm11) | S08343-1 | 96347 | 30 | GATGATYCCAAATCTGCTTCA | C/A |
| 37020092 | B1 (Gm11) | S08346-1 | 136886 | 31 | TTGTTCTCCCGYTTACACCA | CA...G/ GA...T |

TABLE 2-continued

Non-Limiting Examples of Primer Sequences.

| Marker position | Linkage Group (ch) | Locus | Primer Name | SEQ ID NO | Primer Sequence | Allele (Res/Sus) |
|---|---|---|---|---|---|---|
| 37020092 | B1 (Gm11) | S08346-1 | 136887 | 32 | TGATACAACGYCCCATTCTTC | CA . . . G/ GA . . . T |
| 37020092 | B1 (Gm11) | S08346-1 | P8584A-1-F2, 82593 | 33 | GGTCAAACTCATTTGGTAAGTCT RAGTTTGC | CA . . . G/ GA . . . T |
| 37020092 | B1 (Gm11) | S08346-1 | Reverse primer 15081 | 34 | CCCATTCTTCATGTACTCATACA CCAAGAG | CA . . . G/ GA . . . T |
| 37020092 | B1 (Gm11) | S08346-1 | 136884 | 35 | TTCTCCCGYTTACACCACAA | CA . . . G/ GA . . . T |
| 37020092 | B1 (Gm11) | S08346-1 | 136885 | 36 | CAACGYCCCATTCTTCATGT | CA . . . G/ GA . . . T |
| 37020092 | B1 (Gm11) | S08346-1 | 136888 | 37 | GGTTGCAATCAAGAGGGGTA | CA . . . G/ GA . . . T |
| 37020092 | B1 (Gm11) | S08346-1 | 136889 | 38 | TGATGATACAACGYCCCATTC | CA . . . G/ GA . . . T |
| 37311443 | B1 (Gm11) | S06786-1 | 144687 | 39 | GCTTTAGACGTGTCCTCCTCA | A/C |
| 37311443 | B1 (Gm11) | S06786-1 | 144688 | 40 | CCACTTGGAAAGAGTGGGTTA | A/C |
| 37311443 | B1 (Gm11) | S06786-1 | S06786-1-Q1F | 41 | AGACGTGTCCTCCTCAACCA | A/C |
| 37311443 | B1 (Gm11) | S06786-1 | S06786-1-Q1R | 42 | AGGAGAACCCTTCACACTCG | A/C |
| 37311443 | B1 (Gm11) | S06786-1 | S06786-1-Q2R | 43 | CACACTCGCGAGCATAGAAC | A/C |
| 37311443 | B1 (Gm11) | S06786-1 | S06786-1-Q3F | 44 | TTCAATTTGTTGAAGCCTTTTCA | A/C |
| 37311443 | B1 (Gm11) | S06786-1 | S06786-1-Q3R | 45 | GAGGAGAACCCTTCACACTCG | A/C |
| 37311443 | B1 (Gm11) | S06786-1 | S06786-1-Q4F | 46 | TAGACGTGTCCTCCTCAACCAT | A/C |
| 37311443 | B1 (Gm11) | S06786-1 | S06786-1-Q4R | 47 | AACCACTTGGAAAGAGTGGGTT A | A/C |
| 37311443 | B1 (Gm11) | S06786-1 | S06786-1-Q5F | 48 | TCAATTTGTTGAAGCCTTTTCA | A/C |
| 37311443 | B1 (Gm11) | S06786-1 | S06786-1-Q5R | 49 | TGAGGCTTTTGAGGAGAACC | A/C |
| 37333894 | B1 (Gm11) | S06787-1 | 142755 | 50 | TGCTGTTCCATAATTAGAATTGG AG | G/T |
| 37333894 | B1 (Gm11) | S06787-1 | 142756 | 51 | CCTGCATCAAGATGAACAAGAA | G/T |
| 37334507 | B1 (Gm11) | S06803-1 | 142759 | 52 | GCCAATGGTCCATCAAAATG | A/G |
| 37334507 | B1 (Gm11) | S06803-1 | 142760 | 53 | AACATCGAAGGCTGAGAACG | A/G |
| 37334507 | B1 (Gm11) | S06803-1 | S06787-1-Q2F | 54 | GTGTTGTGTGTGCTGTTCCA | A/G |
| 37334507 | B1 (Gm11) | S06803-1 | S06787-1-Q2R | 55 | GTTGGCCAATCAATGAAGGT | A/G |

TABLE 2-continued

Non-Limiting Examples of Primer Sequences.

| Marker position | Linkage Group (ch) | Locus | Primer Name | SEQ ID NO | Primer Sequence | Allele (Res/Sus) |
|---|---|---|---|---|---|---|
| 37334507 | B1 (Gm11) | S06803-1 | S06787-1-Q3R | 56 | GGTTTCAGTTCCACCACCTG | A/G |
| 37334507 | B1 (Gm11) | S06787-1-Q4F | | 57 | AGTGTTGTGTGTGCTGTTCCA | A/G |
| 37334507 | B1 (Gm11) | S06803-1 | S06787-1-Q4R | 58 | AGTTCCACCACCTGCATCAA | A/G |
| 37334507 | B1 (Gm11) | S06803-1 | S06803-1-Q1F | 59 | GCTTCAACATCACCAGCAGA | A/G |
| 37334507 | B1 (Gm11) | S06803-1 | S06803-1 Q1R | 60 | GAAGGCTGAGAACGGACAAG | A/G |
| 37334507 | B1 (Gm11) | S06803-1 | S06803-1 Q2F | 61 | CATCACCAGCAGAAACTGGA | A/G |
| 37334507 | B1 (Gm11) | S06803-1 | S06803-1-Q3F | 62 | CTGCTTCAACATCACCAGCA | A/G |
| 37334507 | B1 (Gm11) | S06803-1 | S06803-1-Q3R | 63 | TGCATCCTGCTTTTCTGCTT | A/G |
| 37117244 | B1 (Gm11) | S04197-1 | 142386 | 64 | TGCCTAATGGGAGAGATGAAG | C/A |
| 37117244 | B1 (Gm11) | S04197-1 | S04197-1-F2 | 65 | CGCAGGTTCTGTTACTCGAAG | C/A |
| 37117244 | B1 (Gm11) | S04197-1 | S04197-1-F2 | 66 | AATGCCTAATGGGAGAGATGAA | C/A |
| 37117244 | B1 (Gm11) | S04197-1 | S04197-1-R2 | 67 | TTTATATTGTAGTGTAGGTGCCTTGTC | C/A |
| 37117244 | B1 (Gm11) | S04197-1 | S04197-1-F3 | 68 | TGAATATATAAATGCCTAATGGGAGAGA | C/A |
| 37117244 | B1 (Gm11) | S04197-1 | S04197-1-R3 | 69 | TTGGGTTGAAGCCTTTTATGG | C/A |
| 37117244 | B1 (Gm11) | S04197-1 | S04197-1-F4 | 70 | ACAAGTAAAGTATGGATAAGATGTGCAA | C/A |
| 37117244 | B1 (Gm11) | S04197-1 | S04197-1-R4 | 71 | TCGCAGGTTCTGTTACTCGAA | C/A |
| 42916770 | C1 (Gm04) | S07162-1 | 136849 | 72 | AATGCAGGGCCAGTTACAAT | C/T |
| 42916770 | C1 (Gm04) | S07162-1 | 136850 | 73 | AATTGCCCCATCTTTTCTC | C/T |
| 42916770 | C1 (Gm04) | S07162-1 | 80907 | 74 | CAGTTACAATACATACATACGCATAACCAAAACAGTAACA | C/T |
| 42916770 | C1 (Gm04) | S07162-1 | 80908 | 75 | ACTACTGGATTTTAATGTAGGTTTCTTCCATGTAGCTATG | C/T |
| 42916770 | C1 (Gm04) | S07162-1 | 87501 | 76 | AACCAAAACAGTAACATCAATGGAAC | C/T |
| 42916770 | C1 (Gm04) | S07162-1 | 87504 | 77 | CAAATGGTTGTGTTTTCTTAGAAATTTC | C/T |
| 42916770 | C1 (Gm04) | S07162-1 | 136845 | 78 | ACCAAAACAGTAACATCAATGGAA | C/T |
| 42916770 | C1 (Gm04) | S07162-1 | 136846 | 79 | TTTAATGTAGGTTTCTTCCATGTAGC | C/T |
| 42916770 | C1 (Gm04) | S07162-1 | 136847 | 80 | ACGCATAACCAAAACAGTAACATC | C/T |

TABLE 2-continued

Non-Limiting Examples of Primer Sequences.

| Marker position | Linkage Group (ch) | Locus | Primer Name | SEQ ID NO | Primer Sequence | Allele (Res/Sus) |
|---|---|---|---|---|---|---|
| 42916770 | C1 (Gm04) | S07162-1 | 136848 | 81 | ATGTAGGTTTCTTCCATGTAGCTATG | C/T |
| 34888681 | D2 (Gm17) | S07161-1 | 137370 | 82 | TGCTTATCTTGTCTGAAAACCACT | A/T |
| 34888681 | D2 (Gm17) | S07161-1 | 137374 | 83 | TGACTTTAAGGCAATTCAACTGTATC | A/T |
| 34888681 | D2 (Gm17) | S07161-1 | 137371 | 84 | ACCTAATGTGATGAGCATCCTTAAT | A/T |
| 34888681 | D2 (Gm17) | S07161-1 | 137372 | 85 | CTTGTCTGAAAACCACTAATGCTC | A/T |
| 34888681 | D2 (Gm17) | S07161-1 | 137373 | 86 | CTAATGTGATGAGCATCCTTAATTG | A/T |

TABLE 3

Non-Limiting Examples of Primer Sequences.

| Marker | Linkage Group (ch) | SEQ ID | Primer Sequence | Allele (Res/Sus) |
|---|---|---|---|---|
| S02621-1-A | D1b (2) | 159 | GCAATTCGTCCTTCCAAATG | G/A |
| | | 160 | GAGTGTGCTTTTGCTCGTTG | |
| S01519-1-A | D1b (2) | 161 | cttgtagcgcagctccagat | C/T |
| | | 162 | accatgaagtccttgaagcag | |
| S08177-1-Q1 | D1b (2) | 163 | tttgggaatggagacagagg | T/G |
| | | 164 | gccctattggcattcttgat | |
| S00479-1-A | D1b (2) | 165 | TCATGCACTGCCCATACCTAAAGG | A/G |
| | | 166 | AAACGGATGTGGATGGTTAAGAATTAGAC | |
| S02136-1-A | D1b (2) | 167 | GGCTGCCGTTTATGTTGTTAGCAT | T/C |
| | | 168 | AGGTATTTAGAATCAGTCCAAGAAGTGAATTAACT | |
| S00875-1-A | D1b (2) | 169 | ACGCCTCATTATCCGTGACCCT | A/G |
| | | 170 | TTCACAATTCTGTGCAGCCGAC | |
| S12875-1-Q1 | D1b (2) | 171 | ggacgtggctcaagagagtt | T/C |
| | | 172 | tgaatgtgatcaaaagcgaga | |
| S12950-1-Q1 | D1b (2) | 173 | ggtatgtgcacagatcctatgg | G/T |
| | | 174 | ggcatcatgcaaaacaaaaa | |
| S12947-1-Q1 | D1b (2) | 175 | ttggtgactgatcacaagatacg | A/T |
| | | 176 | tggacaaaaagaagccaaagg | |
| S12933-1-Q1 | D1b (2) | 177 | tcttaggtcgcaaatcacga | G/C |
| | | 178 | tgcaatcatataaggtttcgttg | |
| S12853-1-Q1 | D1b (2) | 179 | tttccgcgatcaactatttt | A/G |
| | | 180 | acgatccctaattgctttgc | |
| S03246-1-A | D1b (2) | 181 | tccgacggtatttgagttaagg | A/G |
| | | 182 | gcaacgtatttatgcaactcca | |
| S12962-1-Q1 | D1b (2) | 183 | ttgccatggaagggtaaagt | A/G |
| | | 184 | tgcaccactgcaattagtttg | |
| S00144-1-A | D1b (2) | 185 | AGCTTCAGAGGCACGACTACCAG | G/C |
| | | 186 | GGCACCATCATCTCCACCAATC | |
| S08166-1-Q1 | D1b (2) | 187 | ttgaattccacacgacatttg | T/C |
| | | 188 | gagcgttatggggagctaga | |

TABLE 3-continued

Non-Limiting Examples of Primer Sequences.

| Marker | Linkage Group (ch) | SEQ ID | Primer Sequence | Allele (Res/Sus) |
|---|---|---|---|---|
| S01081-1-A | D1b (2) | 189<br>190 | aacagctttagccttcaacca<br>gttgtgtccaagaagcagca | A/C |
| S02183-1-A | E (15) | 191<br>192 | caggctcgYagtagttttgga<br>ccaacctctGtagcaa | A/G |
| S00350-1-A | D1b (2) | 193<br>194 | TTCCTTTTAATTTGCCCAATGTGAGA<br>TCCTATGTTAGTCCCAGCATGAAACTTC | G/C |
| S08166-1-A | D1b (2) | 195<br>196 | ccttccttgatatcttgaggttg<br>cattacaatgtgtgccctgtg | A/G |
| S03991-1-A | L (19) | 197<br>198 | ctgtcagccatgtcgatttc<br>ctgccagcaaaaacagctaa | A/T |
| S04785-1-A | B2 (14) | 199<br>200 | tccgaaataaggcacctgtt<br>ttgcgtgagtttgggtatga | T/C |
| S02874-1-A | B2 (14) | 201<br>202 | gcatggtcttgcacctttt<br>catggctcatttcccttgtt | T/G |
| S04348-1-A | B1 (11) | 203<br>204 | caatcacaccaccaccaaga<br>ctttgacaaggccatcgagt | T/C |
| S01209-1-A | B1 (11) | 205<br>206 | ttcctgaagagcggagacag<br>gcacggagcttctcataagg | A/G |
| S01999-1-A | B1 (11) | 207<br>208 | ccccaaagtcggagaagaat<br>tgttatgggagggggtga | T/G |
| S04937-2-A | B1 (11) | 209<br>210 | gcttcttgactttatcrttctctcc<br>agctagggaaggatttgggta | Null/C |
| S04937-1-Q1 | B1 (11) | 211<br>212 | TCAACCGTGGAAAGTAACCA<br>TCAATTTAGTTCTTGAAAGTTGGAGAC | A/G |
| S04348-1-A | B1 (11) | 213<br>214 | ccacaacctattgttgaagcac<br>tgtgcactcctgactgctttt | G/A |
| S04938-2-A | B1 (11) | 215<br>216 | tcaaaaccattgttcatctgg<br>gaatagaagatgacaacrcattaaagat | T/G |
| S06786-2-Q1 | B1 (11) | 217<br>218 | cggacaaggtcctgtaaggt<br>ttttgtggattgaattcatggt | G/A |
| S06786-3-Q1 | B1 (11) | 219<br>220 | tgcaaacactgtaaataacactaatagg<br>aaatggttgaggaggacacg | C/T |
| S06786-1-Q1 | B1 (11) | 221<br>222 | agacgtgtcctcctcaacca<br>aggagaacccttcacactcg | A/C |
| S06787-2-Q1 | B1 (11) | 223<br>224 | attgctggatgtgaggttcc<br>tggccaacaaggatgaaaat | A/G |
| S06787-1-Q1 | B1 (11) | 225<br>226 | tgctgttccataattagaattggag<br>cctgcatcaagatgaacaagaa | G/T |
| S06803-1-Q1 | B1 (11) | 227<br>228 | gcttcaacatcaccagcaga<br>gaaggctgagaacggacaag | A/G |
| S06804-1-Q1 | B1 (11) | 229<br>230 | aggtttctgtccatgcttcag<br>gccaataaagcttggtggaa | C/A |
| S06787-2-Q1 | B1 (11) | 231<br>232 | aagaaaccccaccaataggg<br>aacggtttcagggaacattg | G/A |
| S06805-1-Q1 | B1 (11) | 233<br>234 | gatgaaatgtttctggcttgaaatta<br>cctggaaacttgcatgagtg | T/C |
| S06789-1-Q1 | B1 (11) | 235<br>236 | cgtcagctattccacccttc<br>ggtgagatcaagagggcatt | A/G |
| S06790-1-Q1 | B1 (11) | 237<br>238 | tcctgaaatcccaagcaatc<br>cttcaatgggtcgcaaaaag | T/G |

TABLE 3-continued

Non-Limiting Examples of Primer Sequences.

| Marker | Linkage Group (ch) | SEQ ID | Primer Sequence | Allele (Res/Sus) |
|---|---|---|---|---|
| S06791-2-Q1 | B1 (11) | 239<br>240 | atgcggaagatcaayagcag<br>atgcagacccaattcatgct | A/T |
| S06791-1-Q1 | B1 (11) | 241<br>242 | acaacgwaaggtatgaggtcaa<br>atcggtgagcaagggaaac | C/T |
| S06792-1-Q1 | B1 (11) | 243<br>244 | tcaaccaaaagtttcccttcc<br>gcagccacctaacagaacaaa | C/G |
| S02112-1-A | C2 (6) | 245<br>246 | CATGTTGCTCGCGACCTTGAC<br>GAAGGTGATTGAGGTGGTGAAGGA | A/G |
| S03252-1-A | C2 (6) | 247<br>248 | gcttggaatattaatctatggctgt<br>cgcgttacaaattaaagcatgt | G/A |

TABLE 4

Non-Limiting Examples of Probe Sequences.

| Marker Position | Linkage Group (ch) | Locus | Probe 1 Name | Probe 1 Sequence | Probe 2 Name | Probe 2 Sequence |
|---|---|---|---|---|---|---|
| 37220579 | B1 (Gm11) | S04196-1 | 141540 | ATTCCTAAAGATAGTC CAAT (SEQ ID NO: 87) | 141539 | CTAAAGATACATGCA AGTC (SEQ ID NO: 88) |
| 36954994 | B1 (Gm1) | S04938-1 | 504938-1-P1 | TTCTGATAGACGAAAC C (SEQ ID NO: 89) | S04938-1-P2 | CTGATAGATGAAACC CA (SEQ ID NO: 90) |
| 36954799 | B1 (Gm11) | S04937-1 | 141537 | CAAACTGCAAGATT (SEQ ID NO: 91) | 141538 | CACAAACCGCAAGAT (SEQ ID NO: 92) |
| 36781754 | B1 (Gm11) | S08344-1 | 102404 | CGGAGAATAAATAAAT AAG (SEQ ID NO: 93) | 102405 | CGGAGAATAAATAAG TAAG (SEQ ID NO: 94) |
| 37020399 | B1 (Gm11) | S08343-1 | 102406 | TTAGTGGACAGTGCCA (SEQ ID NO: 95) | 102407 | TTAGTTGACAGTGCC ATA (SEQ ID NO: 96) |
| 37020092 | B1 (Gm11) | S08346-1 | 102384 | TTTGTGAAGAAAAATA TGAAA (SEQ ID NO: 97) | 102385 | TTGTGAACAAAAGA TGAA (SEQ ID NO: 98) |
| 37311443 | B1 (Gm11) | S06786-1 | 142753 | CTCAGTATATCATCTTC (SEQ ID NO: 99) | 142754 | CCCTCAGTAGATCAT (SEQ ID NO: 100) |
| 37333894 | B1 (Gm11) | S06787-1 | 142757 | CACCTAAGGAACAAT (SEQ ID NO: 101) | 142758 | CCTAATGAACAATAC C (SEQ ID NO: 102) |
| 37334507 | B1 (Gm11) | S06803-1 | 142761 | CTTCCAGTGGCTGCT (SEQ ID NO: 103) | 142762 | CCTTCCAGCGGCT (SEQ ID NO: 104) |
| 37117244 | B1 (Gm11) | S04197-1 | 142389 | CTACTACCATACCTAA AC (SEQ ID NO: 105) | 142388 | TACTACCATCCCTAAA C (SEQ ID NO: 106) |
| 42916770 | C1 (Gm04) | S07162-1 | 102396 | AATAGGACACAATTAT TA (SEQ ID NO: 107) | 102397 | ATAGGACACAATCAT TA (SEQ ID NO: 108) |
| 34888681 | D2 (Gm17) | S07161-1 | 125316 | TCAGTGAGAATAAAA (SEQ ID NO: 109) | 125331 | TCAGTGTGAATAAAA (SEQ ID NO: 110) |

TABLE 5

Non-Limiting Examples of Probe Sequences.

| Marker | Linkage Group (ch) | Probe 1 Sequence | SEQ ID | Probe 2 Sequence | SEQ ID |
|---|---|---|---|---|---|
| S02621-1-A | D1b (2) | CTCTATTACTaTCTGTC TTT | 249 | TCTATTACTgTCTGTC TTT | 294 |

TABLE 5-continued

Non-Limiting Examples of Probe Sequences.

| Marker | Linkage Group (ch) | Probe 1 Sequence | SEQ ID | Probe 2 Sequence | SEQ ID |
|---|---|---|---|---|---|
| S01519-1-A | D1b (2) | acaggaCgatactc | 250 | acaggaTgatactcac | 295 |
| S08177-1-Q1 | D1b (2) | ctttgcatttTagatcat | 251 | ctttgcatttGagatca | 296 |
| S00479-1-A | D1b (2) | CAAGTGATGTTtATTTT | 252 | CAAGTGATGTTcATTTT | 297 |
| S02136-1-A | D1b (2) | actcgaaTgtactctc | 253 | ctcgaaCgtactctc | 298 |
| S00875-1-A | D1b (2) | TCAAGATCATtCACTATT | 254 | TCAAGATCATcCACTATT | 299 |
| S12875-1-Q1 | D1b (2) | ccacgtAttgttctt | 255 | ccacgtGttgttct | 300 |
| S12950-1-Q1 | D1b (2) | ccagccttCgtagca | 256 | ccagccttAgtagcag | 301 |
| S12947-1-Q1 | D1b (2) | aaaTtttgtgctatccac | 257 | aaaAtttgtgctatccac | 302 |
| S12933-1-Q1 | D1b (2) | tcaaacaCtgattctc | 258 | tcaaacaGtgattctc | 303 |
| S12853-1-Q1 | D1b (2) | atgctacccgtgtAtat | 259 | ctacccgtgtGtatac | 304 |
| S03246-1-A | D1b (2) | cctatgctatcAgtttt | 260 | cctatgctatcGgtttt | 305 |
| S12962-1-Q1 | D1b (2) | ttgaaTggtctccacatg | 261 | tttgaaCggtctccac | 306 |
| 500144-1-A | D1b (2) | TTCACAAGTgTATAACC | 262 | TTCACAAGTcTATAACCT | 307 |
| S08166-1-Q1 | D1b (2) | acatctcccacTggc | 263 | catctcccacCggc | 308 |
| S01081-1-A | D1b (2) | caaccatgActttc | 264 | caaccatgCcttc | 309 |
| S02183-1-A | E (15) | ccaacctctAtagcaa | 265 | ccaacctctGtagcaa | 310 |
| S00350-1-A | E (15) | TCTTTcACAATCTAC | 266 | TCTTTgACAATCTAC | 311 |
| S02074-1-A | L (19) | ctactcttgcgTtgtt | 267 | ctcttgcgCtgttaa | 312 |
| S03991-1-A | L (19) | tcaaacTaggatctcc | 268 | tcaaacTaggatctcc | 313 |
| 504785-1-A | B2 (14) | attctggtTcttcacttg | 269 | attctggtCcttcactt | 314 |
| S02874-1-A | B2 (14) | cctcacAaattacca | 270 | cctcacCaattac | 315 |
| S04348-1-A | B1 (11) | acaaaTgtacaccgcc | 271 | acaaaCgtacaccgcc | 316 |
| S01209-1-A | B1 (11) | cttccagagcagTgc | 272 | ttccagagcagCgc | 317 |
| 501999-1-A | B1 (11) | catacccCTtacaagc | 273 | ccatacccCGtacaa | 318 |
| S02112-1-A | C2 (6) | tcctatgTtggtctggtc | 274 | tcctatgCtggtctggt | 319 |

TABLE 5-continued

Non-Limiting Examples of Probe Sequences.

| Marker | Linkage Group (ch) | Probe 1 Sequence | SEQ ID | Probe 2 Sequence | SEQ ID |
|---|---|---|---|---|---|
| S03252-1-A | C2 (6) | ttggctttgaatCac | 275 | ttggctttgaatTac | 320 |
| S04937-2-A | B1 (11) | ccgaacg:tgtcatat | 276 | ccgaacgCtgtcat | 321 |
| S04937-1-Q1 | B1 (11) | caaacTgcaagatt | 277 | cacaaacCgcaagat | 322 |
| S04938-1-A | B1 (11) | ttctgatagaCgaaacc | 278 | ctgatagaTgaaaccca | 323 |
| S04938-2-A | B1 (11) | attaactTccttattttac | 279 | attaactGccttctt | 324 |
| S06786-2-Q1 | B1 (11) | ttacttgGCaacaat | 280 | acttgTTaacaatgtcac | 325 |
| S06786-3-Q1 | B1 (11) | caatttGttgaagcct | 281 | caatttAttgaagccttt | 326 |
| S06786-1-Q1 | B1 (11) | ctcagtaTatcatcttc | 282 | ccctcagtaGatcat | 327 |
| S06787-2-Q1 | B1 (11) | aagccacgagTcat | 283 | aagccacgagCcat | 328 |
| S06787-1-Q1 | B1 (11) | cacctaaGgaacaat | 284 | cctaaTgaacaatacc | 329 |
| 506803-1-Q1 | B1 (11) | cttccagTggctgct | 285 | ccttccagCggct | 330 |
| 506804-1-Q1 | B1 (11) | ctcacCggagcaat | 286 | caacttgctcacAgga | 331 |
| S06788-1-Q1 | B1 (11) | ctaacctcCagaacac | 287 | ctctctaacctcTagaac | 332 |
| S06805-1-Q1 | B1 (11) | cacttgTctttacaacat | 288 | acacttgCctttacaac | 333 |
| S06789-1-Q1 | B1 (11) | tctctattTtccgaaatg | 289 | tctctattCtccgaaatg | 334 |
| S06790-1-Q1 | B1 (11) | ccacatttTcttcc | 290 | ccacatttGcttcc | 335 |
| S06791-2-Q1 | B1 (11) | accttAcgttgtagatc | 291 | accttTcgttgtagatc | 336 |
| S06791-1-Q1 | B1 (11) | ctgctGttgatctt | 292 | ctgctAttgatcttc | 337 |
| S06792-1-Q1 | B1 (11) | acgaacaCgtcctga | 293 | caacgaacaGgtcct | 338 |

TABLE 6

Non-Limiting Examples of Genomic Loci Comprising the Various Marker Loci Provided Herein.

| Marker Position | Locus | SEQ ID NO (Res/Sus) | Reference Sequence [Res/Sus] |
|---|---|---|---|
| 37220579 | S04196-1 | 135/136 | TGCCATCCTAGCTAGCCCTGTATATTTTGATTANNTTNATGGGAAGAAAAAAT TAAATATTTTTATTTAATTGAAGAGTAAGTTAATTTTATGAAAACAAAAATTT AACATTTTCTTACTTATCTTTTAATTCAAATTTTATTTTATTTTCTCTTATTCCA ACAATAATTCCTAAAGATA[\*\*\*\*\*\*\*/CATGCAA]GTCCAATATGTTTAACTCAT CACATTTAATTTCATTACGAAATAATCAACAGGTCAAGATAATTTTAAGACAA |

TABLE 6-continued

Non-Limiting Examples of Genomic Loci Comprising the Various Marker Loci Provided Herein.

| Marker Position | Locus | SEQ ID NO (Res/Sus) | Reference Sequence [Res/Sus] |
| --- | --- | --- | --- |
| | | | ATTAGATTATAAGGATTGTTATTTTCTTTTAAAATATATTATTACACAACTTTT GTCATATATATTATGCGCCCGATGCCTCGATGACACCTAACACATATATAAAA CCTTTTTTATAATTAAGAATTAAAAAAGAGAGAGAGAGGGAAGAT |
| 36954994 | S04938-1 | 137/138 | AACAGCTATGACCATGCGAACCTTCCAAGGACCAAAATGAATTTTCACTCTAA AATTTATGTGCACTCCTGACTGCTTTTACATTTAGTGTCTTCATTTCATTGGGTT TC[C/T]TCTATCAGAATTCAGTGATAAGAAACAGTGCTTCAACAATAGGTTGTG GAACATGTTTTTCTGAGAGGTAAGGTAGTCACAATGAAAAAAAGGACAAAAC TTAGATCCAAAGCTATGTTGCATTGATTAACAAAGTAATCACATAATTTTGGT GTCATTTTCTAATAAGAATTGGAGTTTCATCTTGAAAGTTTATGTTGACCTGTA ATGCAAACCTGTATTGCATAGATTAGTGAAGTAAAACTTTGTTTTTTATTAGA GAATAACATCAAAAGCATTTATGGATCTGCATGAGTTTTTCCTAAAAAGGTGT GAAATAGGGGGAAAAAAGCCACACTGGATGTCAAAACCATTGTTCATCTGGT ATATATMCATCTCCWTATGATARTTTTTTTTTTCTTTTCTGATTTCTTGTGAAA TATATTAATTAACTKCCTTCTTTTACATGTAAATGAGAATGTTGTTAATTAATA TGTTAACCTAAACGATATCTTTAATGYGTTGTCATCTTCTATTCGTTTTGCAGT GATGGTATCC |
| 36954799 | S04937-1 | 139/140 | GAATGCTTGTTTCACGTAAGCTTCTTGACTTTATCRTTCTCTCCCCCGCCCCCC AAATACCACAAAAATTCCGAACGCTGTCATATTGCAATCTAATTGTTTAATAC CCAAATCCTTCCCTAGCTCTTTTCCAGTATCTTGAGCTTGTAATCTTCCATCTTA AAAGCATACTGACTGATGCAATCTTCTGATTAATTTAGACCTGCATCAGTTAC TTGCTTGCAAGTTGTAGAATCTCTTATTTTYCTTTTCACTTCACTGGTTTGCATG TCCATACAATTCGAACTATTTTTTATCTTTCAAAGATTGGAATGACATTAACTT GGTTTTTGATCCTAATAGATAAGTCATATCAATTTAGTTCTTGAAAGTTGGAG ACTRAATGTCCTCTAAATAAATTGACATCAATGTAGATCCTCAATAATAGAAA GATGACATCANTTTASTCCCTAAATCTTGC[T/C]GTTTGTGCATAGAAGGATGG TTTTTTGGTTACTTTCCACGGTTGAGGTACTAAATTGATGCAATATCTCTTAGG GAGTTAGAGGACAAAGTGATGTCTACCGAACCTTCCAAGGAACTGGCCGTCG TTT |
| 36781754 | S08344-1 | 141/142 | AATCCCTCGTTCTTCATGCCCCCCAACCCAACATTCCCAGTCGACACGTCTTCT ACTCCTTAATTTCCTCCTTCTTTCAAACTTGACAAAGCCACAACTCTTCTCTCA TCTCATATAAATACCCTTCCACGACACCAATTTCTCCATCCTCTCATTGAAAAA CAAAATTAATCATCTTA[C/T]TTATTTATTCTCCGAAAATGGTTGATTTACATTG GAAATCAAAGATGCCAAGTTCCGACATGCCTTCCAAAACTCTAAAACTCTCTC TCTCCGACAACAAGTCCTTACCCTCTTTGCAAC |
| 37020399 | S08343-1 | 143/144 | CAAGCAAACTTAGACTTACCAAATGAGTTTGACCAGGTTTTACCCCTCTTGAT TGCAACCTCACGACCATCAACGAGTTTGCCTCTGTACTCAACAACAAAGCCTC CGGTACCAATCTTGTTGTCAAATGAGAAATTATTGGTGGCTGCTTTAAGTTCA GCGAGGGTGAATAATGGTGCAGCAAAAGCATGCACTGGGGAAGGGGATGATY CCAAATCTGCTTCACTGGCACTACTACTCCTTATGGCACTGTC[C/T]ACTAATG AAGCAAAACTACGGACACGAGATTCTCCAAAAATGGACCCAGTATCACTCCTT ATGTCGCTGTCGACTGCCATGCTAAAACTCCTTGCATCATCTGTGTTATCCCTC ACATCAATTCTCTCAACGGTTTCAGTATCCATTTTATTTGATTTGGTAAGTGAA AGTATGTACTAAGTGCTTTGGCAGAGGCACTGAGCACATATRTCATATACAGA GACCAAAGCACATACATATATATATATATATTAATTGAG |
| 37020092 | 508346-1 | 145/146 | CTTCNCNGCACCTTCTCAATTAATATATATATGTATGTGGTTTGGTGTCTGTAT ATGACATATGTGCTCAGTGCCTCCGCCAAAGCAAATAAAATGGATACTGAAAT GGTTGAGAGCATTGATGTCACAGATGATGCAAGGAGTTTTAGCTGGGCAGTG GACAGCGCCATAAGGAGTGATACTGGGTCCATTTTTGGAGAATCTCGTGTCCG TAGCTTTGCTTCGTTAGTGGACAGTGCCATAAGGAGTAGTAGTGCTACTGAAG CAGATTTGGAATCATCCCTTGTCCAGGCAGAAGACAGGGCGATGAGGACTGTT GCAGCACGATTAACAAAAGCCGMTCAAATGCAAAAAGACATTTTGCTAAAG GATTATTTACCCGGGCTGAGCTTATACCAGTCACCCAGGCTGAGCTTGAACCA GCCACCAACAATTTCCMRSSAYYAWTAWTTWCYCWKKATSACCWYARMKCC AGCCACCAATAATTTCTCATTTGACAACAAGATTGGTACTGGAGGCTTTGGTG TTGTTGAGT:ACAGAGGCAAACTCATTGATGGTCGTGAGGTTGCAATCAAGAG GGGTAAAACCTGGTCAAACTCATTTGGTAAGTCTRAGTTTGCCTTGTTCTCCCG YTTACACCACAAGAATTTGTTGGGCTGGTTGGATTTTGTGAA[C/G][A/A]AAA A[G/T]ATGAAAGGCTCTTGGTGTATGAGTACATGAAGAATGGGRCGTTGTATC ATCATTTGCATRRCAAGAAGGGTARCAGTGTGTTGAATTGGTAAAWANRYGR ASRWRGSWATSWGTGK |
| 37311443 | 506786-1 | 147/148 | STATTGCACSCGCTTTTCGTCCCGGTCAAGAAAAGATGGTTTATGTGTATCAGC TCTTGGCAAGAGGCACATTGAGGAGATAAGTACATAAGAACCACTTGGAA AGAGTGGGTTACTAGCATGATTTTTAGTGAGGCTTTTGAGGAGAACCCTTCAC ACTCGCGAGCATAGAACATTGAAGATGAT[A/C]TACTGAGGGAAATGGTTGAG GAGGACACGTCTAAAGCAATTCATATGATTCTAAAGAATGAAAAGGCTTCAA YAAATTGAAGAGAGGTAATTACGCTTTTTTCATATGAAAACATGTGCTTAATT TATGTTTATATATCTTAATCCTACATTCTCCCTATTAGTGTTATTTACAGTGTTT |

TABLE 6-continued

Non-Limiting Examples of Genomic Loci Comprising the Various Marker Loci Provided Herein.

| Marker Position | Locus | SEQ ID NO (Res/Sus) | Reference Sequence [Res/Sus] |
|---|---|---|---|
| | | | GCACTAGATCACTAGAATGCTTGTTGGCATTCACCTTCAGTGTTGGAGACAGA<br>TTTGACACTTGTCGTCTCGAATGCCAGGGCAAGTTCGAGTTTAGTAGAAACTT<br>ATCATCCAAAATTAAAATTGAAAGCACTAATACAAAATGCACAATTTGAAGC<br>CATTCATGTCCTCTCTTGGTCTGAGTCTTGTCATTTTGTGGATTGAATCATGG<br>TTTCTCTTATCCGGTGACATTGTTRMCAAGTAATACTACTATAAATTCAGATTT<br>GGATATCAGATAACCATGGTCATTAATAGTAATACTAACATACTATACATATA<br>ATACCTTACAGGACCTTGTCCGAAACTTGAAACAGGATCAGGGACAGCGAAA<br>AACAAACATGGTCAWAnCYKKTTYY |
| 37333894 | 506787- | 149/150 | TTACAAATAGGAGAAAACTTAGATATACATAGTTCTTTAAGTTTGATTACATT<br>ACAAATAGGAGAAAACTTAAACATACATAGTTCTTTAAGTGTTGTGTGTGCTG<br>TTCCATAATTAGAATTGGAGTTTTACTTACCTTAGTAATATGTATAATTCTAAT<br>TGGAGAACAGTACAAACAAAAACACCTAA[G/T]GAACAATACCTTAGTTTTAA<br>TCATATTTGTTTTGTTCATATAGCTTATCAATAAGTGAAGTATTTCTTGTTCAT<br>CTTGATGCAGGTGGTGGAACTGAAACCTTCATTGATTGGCCAACAAGGATGAA<br>AATAGCACAGGACATGACTCGMGCTTGTTTTGTCTTCATTCCCTGGAGAACA<br>TTATACATGGGAACCTCACATCCAGCAATGTGTTGCTTGATGAGAACACAAAT<br>GCTAAAATTGCAGATTTTGGTCTTTCTCGGTTGATGTCAACTGCTGCTAACTCC<br>AACGTGATAGCTACTGCTGGAGCATTGGGATACCGGGCACCAGAGCTCTCAA<br>AGCTCAAGAAAGCAAACACTAAAACTGATATATACAGTCTTGGTGTTATCTTG<br>TTAGAACTCCTAACTAGGAAGTCACCTGGGGTGTCTATCATGGTCATAGCTGT<br>T |
| 37334507 | 506803-1 | 151/152 | TTGCGTAATCTTTCTGTTCTGATTTTGAGTAGGAACCAATTTAGTGGACATATT<br>CCTTCAAGCATTGCAAACATTTCCATGCTTAGGCAGCTTGATTTGTCACTGAAT<br>AATCTCAGTGGAGAAATTCCAGTCTCCTTTGAAAGTCAACGTAGTCTTGATTT<br>CTTCAATGTTTCTTACAATAGCCTTTCAGGTTCTGTTCCACCTCTACTTGCCAA<br>GAAATTTAACTCAAGCTCATTTGTGGGAAATATTCAACTATGTGGGTATAGCC<br>CTTCAACCCCATGTCTTTCACAAGCTCCATCACAAGGAGTCATTGCCCCAACT<br>CCAGAAGTACTGTCAGAACAGCACCATCGTAGGAACCTCAGTACCAAAGACA<br>TAATTCTCATAGTAGCAGGAGTTCTCCTAGTAGTCCTGATTATACTTTGTTGCA<br>TCCTGCTTTTCTGCTTGATCAGAAAGAGATCAACATCGAAGGCTGAGAACGGA<br>CAAGCCACGGGGAGAGCAGCC[A/G]CTGGAAGGACAGAAAAAGGAGTCCCTC<br>CAGTTTCTGCTGGTGATGTTGAAGCAGGTGGGGAGGCTGGAGGGAAACTAGT<br>CCATTTTGATGGACCATTGGCTTTTACAGCCGATGATCTCTTGTGTGCAACTGC<br>TGAGATCATGGGAAAGAGCCATGGTCATAGCCTGT |
| 37117244 | S04197-1 | 153/154 | TTTCTTAAGTTATATGTTATTTCATTTAAGTCCTAACTGTCNNTTNACTCCTCTT<br>CTTGCTATTGTCATTAGTATTCACTTNNTTTNAATAACTGTGGAAGCAAAATG<br>ATCGTTGTGTAATTTTTTATTGTATATTAGATTATTAGGTTTATAATGTTGTTTT<br>GTTATGTTATATATTTGAATGACTCGAGTTTATGTTTTTATTTTTAATGCTACGT<br>TTGGATGATTTAAGAGTAAAATATTAATTTATTTATAGTAAATTTTTTAATTAA<br>TATTTTGTATTCATTGGTTGAATTTATAACAAGTAAAGTATGGATAAGATGTG<br>CAATAATGAATATATAAATGCCTAATGGGAGAGATGAAGATTAAAGTTATTAT<br>TATATACATAAATATAAAATTGGAAATGAATATTTGTTTTAAATGGAGTATGA<br>AGATCATACCCTATCCAGTATCTACTACCRGTATCTACTACCAT[C/A]CCTAAA<br>CTCGACAAGGCACCTACACTACAATATAAATATAGTAAGGCTTCGAGTAACA<br>GAACCTGCGACATATAATAAGCCATAAAAGGCTTCAACCCAAAGACCCTACG<br>TTACGAGAAAAGAAGAAAACATTTGTTGAAGTGAACCACAACAACGCAATGG<br>CATGGTCAT (CONSENSUS) |
| 42916770 | S07162-1 | 155/156 | CGCAATTAACCCTCACTAAAGGGAACAAAAGCTTGCATGCCTGCAGCAATAT<br>AACCAGGATTCAGAATTAATCTAGTTAGTATATCATACAATGCAGGGCCAGTT<br>ACAATACATACATACGCATAACCAAAACAGTAACATCAATGGAACAGTAATA<br>GGACACAAT[C/T]ATTATTATTTTTTTGTTAAGGAAATTTCTAAGAAAAACACA<br>ACCATTTGTACAAAAAAGGTATTAATACATAGCTACATGGAAGAAACCTACAT<br>TAAAATCCAGTAGTGAGAAAAGATGGGGGCAATTATGATAATCTCGGAAAGC<br>CTCTGCCAAGGGTCAGCATTCAAAATTGAGTTCCTTAGCCTGCTGTCTGCATAT<br>GCTTATCCACAAGGAATATTGTCTCCGTGAGGATTAACCAAAAGCATACCTCA<br>ATGGGTCCAGATATCCTGAAGATAGCGCCCAATTTGCTGAGCACCAAAATATA<br>GGGCATCGGCAACGAGAAAGACTCCAATCTACGCCACAAATGTCAAACTTGT<br>GAATGTCAAGGTTAAGAAATAAGATTTACAATTGAAGGTCTACAGCAGATAG<br>ATTACCAGGCGTGCAGAAAACACTAATCTATATCCCCAACCTTCCTTGGCTGC<br>AGGTCGACTCTAGAGGATCCCCGGGTACCGAGCTCGAATTCGCCCTATAGTGA<br>GTCGTATTACACCCTATAGTGAGTCGTATTACGCCCTATAGTGAGTCGTATTAC |
| 34888681 | S07161-1 | 157/158 | CTTG:AAGTTATAAGTTTTGAGAGAGATTTTATGCTTATCTTGTCTGAAAACCA<br>CTAATGCTCTCTTCAGTG[A/T]GAATAAAAGGGCTACAAGATATCATACATAT<br>GCTTTAATATTATATCACTAAATACAATTAAGGATGCTCATCACATTAGGTTA<br>GGTTAGATACAGTTGAATTGCCTTAAAGTCAAATTTCCACAAG:::AC:::AACA<br>GTAACAGTTACCAAAAACCATGCCCACAACAAGCAATATTGGCTGCGTGACTT<br>AAAAACTGTTTAAACATCTCAACTGATGTCTTACAAGGAAAGGTAACCTAATG<br>AAAAGACATCAATCTAGAAAATCAAGGCACTTCAGTGAGAAGACAAATGAAGT |

TABLE 6-continued

Non-Limiting Examples of Genomic Loci Comprising the Various Marker Loci Provided Herein.

| Marker Position | Locus | SEQ ID NO (Res/Sus) | Reference Sequence [Res/Sus] |
|---|---|---|---|
| | | | CCAACTGATTGCATTTTGTCTTGTCATATTAGGACTTAACATTAGAAGCAAGTT GCATATAGAACAAATCTGAAGGATCATTTTATATATATTTAACAACTACTGGT TGACCACCCAATACGATAAACAGGAACAACCACACAAAAGCTCTTGATCAAC ATAAAGAAAACAAAATTAAACACAAAAAACTGCTACAGAATTTAAAAAACAC TTTAGCAGACGTAACAGAAGTACAGAACAAATTCTGTCAGCAATTAAGCTAA CTAGATACCAAACAGGATACTTCCATTGTAGTAGAAAAGGTGAAACACTATA GAAAAATTCAACAGTCTAGGTGATTAAATCTAGACTCAAATCTCTCAATGTAT AAATGGTCCTCTTAAAAACCAACCCTGCCAATGGTAGCAAATCCCCTGGACAT AATGAAGCACACGAACCAACAAAGAATCCAATAGAATAAAACCAAAAACCA AAAAACTTAAAGTCCAAACAACAAATACACAGGCAATCAAATCAACCAAACA AAATGATGTACACACATACACAAAATGATGTACACATACATATAATTAGGCTT AAATATGTTTTTGATTCCTTAAATTTGGAGTTTGAACAATTTTG |

TABLE 7

Non-Limiting Examples of Genomic Regions Comprising the Various Marker Loci Provided Herein.

| Locus Name | SEQ ID NO | Sequence |
|---|---|---|
| S02621 | 339 | MMRGCTATGACCATGGGGAAGTGCATGAGTGCTTTTTCAGATACCTACTTATA AGTAGGTTTGAATTAAATTGATTATATTGTCCTAGTAGAAGTGGCTATATAAT ATTTTTTGAGTGAGTGTGCTTTTGCTCGTTGCATGATATAGCAGATATGCTATC TGAATGCTAAAGGTACTCTATTACTRTCTGTCTTTTCTTCTCATTCCTTATCCAT ACATATTTTGAACCAATTTTACATTTGAAGGACGAATTGCTGCCAATGGTGC AATCTAGCAATCTTACCTTGTCATTTTCAACTGAAAGTTCAATTGAGGAAGAA CTAAAGAGAGAAAGCACTGCAGATGTCATAACAATACTCGTAAGAAATTTCT GTTTCTTTCAACTAAATGTGAAAACATGATTTGTGTTGTGTGTAAGCTAATGA ACTGATTAGTTTGGTTGTGGCTTCATAAAGATGTGCTTTATTGGAATATACAAT AAATGTCTTCTCCAACATATTATTAGGTGAGCTATATTGTAATGTTGCTTA |
| S01519 | 340 | GatGGGTAGACCAATACACAAGTTTGCAAGCATTGTAGGATATAGAGAGGGTA AGATGTATACAACTTTACCACCATAAGAAGAGAGGCTGCTTCTGAGACTAGA AAATTTGACCACCAGGTCACAAGCTTACAACCTTATAACTGCACGAAGGTTTA CTTTCTAATATGAAGAAATACCACCTTTTGTCATGTAAATATTTAAGTTTACTA AATTGAAATGTTGATAACAATGCAAAGAAAAGAGTAGTCAGTGACTCAATTC AAAAGTTGATGATACCAAACAAACCTGAAGCTTGTAGCGCAGCTCCAGATTTC ATGATTGGCTCCCCAACAGGAYGATACTCACAGCCTGCTTCAAGGACTTCATG GT |
| S08177 | 341 | AGTACCAAGGGAGGACATGCATTGTGTTGCACAGTTTTTTTCCAGGACATGGG AACTGCAAGTGCTGGTTGCTGCTTGTTTAGCCCCTTCCATGATAAAAGAAAATG CCCCAAAAGTGAGACAGCTCTGCAGAAGAGCTTGTGGTGCACCTGTAAAACC CTAGAATATAAGTCCTAATAACAAAACAAGTACACAGAATGAAATTTACATG TGTATTTAGCTGAACANTGAATTGTTGAATTTTAACAATAGCAATGATTGGAA GCCATTCTGAGTCAGCAAAATTTCCCCCCTCCTCCATTTAAGGTGATGGTTTGG GAATGGAGACAGAGGATTCCAGAGTAATACATCTCAAGAAACAAATTACCAC ACTGATTATGGACAAAATTATCTTTGCATTTKAGATCATATGACTATGCTTTTA AAGAGAGATCAAGAATGCCAATAGGGCCTATTCAGAATAGTCAGATTGGCAA GTCCTTTATCCTAATTCTTTCTTATAGATTTCAAAAAGAGGGCAAACCCATCAA TTTGAATAAATAAATAAGAGATACCTGGAAAACTTAGAGCAAGACCAGTGCA ACATCCAGCAACACCCGCATTAATGACTGCAAATGCAAAAGAATTCACATTAC CAGAGGAAGATCACTTAAAAGCAAAAGTGACAAATTTTACAACTAAATATTC ATACCATCATCTTTTCCTCTAAGCCTTTTCAAGATGCAAACAACCAAACTATG AACTCCAGACAAAACTGCAAATGTCTAATGACATAAAGAACAACACAATTAC TTACAATCTA |
| S00479 | 342 | MTgcaTGCATGGATTTTAAGCAAATAAATTAATGTGAAGTATTTCAATGTATGC CCGTGCMYHKAHCACATCTCATGCACTGCCCATACCTAAAGGATAAAATATC AAGTGATGTTYATTTTTTAATCTCCCCTTCAAAATGACCAATTAATGTAGAGA ACCTTCTAAGTTCTATAGATTTTAACACTTGTCTAATTCTTAACCATCCACATC CGTTTCTCATGTACCTTTATAGTTTCAATTATTTCAACAATAACGCCAACACTG TAAAGTTTTTGCCGTTACCAGTTCCAAATTCTACCTTTTTTCTTTTCTGTAACAG CTGGATTCACTGTACTAAAATCCAAAAAGTGTCTGAAACCGGAGTTTGTCTAT TTGCCATGGTcaaRBBBDDTYYCYVVBDDDBBRBRDVBBVBDBVBBHDVMVBB BRVHDDVVDDRDRBBRVVDDBBBWBVHBWBBDHHHWBYBMBHDHBBBMBB HRBHBWBBBBBVBBBBDRBBDRBBKRBBDVBBDWDWKKWDWSaMaRKD |

TABLE 7-continued

Non-Limiting Examples of Genomic Regions Comprising the Various Marker Loci Provided Herein.

| Locus Name | SEQ ID NO | Sequence |
|---|---|---|
| 502136 | 343 | ATTTTATTTTATTTTTTCTGAGATAAACAATGAGCCAATAGTTTAAAATGGCTG<br>CCGTTTATGTTGTTAGCATATAAAGATTCTCAATAATATTCAATTACTCGAAYG<br>TACTCTCTAAAATAAACAAGTTAATTCACTTCTTGGACTGATTCTAAATACCTG<br>TTAACTGCAGCATATAACCTGTACTAACTTCCCAATTTAAGAGTAATCTAACA<br>AACAATATTAAGAATTTTATAATGCAAATAGACAGAAAGAATCTTACTCCCAC<br>ATGGTTAACTATTTTAGCCTAGGTGGTGCATTGTAATTTGCTATTATACAGTAA<br>TTTTGTAATTACARTACATAGAAAAAGGTCAAGAGTAAGTGAATTAGATTTTA<br>GAATTAATAGGTGCTGACACTATAGATCCACACCTATGAAGGTCTCCAGGTTG<br>TCCTGATGAGGTCCTAAACTTACCCATATGCCATGCATGTCTGACAGAATGAC<br>ACTTCACCACCACATGGTCATAGCYKKKT |
| S00875 | 344 | tCgCGaccATCcaAGAGTTTGCCTTTATAAACAACACCATAGCTTCCAGCACCAAT<br>CTYTCAatCAAGGGCGAAATTATTGGTGGCAGCAACAAGCTCAGCCAAAGTGA<br>ACTCCTCAGCCCTCTCAGGATGCTTTGTGGATGATGTTCCACTCCTTTGACGCC<br>TCATTATCCGTGACCCTTGACGCCTAATAGTGRATGATCTTGAAGGAGGACTA<br>ATGCTATTATTAGAACCACCCACACCATTTACACTGCCACCTCTAGTGATTGTC<br>GGCTGCACAGAATTGTGAACTTTCTTCTTCCCAAAACAAACCCCAGTCCACAA<br>ACAATAAATCGCAGTGCATATCCCAGCAACACCTCCCACGCATCCAACAATGG<br>CAAATGCCAACAACCCCTTAGTCAAGGCCTTCGACCGAGAAGCTGCAGGCCC<br>CGGTGGTGATGCTGGCACCACCGCAGGTGGAGCCGGCACCAGCNTTTCAGGC<br>CAACAAGCATGGTcaTAgaatGTTTccaa |
| S12875 | 345 | TAAACAGTTTTCTAACTAGTGAAATTTCATTTCGGTATCATTGGAAACGGAGA<br>ATTCCAATATAGCAGAAAACATGAACAGAACGCGTTGTTCCAAAGCAAAGCC<br>AATAATAACTCACAGTGTTCCCACTGCTAATAGACGTTGAATGTGATCAAAAG<br>CGAGAATAGACGCATTAGATGGAACGCCATAGTGAAGAACAAYACGTGGATC<br>AAAATTCCCCGACGGAAAACTCTCTTGAGCCACGTCCTGTTGCTGAACGGCGC<br>GAAAAATGTTCAGAAACAACGTCAGCTTCAGGATTTGCGTTCATATATAAATA<br>AACTTCTACGAATGCACTATTATTATCATTAAAAAAAAACAAAAACAAAAG<br>GCTCCCTAGCATTATTCGTAACCGCAAGAAAAA |
| 512950 | 346 | TCGGCGCCCAATTTCACCCTGAAAAAAATACATATAGATGTAGGGGAAGACC<br>TAAAAGAAGAAATTAAATCAAACAGAAACATAGGAGACAAACAATTTAGTAA<br>ATTGAGAAACATAGGAGACATAGGTATTATTATTTAGAATGAAACGGCATCAT<br>GCAAAACAAAAAAGAATCATGAAAGAAATTTATGCACTGCTACKAAGGCTGG<br>TTTGTTCAAAATACAGACCCATAGGATCTGTGCACATACCAGACAGATAATATC<br>ATGCAAGCAAACAACTTTGATAAACCAATTCCTAAACACACAAGTGCACAAA<br>TGATAATAGATTATAAATATCAAAACTTCAAGCTAATTGCATATAATGGAA<br>GTGGAAAGAGGAAACAATAATGTAAAACATAGTA |
| S12947 | 347 | AACTGCAAAACATAATGGACCAAGACATTAAGCCATTTTTAAAATAGTCCAA<br>GTTCMGACAAAAAGAAGCCAAAGGGTTAATTTAAAAAAAAAAAAAAAAATT<br>GTAATCTTTTTTCCTAGATCCTTTTTTATAAATGTTACACAACATAAAAGGTAT<br>AGTAGTAAATTTTGCAGTGTATCAATTGGTGGATAGCACAAAWTTTTTTTTCGT<br>ATCTTGTGATCAGTCACCAAACAGCTCCTATACAAATAATATCCTGTGACTCA<br>ACGAGTTGAAATGCTGTTTTGTTTGTTTGTCTCTCCATACACATCAAATACA<br>AAAAATTATACAATTTTACATAAGTGGAGGGCAGGGAGCACAACCCTCACTCT<br>ATGAGCTGGCTATTGGAGTTGAGTTAGGCT |
| S12933 | 348 | AAGACCTAAAAAATTATAATTTTTTTTTTATAAATTTTAGTCAATTATAAAAA<br>TGATACTCAAAAGAATGTGTTAAAAAGTATGTTATCAACATTTTTTTAATATTA<br>TATACATATTTCTAACACAAATGATTGATGCAATCATATAAGGMCGTTGTGT<br>TTATATAAGTGAAAACGATCTAGTTAATATGAGAATCASTGTTTGATTCCCACT<br>ATTGCAAAATTTTATCAAACAAACAAATTAGGGAACACTCGTGATTTGCGAC<br>CTAAGACAAAAGAGACATCAAAGTTCAAAAAACACTACTTACATATCAAGTT<br>AAGTTATGGATTACAAGATCTTCGTATTTACAATGAAAATTCATATTGCATAT<br>GAAAAGTAGATTATGCATTTCAGTTAT |
| S12853 | 349 | ATGACATATCTCTTTTTGTTTMCAAATGTTAAATTAATATTGAGGTGCTTAT<br>ATTTGGCAATTTTGAATTAAGTCTGAATATTTTAAAAATTTGTGATTGAGACA<br>ATGTTATAATATTTTAACGTGCTCTAACTATTAATTTTCCTTTTTTTTCCGCG<br>ATCAACTATTTTAATTTCCAATAGTATGCTACCCGTGTTRTATACACAGGYTATC<br>TAAGAATTGAGATCTGCTAGAAATGCAAAGCAATTAGGGATCGTGTACAAGA<br>TATATTAAACATTTTACCAACTAACCATAGAATCTTTTTCATCAACACGACTAG<br>ATATTMAAAAGAAATCAACACAAGTATTTAAGCAAGTTTTGATTTGAAAAT<br>TCTGCATAATCCCCCAAAAGGAAAAG |
| S03246 | 350 | aACTTTTTATGATTGACTTGGTTCTCAAATTCCGACGGTATTGAGTTAAGGAAT<br>TTTAATGGTGCCTATGCTATCRGTTTMGAATAACGATTATGAGGTTTGGATGA<br>ATATTTGGAGTTGCATAAATACGTTGCTACAAAGGTTTATTTTTCTCTTCTGGT<br>AGTAATATGGAATAACAGGTTACAACCTATTGATTTAATATTAATATAATAGG<br>GGAGGAGTGTATTTTTTGAAACAGAATATTTTTGGAAATCGGGCACTGCCTCC |

TABLE 7-continued

Non-Limiting Examples of Genomic Regions Comprising the Various Marker Loci Provided Herein.

| Locus Name | SEQ ID NO | Sequence |
|---|---|---|
| | | TAGACGTTAAGACTGAAATCTACAGTTTTGGGCTTATATTGGGTTTGCTTTTAT<br>TACTATTGGGCTGCATACATACAATATAGTTATTTTAATTAATTTTCTTTATGC<br>TCTAACACTTTGGTTGGCAGGGTACAATTTGCAGCTCATGGT |
| S12962 | 351 | TGCAATGGTCAGACTACTCAACACAACTCTTGTTGACTTATTGTTCTTTAAATT<br>TCTAATTTCTTTCTTCCAAAAATGATTTTGAGAGGATGAATAGAATAAAATTCT<br>TAGAAGCTTCCTTCCTGCAAGCTGAGGAAGATTACTTACTAGGAGTGATAACT<br>TGGTGCACCACTGCAATTAGTTTGATCCATUMGAGACCRTTCAAAAAAATTT<br>ACATTGATTTCTCTAGATGCATCATGGATCGCAATTCAAAACTAAACTTTACC<br>CTTCCATGGCAATGACTTCCCTACCTTATTGAGGAACTCCACTTTTTTATTAC<br>AGAAGAAGTGGCTCAAGGAATTTTTGTGTAACTTACAAAATAAGTAAGTGCTA<br>AAGAACCAAAGACTCTTGGCAGCTTAA |
| S00144 | 352 | TTTTTTTTTTTTTTTTTTTTTTTTTTTTTTTAGAAAATATCCACTCATTATTA<br>TTTCCAACATGAAACGCTTGTTCCACATATTCAACAAACCATTTTATTTTCTTT<br>TTTCAAGAAGAAAGAAACTTCCAAACATGCATCAATTTTATTGTACTAATCTC<br>TCCCTTGCCTTGAGCTTACAGGAACATTGTTACAATTGGTGTTCTGCTTGCTCA<br>TGATAAAACCCAAATCAACACCACATAATTTAGGAAGTGAATTGGCCTTGTTT<br>TCGAGCAAGGAAGGAAGGCGAGTTGCTACGTCGAAAAAGCACTTACATGCAG<br>CCATTCGTTGAATTTGTGTTGGTGCTGATGCTTTCACTGCATTAACACTTTGGC<br>AACAAACACCTGAAGGGGCACCATCATCTCCACCAATCATGTAATCTACGCAC<br>GAAACTAACAGGTTATASACTTGTGAACAATTGTAGTCATTTGATGCTGAATT<br>TGTTTTAACTGGTAGTCGTGCCTCTGAAGCTTTCGCTGTAAGAACAAATACAA<br>CTAGCACAGCTAAAAATGTGACAAACACTTTCTTCATTTTGTGAAATTGAAGC<br>TAGTTTCTATATATCTCAATCAACTTTTAGGATTTGCTTGTGTTTTGCCGCGTG<br>GGTCGACCAGGGTATTCCGGACCGGTACCMCAGGCGTACCAGCTTTCCCT |
| 508166 | 353 | ATGAGTTCCGTATGAAAAATATACTGTTCTGGATGAATTGTGGCACGAACCAT<br>ACATCCATGTATATATATCCTAATACTGTCCTACCGTCCACTTACAATGATTGT<br>GCAAAGTTCTTCAATGAGAAAATAAGTCCTAAAAACGGTAGAGCTTAATGAC<br>AACAAAGAAAATAACCAATGCGTTACCATATTGGCAACTATAACTAAATGTG<br>AGTGCATGTCATTCCAAATTACGCATTTCTGCGTTATTCACGAGATTATTCATA<br>CTCTGGGAGTCACAGCACCTCCCATTGAATTCCACACGACATTTGACAATGGA<br>TGCCACCCGGAAGAGGGCTGCATAAAGTCTCCTGAGATTACAAACGAGAGAT<br>CTGGAGGGGTATCACTGAAACATCTCCCACYGGCGGGAACAAATCTAGCTCC<br>CCATAACGCTCCAGGACACGCATCCTGCAGTCCTCAGCAGCCATCATTCCAGT<br>AGAGTATGCACCATGCACAGACCCCGTATACAACATACTTGTTGCTTCCCCTG<br>CAAAGAATAAATTGTCTACAGGAACCCGTAGCTTCTCATACAGATCATGTGGT<br>TTCCCAACTGCATCATAGCTATAGGAACCTAGTGTATTAATATCTGTACCCCAT<br>CGAGACACAAGATACTGAATCTGCATGATTGAAACAAATTGCATCTTCAAAAC<br>ACCAACAACATACTAGTCACTGAAAAACAACTTATTAAATTCAATCATATAGC<br>GATTGAACTAAAATGAATAAAACTTAGGAGTAGGAGTCTGCCACTTATAAA<br>AATATGG |
| S01081 | 354 | ACGTACTTtcnTTTTCTTTTTATTATTAATTCTAACAGCTTTAGCCTTCAACCATT<br>TTTTATGGTTTGTTCAACCATGMCTTTCCGTTCCTTGAGACTGGTTTAAACTTG<br>TGGTCAAAAGCCTTTTTGCTGCTGCTGCTTCTTGGACACAACATGGGTGTGAT<br>ACAAAATGATATTAGGCTTCATATCGAAGTACCTTATAAAATGATCTGCTGTT<br>GCATCTTGTACCTGTTGATCTTGAAKAAGATCTTTAATTGCTTCAGGCATRGGT<br>TSGTCATTCATCATTTTCTTCCAATAATCCCCCAGGTCTMCTTGCATGGCTTA<br>AGTTGATGTTGGCAACCTATTTATTAGTAGAGATAACATAGAAAASTCATAAA<br>CCATAATTAGCACAAACTCAATGGTTCAAATTTTAAAACAAATRAGTTRCTAC<br>TGAAAAGCTTACCAGGAGAAGMGAMAAGACTAMGAASAAGGCAAAGRTCAK<br>GGTCATAGCYKKT |
| 502183 | 355 | gaccnntgctTACATCCAGTCCCCAMRWMMCSYnntYRGGAGWTnCAntWKSKRKCn<br>AATCnnnnaCAnWTTnTGAAAnncnnTnnnTnnnnnnnnnnACCATGGGAGGACC<br>TTGATGATGTCGGATCACCATACCCCCACTTTGCTTTTCAAACRAAGTATTATG<br>AGGAACATCTTTCTCAYCTAAAAACATAATTCTATGTTCAAAAACAAATATAC<br>AAGGCATAAAAGTACRTGTATCCAAAAKTAGCATGAATAAAAACTCGATACC<br>TTGGGGTTGATTAGAAGGAATCAAAGTAGTCGACTTCTCCACGTGCTTGTCAT<br>TAACATCAACATTAGTGATCGACTTCTCATCGTTATKTGGTTGGATCACATCA<br>ACATTCCTACCCTTAGTAGCAGGCTGCYAGTAGTTTTGGACTRRGCTTGTTYA<br>GTTTTGTCACTTTGTTGGCCAACCTCTRTAGCAACTCTTTTCCTTTTCTTTGGCT<br>TCACTAGGTCGGCAAAGTGTTGGTGGTATGCTAnGATTATGAGATTTCGACAT<br>GGAAGCCCAAACCTTCCTGAAAT |
| S00350 | 356 | TGggttgtttggtgagaacgaTAAGTTTGCCACAGGAACAGAGGTAAGAATAATAAAATA<br>ATAAATCATCCATTGCTTTTGAAAGATTTTGCAAGACTGTCTCACTGTAAAGT<br>ACTTCCAGTCCAAATATTGGATTCTTCTTTATAAGCCTGGTTACATCACTTGTA<br>CTCAAGTCTTCAGATTTGGGCCATTATTCATGGATCAAACTGTGAAAAAAAG<br>TTAAACAAAATTTATTTACAATTGAAAATCAGTTATCTTCCTTTTAATTTGCCC<br>AATGTGAGAGAAATGCAYTAGAGTCTTTSACAATCTACAATGGGAAGTTTCAT |

TABLE 7-continued

Non-Limiting Examples of Genomic Regions Comprising the Various Marker Loci Provided Herein.

| Locus Name | SEQ ID NO | Sequence |
|---|---|---|
| | | GCTGGGACTAACATAGGACGACAATTTTTATCTATTTTCTTTTACTTATTTCAT<br>GCTTCTGTTGTAGGTTAGAAAAYGATACTGCCATAGTGGTATTAGTATAATAT<br>AATATACTACATCTGYTYTAGAAAAAGATATGCATTTATCTGAAACTATATCA<br>TGCATATGTTAAACTCTGAGAAGCTCTTTGATAGATGTGCAACTGTAAAACTT<br>CAGAGCATTACATGCACTAATGAAAAGCTCTTTGATGCTTTAAAATCTGATAC<br>TTGAAACTTCTATAAAATTTGATGTACTTGATCACTAGTAACTGAAGACTCTA<br>CCCTTTTTGTGCACAGGCTATAGCCAAGAAACTGGCAGAGCTGAGTGGGAAG<br>GGAGTGACAACCATCATTGGAGGAGGTGACTCCGTTGCCGCTGTGGAGAAGG<br>TTGGACTTGCAGACAAGATGAGCCACATCTCCACTGGTGGTGGTGCCAGCTTA<br>GAGMCTTGAGGGAAAGCAACTCCCTGGTGTCCTTGCTCTTGATGATGCTTG<br>AGCAAAAATCATTCGTTCCTTTGAAGTTTGTGCTTTATATTATTATTATGGTTG<br>GGTTTCAGCCAACAGTGGATTAAGGTACAATGAGAGCTGCGAagttctTgcTCCctga<br>aaGGCTTAA |
| S02074 | 357 | ATGGanTTCTAAAAGAATGCCTTGTATGTGACGCGTACCATTCTAATCCTAaCT<br>ATATTTCTTTATATTCCTTATTTCACAAAAAGACACATTACAATGTGTGCCCTG<br>TGAGGGAAATATTGTAAATGTTAACARCGCAAGAGTAGTTTACACAACCTCAA<br>GATATCAAGGAAGGTATTAGTGTGTAATTTTGCTCATTTTTTTAAGAGACAAC<br>AAAATTVTATTCTCATATACTTATCAAAGCCACAAGATGTGACCTAAATATAT<br>AAGCCAAACATTACAGAAATTATTTTTTGCCATATGGTTGCAGCACCAAATTA<br>ACATCATCCCTAAACACAAGAAAATTTGAACACTAAATCCATCTAGAAAGCCT<br>TCKTAAACATAGTTTTTCTAGGCTTAGAAACCAAATCCTAGAATCAAATAAA<br>CATAAAGACTCCAACCATAGTGTAATTTTGCTCATTTTTATTTTGATACAAAGT<br>GCTAGGACATTAAAACATATTCTTTCTCTAATGAAACCTCCTCTAAAAAACTA<br>GYCGGAGAATCCCACCAACAGAACCATGTGTCATGGT |
| S03991 | 358 | agcttatYCCCCaaGAcgCTGTCAGCCATGTCGATTTCATTGTCAAACWAGGATCTC<br>CTCCCTATGAAGTTCCACTCCCAACCTACATCTGTGTGACTCCCATGTGCTGA<br>ATTAGCTGTTTTTGCTGGCAGGAAATGTGATATAGCTTAGGATATTTGTTATT<br>AGTGGAGCATCATTAGCAATTCCATTTTGAAAGACATTGCCCTGTTGCGATTG<br>GTGGAACACCGCCTTTAGGTCCTGCCACCATAAAGATTCATTGTTGCCTCTTGT<br>TACGTCATCCATGCACCTCCAGCCACCATATTTTGAATCCAATATTCTGGCCCA<br>TAGTTCCCCTKGGTGCTGAAATARAWCCSATCTCCATCTTCCAAGCAGTGCTA<br>GAKTGRAGGTGTTGATGTCcttcatgctctaacacatacctgtttccatcc |
| 504785 | 359 | ATTCAGTGATTTTACCTGTTTGCTTGCGAGATTCAGGAGGAGGGCCCCATAT<br>TGACGAGGCAAGAAAACCCCYGTTCCAGCGCAACCCCTTTTAGTAACACCGG<br>ATCCACCTTGCAACCCGGGTCGCGACCCGGATCCGAAATAAGGCACCTGTTGG<br>GTATTCTGGTYCTTCACTTGAAGAGGGTGCCATGCARGTGAGGCAAAACGTG<br>CGTGCAWTTCACAGCTTCATAGTCATACC |
| S02874 | 360 | GTATTATGCAGCTATGGTCAAGACATACTCATACTAGCAAAACAGCATTAATT<br>TGATGATTTGACTCATGGCTCATTTCCCTTGTTTAAATATAGCCATGTGGAAGT<br>TCACTUGTTATGGATTCCAYTTTCCTATTCATUTGAGGGATTTGGTAATTKGT<br>GAGGCACGACCAAGGAGAAGGGAAAATAAAAAAGGTGCAAGACCATGCTAA<br>AAAGGCTAGAAGAAACTATAAATCCTGATATTGTTGTTGAGAAAGAAGTGGT<br>TTGATTTGTGATAAATAAATGATAATATCTCACACAACCGGCCWGCTTCATCT<br>TACCCACACAGTTATTTCATAAACTTTAGAAGAWAACGTAAACTTATAGTAGT<br>TGATTAGAAAATTAACAGTTGAAATTGTGATTAAATACATTCACATATGTTCG<br>AAAAATATAGAATTGTTATCCACTAACGTGTATCAAGCTCTTTTTGCGGGATCTT<br>GCATGGTCATAGCYKKTT |
| S04348 | 361 | KHVKWYWHAAYYWRATGARMAGKGMATRKGRTAACWKRSMKWSCAgAgnnn<br>nnGAGACTAGAACCATTAACATTAGCCAGAGCCACAAAAGGTCTAATAAAAAC<br>ATATCATGAAAATAATTTTCTAAAAAGAGCAGCAAAAGACCTGTGCCATCAC<br>AGTTGTAGGAATCTGAATAAAATTAACACCACGTAGGAAGGCAGAGGCAGCA<br>AAGCCACACATGTCGCCAATCACACCACCACCAAGAGCAACAAAYGTACACC<br>GCCGGTCGAGCCGCGACTCGATGGCCTTGTCAAAGACTTTCATAAGAGTATCC<br>TATCAGTTGAACACACAAAGACTTTCTTATGCAATTCTCAAGAGTGCCAACAA<br>ACACCACAGCCAATTCAAAACACATGAGACCTACCATGTCCTTGTACTGCTCA<br>CCATCAGGTAAAATTACACTCTCCACAGAAACATTCGGGTTTCCCCTTGTCAA<br>AGCATCAACAACCTTGTCTAGATAAAGTGGCGCAACGGTTTCGTTAGTTACAA<br>CTAGGACTCTCTTTCCATGCACATGCCTATTCCAATAGTGAGAACAGAGCACT<br>TCAGAATAAATATTAAACAAGAAATAAAATCCATGCCTTGTTAGAAACTTTAA<br>TTGAATTGAACTTCTCCCACATACYATTAAATTTTATAGAAGCTCTTTCATTTA<br>AAGTCTCCAAAAGTTGAGGCACATATGTTGATTTTAGCTTAGAGGAGACTTCA<br>ATTCATTCTATCTTCT |
| 501209 | 362 | AATACTAAGCTGAAGGAATCGATTGCAAAATAATAACCCTTAGAAAACACTA<br>CGGCTTTGTAAATCATAAACCCTAAGCTCTCTCGCCCCTAATCCTACGAGCTA<br>GCTGAATGTCCTTGGGCATAATGGTAACCCTCTTAGCATGAATAGCGCAGAGG<br>TTGGTATCCTCAAAGAGCCCAACGAGGTAGGCCTCAGCGGCTTCCTGAAGAGC<br>GGAGACAGCRCTGCTCTGGAAGCGTAGATCGGTCTTGAAGTCYTGAGCGATTT |

TABLE 7-continued

Non-Limiting Examples of Genomic Regions Comprising the Various Marker Loci Provided Herein.

| Locus Name | SEQ ID NO | Sequence |
|---|---|---|
| | | CCCTTACGAGCCTCTGGAAAGGAAGCTTCCTTATGAGAAGCTCCGTGCTCTTC<br>TGGTACTTCCGAATCTCCCTCAGAGCCACTGTCCCCGGCCTGAAACGGTGGGG<br>CTTCTTCACGCCGCCCGTCGCCGGAGCGGACTTRCSTGCTGCCTTGGTGGCGA<br>GCTGCTTCCTTGGAGCTTTTCCTCCATGGTCATAGCTGTTT |
| S01999 | 363 | CaMCGGCGATTAAGCAGCCATATTTnCTGGTCAACACCAAGMGNGTCTTAAGT<br>TCCCTTCAGCTACTCTTTGGTCTAATTTTGATAGGAACCTGTCTCAGACCAAGC<br>CTAAGGTTTAATTCCATAGGCCCAAAAGGGCAAATGCGTCCTAGGTGAAAAG<br>AAGTTAGTTAGAGATGAGACAGTGTGAGTGAGGGGTCTGTTATATGGGAGGG<br>GGTGAGGCTTGTAMGGGGTATGGATGAATTTGGAATGTGAATTGGAGTCTAG<br>AGATTCTTCTCCGACTTTGGGGAGCACTTGCTCTCACTTCTTTCTGTGTGTTTTC<br>TGTTTTCAGCTTGTTTTTCTAATTCTGCAGCTTCCCTCTGATACAATATGTATCA<br>TTGGTGCTTTCATTGAGAGATTTGTTCCAATCASCATATGCAAACGAGGATGA<br>CGTCCMCCTYGATGCTGTTGAATAAAAAAWMTCTACCATCGACTTCMTCCTT<br>MAAWCWCATCWYCAAYMAMTTMAKYWACATTCCDYYCMCATGGTCAWAG<br>SHDKT |
| S02112 | 364 | CCATAGATCTGAAACAGAGATCACAAGGTTAACGCTTTTATTCtccaTTGGATGT<br>TACCCCAAACACCCCGYACCTATAATCTAGCACCAATCCAACCCGTTTTCACT<br>CGGATCTAGGACCTCAGGTAATCCCCCATGAATTTTCAATTATTATCAATGCTT<br>TTTCAACTTTAGTTTATTAATTCAGCYAGGGTTTAGTGTCTAAGTGAATAAGGT<br>TGGGATTTGYGATGGCTCCGACRATGRTCCGGAAGGTGATTGAGGTGGTGAA<br>GGACCAGACCARCATAGGAATAGTCAAGGTCGCGAGCAACATGGCGTCGGAG<br>ATGGAGGTCACGATTGTGAAGGCGATGAGCCACGAAGATGACCCTGYCAGTG<br>ACAAGTACATAAGARAGATCTTGAACCTCATGTCTCACTCRYRCGRCTACATC<br>CACACATGTGTCACCGCCATGTCCAAGCGATTGGGTAAGATGCRCGAATGGAT<br>TGTGTCGCTCAAGGCRCTGATGCTCGTGAACAGGCTCATG |
| S03252 | 365 | GtAGCATAACTGAaAATATAAATTVCCAATGCTCCTATTCTTCAAGAAGCAATT<br>CAAACTATAAGACAAGTTATATGACCTTCAAAAGTGTGCCCATAGAAAGTGTG<br>TTTTTAAGGTTTTTCGTTGTCCTGGTAATAATTTAACTAACTAGATGGCTTGTA<br>GTACTGTCAGAACATGTTCTCACTTGTTAAATTTCTATTTTGTGGTACGGTCCC<br>AGCTCAAAGATGTTTGCTTTATACAAATTACGCGTTACAAATTAAAGCATGTT<br>AAACAAGGTTTATGAGAGAGGAAGTTTTGACGTRATTCAAAGCCAAACCAAT<br>AAGTGGTTAGACATGTATTTATAATAGAACATAGATTTACCATAACAGCCATA<br>GATTAATATTCCAAGCTAATTAAGTGGTTGACAACCCCGACAATACCAATATA<br>TACTGAAATTCCTGATTACACGCCCTCTCTCCAACGTGTTGCTGAATTKTCAAG<br>AGGCTTTCCTATGTGGCTGGATATATTGCATCACACAACATCTGGGCACCAT |
| S04937 | 366 | gaatgcttgtttcacgtaagcttcttgactttaTCRTTCTCTCCCCCGCCCCCC<br>AAATACCACWAAAATTCCGAACGCTGTCATATTGCAATCTAATTGTTTAATACC<br>CAAATCCTTCCCTAGCTCTTTTCCAGTATCTTGAGCTTGTAATCTTCCATCTTA<br>AAAGCATACTGACTGATGCAATCTTCTGATTAATTTAGACCTGCATCAGTTACT<br>TGCTTGCAAGTTGTAGAATCTCTTATTTTYCTTTTCACTTCACTGGTTTGCATG<br>TCCATACAATTCGAACTATTTTTTATCTTTCAAAGATTGGAATGACATTAACTT<br>GGTTTTTGATCCTAATAGATAAGTCATATCAATTTAGTTCTTGAAAGTTGGAGA<br>CTRAATGTCCTCTAAATAAATTGACATCAATGTAGATCCTCAATAATAGAAAGA<br>TGACATCAATTTASTCCCTAAATCTTGCRGTTTGTGCATAGAAGGATGGTTTTT<br>TGGTTACTTTCCACGGTTGAGGTWCTAAAYTGATGCAATATCTCTTAKGGAGTT<br>ARRRVMMAAAGTGATGTCTACCGAACCTTCCAAGGAACTGGCCGWMgTTT |
| S04938 | 367 | aMMAKYTATGACCCATKCGAACCTTCCAASSMCCAAAAKGRAWTTTCACTCYW<br>AAATWTATGTSCACTCCTGACTGCTTTTACATTTAGTGTYTTCATTTCATTGGG<br>TTTCRTCTATCAGAATTCAGTGATAAGAAACAGTGCTTCAACAATAGGTTGTG<br>GAACATGTTTTYTGAGAGGTAAGGTAGTCACAATGAAAAAAAGGACAAAAC<br>TTAGATCCAAAGCTATGTTGCATTGATTAACAAAGTAATCACATAATTTTGGT<br>GTCATTTTCTAATAAGAATTGGAGTTTCATCTTGAAAGTTTATGTTGACCTGTA<br>ATGCAAACCTGTATYGCATAGATTAGTGAAGTAAAACTTTGTTTMATTAGA<br>GAATAACATCAAAAGCATTTATGGATCTGCATGAGTTTTKTCCTAAAAAGGTG<br>TGAAATAGGGGGAAAAAAGCCACACTGGATGTCAAAACCATTGTTCATCTGG<br>TATATAATTTCATCTCCWTATGGATARTTTTTTTTCTTTTCTGATTTCTTGTGAA<br>ATATATTAATTAACTKCCTTCTTTTACAKGTAAATGAGAATGTTGTTAATTAAT<br>ATGTTAACCTAAACSATATCTTTAATGYGTTKYCATYTTCTWTTCGTTTTGCAG<br>TGATGGTATCC |
| S06786 | 368 | STATTGCACSCGCTTTTCGTCCCGGTCAAGAAAAGATGGTTTATGTGTATCAGC<br>TCTTGGCAACAGGCACATTGGAGGAAGATAAGTACATAAGAACCACTTGGAA<br>AGAGTGGGTTACTAGCATGATTTTTAGTGAGGCTTTTGAGGAGAACCCTTCAC<br>ACTCGCGAGCATAGAACATTGAAGATGATMTACTGAGGGAAATGGTTGAGGA<br>GGACACGTCTAAAGCAATTCATATGATTCTAAAGAATGAAAAGGCTTCAAYA<br>AATTGAAGAGAGGTAATTACGCTTTTTTCATATGAAAACATGTGCTTAATTTA<br>TGTTTATATATCTTAATCCTACATTCTCCCTATTAGTGTTATTTACAGTGTTTGC<br>ACTAGATCACTAGAATGCTTGTTGGCATTCACCTTCAGTGTTGGAGACAGATT |

TABLE 7-continued

Non-Limiting Examples of Genomic Regions Comprising the Various Marker Loci Provided Herein.

| Locus Name | SEQ ID NO | Sequence |
|---|---|---|
| | | TGACACTTGTCGTCTCGAATGCCAGGGCAAGTTCGAGTTTAGTAGAAACTTAT<br>CATCCAAAATTAAAATTGAAAGCACTAATACAAAATGCACAATTTGAAGCCA<br>TTCATGTCCTCTCTTGGTCTGAGTCTTGTCATTTTGTGGATTGAATTCATGGTTT<br>CTCTTATCCGGTGACATTGTTRMCAAGTAATACTACTATAAATTCAGATTTGG<br>ATATCAGATAACCATGGTCATTAATAGTAATACTAACATACTATACATATAAT<br>ACCTTACAGGACCTTGTCCGAAACTTGAAACAGGATCAGGGACAGCGAAAAA<br>CAAACATGGTCAWAnCYKKTTYY |
| S06787 | 369 | TTACAAATAGGRRAAAACTTAGATATACATAGTTCTTTAAGTTTGATTACATT<br>ACAAATAGGAGAAAACTTAAAYATRCATAGTTMTAAGTGTTGTGTGTGCTG<br>TTCCATAATTAGAATTGGAGTTTTACTTACCTTAGTAATATGTATAATTCTAAT<br>TGGAGAACAGTACAAACAAAAACACCTAAKGAACAATACCTTAGMTAATC<br>ATATTTGTTTTGTTCATATAGCTTATCAATAAGTGAAGTATTTTCTTGTTCATCT<br>TGATGCAGGTGGTGGAACTGAAACCTTCATTGATTGGCCAACAAGGATGAAA<br>ATAGCACAGGACATGRCTCGTGGCTTGTTTTGTCTTCATTCCCTGGAGAACATT<br>ATACATGGGAACCTCACATCCAGCAATGTGTTGCTTGATGAGAACACAAATGC<br>TAAAATTGCAGATTTTGGTCTTTCTCGGTTGATGTCAACTGCTGCTAACTCCAA<br>CGTGATAGCTACTGCTGGAGCATTGGGATACCGGGCACCAGAGCTCTCAAAG<br>CTCAAGAAAGCAAACACTAAAACTGATATATACAGTCTTGGTGTTATCTTGTT<br>AGAACTCCTAACTAGGAAGTCACCTGGGGTGTCTATCATGGYCAWAGCTKKT |
| S06803 | 370 | ttgcgtaatctttctgttctgattttgagtaggaaccaatttagtggacatat<br>tccttcaagcattgcaaacatttccatgcttaggcagcttgatttgtcactga<br>ataatctcagtggagaaattccagtctcctttgaaagtcaacgtagtcttgat<br>ttcttcaatgtttcttacaatagcctttcaggttctgttccacctctacttgc<br>caagaaatttaactcaagctcatttgtgggaaatattcaactatgtgggtata<br>gcccttcaaccccatgtctttcacaagctccatcacaaggagtcattgcccca<br>actccagaagtactgtcagaacagcaccatcgtaggaacctcagtaccaaaga<br>cataattctcatagtagcaggagttctcctagtagtcctgattatactttgtt<br>gcatcctgcttttctgcttgatcagaaagagatcaacatcgaaggctgagaac<br>ggacaagccacggggagagcagccRctggaaggacagaaaaaggagtccctcc<br>agtttctgctggtgatgttgaagcaggtggggaggctggagggaaactagtcc<br>attttgatggaccattggcttttacagccgatgatctcttgtgtscaactgct<br>gagatcatgggaaagagccatggtcatagcctgt |
| S06804 | 371 | tttgtttcttatgatgtggagtcttgttgtgctcccttcatgcgtgagaccag<br>ctttgtgtgaagatgaaagttgggacggagtggttgtgacagcatcaaacctc<br>ttagcacttcaagcttcaagcaagagttggtggacccagaagggttcttgcg<br>gagctggaacgacagtggctatggtgcttgttcaggaggttgggttggaatca<br>agtgtgctcagggacaggttatcgtgatccagcttccttggaagggtttgaag<br>ggtcgaatcactgacaaaattggccaacttcaaggccttaggaagcttagtct<br>tcatgataaccaaattggtggacaatcccttcaactttgggacttcttcccaa<br>ccttagaggggttcagttattcaacaataggttaactggttccatcccttctt<br>ctttaggatctgtcctttgcttaagtctcttgacctcagcaacaacttgctca<br>cMggagcaatcccttatagccttgccaattccaccaagctttattggcttaac<br>ttgagtttcaactccttctctggtactttaccaactagcctaactcactcatt<br>ttctctcactttcctttctatcaaaataataatctttctggcaaccttcctaa<br>ctcttgggtgggagtcccaagagggcttctttaggcatggtcatagctgtt |
| S06788 | 372 | gTATTTGATTAGTTAAACCGCAACGCGGAATCTCTTTTCTCGAACTGGCTAACT<br>CTCAGGCAAGTGGTTCGGACGCTGATTCCAGCAACAAGCGGCTGGTGCTCGCA<br>CTGTATGACGCCCTAAACTCCGGCGACTCCGACGCCGTCGTCAAGATCGTCGC<br>CGCCGACCTCGAGTGGTGGTTCCATGGTCCGCCCTCACACCAGTTTTTGATGC<br>GCATGCTCACCGGCGACTCCGCTGCCGACAACTCCTTCCGCTTCCTTCCGCAGT<br>CCATCGCCGCMCGGCTCCACCGTCATCGTCGAGGGCTGCGACACCGCCCGC<br>AACATTGCCTGGGTCCACGCCTGCACCGTCACGGATGGGATAATTACTCAGAT<br>CAGAGAGTACTTVAACACCGCCCTCACCGTCACCCGCATCCACGATTCCGGCG<br>AGATTGTTCCGGCTAGCTCCGGCGCCGGCCGTTTGCCCCTUTGTCTGGGAAAG<br>CAGCGTCTCCGGTCGGTCGGGAAATCCGTACCCGGTTTGGTTCTTGCAATAT<br>AAAATAATTATTAACAAGTAATTAGGGAAGAACGCGGTCACGTGTGAATAAT<br>ANTTAAATAAGGAGGTTGTGCACGTGGCGGTGACTGGGTCGAACGGTTTCAG<br>GGAACATTGATATATTTTCGTAGTATTGGTGTGTTCTRGAGGTTAGAGAGATG<br>TGAGACCCTATTGGTGGGGTTTCTTATTTCTTTAATTTTCTCAGGTTTGGYTTGT<br>TTTTGTTTTGTTTGCTTGTGTGTMGGGCATGGTCATAGCCKK |
| S06805 | 373 | TATTTTAATTAAGAAAATAAAGGAGTTTGTTTATGCTGCAATTTATGATCTAG<br>ATCCAATATAGGGAAGATGANTGCTAGTAAGGCACTATTTATTGGGTAAAATC<br>CATGTGGGTCCCAATCCATATTTACTAGTTCTCACTCCGTACTTAGTGTAACTT<br>ACATGTGTCATCCGATTATGGAGTGTTGTGCTAGCATTTCTCTTATATAGGGAA<br>TTAGGGATACAAAATGGCTTTCCCTACTTTTCGTGGGCAACCCCAATTTGATA<br>ACTTGGCCACTTTATGGCTAGACTTCAGCCTAATTTATGTACTAGATATAGTAT<br>ATGAATTTATACATAACTTCACATGCCCTGAAATTTTCCACTTGATTTGCAGGC<br>AATTGTGACAGAAGAGGATGGAATGGAGTCAATAGCTCATAGATTTCTTTCTG |

TABLE 7-continued

Non-Limiting Examples of Genomic Regions Comprising the Various Marker Loci Provided Herein.

| Locus Name | SEQ ID NO | Sequence |
|---|---|---|
| | | CTGCTGTCAAGGTAGAGTTCCATCCACCTGATTCTATTTTTGATGAAATUTTTC<br>TGGCTTGAAATTATTACTATATTTATTATTGTATTTTAACACTTGYCTTTACAA<br>CATGTAGTATAATACTATAATTACACTCATGCAAGMCCAGGTCCATCTTTAC<br>AAAATTGTAAATACTAACACTGCAGRAATTTGGAAAGTTATAGTAGTAGTCGT<br>CTACCATCTACGGccAAAMCMWKGKYMWWRSYBKKt |
| S06789 | 374 | ggSttYcccaaaTAggtcagcctctccataaaccctcaagagcgtattatagct<br>aatgacgttgggttgaatcccatttcctcatgctccagaagaggcggtcggc<br>ttccttgggcatgtgaagctggccataaacatcaatcatgatgttacaagtggt<br>gagatcaagagggcatttagcttcattcatttcggaRaatagagaaagtgcttc<br>aacaaacttttggttgtcaacgtagatggcaagaagggtggaatagctgacggt<br>gtcgggttganggcattgtctctcatctcttgaagaagaaggcgagcctcacgg<br>aagagcttggcttttccaaagacattgatcatggagttataagcaataaggtcg<br>ggggtaatagtggaggctttcAatctggagaaGatagaaatggccttggaataa<br>toGgacaacttgcgggcaaggtcaatcaagttactgtagagaacgaggtcgccg<br>gagacGttgtcttgctccatctgctggagccaaaagagggaagaatcAaacaag<br>ccgtgtttgccgaaacaagtaattagggtggagtaagtgtacctatcgggggag<br>aggcccttttggcGcattTcATcGaacaggccgtgtgcgaggtgccactgcttg<br>gcccGaaggacgttgcggagaaGgACGTgGTgGGCGaMGWKGSRGTZRAMRTZW<br>MGWKgBMCKYSWMSWKKTZWSSVWBGDYMKAGSBBBttBYMnWtgatccMtggt<br>catagcYKKtt |
| 506790 | 375 | gWcWMKWWTTKGCAMASRMKCVARGCTCGACMCTGKTCTATAATCTTACCC<br>CTGATAGAACCTTCAAGTTCAGGCCTTGGAGCTCCGGTGAAAGTGAACAAGTA<br>TGGCCGCTTTTGATGTCTGATTTTTCTCTGCCACCGGTAAACATGAGTGTCCTC<br>TGATGGGTGGAAAGAAGTTGGGTACGGAATTGCGTAGTCATTATTCCACGAAC<br>TTGCTTVAACTGCTAACATGGACATGTTCATGGATTCGGGTATAAACCTGAAC<br>TTACTACCCCAATAGGACGCATCATCATATTGTCTCCTGAAATCCCAAGCAAT<br>CCTCCCAGAAACAAGGAATGATCTCTGCCCCACATTTKCTTCCACTCGGGTC<br>TTTTTGCGACCCATTGAAGAAGATCACGACCAGAGGAATCTCTCTCTGTGAGA<br>TTAGAGAGCCAAAGGAAACGGCTAACATCAAGACCAGCATAGAATGGGACGA<br>AAATTGCAGAGGCGAGGGAGGAATCGTTGGTCAAGCAGCCATATTTGGTCAT<br>CCTGTTGTGAAAAATAACTTCCAACAAGAACTGGTTGGTGGCATAGCAAGTGT<br>TGTTGGAGAAAAGCCCTTGGGAGTAGGTAATGTGAGGACCTAAACCATTGTTT<br>TGCATGTATGGACACATGTTGGGTTTGTCAGTGCCTCTAGTGAGGGACTGGCA<br>ATTCTGAAGCAAGTAATCgTTnAAGCGGGAGCATGGTCATAGCBKKTTT |
| 506791 | 376 | tACBTAATTTTAAGTAGGTTGAAATGTYTCTTACCCTTTGTATGAGATCTCTGTT<br>TGATTCACCTAGAAAGTGTTCCTTCACAAGTGACATATATAATTGAATCGGTG<br>AGCAAGGGAAACATGCGGAAGATCAAYAGCAGTTAAACATTGAYMAAAGAA<br>AGAAAGSATAATTGACCTCATACCTTWCGTTGTAGATCAGAAAGCTGATCCAG<br>CATGAATTGGGTCTGCATATATAGAATGCTATGAGAAAAGTTGATATAGACCA<br>TTGACCATTGAGATTATATATGAAGTTATGAGAAAGATCAACTAATTTCTTCT<br>ATTCTTTATTGCACAGCTAAAAAAAAAATGATTATATATGTCAAAATGGAAAT<br>TGGCAACGTTGGAAACTTTAGTACCCTTATTGATCTGATTTGTTTCAAAGACG<br>AATCTAGCTGCCTTTCAAGTGACTCAAGCTCTTTGCTGCTTAGAGGACCAAGA<br>TCTTCTCCCATAAGGTTCCTAATGAGTATCGACCAGTCAAATATATATTAATA<br>ACTCATCAGTTCGTATTATGTAGCTAGCATATACTTCTAGACATAGTCGAGTCT<br>AGCTCTTTACCTTTGAGAACGCTGAAGAGCTTCATAACGCGCTTTCAGCCTCA<br>AGTATTCTTCATGGTCATAGCYKKTT |
| 506792 | 377 | KWRTWAACTTCnaTTCCWTATCRTCTCTATGATCARYATSRGCATAAGTTTCAG<br>AAGAAGTAATTGGAGAGTTGTCTTCAACCAAAAGTTTCCCTTCCTTAGCTGCA<br>ACGAACASGTCCTGAATAGGACCATACAAGGCATTGTGATTTGTTCTGTTAGG<br>TGGCMCGGAAAATCAGTCAAACTCTCCCTTATCAAACTACATTGTTTCTCTAT<br>GCTTAATGCCCCAGGAATAAAATAAAAGCCTGCAAATTAAGTATCACCAAGT<br>GTGCTTGAGTTCATTAGTTACAAATGCACTTATGATTAGTTTCTAATCACTAAT<br>TAATTATCCCAGTCAAGTACAATTCAAGCCATTTGTTTCAAGTTACTAAGATA<br>AACGGCAAATAAAAGAAAAAAGAAAATACCTGGGCGATTTTGTAAAGCAAAA<br>ACCGGAGAGGTGAACTTGTCGTGAAGAACGATAACACCCGAAGGAAGCACAG<br>CGTTTTGGTGATAGCATTCTAGAATAGATCTAAAGTCAAGGACCTCCGCTAAG<br>TCCACGGGTTTAGGTTGTTTTTTCCTGTTAAGAAAGGGAATTTCAATTASAATT<br>TGCAGAGATTACAACTGAAACAATCTACGTTCAAAGGAAATGAAATAGTAAA<br>ATACTTTTTGTTCTTGGAAGAAGCATTGTAGTCSTAGTAGAGCTTGTACTTCTT<br>CTCTGCATGGTCAWAGCSKKTT |

TABLE 8

Non-limiting Examples of Amplicons Comprising the Various Marker Loci Provided Herein.

| Locus | Linkage Group (cm) | Primer 1 | Primer 2 | Amplicon SEQ ID NO (R/S) | Amplicon Sequence [Res/Sus] | Amplicon Size (bp) |
|---|---|---|---|---|---|---|
| S04196-1 | B1 (Gm11) | 141527 | 141528 | 111/112 | GCCATCCTAGCTAGCCCTGTATATTTTGATTANNTTNATGGGAAGAAAAAATTAAATATTTTTATTTAATTGAAGAGTAAGTTAATTTTATGAAAACAAAAATTTAACATTTTCTTACTTATCTTTTAATTCAAATTTTATTTTATTTTCTCTTATTCCAACAATAATTCCTAAAGATA[****/CATGCAA**]GTCCAATATGTTTAACTCATCACATTTAATTTCATTACGAAATAATCAACAGGTCAA | 236/243 (12/S) |
| S04938-1 | B1 (Gm11) | S04938-P1 | S04938-R1 | 113/114 | TGTGCACTCCTGACTGCTTTTACATTTAGTGTCTTCATTTCATTGGGTTTC[C/T]TCTATCAGAATTCAGTGATAAGAAACAGTGCTTCAACAATAGGTTGTGG | 101 |
| S04937-1 | B1 (Gm11) | 148638 | 148639 | 115/116 | TCAATTTAGTTCTTGAAAGTTGGAGACTRAATGTCCTCTAAATAAATTGACATCAATGTAGATCCTCAATAATAGAAAGATGACATCAATTTASTCCCTAAATCTTGC[T/C]GTTTGTGCATAGAAGGATGGTTTTTTGGTTACTTTCCACGGTTGAGGTACTAAATTGATGCAATATCTCTTAGGGAGTTAGAGGACAAAGTGATGTCTACCGAACCTTCCAAGGA | 224 |
| S08344-1 | B11 (Gm11) | 136830 | 136831 | 117/118 | CGACACCAATTTCTCCATCCTCTCATTGAAAAACAAAATTAATCATCTTA[C/T]TTATTTATTCTCCGAAAATGGTTGATTTACATTGGAAATCAAAGATGCCAAGTTCCGACAT | 112 |
| S08343-1 | B1 (Gm11) | 136886 | 136887 | 119/120 | GACTTACCAAATGAGTTTGACCAGGTTTTACCCCTCTTGATTGCAACCTCACGACCATCAACGAGTTTGCCTCTGTACTCAACAACAAAGCCTCCGGTACCAATCTTGTTGTCAAATGAGAAATTATTGGTGGCTGCTTTAAGTTCAGCGAGGGTGAATAATGGTGCAGCAAAAGCATGCACTGGGGAAGGGGATGATYCCAAATCTGCTTCACTGGCACTACTACTCCTTATGGCACTGTC[C/A]ACTAATGAAGCAAAACTACGGACACGAGATTCTCCAAAAATGG | 286 |
| S08346-1 | B1 (Gm11) | 136886 | 136887 | 121/122 | TTGTTCTCCCGYTTACACCACAAGAATTTGGTTGGGCTGUTTGGATTTTGTGAA[C/G][A/A]AAAA[G/T]ATGAAAGGCTCTTGGTGTATGAGTACATGAAGAATGGGRCGTTGTATCA | 110 |
| S06786-1 | B1 (Gm11) | 144687 | 144688 | 123/124 | CCACTTGGAAAGAGTGGGTTACTAGCATGATTTTAGTGAGGCTTTTGAGGAGAACCCTTCACACTCGCGAGCATAGAACATTGAAGATGAT[A/C]TACTGAGGGAAATGGTTGAGGAGGACACGTCTAAAGC | 130 |
| S06787-1 | B1 (Gm11) | 142755 | 142756 | 125/126 | TGCTGTTCCATAATTAGAATTGGAGTTTTACTTACCTTAGTAATATGTATAATTCTAATTGGAGAACAGTACAAACAAAAACACCTAA[G/T]GAACAATACCTTAGYTTTAATCATATTTGTTTTGTTCATATAGCTTATCAATAAGTGAAGTATTTTCTTGTTCATCTTGATGCAGG | 175 |

TABLE 8-continued

Non-limiting Examples of Amplicons Comprising the Various Marker Loci Provided Herein.

| Locus | Linkage Group (cm) | Primer 1 | Primer 2 | Amplicon SEQ ID NO (R/S) | Amplicon Sequence [Res/Sus] | Amplicon Size (bp) |
|---|---|---|---|---|---|---|
| S06803-1 | B1 (Gm11) | 142759 | 142760 | 127/128 | AACATCGAAGGCTGAGAACGGA CAAGCCACGGGGAGAGCAGCC[A/ G]CTGGAAGGACAGAAAAAGGA GTCCCTCCAGTTTCTGCTGGTGAT GTTGAAGCAGGTGGGGAGGCTG GAGGGAAACTAGTCCATTTTGAT GGACCATTGGC | 144 |
| S04197-1 | B1 (Gm11) | 142386 | 142387 | 129/130 | TGCCTAATGGGAGAGATGAAGAT TAAAGTTATTATTATATACATAA ATATAAAATTGGAAATGAATATT TGTTTTAAATGGAGTATGAAGAT CATACCCTATCCAGTATCTACTA CCRGTATCTACTACCAT[C/A]CCT AAACTCGACAAGGCACCTACACT ACAATATAAATATAGTAAGGCTT CGAGTAACAGAACCTGCG | 200 |
| S07162-1 | C1 (Gm04) | 136849 | 136850 | 131/132 | AATGCAGGGCCAGTTACAATACA TACATACGCATAACCAAAACAGT AACATCAATGGAACAGTAATAGG ACACAAT[C/T]ATTATTATTTTTT TGTTAAGGAAATTTCTAAGAAAA ACACAACCATTTGTACAAAAAAG GTATTAATACATAGCTACATGGA AGAAACCTACATTAAAATCCAGT AGTGAGAAAAGATGGGGGCAAT T | 205 |
| S07161-1 | D2 (Gm 17) | 137370 | 137374 | 133/134 | TGCTTATCTTGTCTGAAAACCACT AATGCTCTCTTCAGTG[A/T]GAAT AAAAGGGCTACAAGATATCATAC ATATGCTTTAATATTATATCACTA AATACAATTAAGGATGCTCATCA CATTAGGTTAGGTTAGATACAGT TGAATTGCCTTAAAGTCA | 156 |

TABLE 9

Positions of various markers

| Locus | Linkage Group (ch) | Genetic (cM) | SNP Position (bp) |
|---|---|---|---|
| S02621 | D1b (2) | 133.95 | 51490811 |
| S01519 | D1b (2) | 120.16 | 48686902 |
| S08177 | D1b (2) | 131.45 | 50529112 |
| S00479 | D1b (2) | 91.61 | 42982998 |
| S02136 | D1b (2) | 94.75 | 44096100 |
| S00875 | D1b (2) | 113.96 | 47471551 |
| S12875 | D1b (2) | 114.51 | 47529446 |
| S12950 | D1b (2) | 114.71 | 47556177 |
| S12947 | D1b (2) | 114.78 | 47576630 |
| S12933 | D1b (2) | 115.35 | 47765197 |
| S12853 | D1b (2) | 116.68 | 48204176 |
| S03246 | D1b (2) | 117.97 | 4833665 |
| S12962 | D1b (2) | 125.66 | 49371792 |
| S00144 | D1b (2) | 126.03 | 49461261 |
| S08166 | D1b (2) | 126.17 | 49505295 |
| S01081 | D1b (2) | 132.07 | 50775206 |
| S02183 | E (15) | 90.49 | 49934844 |
| S00350 | E (15) | 85.49 | 48657373 |
| S02074 | L (19) | 17.63 | 2901398 |
| S03991 | L (19) | 29.32 | 18029354 |
| S04785 | B2 (14) | 26.08 | 5096522 |
| S02874 | B2 (14) | 20.07 | 3945680 |
| S04348 | B1 (11) | 37.62 | 5916329 |
| S01209 | B1 (11) | 54.57 | 9963410 |
| S01999 | B1 (11) | 63.22 | 11202391 |
| S04937-2 | B1 (11) | 97.94 | 36954416 |
| S04937-1 | B1 (11) | 97.95 | 36954799 |
| S04938-1 | B1 (11) | 97.95 | 36954994 |
| S04938-2 | B1 (11) | 97.95 | 36955430 |
| S06786-2 | B1 (11) | 99.96 | 37311026 |
| S06786-3 | B1 (11) | 99.97 | 37311730 |
| S06786-1 | B1 (11) | 99.97 | 37311443 |
| S06787-2 | B1 (11) | 100.09 | 37333749 |
| S06787-1 | B1 (11) | 100.09 | 37333894 |
| S06803 | B1 (11) | 100.10 | 37334507 |
| S06804 | B1 (11) | 100.10 | 37335483 |
| S06788 | B1 (11) | 100.50 | 37405385 |
| S06805 | B1 (11) | 100.99 | 37492596 |
| S06789 | B1 (11) | 109.51 | 37923651 |
| S06790 | B1 (11) | 109.97 | 38041618 |
| S06791-2 | B1 (11) | 110.26 | 38197612 |
| S06791-1 | B1 (11) | 110.26 | 38197663 |
| S06792 | B1 (11) | 110.45 | 38279360 |
| S02112 | C2 (6) | 108.15 | 45770644 |
| S03252 | C2 (6) | 102.83 | 21822996 |

In another embodiment, the method of detecting comprises DNA sequencing of at least one of the marker loci provided herein. As used herein, "sequencing" refers to sequencing methods for determining the order of nucleotides in a molecule of DNA. Any DNA sequencing method known in the art can be used in the methods provided herein. Non-limiting examples of DNA sequencing methods useful in the methods provided herein include Next Generation Sequencing (NGS) technologies, for example, as described in Egan, A. N, et al. (2012) *American Journal of Botany* 99(2): 175-185; genotyping by sequencing (GBS) methods, for example, as described in Elshire, R. J., et al. (2011) *PLoS ONE* 6(5):e19379; Molecular Inversion Probe (MIP) genotyping, as described, for example, in Hardenbol, P., et al. (2003) *Nature Biotechnology* 21(6):673-678; or high throughput genotyping by whole-genome resequencing, as described, for example in Huang, X et al., (2009) *Genome Research* 19:1068-1076. Each of the above references is incorporated by reference in their entirety herein.

An active variant of any one of SEQ ID NOS: 1-377 can comprise a polynucleotide having at least 75%, 80% 85%, 90%, 91%, 92%, 93%, 94%, 95%, 96%, 97%, 98% or 99% sequence identity to SEQ ID NOS: 1-377 as long as it is capable of amplifying and/or detecting the marker locus of interest. By "fragment" is intended a portion of the polynucleotide. A fragment or portion can comprise at least 5, 6, 7, 8, 9, 10, 11, 12, 13, 14, 15, 16, 17, 18, 19, 20, 25, 30, 40, 50, 75, 100, 150, 200, 250, 300, 350, 400 contiguous nucleotides of SEQ ID NOS: 1-158 as long as it is capable of amplifying and/or detecting the marker locus of interest.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; or any equivalent program thereof. By "equivalent program" is intended any sequence comparison program that, for any two sequences in question, generates an alignment having identical nucleotide residue matches and an identical percent sequence identity when compared to the corresponding alignment generated by GAP Version 10.

Traits or markers are considered to be linked if they co-segregate. A 1/100 probability of recombination per generation is defined as a map distance of 1.0 centiMorgan (1.0 cM). Genetic elements or genes located on a single chromosome segment are physically linked. Two loci can be located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. Genetic elements located within a chromosome segment are also genetically linked, typically within a genetic recombination distance of less than or equal to 50 centimorgans (cM), e.g., about 49, 40, 30, 20, 10, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). In specific embodiments, a closely linked marker is within 10 cM, 9 cM, 8 cM, 7 cM, 6 cM, 5 cM, 4 cM, 3 cM, 2 cM or 1 cM of any given marker disclosed herein. In further embodiments, a marker associated with one of the markers disclosed herein can be within 75 Kb, 60 Kb, 50 Kb, 40 Kb, 30 Kb, 20K, 10 Kb, 5 Kb or less of the disclosed marker.

Put another way, closely linked loci co-segregate at least about 90% of the time. Genetic linkage as evaluated by recombination frequency is impacted by the chromatin structure of the region comprising the loci. Typically, the region is assumed to have a euchromatin structure during initial evaluations. However, some regions, such are regions closer to centrosomes, have a heterochromatin structure. Without further information, the predicted physical distance between genetic map positions is based on the assumption that the region is euchromatic, however if the region comprises heterochromatin the markers may be physically closer together. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 2 Kb, about 1 Kb, about 500 nucleotides, about 250 nucleotides, or less.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

Markers are used to define a specific locus on the soybean genome. Each marker is therefore an indicator of a specific segment of DNA, having a unique nucleotide sequence. Map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in soybeans.

Favorable genotypes associated with at least trait of interest may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) Nat Biotech 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GB S) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis.

The use of marker assisted selection (MAS) to select a soybean plant or germplasm which has a certain marker locus, haplotype or marker profile is provided. For instance, in certain examples a soybean plant or germplasm possessing a certain predetermined favorable marker locus or haplotype will be selected via MAS. In certain other examples, a soybean plant or germplasm possessing a certain predetermined favorable marker profile will be selected via MAS.

Using MAS, soybean plants or germplasm can be selected for markers or marker alleles that positively correlate with soybean cyst nematode resistance, without actually raising soybean and measuring for resistance (or, contrawise, soybean plants can be selected against if they possess markers that negatively correlate with resistance). MAS is a powerful tool to select for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some embodiments, the molecular markers or marker loci are detected using a suitable amplification-based detection method. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage and Caruthers (1981) Tetrahedron Letts 22:1859-1862, e.g., using a commercially available automated synthesizer, e.g., as described in Needham-VanDevanter, et al. (1984) Nucleic Acids Res. 12:6159-6168. Oligonucleotides, including modified oligonucleotides, can also be ordered from a variety of commercial sources known to persons of skill in the art.

It will be appreciated that suitable primers and probes to be used can be designed using any suitable method. It is not intended that the invention be limited to any particular primer, primer pair or probe. For example, primers can be designed using any suitable software program, such as LASERGENE® or Primer3.

It is not intended that the primers be limited to generating an amplicon of any particular size. For example, the primers used to amplify the marker loci and alleles herein are not limited to amplifying the entire region of the relevant locus. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Non-limiting examples of polynucleotide primers useful for detecting the marker loci provided herein are provided in Table 2 and 3 and include, for example, SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, and/or 248 or variants or fragments thereof.

PCR, RT-PCR, and LCR are in particularly broad use as amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous journal and patent references, such as Mullis, et al. (1987) U.S. Pat. No. 4,683,202; Arnheim & Levinson (Oct. 1, 1990) C&EN 36-47; Kwoh, et al. (1989) Proc. Natl. Acad. Sci. USA 86:1173; Guatelli, et al., (1990) Proc. Natl. Acad. Sci. USA 87:1874; Lomell, et al., (1989) J. Clin. Chem. 35:1826; Landegren, et al., (1988) Science 241:1077-1080; Van Brunt, (1990) Biotechnology 8:291-294; Wu and Wallace, (1989) Gene 4:560; Barringer, et al., (1990) Gene 89:117, and Sooknanan and Malek, (1995) Biotechnology 13:563-564.

Such nucleic acid amplification techniques can be applied to amplify and/or detect nucleic acids of interest, such as nucleic acids comprising marker loci. Amplification primers for amplifying useful marker loci and suitable probes to detect useful marker loci or to genotype SNP alleles are provided. For example, exemplary primers and probes are provided in SEQ ID NOS: 1-110 and in Tables 2 and 4, and the genomic loci comprising the various marker loci provided herein are provided in SEQ ID NOS: 135-158 and in Table 6. Non-limiting examples of amplicon sequences comprising the marker loci provided herein are provided in Table 8. In other embodiments, exemplary primers and probes are provided in SEQ ID NOS: 159-248 and in Tables 3 and 5, and the genomic loci comprising the various marker loci provided herein are provided in SEQ ID NOS: 339-337 and in Table 7. However, one of skill will immediately recognize that other primer and probe sequences could also be used. For instance primers to either side of the given primers can be used in place of the given primers, so long as the primers can amplify a region that includes the allele to be detected, as can primers and probes directed to other SNP marker loci. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the compositions and methods are not limited to the primers and probes specifically recited herein.

In certain examples, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.).

Detectable labels may also include reporter-quencher pairs, such as are employed in Molecular Beacon and TaqMan™ probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent, depending on the embodiment. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules*, 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland, *Handbook of Fluorescent Probes and Research Chemicals*, Molecular Probes of Eugene, Oreg., 1992, the content of which is incorporated herein by reference.

In certain examples, reporter-quencher pairs are selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters are the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like. In certain other examples, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from Applied Biosystems, and the like. Suitable examples of quenchers may be selected from 6-carboxy-tetramethyl-rhodamine, 4-(4-dimethylaminophenylazo) benzoic acid (DABYL), tetramethylrhodamine (TAMRA), BHQ-O™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

In one aspect, real time PCR or LCR is performed on the amplification mixtures described herein, e.g., using molecular beacons or TaqMan™ probes. A molecular beacon (MB) is an oligonucleotide which, under appropriate hybridization conditions, self-hybridizes to form a stem and loop structure. The MB has a label and a quencher at the termini of the oligonucleotide; thus, under conditions that permit intramolecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone, et al., (1995) Molecular beacon probes combined with amplification by NASBA enable homogenous real-time detection of RNA, Nucleic Acids Res. 26:2150-2155; Tyagi and Kramer, (1996) Molecular beacons: probes that fluoresce upon hybridization, Nature Biotechnology 14:303-308; Blok and Kramer, (1997) Amplifiable hybridization probes containing a molecular switch, Mol Cell Probes 11:187-194; Hsuih. et al., (1997) Novel, ligation-dependent PCR assay for detection of hepatitis C in serum, J Clin Microbiol 34:501-507; Kostrikis, et al., (1998) Molecular beacons: spectral genotyping of human alleles, Science 279:1228-1229; Sokol, et al., (1998) Real time detection of DNA:RNA hybridization in living cells, Proc. Natl. Acad. Sci. U.S.A. 95:11538-11543; Tyagi, et al., (1998) Multicolor molecular beacons for allele discrimination, Nature Biotechnology 16:49-53; Bonnet, et al., (1999) Thermodynamic basis of the chemical specificity of structured DNA probes, Proc. Natl. Acad. Sci. U.S.A. 96:6171-6176; Fang, et al. (1999) Designing a novel molecular beacon for surface-immobilized DNA hybridization studies, J. Am. Chem. Soc. 121:2921-2922; Marras, et al., (1999) Multiplex detection of single-nucleotide variation using molecular beacons, Genet. Anal. Biomol. Eng. 14:151-156; and Vet, et al., (1999) Multiplex detection of four pathogenic retroviruses using molecular beacons, Proc. Natl. Acad. Sci. U.S.A. 96:6394-6399. Additional details regarding MB construction and use is found in the patent literature, e.g., U.S. Pat. Nos. 5,925,517; 6,150,097; and 6,037,130.

Another real-time detection method is the 5'-exonuclease detection method, also called the TaqMan™ assay, as set forth in U.S. Pat. Nos. 5,804,375; 5,538,848; 5,487,972; and 5,210,015, each of which is hereby incorporated by reference in its entirety. In the TaqMan™ assay, a modified probe, typically 10-25 nucleic acids in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are preferably attached to the probe within a few nucleotides of one another, usually within 30 nucleotides of one another, more preferably with a separation of from about 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook, et al., *Molecular Cloning—A Laboratory Manual* (3d ed.), Vol. 1-3, Cold Spring Harbor Laboratory, Cold Spring Harbor, N.Y., 2000 ("Sambrook"); *Current Protocols in Molecular Biology*, F. M. Ausubel, et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis, et al., eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

Other techniques for detecting SNPs can also be employed, such as allele specific hybridization (ASH). ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Real-time amplification assays, including MB or TaqMan™ based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain examples, each allele-specific probe for a certain SNP locus is 11-20 nucleotides in length, dual-labeled with a florescence quencher at the 3' end and either the 6-FAM (6-carboxyfluorescein) or VIC (4,7,2'-trichloro-7'-phenyl-6-carboxyfluorescein) fluorophore at the 5' end.

To effectuate SNP allele detection, a real-time PCR reaction can be performed using primers that amplify the region including the SNP locus, for instance the sequences listed in Table 4, the reaction being performed in the presence of all allele-specific probes for the given SNP locus. By then detecting signal for each detectable label employed and determining which detectable label(s) demonstrated an increased signal, a determination can be made of which allele-specific probe(s) bound to the amplicon and, thus, which SNP allele(s) the amplicon possessed. For instance, when 6-FAM- and VIC-labeled probes are employed, the distinct emission wavelengths of 6-FAM (518 nm) and VIC (554 nm) can be captured. A sample that is homozygous for one allele will have fluorescence from only the respective 6-FAM or VIC fluorophore, while a sample that is heterozygous at the analyzed locus will have both 6-FAM and VIC fluorescence.

The KASPar® and Illumina® Detection Systems are additional examples of commercially-available marker detection systems. KASPar® is a homogeneous fluorescent genotyping system which utilizes allele specific hybridization and a unique form of allele specific PCR (primer extension) in order to identify genetic markers (e.g. a particular SNP locus associated with soybean cyst nematode resistance). Illumina® detection systems utilize similar technology in a fixed platform format. The fixed platform utilizes a physical plate that can be created with up to 384 markers. The Illumina® system is created with a single set of markers that cannot be changed and utilizes dyes to indicate marker detection.

These systems and methods represent a wide variety of available detection methods which can be utilized to detect markers associated with improved resistance to soybean cyst nematode, but any other suitable method could also be used.

Introgression of soybean cyst nematode resistance into non-tolerant or less-tolerant soybean germplasm is provided. Any method for introgressing one or more marker loci into soybean plants known to one of skill in the art can be used. Typically, a first soybean germplasm that contains soybean cyst nematode resistance derived from a particular marker locus, haplotype or marker profile and a second soybean germplasm that lacks such resistance derived from the marker locus, haplotype or marker profile are provided. The first soybean germplasm may be crossed with the second soybean germplasm to provide progeny soybean germplasm. These progeny germplasm are screened to determine the presence of soybean cyst nematode resistance derived from the marker locus, haplotype or marker profile, and progeny that tests positive for the presence of resistance derived from the marker locus, haplotype or marker profile are selected as being soybean germplasm into which the marker locus, haplotype or marker profile has been introgressed. Methods for performing such screening are well known in the art and any suitable method can be used.

One application of MAS is to use the resistance markers, haplotypes or marker profiles to increase the efficiency of an introgression or backcrossing effort aimed at introducing a resistance trait into a desired (typically high yielding) background. In marker assisted backcrossing of specific markers from a donor source, e.g., to an elite genetic background, one selects among backcross progeny for the donor trait and then uses repeated backcrossing to the elite line to reconstitute as much of the elite background's genome as possible.

Thus, the markers and methods can be utilized to guide marker assisted selection or breeding of soybean varieties with the desired complement (set) of allelic forms of chromosome segments associated with superior agronomic performance (resistance, along with any other available markers for yield, disease resistance, etc.). Any of the disclosed marker loci, marker alleles, haplotypes, or marker profiles can be introduced into a soybean line via introgression, by traditional breeding (or introduced via transformation, or both) to yield a soybean plant with superior agronomic performance. The number of alleles associated with resistance that can be introduced or be present in a soybean plant ranges from 1 to the number of alleles disclosed herein, each integer of which is incorporated herein as if explicitly recited.

The markers and methods provided herein can also be utilized to guide marker assisted selection or breeding of soybean varieties comprising other soybean cyst nematode resistance markers or alleles to create a molecular stack for soybean cyst nematode resistance. For example, any of the marker loci provided herein can be introduced into a soybean line having one or more of the soybean cyst nematode resistance alleles rhg1, rhg2, rhg3, rhg4 or rhg5. In one embodiment, any one or more of the marker loci provided herein can be stacked with the rhg1 allele. In another embodiment, any one or more of the marker loci provided herein can be stacked with the rhg4 allele. In a further embodiment, any one or more of the marker loci provided herein can be stacked with the rhg1 and rhg4 alleles. For example, any of the marker loci provided herein can be introduced into a soybean line having one or more of the soybean cyst nematode resistance loci rhg1, rhg2, rhg3 or rhg5. In one embodiment, any one or more of the marker loci provided herein can be stacked with the rhg1 locus. In another embodiment, any one or more of the marker loci provided herein can be stacked with the rhg2 locus. In a further embodiment, any one or more of the marker loci provided herein can be stacked with the rhg1 and rhg2 loci.

This also provides a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with resistance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant in that it comprises at least one of the marker loci or marker profiles, such that the progeny are capable of inheriting the marker locus or marker profile.

Often, a method is applied to at least one related soybean plant such as from progenitor or descendant lines in the subject soybean plants pedigree such that inheritance of the desired resistance can be traced. The number of generations separating the soybean plants being subject to the methods provided herein will generally be from 1 to 20, commonly 1 to 5, and typically 1, 2, or 3 generations of separation, and quite often a direct descendant or parent of the soybean plant will be subject to the method (i.e., 1 generation of separation).

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provides an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers, haplotypes, primers, probes, and marker profiles can be used for MAS in crosses involving elite x exotic soybean lines by subjecting the segregating progeny to MAS to maintain major yield alleles, along with the resistance marker alleles herein.

As an alternative to standard breeding methods of introducing traits of interest into soybean (e.g., introgression), transgenic approaches can also be used to create transgenic plants with the desired traits. In these methods, exogenous nucleic acids that encode a desired marker loci, marker profile or haplotype are introduced into target plants or germplasm. For example, a nucleic acid that codes for a resistance trait is cloned, e.g., via positional cloning, and introduced into a target plant or germplasm.

Experienced plant breeders can recognize tolerant soybean plants in the field, and can select the tolerant individuals or populations for breeding purposes or for propagation. In this context, the plant breeder recognizes "resistant" and "non-resistant" or "susceptible" soybean plants. However, plant resistance is a phenotypic spectrum consisting of extremes in resistance and susceptibility, as well as a continuum of intermediate resistance phenotypes. Evaluation of these intermediate phenotypes using reproducible assays are of value to scientists who seek to identify genetic loci that impart resistance, to conduct marker assisted selection for tolerant populations, and to use introgression techniques to breed a resistance trait into an elite soybean line, for example.

By "improved resistance" is intended that the plants show a decrease in the disease symptoms that are the outcome of plant exposure to soybean cyst nematode. That is, the damage caused by soybean cyst nematode is prevented, or alternatively, the disease symptoms caused by soybean cyst nematode is minimized or lessened. Thus, improved resistance to soybean cyst nematode can result in reduction of the disease symptoms by at least about 2% to at least about 6%, at least about 5% to about 50%, at least about 10% to about 60%, at least about 30% to about 70%, at least about 40% to about 80%, or at least about 50% to about 90% or greater. Hence, the methods provided herein can be utilized to protect plants from soybean cyst nematode.

Screening and selection of soybean cyst nematode tolerant soybean plants may be performed, for example, by exposing plants to soybean cyst nematode and selecting those plants showing resistance to soybean cyst nematode. Various assays can be used to measure resistance or improved resistance to soybean cyst nematode. For example, soybean cyst nematode resistance can be determined by visual observations after plant exposure to a particular race of soybean cyst nematode, such as race 1, 2, 3, 5 or 14. Scores range from 1 to 9 and indicate visual observations of resistance as compared to other genotypes in the test. A score of 1 indicates soybean cyst nematode are able to infect the plant and cause yield loss, while a score of 9 indicates soybean cyst nematode resistance. Preliminary scores are reported as double digits, for example, '55' indicates a preliminary score of 5 on the scale of 1 to 9.

Non-limiting examples of soybean cyst nematode resistance phenotypic screening are described in detail below.

Multiple populations of Heterodera glycines are maintained and increased on host plants. These populations are used to identify, purify, and characterize elite soybean varieties for resistance to soybean cyst nematode. The following races of soybean cyst nematode are maintained: Race 1 (Type HG 2.5), Race 2 (Type HG 1.2.5.7), Race 3 (Type HG 0 or Type HG 7), Race 5 (Type HG 2.5.7), and Race 14 (Type HG 1.3.6.7).

Eggs or second stage juveniles (J2) are used to inoculate host plants to increase their population. Soybean cyst nematode infestation requires a minimum 35 days before the cysts reach maturity and can be used to inoculate soybean experiments. Cyst eggs/J2 inoculant is harvested through a series of washings, grindings, and screenings. Screens are used progressing from larger to smaller sizes, ending with a #500 (25 μm) screen.

Soybean plants are grown in cones. Cones are long containers approximately 12 inches long and 1.5 inches in diameter at the top (e.g., Ray Leach Cone-tainers™). The cone is designed to easily remove the root mass. Three to seven days after planting, an inoculum channel is made in the cone containing the experimental line by poking a 4 inch hole with a 10 ml pipette tip. One ml of inoculum is dispensed into the channel. The plants are watered manually for the duration of the test, with watering being moderately light during the first 3-5 days until J2 infects the roots.

Plants are scored approximately 28-35 days following inoculation when cyst reproduction on susceptible checks is sufficiently high. Plants are removed from their cones and the soil is removed from the roots by gently dipping the roots into a bucket of water. The plants are screened to identify native resistance to one or more of the five races of soybean cyst nematode inoculated using a combination of three methods (1) visual 9-6-1 score; (2) visual full count; and/or (3) microscope count score depending on the stage of the line when screened. In general, lines earlier in the development cycle (R1-R2) are screened by the visual 9-6-1 method, and lines that have progressed to later development phases (R3-R5) are screened by the visual full count and/or microscope count method(s).

One typical phenotyping method is a visual evaluation of the roots. Susceptible checks are first evaluated for the development of cysts on the root system. These counts are recorded and averaged across the experiment to determine the susceptible (SUS) check average. Roots from the test plants are then scored based on a comparison with the average of the susceptible checks as follows:

9=0-15% of the susceptible checks average

6=16-40% of the susceptible checks average

1=≥41% of the susceptible checks average

Visual Counts:

In this method, known checks are counted and reported in full. Observed cysts on the test plants are counted for comparison to the susceptible check plant scores. Cyst counts are converted to 1-9 scores based on the female index (FI). The female index (FI) is the percentage of the number of females cysts produced on each experimental line divided by the number produced on a standard susceptible soybean check, then the result is multiplied by 100. A low FI (<10) means that the soybean cyst nematode population is not able to reproduce well on the test line, a high FI means that the soybean cyst nematode population is able to reproduce well on the test line.

Microscope Counts:

Cysts counts for soybean cyst nematode assays for checks and experimental line are determined by washing cysts from roots and counting the number of cysts under the microscope.

At about 28-35 days after inoculation, roots from the susceptible check controls are examined for yellow cysts to assess whether to begin the process of evaluating the test. Experimental lines are compared with known standard checks. Once adequate levels of cysts are detected on the check varieties, plants from the test lines are removed from cones one at a time. Soil is removed from roots by gently dipping the roots into a bucket of water. The root tissue is placed on a 850 micron (#20) pore sieve stacked over a 250 micron (#60) pore sieve and sprayed with a jet of water to dislodge cysts from the roots. Collected cysts are rinsed from the #60 sieve into a clean labeled cup using no more than 30 mls of additional water.

Once all the samples are collected, each sample is counted using a gridded counting dish under a stereo microscope. The number of cysts counted are recorded for each sample. Cyst counts on the test plants are converted to the 1-9 scoring scale based on the female index (FI) described above.

The following exemplary soybean cyst nematode checks, as depicted in Table 6, can be planted and used to monitor cyst development:

TABLE 10

Exemplary soybean cyst nematode checks.

| Race 1 | Race 2 | Race 3 | Race 5 | Race 14 |
|---|---|---|---|---|
| 92B12 RES | 95M60 RES | 9182 RES | 92B12 RES | 9182 RES |
| 9281 SUS | 9281 SUS | 9281 SUS | 9281 SUS | 9281 SUS |
| 9234 RES | PI437654 RES | 9234 RES | 9234 RES | 9234 SUS |
| 9392 SUS | 9392 SUS | 9392 SUS | 9392 SUS | 9392 SUS |
| 91M12 MR | 9234 MR | 93B15 MR | 91M12 SUS | 93B15 MR |

RES = Resistant;
SUS = Susceptible; and,
MR = Moderately Resistant

In some examples, a kit or an automated system for detecting marker loci, haplotypes, and marker profiles, and/or correlating the marker loci, haplotypes, and marker profiles with a desired phenotype (e.g., soybean cyst nematode resistance) are provided. As used herein, "kit" refers to a set of reagents for the purpose of performing the various methods of detecting or identifying herein, more particularly, the identification and/or the detection of a soybean plant or germplasm having improved resistance to soybean cyst nematode.

In one embodiment, a kit for detecting or selecting at least one soybean plant or soybean germplasm with improved resistance to soybean cyst nematode is provided. Such a kit comprises (a) primers or probes for detecting one or more marker loci associated with resistance to soybean cyst nematode, wherein at least one of the primers and probes in the kit are capable of detecting a marker locus, wherein the marker locus is: (i) between about marker Sat_123 and about marker Satt453 on linkage group B1; (ii) between about marker Sat_207 and about marker Satt713 on linkage group C1; or (iii) between about marker Satt574 and about marker Satt615 on linkage group D2; and (b) instructions for using the primers or probes for detecting the one or more marker loci and correlating the detected marker loci with predicted resistance to soybean cyst nematode.

In a specific embodiment, the primers and probes of the kit are capable of detecting a marker locus comprising: (a) S04196-1-B, S04938-1-A, S04937-1-Q1, S08344-1-Q1, S08343-1-Q1, S08346-1-Q1, S06786-1, S06787-1, S06803-1, S04197-1 on linkage group B1, or a closely linked marker; (b) S07162-1-Q1 on linkage group C1, or a closely linked marker; or (c) S07161-1-Q1 on linkage group D2, or a closely linked marker.

In one embodiment, a kit for detecting or selecting at least one soybean plant or soybean germplasm with improved resistance to soybean cyst nematode is provided. Such a kit comprises (I) primers or probes for detecting one or more marker loci associated with resistance to soybean cyst nematode, wherein at least one of the primers and probes in the kit are capable of detecting a marker locus, wherein the marker locus is: (a) is flanked by S04348 and S01999 on linkage group B1; (b) two or more marker locus within 30 cM of one or more of S04348, S01209, or S01999 on linkage group B1; (c) is within 10 cM of one or more of S04348, S01209, or S01999 on linkage group B1; (d) comprises S04348-1-A, S01209-1-A, S01999-1-A, or a marker closely linked thereto on linkage group B1; (e) is flanked by S01209 and S01999 on linkage group B1; (f) is selected from the group consisting of S04937-2-A, S04937-1-Q1, S04938-1-A, S04938-2-A, S06786-2-Q1, S06786-3-Q1, S06786-1-Q1, S06787-2-Q1, S06787-1-Q1, S06803-1-Q1, S06804-1-Q1, S06788-1-Q1, S06805-1-Q1, S06789-1-Q1, S06790-1-Q1, S06791-2-Q1, S06791-1-Q1, or S06792-1-Q1 or a marker closely linked thereto on linkage group B1; (g) is flanked by Satt557 and Satt307 on linkage group C2; (h) is flanked by S03252 and S02112 on linkage group C2; (i) is within 30 cM of one or more of S03252 or S02112 on linkage group C2; (j) is within 10 cM of one or more of S03252 or S02112 on linkage group C2; (k) comprises S03252-1-A, S02112-1-A, or a marker closely linked thereto on linkage group C2; (l) is in an interval comprising the bottom 30 cM of linkage group E, for example from about 66 cM to the end; (m) is flanked by BARC-062799-18070 to the end of linkage group E; (n) is flanked by Sat_107 to the end of linkage group E; (o) is flanked by S00350 to S02183 on linkage group E; (p) is within 30 cM of one or more of S00350 or S02183 on linkage group E; (q) is within 10 cM of one or more of S00350 or S02183 on linkage group E; (r) comprises S00350-1-A, S02183-1-A, or a marker closely linked thereto on linkage group E; (s) is in an interval comprising the top 30 cM of linkage group L, for example from about 0-30 cM; (t) is in an interval is flanked by S02074 and S03991 on linkage group L; (u) is within 30 cM of one or more of S02074 or S03991 on linkage group L; (v) is within 10 cM of one or more of S02074 or S03991 on linkage group L; (w) comprises S02074-1-A, S03991-1-A, or a marker closely linked thereto on linkage group L; (x) is flanked by marker locus S00875 and about marker S02621 on linkage group D1b; (y) is flanked by S00479 and S02136 on linkage group D1b; (z) is within 30 cM of one or more of S00479, S02136, S00875, S12875, S12950, S12947, S12933, S12853, S03246, S01519, S12962, S00144, S08166, S08177, S01081, and S02621 on linkage group D1b; (aa) is within 10 cM of one or more of S00479, S02136, S00875, S12875, S12950, S12947, S12933, S12853, S03246, S01519, S12962, S00144, S08166, S08177, S01081, and S02621 on linkage group D1b; (ab) comprises one or more of S01519-1-A, S08177-1-Q1, S00479-1-A, S02136-1-A, S00875-1-A, S12875-1-Q1, S12950-1-Q1, S12947-1-Q1, S12933-1-Q1, S12853-1-Q1, S03246-1-A or S12962-1-Q1 S00144-1-A, S08166-1-Q1, S01081, and S02621-1-A, or a marker closely linked thereto on linkage group D1b; (ac) is flanked by Sat_264 and about BARC-020449-04623 on linkage group B2; (ad) is flanked by S02874 and S04785 on linkage group B2; (ae) is within 30 cM of one or more of S02864 and S04785 on linkage group B2; (af) is within 10 cM of one or more of S02864 and S04785 on linkage group B2; and/or (ag) comprises S02874-1-A, S04785-1-A, or a marker closely linked thereto on linkage group B2; and (II) instructions for using the primers or probes for detecting the one or more marker loci and correlating the detected marker loci with predicted resistance to soybean cyst nematode.

In a specific embodiment, the primers and probes of the kit are capable of detecting a marker locus comprising a marker that: (a) is flanked by S04348 and S01999 on linkage group B1; (b) two or more marker locus within 30 cM of one or more of S04348, S01209, or S01999 on linkage group B1; (c) is within 10 cM of one or more of S04348, S01209, or S01999 on linkage group B1; (d) comprises S04348-1-A, S01209-1-A, S01999-1-A, or a marker closely linked thereto on linkage group B1; (e) is flanked by S01209 and S01999 on linkage group B1; (f) is selected from the group consisting of S04937-2-A, S04937-1-Q1, S04938-1-A, S04938-2-A, S06786-2-Q1, S06786-3-Q1, S06786-1-Q1, S06787-2-Q1, S06787-1-Q1, S06803-1-Q1, S06804-1-Q1, S06788-1-Q1, S06805-1-Q1, S06789-1-Q1, S06790-1-Q1, S06791-2-Q1, S06791-1-Q1, or S06792-1-Q1 or a marker closely linked thereto on linkage group B1; (g) is flanked by Satt557 and Satt307 on linkage group C2; (h) is flanked by S03252 and S02112 on linkage group C2; (i) is within 30 cM of one or more of S03252 or S02112 on linkage group C2; (j) is within 10 cM of one or more of S03252 or S02112 on linkage group C2; (k) comprises S03252-1-A, S02112-1-A, or a marker closely linked thereto on linkage group C2; (l) is in an interval comprising the bottom 30 cM of linkage group E, for example from about 66 cM to the end; (m) is flanked by BARC-062799-18070 to the end of linkage group E; (n) is flanked by Sat_107 to the end of linkage group E; (o) is flanked by S00350 to S02183 on linkage group E; (p) is within 30 cM of one or more of S00350 or S02183 on linkage group E; (q) is within 10 cM of one or more of S00350 or S02183 on linkage group E; (r) comprises S00350-1-A, S02183-1-A, or a marker closely linked thereto on linkage group E; (s) is in an interval comprising the top 30 cM of linkage group L, for example from about 0-30 cM; (t) is in an interval is flanked by S02074 and S03991 on linkage group L; (u) is within 30 cM of one or more of S02074 or S03991 on linkage group L; (v) is within 10 cM of one or more of S02074 or S03991 on linkage group L; (w) comprises S02074-1-A, S03991-1-A, or a marker closely linked thereto on linkage group L; (x) is flanked by marker locus S00875 and about marker S02621 on linkage group D1b; (y) is flanked by S00479 and S02136 on linkage group D1b; (z) is within 30 cM of one or more of S00479, S02136, S00875, S12875, S12950, S12947, S12933, S12853, S03246, S01519, S12962, S00144, S08166, S08177, S01081, and S02621 on linkage group D1b; (aa) is within 10 cM of one or more of S00479, S02136, S00875, S12875, S12950, S12947, S12933, S12853, S03246, S01519, S12962, S00144, S08166, S08177, S01081, and S02621 on linkage group D1b; (ab) comprises one or more of S01519-1-A, S08177-1-Q1, S00479-1-A, S02136-1-A, S00875-1-A, S12875-1-Q1, S12950-1-Q1, S12947-1-Q1, S12933-1-Q1, S12853-1-Q1, S03246-1-A or S12962-1-Q1 S00144-1-A, S08166-1-Q1, S01081, and S02621-1-A, or a marker closely linked thereto on linkage group D1b; (ac) is flanked by Sat_264 and about BARC-020449-04623 on linkage group B2; (ad) is flanked by S02874 and S04785 on linkage group B2; (ae) is within 30 cM of one or more of S02864 and S04785 on linkage group B2; (af) is within 10 cM of one or more of S02864 and S04785 on linkage group B2; and/or (ag) comprises S02874-1-A, S04785-1-A, or a marker closely linked thereto on linkage group B2.

Thus, a typical kit or system can include a set of marker probes or primers configured to detect at least one favorable allele of one or more marker loci associated with resistance to soybean cyst nematode, for instance a favorable marker locus, haplotype or marker profile. These probes or primers can be configured, for example, to detect the marker loci noted in the tables and examples herein, e.g., using any available allele detection format, such as solid or liquid phase array based detection, microfluidic-based sample detection, etc. The systems and kits can further include packaging materials for packaging the probes, primers, or instructions, controls such as control amplification reactions that include probes, primers or template nucleic acids for amplifications, molecular size markers, or the like.

A typical system can also include a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, scanning detectors, phototubes and photodiodes, microscope stations, galvo-scans, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector examples include light (e.g., fluorescence) detectors or radioactivity detectors. For example, detection of a light emission (e.g., a fluorescence emission) or other probe label is indicative of the presence or absence of a marker allele. Fluorescent detection is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele. The detector(s) optionally monitors one or a plurality of signals from an amplification reaction. For example, the detector can monitor optical signals which correspond to "real time" amplification assay results.

System or kit instructions that describe how to use the system or kit or that correlate the presence or absence of the favorable allele with the predicted resistance are also provided. For example, the instructions can include at least one look-up table that includes a correlation between the presence or absence of the favorable alleles, haplotypes, or marker profiles and the predicted resistance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical example, the system instructions include at least one look-up table that includes a correlation between the presence or absence of the favorable alleles and predicted resistance. The instructions also typically include instructions providing a user interface with the system, e.g., to permit a user to view results of a sample analysis and to input parameters into the system.

Isolated polynucleotides comprising the nucleic acid sequences of the primers and probes provided herein are also encompassed herein. In one embodiment, the isolated polynucleotide comprises a polynucleotide capable of detecting a marker locus of the soybean genome comprising S04196-1-B, S04938-1-A, S04937-1-Q1, S08344-1-Q1, S08343-1-Q1, S08346-1-Q1, S06786-1, S06787-1, S06803-1, S04197-1, S07162-1-Q1, S07162-1-Q1, or a marker closely linked thereto.

Isolated polynucleotides comprising the nucleic acid sequences of the primers and probes provided herein are also encompassed herein. In one embodiment, the isolated polynucleotide comprises a polynucleotide capable of detecting a marker locus of the soybean genome comprising a marker locus (a) is flanked by S04348 and S01999 on linkage group B1; (b) two or more marker locus within 30 cM of one or more of S04348, S01209, or S01999 on linkage group B1; (c) is within 10 cM of one or more of S04348, S01209, or S01999 on linkage group B1; (d) comprises S04348-1-A, S01209-1-A, S01999-1-A, or a marker closely linked thereto on linkage group B1; (e) is flanked by S01209 and S01999 on linkage group B1; (f) is selected from the group consisting of S04937-2-A, S04937-1-Q1, S04938-1-A, S04938-2-A, S06786-2-Q1, S06786-3-Q1, S06786-1-Q1, S06787-2-Q1, S06787-1-Q1, S06803-1-Q1, S06804-1-Q1, S06788-1-Q1, S06805-1-Q1, S06789-1-Q1, S06790-1-Q1, S06791-2-Q1, S06791-1-Q1, or S06792-1-Q1 or a marker closely linked thereto on linkage group B1; (g) is flanked by Satt557 and Satt307 on linkage group C2; (h) is flanked by S03252 and S02112 on linkage group C2; (i) is within 30 cM of one or more of S03252 or S02112 on linkage group C2; (j) is within 10 cM of one or more of S03252 or S02112 on linkage group C2; (k) comprises S03252-1-A, S02112-1-A, or a marker closely linked thereto on linkage group C2; (l) is in an interval comprising the bottom 30 cM of linkage group E, for example from about 66 cM to the end; (m) is flanked by BARC-062799-18070 to the end of linkage group E; (n) is flanked by Sat_107 to the end of linkage group E; (o) is flanked by S00350 to S02183 on linkage group E; (p) is within 30 cM of one or more of S00350 or S02183 on linkage group E; (q) is within 10 cM of one or more of S00350 or S02183 on linkage group E; (r) comprises S00350-1-A, S02183-1-A, or a marker closely linked thereto on linkage group E; (s) is in an interval comprising the top 30 cM of linkage group L, for example from about 0-30 cM; (t) is in an interval is flanked by S02074 and S03991 on linkage group L; (u) is within 30 cM of one or more of S02074 or S03991 on linkage group L; (v) is within 10 cM of one or more of S02074 or S03991 on linkage group L; (w) comprises S02074-1-A, S03991-1-A, or a marker closely linked thereto on linkage group L; (x) is flanked by marker locus S00875 and about marker S02621 on linkage group D1b; (y) is flanked by S00479 and S02136 on linkage group D1b; (z) is within 30 cM of one or more of S00479, S02136, S00875, S12875, S12950, S12947, S12933, S12853, S03246, S01519, S12962, S00144, S08166, S08177, S01081, and S02621 on linkage group D1b; (aa) is within 10 cM of one or more of S00479, S02136, S00875, S12875, S12950, S12947, S12933, S12853, S03246, S01519, S12962, S00144, S08166, S08177, S01081, and S02621 on linkage group D1b; (ab) comprises one or more of S01519-1-A, S08177-1-Q1, S00479-1-A, S02136-1-A, S00875-1-A, S12875-1-Q1, S12950-1-Q1, S12947-1-Q1, S12933-1-Q1, S12853-1-Q1, S03246-1-A or S12962-1-Q1 S00144-1-A, S08166-1-Q1, S01081, and S02621-1-A, or a marker closely linked thereto on linkage group D1b; (ac) is flanked by Sat_264 and about BARC-020449-04623 on linkage group B2; (ad) is flanked by S02874 and S04785 on linkage group B2; (ae) is within 30 cM of one or more of S02864 and S04785 on linkage group B2; (af) is within 10 cM of one or more of S02864 and S04785 on linkage group B2; and/or (ag) comprises S02874-1-A, S04785-1-A, or a marker closely linked thereto on linkage group B2.

In specific embodiments, the isolated polynucleotide comprises: (a) a polynucleotide comprising SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, and/or 248; (b) a polynucleotide comprising SEQ ID NOs: 87, 88, 89, 90, 91, 92, 93, 94, 95, 96, 97, 98, 99, 100, 101, 102, 103, 104, 105, 106, 107, 108, 109, 110, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, and/or 338; (c) a polynucleotide having at least 90% sequence identity to SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, and/or 338; or (d) a polynucleotide comprising at least 10 contiguous nucleotides of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, and/or 338.

In certain embodiments, the isolated nucleic acids are capable of hybridizing under stringent conditions to nucleic acids of a soybean cultivar tolerant to soybean cyst nematode, for instance to particular SNPs that comprise a marker locus, haplotype or marker profile.

As used herein, a substantially identical or complementary sequence is a polynucleotide that will specifically hybridize to the complement of the nucleic acid molecule to which it is being compared under high stringency conditions. A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Appropriate stringency conditions which promote DNA hybridization, for example, 6× sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Non-limiting examples of methods and compositions disclosed herein are as follows:
1. A method of identifying a first soybean plant or a first soybean germplasm that displays improved resistance to soybean cyst nematode, the method comprising detecting in the genome of said first soybean plant or in the genome of said first soybean germplasm at least one marker locus that is associated with the resistance, wherein:
  (a) the at least one marker locus is between about marker Sat_123 and about marker Satt453 on linkage group B1;
  (b) the at least one marker locus is between about marker Sat_207 and about marker Satt713 on linkage group C1; or
  (c) the at least one marker locus is between about marker Satt574 and about marker Satt615 on linkage group D2.
2. The method of embodiment 1, wherein the at least one marker locus of part (a) comprises S04196-1-B, S04938-1-A, S04937-1-Q1, S08344-1-Q1, S08343-1-Q1, S08346-1-Q1, S06786-1, S06787-1, S06803-1, S04197-1 or a marker closely linked thereto.
3. The method of embodiment 1, wherein the at least one marker locus of part (b) comprises S07162-1-Q1 or a marker closely linked thereto.
4. The method of embodiment 1, wherein the at least one marker locus of part (c) comprises S07161-1-Q1 or a marker closely linked thereto.
5. The method of any one of embodiments 1-4, wherein at least two marker loci are detected.
6. The method of embodiment 5, wherein the at least two marker loci comprise a haplotype that is associated with said resistance.
7. The method of embodiment 5, wherein the at least two marker loci comprise a marker profile that is associated with said resistance.
8. The method of any one of embodiments 1-7, wherein the germplasm is a soybean variety.
9. The method of any one of embodiments 1-8, wherein the method further comprises selecting the first soybean plant or first soybean germplasm or a progeny thereof having the at least one marker locus.
10. The method of embodiment 9, further comprising crossing the selected first soybean plant or first soybean germplasm with a second soybean plant or second soybean germplasm.
11. The method of embodiment 10, wherein the second soybean plant or second soybean germplasm comprises an exotic soybean strain or an elite soybean strain.
12. The method of any one of embodiments 1-11, wherein the detecting comprises amplifying at least one of said marker loci and detecting the resulting amplified marker amplicon.
13. The method of embodiment 12, wherein the amplifying comprises:
  a) admixing an amplification primer or amplification primer pair for each marker locus being amplified with a nucleic acid isolated from the first soybean plant or the first soybean germplasm, wherein the primer or primer pair is complementary or partially complementary to a variant or fragment of the genomic locus comprising the marker locus, and is capable of initiating DNA polymerization by a DNA polymerase using the soybean nucleic acid as a template; and
  b) extending the primer or primer pair in a DNA polymerization reaction comprising a DNA polymerase and a template nucleic acid to generate at least one amplicon.
14. The method of embodiment 13, wherein said method comprises amplifying a variant or fragment of one or more polynucleotides comprising SEQ ID NOs: 135, 136, 137, 138, 139, 140, 141, 142, 143, 144, 145, 146, 147, 148, 149, 150, 151, 152, 153 or 154.
15. The method of embodiment 13, wherein said primer or primer pair comprises a variant or fragment of one or more polynucleotides comprising SEQ ID NOs: 135, 136, 137, 138, 139, 140, 141, 142, 143, 144, 145, 146, 147, 148, 149, 150, 151, 152, 153, 154, or complements thereof.
16. The method of embodiment 15, wherein said primer or primer pair comprises a nucleic acid sequence comprising SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 or variants or fragments thereof.
17. The method of embodiment 16, wherein said primer pair comprises:
  a) SEQ ID NO: 1 and SEQ ID NO:2;
  b) SEQ ID NO: 8 and SEQ ID NO:9;
  c) SEQ ID NO: 10 and SEQ ID NO: 13;
  d) SEQ ID NO: 18 and SEQ ID NO: 19;
  e) SEQ ID NO: 31 and SEQ ID NO:32;
  f) SEQ ID NO: 39 and SEQ ID NO:40;
  g) SEQ ID NO: 50 and SEQ ID NO:51;
  h) SEQ ID NO: 64 and SEQ ID NO:65; or
  i) SEQ ID NO: 66 and SEQ ID NO:67.
18. The method of embodiment 13, wherein said method comprises amplifying a variant or fragment of SEQ ID NOs: 155 or 156.
19. The method of embodiment 13, wherein said primer or primer pair comprises a variant or fragment of SEQ ID NOs: 155, 156 or complements thereof.

20. The method of embodiment 19, wherein said primer or primer pair comprises a nucleic acid sequence comprising SEQ ID NOs: 72, 73, 74, 75, 76, 77, 78, 79, 80, 81 or variants or fragments thereof.

21. The method of embodiment 20, wherein said primer pair comprises SEQ ID NO: 72 or SEQ ID NO: 73.

22. The method of embodiment 13, wherein said method comprises amplifying a variant or fragment of SEQ ID NOs: 157 or 158.

23. The method of embodiment 13, wherein said primer or primer pair comprises a variant or fragment of SEQ ID NOs: 157, 158 or complements thereof.

24. The method of embodiment 23, wherein said primer or primer pair comprises a nucleic acid sequence comprising SEQ ID NOs: 82, 83, 84, 85, 86 or variants or fragments thereof.

25. The method of embodiment 23, wherein said primer pair comprises SEQ ID NO: 82 and SEQ ID NO: 83.

26. The method of embodiment 13, wherein the method further comprises providing one or more labeled nucleic acid probes suitable for detection of each marker locus being amplified.

27. The method of embodiment 26, wherein said labeled nucleic acid probe comprises a nucleic acid sequence comprising a variant or fragment of one or more polynucleotides comprising SEQ ID NOs: 135, 136, 137, 138, 139, 140, 141, 142, 143, 144, 145, 146, 147, 148, 149, 150, 151, 152, 153, 154 or complements thereof.

28. The method of embodiment 27, wherein the labeled nucleic acid probe comprises a nucleic acid sequence comprising SEQ ID NOs: 87, 88, 89, 90, 91, 92, 93, 94, 95, 96, 97, 98, 99, 100, 101, 102, 103, 104, 105 or 106.

29. The method of embodiment 26, wherein said labeled nucleic acid probe comprises a nucleic acid sequence comprising a variant or fragment of SEQ ID NOs: 155, 156 or complements thereof.

30. The method of embodiment 29, wherein the labeled nucleic acid probe comprises SEQ ID NOs: 107 or 108.

31. The method of embodiment 26, wherein said labeled nucleic acid probe comprises a variant or fragment of SEQ ID NOs: 157, 158 or complements thereof.

32. The method of embodiment 31, wherein the labeled nucleic acid probe comprises a nucleic acid sequence comprising SEQ ID NOs: 109 or 110.

33. The method of any one of embodiments 1-7, wherein the detecting comprises DNA sequencing of at least one of said marker loci.

34. An isolated polynucleotide capable of detecting a marker locus of the soybean genome comprising S04196-1-B, S04938-1-A, S04937-1-Q1, S08344-1-Q1, S08343-1-Q1, S08346-1-Q1, S06786-1, S06787-1, S06803-1, S04197-1 or a marker closely linked thereto.

35. The isolated polynucleotide of embodiment 34, wherein the polynucleotide comprises:
 (a) a polynucleotide comprising SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or 71;
 (b) a polynucleotide comprising SEQ ID NOs: 87, 88, 89, 90, 91, 92, 93, 94, 95, 96, 97, 98, 99, 100, 101, 102, 103, 104, 105 or 106;
 (c) a polynucleotide having at least 90% sequence identity to the polynucleotides set forth in parts (a) or (b); or
 (d) a polynucleotide comprising at least 10 contiguous nucleotides of the polynucleotides set forth in parts (a) or (b).

36. An isolated polynucleotide capable of detecting a marker locus of the soybean genome comprising S07162-1-Q1 or a marker closely linked thereto.

37. The isolated polynucleotide of embodiment 36, wherein the polynucleotide comprises:
 (a) a polynucleotide comprising SEQ ID NOs: 72, 73, 74, 75, 76, 77, 78, 79, 80 or 81;
 (b) a polynucleotide comprising SEQ ID NOs: 107 or 108;
 (c) a polynucleotide having at least 90% sequence identity to the polynucleotides set forth in parts (a) or (b); or
 (d) a polynucleotide comprising at least 10 contiguous nucleotides of the polynucleotides set forth in parts (a) or (b).

38. An isolated polynucleotide capable of detecting a marker locus of the soybean genome comprising S07161-1-Q1 or a marker closely linked thereto.

39. The isolated polynucleotide of embodiment 38, wherein the polynucleotide comprises:
 (a) a polynucleotide comprising SEQ ID NOs: 82, 83, 84, 85 or 86;
 (b) a polynucleotide comprising SEQ ID NOs: 109 or 110;
 (c) a polynucleotide having at least 90% sequence identity to the polynucleotides set forth in parts (a) or (b); or
 (d) a polynucleotide comprising at least 10 contiguous nucleotides of the polynucleotides set forth in parts (a) or (b).

40. A kit for detecting or selecting at least one soybean plant or soybean germplasm with improved resistance to soybean cyst nematode, the kit comprising:
 a) primers or probes for detecting one or more marker loci associated with resistance to soybean cyst nematode, wherein the primers or probes are capable of detecting a marker locus, wherein:
  (i) the marker locus is between about marker Sat_123 and about marker Satt453 on linkage group B1;
  (ii) the marker locus is between about marker Sat_207 and about marker Satt713 on linkage group C1; or
  (iii) the marker locus is between about marker Satt574 and about marker Satt615 on linkage group D2; and
 b) instructions for using the primers or probes for detecting the one or more marker loci and correlating the detected marker loci with predicted resistance to soybean cyst nematode.

41. The kit of embodiment 40, wherein the primers or probes are capable of detecting a marker locus comprising
 (a) S04196-1-B, S04938-1-A, S04937-1-Q1, S08344-1-Q1, S08343-1-Q1, S08346-1-Q1, S06786-1, S06787-1, S06803-1, S04197-1 or a marker closely linked thereto;
 (b) S07162-1-Q1 or a marker closely linked thereto; or
 (c) S07161-1-Q1 or a marker closely linked thereto.

42. A method of identifying a first soybean plant or a first soybean germplasm that displays improved resistance to soybean cyst nematode, the method comprising detecting in the genome of said first soybean plant or in the genome of said first soybean germplasm at least one marker locus that is associated with the resistance, wherein:
 (a) the at least one marker locus is flanked by marker locus S00875 and S02621 on linkage group D1b;
 (b) the at least one marker locus is flanked by marker locus S00479 and S02136 on linkage group D1b;
 (c) the at least one marker locus is flanked by marker locus Sat_264 and BARC-020449-04623 on linkage group B2;

(d) the at least one marker locus is flanked by marker locus S02874 and S04785 on linkage group B2;
(e) the at least one marker locus is flanked by marker locus S04348 and S01999 on linkage group B1;
(f) the at least one marker locus is flanked by marker locus S01209 and S01999 on linkage group B1;
(g) the at least one marker locus is flanked by marker locus Satt557 and Satt307 on linkage group C2;
(h) the at least one marker locus is flanked by marker locus S03252 and S02112 on linkage group C2; or,
(i) the at least one marker locus comprises S00350-1-A, S02183-1-A, or a marker closely linked thereto; or,
(j) the at least one marker locus is flanked by marker locus S02074 and S03991 on linkage group L.

43. The method of embodiment 42, wherein the at least one marker locus of part (a) comprises S01519-1-A, S08177-1-Q1, S00479-1-A, S02136-1-A, S00875-1-A, S12875-1-Q1, S12950-1-Q1, S12947-1-Q1, S12933-1-Q1, S12853-1-Q1, S03246-1-A, S12962-1-Q1 S00144-1-A, S08166-1-Q1, S01081, and, S02621-1-A or a marker closely linked thereto.

44. The method of embodiment 42, wherein the at least one marker locus of part (c) comprises S02874-1-A, S04785-1-A, or a marker closely linked thereto.

45. The method of embodiment 42, wherein the at least one marker locus of part (e) comprises S04348-1-A, S01209-1-A, S01999-1-A, or a marker closely linked thereto.

46. The method of embodiment 42, wherein the at least one marker locus of part (f) comprises S04937-2-A, S04937-1-Q1, S04938-1-A, S04938-2-A, S06786-2-Q1, S06786-3-Q1, S06786-1-Q1, S06787-2-Q1, S06787-1-Q1, S06803-1-Q1, S06804-1-Q1, S06788-1-Q1, S06805-1-Q1, S06789-1-Q1, S06790-1-Q1, S06791-2-Q1, S06791-1-Q1, or S06792-1-Q1 or a marker closely linked thereto.

47. The method of embodiment 42, wherein the at least one marker locus of part (g) comprises S03252-1-A, S02112-1-A, or a marker closely linked thereto.

48. The method of embodiment 42, wherein the at least one marker locus of part (j) comprises S02074-1-A, S03991-1-A, or a marker closely linked thereto.

49. The method of any one of embodiments 42-48, wherein at least two marker loci are detected.

50. The method of any one of embodiments 42-49, wherein the germplasm is a soybean variety.

51. The method of any one of embodiments 42-50, wherein the method further comprises selecting the first soybean plant or first soybean germplasm or a progeny thereof having the at least one marker locus.

52. The method of embodiment 51, further comprising crossing the selected first soybean plant or first soybean germplasm with a second soybean plant or second soybean germplasm.

53. The method of embodiment 52, wherein the second soybean plant or second soybean germplasm comprises an exotic soybean strain or an elite soybean strain.

54. The method of any one of embodiments 42-51, wherein the detecting comprises amplifying at least one of said marker loci and detecting the resulting amplified marker amplicon.

55. The method of embodiment 54, wherein the amplifying comprises:
a) admixing an amplification primer or amplification primer pair for each marker locus being amplified with a nucleic acid isolated from the first soybean plant or the first soybean germplasm, wherein the primer or primer pair is complementary or partially complementary to a variant or fragment of the genomic locus comprising the marker locus, and is capable of initiating DNA polymerization by a DNA polymerase using the soybean nucleic acid as a template; and
b) extending the primer or primer pair in a DNA polymerization reaction comprising a DNA polymerase and a template nucleic acid to generate at least one amplicon.

56. The method of embodiment 55, wherein said method comprises amplifying a variant or fragment of one or more polynucleotides comprising SEQ ID NOs: 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, and/or 377.

57. The method of embodiment 55, wherein said primer or primer pair comprises a variant or fragment of one or more polynucleotides comprising SEQ ID NOs: 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, and/or 377 or complements thereof.

58. The method of embodiment 57, wherein said primer or primer pair comprises a nucleic acid sequence comprising SEQ ID NOs: 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, and/or 248 or variants or fragments thereof.

59. The method of embodiment 58, wherein said primer pair comprises the pairs as shown in Table 3.

60. The method of embodiment 55, wherein the method further comprises providing one or more labeled nucleic acid probes suitable for detection of each marker locus being amplified.

61. The method of embodiment 60, wherein said labeled nucleic acid probe comprises a nucleic acid sequence comprising a variant or fragment of one or more polynucleotides comprising SEQ ID NOs: 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, and/or 377 or complements thereof.

62. The method of embodiment 61, wherein the labeled nucleic acid probe comprises a nucleic acid sequence comprising SEQ ID NOs: 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, and/or 338.

63. The method of any one of embodiments 41-53, wherein the detecting comprises DNA sequencing of at least one of said marker loci.

64. An isolated polynucleotide capable of detecting a marker locus of the soybean genome comprising
a) S00350-1-A, S02183-1-A, or a marker closely linked thereto;
b) S01519-1-A, S08177-1-Q1, S00479-1-A, S02136-1-A, S00875-1-A, S12875-1-Q1, S12950-1-Q1, S12947-1-Q1, S12933-1-Q1, S12853-1-Q1, S03246-1-A, S12962-1-Q1 S00144-1-A, S08166-1-Q1, S01081, S02621-1-A or a marker closely linked thereto;

c) S02874-1-A, S04785-1-A, or a marker closely linked thereto;
d) S04348-1-A, S01209-1-A, S01999-1-A, or a marker closely linked thereto;
e) S04937-2-A, S04937-1-Q1, S04938-1-A, S04938-2-A, S06786-2-Q1, S06786-3-Q1, S06786-1-Q1, S06787-2-Q1, S06787-1-Q1, S06803-1-Q1, S06804-1-Q1, S06788-1-Q1, S06805-1-Q1, S06789-1-Q1, S06790-1-Q1, S06791-2-Q1, S06791-1-Q1, or S06792-1-Q1 or a marker closely linked thereto;
f) S03252-1-A, S02112-1-A, or a marker closely linked thereto; or,
g) S02074-1-A, S03991-1-A, or a marker closely linked thereto.

65. The isolated polynucleotide of embodiment 64, wherein the polynucleotide comprises:
(a) a polynucleotide comprising SEQ ID NOs: 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, and/or 338;
(b) a polynucleotide having at least 90% sequence identity to the polynucleotides set forth in part (a); or
(d) a polynucleotide comprising at least 10 contiguous nucleotides of the polynucleotides set forth in part (a).

66. A kit for detecting or selecting at least one soybean plant or soybean germplasm with improved resistance to soybean cyst nematode, the kit comprising:
a) a primer or a probe for detecting one or more marker loci associated with resistance to soybean cyst nematode, wherein the primer or probe are capable of detecting a marker locus, wherein:
(i) the at least one marker locus is flanked by marker locus S00875 and S02621 on linkage group D1b;
(ii) the at least one marker locus is flanked by marker locus S00479 and S02136 on linkage group D1b;
(iii) the at least one marker locus is flanked by marker locus Sat_264 and BARC-020449-04623 on linkage group B2;
(iv) the at least one marker locus is flanked by marker locus S02874 and S04785 on linkage group B2;
(v) the at least one marker locus is flanked by marker locus S04348 and S01999 on linkage group B1;
(vi) the at least one marker locus is flanked by marker locus S01209 and S01999 on linkage group B1;
(vii) the at least one marker locus is flanked by marker locus Satt557 and Satt307 on linkage group C2;
(viii) the at least one marker locus is flanked by marker locus S03252 and S02112 on linkage group C2; or,
(iix) the at least one marker locus comprises S00350-1-A, S02183-1-A, or a marker closely linked thereto; or,
(ix) the at least one marker locus is flanked by marker locus S02074 and S03991 on linkage group L; and,
b) instructions for using the primers or probes for detecting the one or more marker loci and correlating the detected marker loci with predicted resistance to soybean cyst nematode.

67. The kit of embodiment 66, wherein the primer or probe is capable of detecting a marker locus comprising
(a) the at least one marker locus comprises S01519-1-A, S08177-1-Q1, S00479-1-A, S02136-1-A, S00875-1-A, S12875-1-Q1, S12950-1-Q1, S12947-1-Q1, S12933-1-Q1, S12853-1-Q1, S03246-1-A, S12962-1-Q1 S00144-1-A, S08166-1-Q1, S01081, S02621-1-A or a marker closely linked thereto;
(b) the at least one marker locus comprises S02874-1-A, S04785-1-A, or a marker closely linked thereto;
(c) the at least one marker locus comprises S04348-1-A, S01209-1-A, S01999-1-A, or a marker closely linked thereto;
(d) the at least one marker locus comprises S04937-2-A, S04937-1-Q1, S04938-1-A, S04938-2-A, S06786-2-Q1, S06786-3-Q1, S06786-1-Q1, S06787-2-Q1, S06787-1-Q1, S06803-1-Q1, S06804-1-Q1, S06788-1-Q1, S06805-1-Q1, S06789-1-Q1, S06790-1-Q1, S06791-2-Q1, S06791-1-Q1, or S06792-1-Q1 or a marker closely linked thereto;
(e) the at least one marker locus of part (g) comprises S03252-1-A, S02112-1-A, or a marker closely linked thereto.
(f) the at least one marker locus of part (j) comprises S02074-1-A, S03991-1-A, or a marker closely linked thereto.

EXPERIMENTAL

The following examples are offered to illustrate, but not to limit the claimed invention. It is understood that the examples and embodiments described herein are for illustrative purposes only, and persons skilled in the art will recognize various reagents or parameters that can be altered without departing from the spirit of the invention or the scope of the appended claims.

Example 1

Markers were developed to characterize, identify, and/or select resistant or susceptible alleles at the SCN loci on linkage groups B1, C1 and D2. Markers were screened against various known resistant and susceptible parents.

During development, these markers were validated and confirmed against a panel of 31 varieties which included proprietary experimental lines, proprietary commercial lines, and public lines.

TABLE 11

| Assay conditions: | |
|---|---|
| H20 | 4.28 ul |
| Hot Tub buffer | 0.5 ul |
| Rox Dye (50X) | 0.075 ul |
| DNTPs (24 mM each) | 0.039 ul |
| Primer (100 uM) | 0.0375 ul |
| Primer (100 uM) | 0.0375 ul |
| Primer (100 uM) | 0.0375 ul |
| FAM Probe (100 uM | 0.005 ul |
| VIC Probe (100 uM | 0.005 ul |
| Hot Tub enzyme | 0.025 ul |
| Total volume | 5.005 ul |

Further development and testing was done to optimize the marker components for high throughput analysis of soybean. From this testing, an optimal set of primer and probe combinations were chosen for high throughput analysis needs, but other versions can be used to detect the polymorphism(s) associated with the phenotype.

Similar development, testing and analysis was done to produce any additional markers to detect polymorphisms associated with the identified SCN loci and soybean cyst nematode resistance, with the results of this work summarized in the Tables provided herein. The markers were validated against the panel of SCN resistant or susceptible varieties described above. The markers are capable of detecting SCN loci likely derived from one or more of PI88788, Peking, PI437654, as well markers from other sources. These markers may have further been optimized for robust and consistent performance in high throughput assay conditions.

These markers can be used in other assays or with other assay conditions. Some markers were assayed under additional conditions, an example of which is summarized below.

The parameters used for the TaqMan assay are as follows in Table 12 and 13.

TABLE 12

| Cycle Settings | | |
| --- | --- | --- |
| 94° C. | 120 sec | 1 cycle |
| 60° C. | 60 sec | 40 cycles |
| 72° C. | 1 sec | |
| 94° C. | 30 sec | |

TABLE 13

| Assay Mix | 1x (ul) |
| --- | --- |
| DNA (1.5 ng) - dried down in assay plate | — |
| ddH$_2$0 | 3.95 |
| Hottub buffer | 0.5 |
| dNTP (2.5 mM) | 0.375 |
| Primer 1 + Pri0mer 2 (100 uM F + R) | 0.02 |
| Probe 1 (10 uM) | 0.05 |
| Probe 2 (10 uM) | 0.05 |
| Hottub enzyme | 0.025 |
| Rox dye (50x) | 0.075 |
| Total | 5.05 |

TABLE 14

Summary of SEQ ID NOs.

| SEQ ID NO | Description | Linkage Group |
| --- | --- | --- |
| 1 | Primer 141527 | B1 |
| 2 | Primer 141528 | B1 |
| 3 | Primer S4196-F2 | B1 |
| 4 | Primer S4196-R2 | B1 |
| 5 | Primer S4196-F3 | B1 |
| 6 | Primer S4196-R3 | B1 |
| 7 | Primer S4196-R4 | B1 |
| 8 | Primer S04938-F1 | B1 |
| 9 | Primer S04938-R1 | B1 |
| 10 | Primer 141535, S04937-F1 | B1 |
| 11 | Primer 141536 | B1 |
| 12 | Primer 148638, S04937-F5 | B1 |
| 13 | Primer 148639, S04937-R3 | B1 |
| 14 | Primer S04937-F3 | B1 |

TABLE 14-continued

Summary of SEQ ID NOs.

| SEQ ID NO | Description | Linkage Group |
| --- | --- | --- |
| 15 | Primer S04937-F4 | B1 |
| 16 | Primer S04937-R4 | B1 |
| 17 | Primer S04937-R5 | B1 |
| 18 | Primer 136830 | B1 |
| 19 | Primer 136831 | B1 |
| 20 | Primer P12198A1-F (128-) 76806 | B1 |
| 21 | Primer 86074: P12198A-1T66A218F | B1 |
| 22 | Primer 86075: P12198A-1T66A218R | B1 |
| 23 | Primer 92472-p12198A1_R | B1 |
| 24 | Primer 136828 | B1 |
| 25 | Primer 136829 | B1 |
| 26 | Primer 136832 | B1 |
| 27 | Primer 136833 | B1 |
| 28 | Primer 19661 | B1 |
| 29 | Primer 19389 | B1 |
| 30 | Primer 96347 | B1 |
| 31 | Primer 136886 | B1 |
| 32 | Primer 136887 | B1 |
| 33 | Primer P8584A-1-F2, 82593 | B1 |
| 34 | Primer Reverse primer 15081 | B1 |
| 35 | Primer 136884 | B1 |
| 36 | Primer 136885 | B1 |
| 37 | Primer 136888 | B1 |
| 38 | Primer 136889 | B1 |
| 39 | Primer 144687 | B1 |
| 40 | Primer 144688 | B1 |
| 41 | Primer S06786-1-Q1F | B1 |
| 42 | Primer S06786-1-Q1R | B1 |
| 43 | Primer S06786-1-Q2R | B1 |
| 44 | Primer S06786-1-Q3F | B1 |
| 45 | Primer S06786-1-Q3R | B1 |
| 46 | Primer S06786-1-Q4F | B1 |
| 47 | Primer S06786-1-Q4R | B1 |
| 48 | Primer S06786-1-Q5F | B1 |
| 49 | Primer S06786-1-Q5R | B1 |
| 50 | Primer 142755 | B1 |
| 51 | Primer 142756 | B1 |
| 52 | Primer 142759 | B1 |
| 53 | Primer 142760 | B1 |
| 54 | Primer S06787-1-Q2F | B1 |
| 55 | Primer S06787-1-Q2R | B1 |
| 56 | Primer S06787-1-Q3R | B1 |
| 57 | Primer S06787-1-Q4F | B1 |
| 58 | Primer S06787-1-Q4R | B1 |
| 59 | Primer S06803-1-Q1F | B1 |
| 60 | Primer S06803-1-Q1R | B1 |
| 61 | Primer S06803-1-Q2F | B1 |
| 62 | Primer S06803-1-Q3F | B1 |
| 63 | Primer S06803-1-Q3R | B1 |
| 64 | Primer 142386 | B1 |
| 65 | Primer 142387 | B1 |
| 66 | Primer S04197-1-F2 | B1 |
| 67 | Primer S04197-1-R2 | B1 |
| 68 | Primer S04197-1-F3 | B1 |
| 69 | Primer S04197-1-R3 | B1 |
| 70 | Primer S04197-1-F4 | B1 |
| 71 | Primer S04197-1-R4 | B1 |
| 72 | Primer 136849 | C1 |
| 73 | Primer 136850 | C1 |
| 74 | Primer 80907 | C1 |
| 75 | Primer 80908 | C1 |
| 76 | Primer 87501 | C1 |
| 77 | Primer 87504 | C1 |
| 78 | Primer 136845 | C1 |
| 79 | Primer 136846 | C1 |
| 80 | Primer 136847 | C1 |
| 81 | Primer 136848 | C1 |
| 82 | Primer 137370 | D2 |
| 83 | Primer 137374 | D2 |
| 84 | Primer 137371 | D2 |
| 85 | Primer 137372 | D2 |
| 86 | Primer 137373 | D2 |
| 87 | Probe 141540 | B1 |
| 88 | Probe 141539 | B1 |
| 89 | Probe S04938-1-P1 | B1 |

TABLE 14-continued

Summary of SEQ ID NOs.

| SEQ ID NO | Description | Linkage Group |
|---|---|---|
| 90 | Probe S04938-1-P2 | B1 |
| 91 | Probe 141537 | B1 |
| 92 | Probe 141538 | B1 |
| 93 | Probe 102404 | B1 |
| 94 | Probe 102405 | B1 |
| 95 | Probe 102406 | B1 |
| 96 | Probe 102407 | B1 |
| 97 | Probe 102384 | B1 |
| 98 | Probe 102385 | B1 |
| 99 | Probe 142753 | B1 |
| 100 | Probe 142754 | B1 |
| 101 | Probe 142757 | B1 |
| 102 | Probe 142758 | B1 |
| 103 | Probe 142761 | B1 |
| 104 | Probe 142762 | B1 |
| 105 | Probe 142389 | B1 |
| 106 | Probe 142388 | B1 |
| 107 | Probe 102396 | C1 |
| 108 | Probe 102397 | C1 |
| 109 | Probe 125316 | D2 |
| 110 | Probe 125331 | D2 |
| 111 | Amplicon for S04196-1-B comprising resistance allele | B1 |
| 112 | Amplicon for S04196-1-B comprising susceptible allele | B1 |
| 113 | Amplicon for S04938-1-A comprising resistance allele | B1 |
| 114 | Amplicon for S04938-1-A comprising susceptible allele | B1 |
| 115 | Amplicon for S04937-1-Q1 comprising resistance allele | B1 |
| 116 | Amplicon for S04937-1-Q1 comprising susceptible allele | B1 |
| 117 | Amplicon for S08344-1-Q1 comprising resistance allele | B1 |
| 118 | Amplicon for S08344-1-Q1 comprising susceptible allele | B1 |
| 119 | Amplicon for S08343-1-Q1 comprising resistance allele | B1 |
| 120 | Amplicon for S08343-1-Q1 comprising susceptible allele | B1 |
| 121 | Amplicon for S08346-1-Q1 comprising resistance allele | B1 |
| 122 | Amplicon for S08346-1-Q1 comprising susceptible allele | B1 |
| 123 | Amplicon for S06786-1 comprising resistance allele | B1 |
| 124 | Amplicon for S06786-1 comprising susceptible allele | B1 |
| 125 | Amplicon for S06787-1 comprising resistance allele | B1 |
| 126 | Amplicon for S06787-1 comprising susceptible allele | B1 |
| 127 | Amplicon for S06803-1 comprising resistance allele | B1 |
| 128 | Amplicon for S06803-1 comprising susceptible allele | B1 |
| 129 | Amplicon for S04197-1 comprising resistance allele | B1 |
| 130 | Amplicon for S04197-1 comprising susceptible allele | B1 |
| 131 | Amplicon for S07162-1-Q1 comprising resistance allele | C1 |
| 132 | Amplicon for S07162-1-Q1 comprising susceptible allele | C1 |
| 133 | Amplicon for S07161-1-Q1 comprising resistance allele | D2 |
| 134 | Amplicon for S07161-1-Q1 comprising susceptible allele | D2 |
| 135 | Reference sequence for S04196-1-B comprising resistance allele | B1 |
| 136 | Reference sequence for S04196-1-B comprising susceptible allele | B1 |
| 137 | Reference sequence for S04938-1-A comprising resistance allele | B1 |
| 138 | Reference sequence for S04938-1-A comprising susceptible allele | B1 |
| 139 | Reference sequence for S04937-1-Q1 comprising resistance allele | B1 |
| 140 | Reference sequence for S04937-1-Q1 comprising susceptible allele | B1 |
| 141 | Reference sequence for S08344-1-Q1 comprising resistance allele | B1 |
| 142 | Reference sequence for S08344-1-Q1 comprising susceptible allele | B1 |
| 143 | Reference sequence for S08343-1-Q1 comprising resistance allele | B1 |
| 144 | Reference sequence for S08343-1-Q1 comprising susceptible allele | B1 |
| 145 | Reference sequence for S08346-1-Q1 comprising resistance allele | B1 |
| 146 | Reference sequence for S08346-1-Q1 comprising susceptible allele | B1 |
| 147 | Reference sequence for S06786-1 comprising resistance allele | B1 |
| 148 | Reference sequence for S06786-1 comprising susceptible allele | B1 |
| 149 | Reference sequence for S06787-1 comprising resistance allele | B1 |
| 150 | Reference sequence for S06787-1 comprising susceptible allele | B1 |
| 151 | Reference sequence for S06803-1 comprising resistance allele | B1 |
| 152 | Reference sequence for S06803-1 comprising susceptible allele | B1 |
| 153 | Reference sequence for S04197-1 comprising resistance allele | B1 |
| 154 | Reference sequence for S04197-1 comprising susceptible allele | B1 |
| 155 | Reference sequence for S07162-1-Q1 comprising resistance allele | C1 |
| 156 | Reference sequence for S07162-1-Q1 comprising susceptible allele | C1 |
| 157 | Reference sequence for S07161-1-Q1 comprising resistance allele | D2 |
| 158 | Reference sequence for S07161-1-Q1 comprising susceptible allele | D2 |

Example 2

Materials and Methods

Population:

Three different homozygous PI90763-derived donor parents were used to create three backcross populations, consisting of five replicates of 92, 83, and 69 progeny, respectively. The respective family names for the populations are LP40401802 (1802), LP40401803 (1803), and LP40401805 (1805). Six punches from separate plants were sampled per line and submitted for genotyping as JB29911. The plates were CTAB extracted to isolate DNA for analysis.

Genotyping:

The putative QTL region on linkage group D1b_(2) was saturated with 16 polymorphic markers for genotyping Phenotyping:

SCN2 scores (1-9 scale) were provided for each replication of each line and the scores were averaged to give one score per line. A haplotype analysis of the D1b region and the results were used to divide the progeny into a recombinant data set and a non-recombinant data set.

QTL Analysis:

Single marker analysis was executed using QTL Cartographer 2.5 (Wang et al. (2011) Windows QTL Cartographer 2.5; Dept. of Statistics, North Carolina State University, Raleigh, N.C. Available online at statgen.ncsu.edu/qtlcart/WQTLCart.htm).

Results:

Genotyping:

Three markers were removed from all three families that were segregating between the two susceptible parents, one monomorphic marker was removed from family 1802, and two monomorphic markers were removed from family 1805.

The remaining allele calls were converted to the A (maternal), B (paternal), H (heterozygous) convention for QTL analysis.

The segregation ratios among the three families varied widely with family 1802 skewed towards the susceptible parents, 1803 skewed towards the resistant parent, and 1805 fairly equal Phenotyping:

The phenotypic distributions for the populations were evaluated with each line represented once using the average score across samples. Each population was evaluated as a whole and then broken down into a recombinant data set and a non-recombinant data set (family 1803 progeny were all classified as recombinant). The average SCN2 score for the parents are as follows: Parent 1=3.0, Parent 2=2.2, and PI090763=8.4.

Single Marker Analysis:

Highly significant markers associated with SCN were found on Lg-D1b. Single marker analysis was conducted for each family and then the families were broken down into recombinant and non-recombinant groups and the analysis was repeated. The tables below show the markers found to be significant at a pr(F)<0.05, and the markers/intervals of highest significance are indicated in bold for each set.

Family LP40401802:

No highly significant associations were identified in family 1802. The highest significance was found in the non-recombinant data set at marker S00479-1-A (91.61 cM), explaining 24% of the variation. Minor significance was found at marker S01519-1-A across all progeny and in the recombinant data set, explaining 11% of the variation.

TABLE 15

| Family | Data Set | Marker | LG | LRS | pr(F) | R2 |
| --- | --- | --- | --- | --- | --- | --- |
| LP40401802 | All progeny | S00479-1-A | D1b_(2) | 3.966 | 0.04957 | 0.046 |
| LP40401802 | All progeny | S00875-1-A | D1b_(2) | 6.084 | 0.01501 | 0.065 |
| LP40401802 | All progeny | S12947-1-Q1 | D1b_(2) | 6.084 | 0.01501 | 0.065 |
| LP40401802 | All progeny | S12933-1-Q1 | D1b_(2) | 9.304 | 0.00263 | 0.087 |
| LP40401802 | All progeny | S01519-1-A | D1b_(2) | 10.743 | 0.00123 | 0.113 |
| LP40401802 | All progeny | S08177-1-Q1 | D1b_(2) | 6.986 | 0.00916 | 0.074 |
| LP40401802 | Non-recombinant | S00479-1-A | D1b_(2) | 9.310 | 0.00324 | 0.239 |
| LP40401802 | Non-recombinant | S01519-1-A | D1b_(2) | 4.478 | 0.04120 | 0.117 |
| LP40401802 | Recombinant | S12933-1-Q1 | D1b_(2) | 5.166 | 0.02643 | 0.083 |
| LP40401802 | Recombinant | S01519-1-A | D1b_(2) | 6.316 | 0.01411 | 0.110 |
| LP40401802 | Recombinant | S08177-1-Q1 | D1b_(2) | 4.278 | 0.04338 | 0.075 |

LRS = likelihood ratio statistic.
pr(F) is the F test statistic testing the null hypothesis. 0.05 is the lowest level of significance, anything <0.0001 is highly significant.

Family LP40401803:

Significance was found in family 1803 between markers S00875-1-A (113.96 cM) and S12933-1-Q1 (cM), explaining 15% of the variation. No recombination was observed in this interval.

TABLE 16

| Family | Data Set | Marker | LG | LRS | pr(F) | R2 |
| --- | --- | --- | --- | --- | --- | --- |
| LP40401803 | Recombinant | S02136-1-A | D1b_(2) | 4.731 | 0.03236 | 0.059 |
| LP40401803 | Recombinant | S00875-1-A | D1b_(2) | 12.686 | 0.00046 | 0.150 |
| LP40401803 | Recombinant | S12875-1-Q1 | D1b_(2) | 11.423 | 0.00088 | 0.125 |
| LP40401803 | Recombinant | S12950-1-Q1 | D1b_(2) | 12.686 | 0.00046 | 0.150 |
| LP40401803 | Recombinant | S12947-1-Q1 | D1b_(2) | 12.037 | 0.00064 | 0.137 |
| LP40401803 | Recombinant | S12933-1-Q1 | D1b_(2) | 12.686 | 0.00046 | 0.150 |
| LP40401803 | Recombinant | S12853-1-Q1 | D1b_(2) | 10.248 | 0.00163 | 0.119 |
| LP40401803 | Recombinant | S03246-1-A | D1b_(2) | 10.744 | 0.00126 | 0.129 |
| LP40401803 | Recombinant | S12962-1-Q1 | D1b_(2) | 7.494 | 0.00707 | 0.092 |
| LP40401803 | Recombinant | S08177-1-Q1 | D1b_(2) | 8.056 | 0.00523 | 0.098 |

Family LP40401805:

Highly significant markers were found in family 1805 between markers S12875-1-Q1 (cM) and S12933-1-Q1 (cM), explaining 31% of the variation using all progeny and 18% of the variation using only recombinant progeny. No recombination was observed in this interval. Significance was not found using the non-recombinant data set.

TABLE 17

| Family | Data Set | Marker | LG | LRS | pr(F) | R2 |
| --- | --- | --- | --- | --- | --- | --- |
| LP40401805 | All progeny | S02136-1-A | D1b_(2) | 4.158 | 0.04537 | 0.059 |
| LP40401805 | All progeny | S00875-1-A | D1b_(2) | 11.254 | 0.00099 | 0.153 |
| LP40401805 | All progeny | S12875-1-Q1 | D1b_(2) | 24.834 | 0.00000 | 0.304 |

TABLE 17-continued

| Family | Data Set | Marker | LG | LRS | pr(F) | R2 |
|---|---|---|---|---|---|---|
| LP40401805 | All progeny | S12950-1-Q1 | D1b_(2) | 24.834 | 0.00000 | 0.306 |
| LP40401805 | All progeny | S12947-1-Q1 | D1b_(2) | 24.129 | 0.00000 | 0.299 |
| LP40401805 | All progeny | S12933-1-Q1 | D1b_(2) | 24.129 | 0.00000 | 0.304 |
| LP40401805 | All progeny | S12853-1-Q1 | D1b_(2) | 22.994 | 0.00000 | 0.285 |
| LP40401805 | All progeny | S03246-1-A | D1b_(2) | 22.994 | 0.00000 | 0.287 |
| LP40401805 | All progeny | S01519-1-A | D1b_(2) | 22.377 | 0.00000 | 0.280 |
| LP40401805 | Recombinant | S12875-1-Q1 | D1b_(2) | 9.076 | 0.00339 | 0.179 |
| LP40401805 | Recombinant | S12950-1-Q1 | D1b_(2) | 9.076 | 0.00339 | 0.179 |
| LP40401805 | Recombinant | S12947-1-Q1 | D1b_(2) | 9.076 | 0.00339 | 0.179 |
| LP40401805 | Recombinant | S12933-1-Q1 | D1b_(2) | 9.076 | 0.00339 | 0.179 |
| LP40401805 | Recombinant | S12853-1-Q1 | D1b_(2) | 7.411 | 0.00811 | 0.149 |
| LP40401805 | Recombinant | S03246-1-A | D1b_(2) | 7.411 | 0.00811 | 0.149 |
| LP40401805 | Recombinant | S01519-1-A | D1b_(2) | 7.411 | 0.00811 | 0.149 |
| LP40401805 | Recombinant | S08177-1-Q1 | D1b_(2) | 7.075 | 0.00969 | 0.163 |

Recombinant and non-recombinant haplotypes were identified in these three populations, and are summarized below in Table ??, where r=resistant, h=heterozygous, and s=susceptible

TABLE 18

| D1b Haplotype | S00875 | S01519 | S00144 | S01081 |
|---|---|---|---|---|
| rrrr | G | C | C | C |
| rrhh | G | C | C, G | A, C |
| rrhs | G | C | C, G | A |
| ssrr | A | T | C | C |
| rrss | G | C | G | A |
| hrrr | A, G | C | C | C |
| rrrh | G | C | C | A, C |
| hrrh | A, G | C | C | A, C |
| rrrs | G | C | C | A |
| rsrr | G | T | C | C |
| srrr | A | C | C | C |
| sssr | A | T | G | C |
| srrh | A | C | C | A, C |
| srsr | A | C | G | C |

Example 3

Materials and Methods

Population.

The population LP40401802 comprised of 204 progeny replicated five times each, was submitted as JB15967 and CTAB extracted for genotyping.

Genotyping:

The putative QTL region on linkage group D1b_(2) was saturated with 17 polymorphic markers, with the rest of the chromosome covered by an additional 13 markers. All marker selections were made using a proprietary software to select markers distributed across the linkage group.

Phenotyping:

Raw cyst counts and the derived 1-9 SCN2 scores were provided for each of the 1020 progeny and parental samples. The scores were averaged for each variety, resulting in 204 progeny scores.

Linkage Analysis:

Map Manager QTX.b20 was used for linkage map construction with the following parameters:

1) Linkage Evaluation: Advanced Backcross 2
2) Search Criteria: $P=1e^{-5}$
3) Map Function: Haldane
4) Cross Type: Line Cross QTL Analysis:

Single marker analysis and composite interval mapping (CIM) were executed using QTL Cartographer 2.5. The standard CIM model and forward and backward regression method was used, and the LRS threshold for statistical significance was set to the default value of 11.5.

Results:

Genotyping:

A consensus call was calculated for each variety and then converted to the A (maternal), B (paternal), H (heterozygous) convention for QTL analysis. Three markers were removed from the analysis because the maternal call was heterozygous while Parent 2 and PI90763 were homozygous for opposite alleles. An additional marker was removed that failed genotyping.

Phenotyping:

The phenotypic distributions were evaluated using an average score across samples for each line. The population was evaluated as a whole and then broken down into a recombinant data set and a non-recombinant data set.

Mapping Analysis:

Linkage mapping was performed in Map Manager QTX.b20 using Advanced Backcross 2 for the Linkage Evaluation setting.

Single Marker Analysis:

Single marker analysis was performed using all 204 progeny, 107 recombinant progeny, and 97 non-recombinant progeny for both the raw cyst counts and SCN2 scores. Highly significant markers were observed at the p=0.0001 level using all progeny and recombinant progeny across both data sets The non-recombinant data set identified peak markers in a similar area, but showed less significance (p=0.001 level). All significant markers among the data sets have effects coming from PI90763.

TABLE 19

| | Chrom | LRS | F(1, n − 2) | pr(F) | R2 |
|---|---|---|---|---|---|
| S00479-1-A | D1b_(2) | 7.605 | 7.672 | 0.00613 | 0.037 |
| S00875-1-A | D1b_(2) | 31.354 | 33.560 | 0.00000 | 0.143 |
| S12875-1-Q1 | D1b_(2) | 39.481 | 43.133 | 0.00000 | 0.176 |
| S12950-1-Q1 | D1b_(2) | 38.950 | 42.497 | 0.00000 | 0.174 |
| S12947-1-Q1 | D1b_(2) | 39.800 | 43.517 | 0.00000 | 0.177 |
| S12933-1-Q1 | D1b_(2) | 41.250 | 45.268 | 0.00000 | 0.183 |
| S12853-1-Q1 | D1b_(2) | 27.427 | 29.068 | 0.00000 | 0.126 |
| S03246-1-A | D1b_(2) | 27.567 | 29.227 | 0.00000 | 0.126 |
| S01519-1-A | D1b_(2) | 14.907 | 15.314 | 0.00012 | 0.071 |
| S12962-1-Q1 | D1b_(2) | 3.521 | 3.517 | 0.06218 | 0.017 |
| S00144-1-A | D1b_(2) | 3.441 | 3.436 | 0.06525 | 0.017 |
| S08166-1-Q1 | D1b_(2) | 3.251 | 3.245 | 0.07313 | 0.016 |
| S01081-1-A | D1b_(2) | 0.298 | 0.295 | 0.58775 | 0.002 |

TABLE 20

| Marker | Chrom | LRS | F(1, n − 2) | pr(F) | R2 |
|---|---|---|---|---|---|
| S00479-1-A | D1b__(2) | 8.533 | 8.628 | 0.00369 | 0.041 |
| S00875-1-A | D1b__(2) | 32.327 | 34.686 | 0.00000 | 0.147 |
| S12875-1-Q1 | D1b__(2) | 40.357 | 44.188 | 0.00000 | 0.180 |
| S12950-1-Q1 | D1b__(2) | 39.963 | 43.713 | 0.00000 | 0.178 |
| S12947-1-Q1 | D1b__(2) | 40.689 | 44.589 | 0.00000 | 0.181 |
| S12933-1-Q1 | D1b__(2) | 42.131 | 46.339 | 0.00000 | 0.187 |
| S12853-1-Q1 | D1b__(2) | 28.012 | 29.732 | 0.00000 | 0.128 |
| S03246-1-A | D1b__(2) | 28.112 | 29.845 | 0.00000 | 0.129 |
| S01519-1-A | D1b__(2) | 14.376 | 14.749 | 0.00016 | 0.068 |
| S12962-1-Q1 | D1b__(2) | 3.272 | 3.266 | 0.07222 | 0.016 |
| S00144-1-A | D1b__(2) | 3.161 | 3.154 | 0.07723 | 0.015 |
| S08166-1-Q1 | D1b__(2) | 3.039 | 3.032 | 0.08318 | 0.015 |
| S01081-1-A | D1b__(2) | 0.263 | 0.260 | 0.61043 | 0.001 |

TABLE 21

| Marker | Chrom | LRS | F(1, n − 2) | pr(F) | R2 |
|---|---|---|---|---|---|
| S00479-1-A | D1b__(2) | 7.644 | 7.776 | 0.00629 | 0.069 |
| S00875-1-A | D1b__(2) | 28.525 | 32.078 | 0.00000 | 0.234 |
| S12875-1-Q1 | D1b__(2) | 38.096 | 44.905 | 0.00000 | 0.300 |
| S12950-1-Q1 | D1b__(2) | 38.096 | 44.905 | 0.00000 | 0.300 |
| S12947-1-Q1 | D1b__(2) | 37.891 | 44.618 | 0.00000 | 0.298 |
| S12933-1-Q1 | D1b__(2) | 41.134 | 49.222 | 0.00000 | 0.319 |
| S12853-1-Q1 | D1b__(2) | 24.658 | 27.212 | 0.00000 | 0.206 |
| S03246-1-A | D1b__(2) | 26.949 | 30.074 | 0.00000 | 0.223 |
| S01519-1-A | D1b__(2) | 1.731 | 1.713 | 0.19349 | 0.016 |
| S12962-1-Q1 | D1b__(2) | 4.397 | 4.405 | 0.03823 | 0.040 |
| S00144-1-A | D1b__(2) | 4.271 | 4.276 | 0.04111 | 0.039 |
| S08166-1-Q1 | D1b__(2) | 4.397 | 4.405 | 0.03823 | 0.040 |
| S01081-1-A | D1b__(2) | 11.558 | 11.977 | 0.00078 | 0.102 |

TABLE 22

| Marker | Chrom | LRS | F(1, n − 2) | pr(F) | R2 |
|---|---|---|---|---|---|
| S00479-1-A | D1b__(2) | 8.402 | 8.577 | 0.00417 | 0.076 |
| S00875-1-A | D1b__(2) | 30.332 | 34.412 | 0.00000 | 0.247 |
| S12875-1-Q1 | D1b__(2) | 39.829 | 47.352 | 0.00000 | 0.311 |
| S12950-1-Q1 | D1b__(2) | 39.829 | 47.352 | 0.00000 | 0.311 |
| S12947-1-Q1 | D1b__(2) | 39.480 | 46.856 | 0.00000 | 0.309 |
| S12933-1-Q1 | D1b__(2) | 42.940 | 51.847 | 0.00000 | 0.331 |
| S12853-1-Q1 | D1b__(2) | 24.825 | 27.419 | 0.00000 | 0.207 |
| S03246-1-A | D1b__(2) | 27.118 | 30.287 | 0.00000 | 0.224 |
| S01519-1-A | D1b__(2) | 1.411 | 1.394 | 0.24048 | 0.013 |
| S12962-1-Q1 | D1b__(2) | 4.729 | 4.744 | 0.03163 | 0.043 |
| S00144-1-A | D1b__(2) | 4.647 | 4.660 | 0.03314 | 0.043 |
| S08166-1-Q1 | D1b__(2) | 4.729 | 4.744 | 0.03163 | 0.043 |
| S01081-1-A | D1b__(2) | 11.842 | 12.288 | 0.00067 | 0.105 |

TABLE 23

| Marker | Chrom | LRS | F(1, n − 2) | pr(F) | R2 |
|---|---|---|---|---|---|
| S00479-1-A | D1b__(2) | 1.159 | 1.142 | 0.28796 | 0.012 |
| S00875-1-A | D1b__(2) | 9.125 | 9.371 | 0.00287 | 0.090 |
| S12875-1-Q1 | D1b__(2) | 11.664 | 12.138 | 0.00075 | 0.113 |
| S12950-1-Q1 | D1b__(2) | 11.198 | 11.625 | 0.00096 | 0.109 |
| S12947-1-Q1 | D1b__(2) | 11.961 | 12.467 | 0.00064 | 0.116 |
| S12933-1-Q1 | D1b__(2) | 11.664 | 12.138 | 0.00075 | 0.113 |
| S12853-1-Q1 | D1b__(2) | 8.358 | 8.549 | 0.00432 | 0.083 |
| S03246-1-A | D1b__(2) | 8.185 | 8.365 | 0.00474 | 0.081 |
| S01519-1-A | D1b__(2) | 9.935 | 10.246 | 0.00186 | 0.097 |
| S12962-1-Q1 | D1b__(2) | 12.522 | 13.091 | 0.00048 | 0.121 |
| S00144-1-A | D1b__(2) | 12.230 | 12.766 | 0.00056 | 0.119 |
| S08166-1-Q1 | D1b__(2) | 11.742 | 12.225 | 0.00072 | 0.114 |
| S01081-1-A | D1b__(2) | 10.448 | 10.804 | 0.00142 | 0.102 |

TABLE 24

| Marker | Chrom | LRS | F(1, n − 2) | pr(F) | R2 |
|---|---|---|---|---|---|
| S00479-1-A | D1b__(2) | 1.412 | 1.393 | 0.24078 | 0.015 |
| S00875-1-A | D1b__(2) | 9.014 | 9.251 | 0.00304 | 0.089 |
| S12875-1-Q1 | D1b__(2) | 11.479 | 11.935 | 0.00083 | 0.112 |
| S12950-1-Q1 | D1b__(2) | 11.116 | 11.535 | 0.00100 | 0.108 |
| S12947-1-Q1 | D1b__(2) | 11.826 | 12.318 | 0.00069 | 0.115 |
| S12933-1-Q1 | D1b__(2) | 11.479 | 11.935 | 0.00083 | 0.112 |
| S12853-1-Q1 | D1b__(2) | 8.593 | 8.800 | 0.00381 | 0.085 |
| S03246-1-A | D1b__(2) | 8.360 | 8.551 | 0.00432 | 0.083 |
| S01519-1-A | D1b__(2) | 10.234 | 10.571 | 0.00159 | 0.100 |
| S12962-1-Q1 | D1b__(2) | 12.627 | 13.207 | 0.00045 | 0.122 |
| S00144-1-A | D1b__(2) | 12.289 | 12.831 | 0.00054 | 0.119 |
| S08166-1-Q1 | D1b__(2) | 11.900 | 12.400 | 0.00066 | 0.116 |
| S01081-1-A | D1b__(2) | 10.442 | 10.797 | 0.00142 | 0.102 |

Example 4

The goal of this study was to confirm the QTLs reported in the paper TAG (2005) 111:965—another F4 population from a biparental cross with PI90763. This population has been previously phenotyped and an initial genotyping job assayed 119 markers from the 7 chromosomes (Lg-A2/B1/E/G/J/L/O) reported as significant in the above literature. Marker regression significant associations on Lg-L and B1 (p=0.001), and interval mapping also indicated Lg-L as significant. However, the chromosome positions of each QTL were inconsistent with the QTL positions reported in the literature. In combination with a subsequent genome-wide scan of the population (an additional 163 markers), a second mapping analysis confirmed the minor QTL on Lg-L and indicated a major QTL on Lg-D1b. The QTL on Lg-L was not consistent with the QTL reported in the literature, while the QTL on Lg-D1b was not reported in either paper. New phenotypic data was analyzed in this study using the previous genotypic calls. A minor QTL was identified on Lg-B2, explaining 8% of the phenotypic variation, and the QTL on Lg-D1b was confirmed from the prior analysis, explaining 40% of the variation. When the first and second sets of phenotypic scores were averaged, one major and six minor QTLs were identified. The major QTL mapped to Lg-D1b in the interval reported previously and explained 39% of the variation. Two minor QTLs were identified on Lg-B1, each explaining 7% of the phenotypic variation, and one minor QTL was identified on each of Lg-C2, E, F, and L, explaining 7%, 8%, 10%, and 9% of the variation, respectively. While QTLs were identified on Lg-B1, E, and L in the literature, the positions do not seem consistent with the current findings.

Materials and Methods:

Population:

An F4 population from a biparental cross with PI90763 PI90763 consisting of 276 progeny was used for the study, PI90763 was the resistant donor. The tissue was lyophilized and submitted for genotyping as JB1048. The tissue was then CTAB extracted to isolate DNA.

Genotyping:

Genotypic data from jobs J-D306 (119 markers) and J-G285 (163 markers) were employed in this analysis.

Phenotyping:

Phenotypic scores, ranged from a score of 1 (susceptible) to 9 (resistant). The new data set was analyzed both alone (Set2_AVE) and as an average with the original data set (Total_AVE).

Linkage Analysis:

Map Manager QTX.b20 was used to construct the linkage map and perform QTL analysis. The initial Map Manager Parameters were set to:
1) Linkage Evaluation: Intercross
2) Search Criteria: P=1e$^{-5}$
3) Map Function: Kosambi
4) Cross Type: Line Cross Genetic Map:

Preliminary analysis showed that 24 markers from J-G285 were non-informative for QTL analysis due to the absence of a heterozygous class. These markers were removed and the data for the remaining 139 markers was combined with the data for 78 markers from J-D306. In all, 45 markers showed segregation distortion but were retained in the analysis. Allele calls for the 217 markers were then converted to the A (maternal), B (paternal), H (heterozygous) convention for QTL analysis. The 217 markers formed 48 linkage groups across the 20 chromosomes, with 19 markers remaining unlinked. Marker arrangement was checked to ensure the distorted markers linked as expected, and four markers were found to have rearrangements. These were removed from the analysis.

Marker Regression Analysis:

Marker regression was performed (p=0.001) across all 217 markers, indicating significant associations on Lg-B2, D1b, E, L, and I in the Set2_AVE data set, and Lg-B1, C2, D1b, E, and L in the Total_AVE data set.

A permutation test was run 1000 times using the free model, establishing the threshold for statistical significance (LOD ratio statistic—LRS) to determine putative QTL. LRS cutoffs were 11.0 for suggestive in Set2_AVE and total_AVE, 17.7 or 17.3 for significant in Set2_AVE and total_AVE, and 26.8 or 28.9 for highly significant in Set2_AVE and total_AVE. Interval mapping was performed using the bootstrap test, free regression model, and the LRS cutoffs determined by the permutation test.

Set2_AVE: Major QTL on Lg-D1b, Minor QTL on Lg-B2

A major QTL was indicated near the bottom of Lg-D1b with a 1-LOD support interval of 3 cM between markers S01519-1-A and S02621-1-A and an LRS of 131.6, explaining 40% of the phenotypic variation. A minor QTL was also indicated near the top of Lg-B2 at marker S02874-1-A with a 1-LOD support interval of 3 cM between markers. The LRS was 21.1 and the QTL explained 8% of the phenotypic variation.

Total_AVE: Major QTL on Lg-D1b, Six Minor QTL on Lg-B1, C2, E, and L

A major QTL was indicated near the bottom of Lg-D1b with a 1-LOD support interval of 3 cM between markers S01519-1-A and S02621-1-A and an LRS of 131.1, explaining 39% of the phenotypic variation.

Two minor QTLs were identified about 28 cM apart in the top half of Lg-B1, each explaining 7% of the phenotypic variation. The first has a 1-LOD support interval of 9 cM and LRS of 19.9. The second minor QTL has a 1-LOD support interval of 5 cM between markers S01209-1-A and S01999-1-A and an LRS of 18.7.

A minor QTL was indicated near the bottom of Lg-C2 at marker S02112-1-A, This QTL had an LRS of 17.3, explaining 7% of the variation.

A minor QTL was identified near the bottom of Lg-E, highly associated with marker S02183-1-A and flanked to the north by S00350-1-A. No markers were linked to the south. The QTL had an LRS of 20.2, explaining 8% of the phenotypic variation.

A minor QTL was found at the top of Lg-L at marker S02074-1-A and flanked to the south by S03991-1-A. No markers were linked to the north. The QTL had an LRS of 20.7 and explained 9% of the phenotypic variation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of selecting a first soybean plant or a first soybean germplasm that displays resistance to soybean cyst nematode compared to a susceptible plant, the method comprising detecting in the genome of said first soybean plant or in the genome of said first soybean germplasm at least one marker locus that is associated with the resistance, wherein
the at least one marker locus is between about marker Sat_123 and about marker Satt453 on linkage group B1,
wherein the at least one marker locus comprises S06787-1,
wherein the detecting comprises amplifying the at least one marker locus and detecting the resulting amplified marker amplicon,
thereby selecting a first soybean plant or a first soybean germplasm that displays resistance to soybean cyst nematode compared to a susceptible plant.

2. The method of claim 1, wherein at least two marker loci are detected.

3. The method of claim 2, wherein the at least two marker loci comprise a haplotype that is associated with said resistance.

4. The method of claim 2, wherein the at least two marker loci comprise a marker profile that is associated with said resistance.

5. The method of claim 1, wherein the germplasm is a soybean variety.

6. The method of claim 1, wherein the method further comprises selecting the first soybean plant or first soybean germplasm or a progeny thereof having the at least one marker locus.

7. The method of claim 6, further comprising crossing the selected first soybean plant or first soybean germplasm with a second soybean plant or second soybean germplasm.

8. The method of claim 7, wherein the second soybean plant or second soybean germplasm comprises an exotic soybean strain or an elite soybean strain.

9. The method of claim 1, wherein the amplifying comprises: (a) admixing an amplification primer or amplification primer pair for each marker locus being amplified with a nucleic acid isolated from the first soybean plant or the first soybean germplasm, wherein the primer or primer pair is complementary or partially complementary to the genomic locus comprising the marker locus, and is capable of initiating DNA polymerization by a DNA polymerase using the soybean nucleic acid as a template; and b) extending the primer or primer pair in a DNA polymerization reaction comprising a DNA polymerase and a template nucleic acid to generate at least one amplicon.

10. The method of claim 9, wherein said method comprises:
amplifying a polynucleotide comprising SEQ ID NO: 149.

11. The method of claim 9, wherein said primer or primer pair comprises:
a polynucleotide comprising SEQ ID NO: 149.

12. The method of claim 11, wherein said primer or primer pair comprises:
a nucleic acid sequence comprising SEQ ID NOs: 50 or 51.

13. The method of claim 12, wherein said primer pair comprises:
SEQ ID NO: 50 and SEQ ID NO:51.

14. The method of claim 9, wherein the method further comprises providing one or more labeled nucleic acid probes suitable for detection of each marker locus being amplified.

15. The method of claim 14, wherein said labeled nucleic acid probe comprises:
a nucleic acid sequence comprising a polynucleotide comprising SEQ ID NO: 149.

16. The method of claim 1, wherein the detecting comprises DNA sequencing of at least one of said marker loci.

* * * * *